(12) United States Patent
Clagett-Dame et al.

(10) Patent No.: US 8,188,064 B2
(45) Date of Patent: *May 29, 2012

(54) VITAMIN D ANALOGS FOR OBESITY PREVENTION AND TREATMENT

(75) Inventors: Margaret Clagett-Dame, Madison, WI (US); Hector F. DeLuca, Deerfield, WI (US); Jamie M. Ahrens, Mt. Horeb, WI (US); James M. Ntambi, Madison, WI (US); Brian Thomson, Madison, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 10/997,698

(22) Filed: Nov. 24, 2004

(65) Prior Publication Data

US 2005/0119242 A1 Jun. 2, 2005

Related U.S. Application Data

(60) Provisional application No. 60/524,798, filed on Nov. 25, 2003, provisional application No. 60/524,813, filed on Nov. 25, 2003.

(51) Int. Cl.
*A61K 31/59* (2006.01)
*C07D 401/00* (2006.01)
(52) U.S. Cl. ....................... 514/167; 552/653
(58) Field of Classification Search ................ 514/167; 552/653
See application file for complete search history.

(56) References Cited

U.S. PATENT DOCUMENTS

| | | | |
|---|---|---|---|
| 5,086,191 A | 2/1992 | DeLuca et al. | |
| 5,246,925 A | 9/1993 | DeLuca et al. | |
| 5,536,713 A | 7/1996 | Deluca et al. | |
| 5,585,369 A | 12/1996 | DeLuca et al. | |
| 5,587,497 A | 12/1996 | DeLuca et al. | |
| 5,843,928 A | 12/1998 | Deluca et al. | |
| 5,936,133 A | 8/1999 | Deluca et al. | |
| 5,945,410 A | 8/1999 | DeLuca et al. | |
| 6,384,087 B1* | 5/2002 | Zemel et al. | 424/755 |
| 6,537,981 B2 | 3/2003 | DeLuca et al. | |
| 6,566,352 B1 | 5/2003 | DeLuca et al. | |
| 6,579,861 B2 | 6/2003 | DeLuca et al. | |
| 6,627,622 B2 | 9/2003 | DeLuca et al. | |
| 7,232,810 B2* | 6/2007 | DeLuca et al. | 514/167 |
| 7,241,749 B2* | 7/2007 | DeLuca et al. | 514/167 |
| 7,241,751 B2* | 7/2007 | DeLuca et al. | 514/167 |
| 2002/0192264 A1* | 12/2002 | Zemel et al. | 424/439 |
| 2004/0220418 A1 | 11/2004 | DeLuca et al. | |
| 2005/0065088 A1* | 3/2005 | Thompson | 514/12 |
| 2005/0065133 A1* | 3/2005 | Lee et al. | 514/167 |
| 2005/0065180 A1* | 3/2005 | Lee | 514/303 |
| 2005/0070511 A1 | 3/2005 | DeLuca et al. | |
| 2005/0070512 A1* | 3/2005 | Lee | 514/167 |

FOREIGN PATENT DOCUMENTS

| | | |
|---|---|---|
| WO | WO 98/41501 | 9/1998 |
| WO | WO 00/59513 | 10/2000 |
| WO | WO 2005/027913 | 3/2005 |
| WO | WO 2005/027915 | 3/2005 |
| WO | WO 2005/027924 | 3/2005 |
| WO | WO 2005/027929 | 3/2005 |
| WO | WO 2005/027931 | 3/2005 |

OTHER PUBLICATIONS

Xue et al., The FASEB Journal. (Nov. 17, 2001), vol. 15, pp. 2527-2529.*
Shi et al., The FASEB Journal (Dec. 2001, vol. 15, pp. 2751-2753.*
Hiroshi, Horikawa et al., abstract of JP 03210156.*
DeLuca, H. F., "Applications of New Vitamin D Compounds to Disease," *DN& P*, vol. 5, No. 2, pp. 87-92, Mar. 1992.

Baggiolini et al., "Stereocontrolled Total Synthesis of 1α,25-Dihydroxyergocalciferol," *J. Org. Chem.*, vol. 51, 3098-3108 (1986); published by American Chemical Society.

Casimir, D.A. et al., "cAMP Activates the Expression of Stearoyl-CoA Desaturase Gene 1 during Early Preadipocyte Differentiation," *J. Biol. Chem.*, 271(47), pp. 29847-29853 (1996); The American Society for Biochemistry and Molecular Biology, Inc.

Chomczynski, P. et al., "Single-Step Method of RNA Isolation by Acid Guanidinium Thiocyanate-Phenol-Chloroform Extraction," *Anal. Biochem.*, 162, pp. 156-159 (1987); Academic Press, Inc.

Cohen, P. et al., "Role for Stearoyl-CoA Desaturase-1 in Leptin-Mediated Weight Loss," *Science*, 297, pp. 240-243 (2002).

Collins et al., "Normal Functional Characteristics of Cultured Human Promyelocytic Leukemia Cells (HL-60) After Induction of Differentiation by Dimethylsulfoxide" *J. Exp. Med.*, 149, pp. 969-974 (1979).

U.S. Appl. No. 10/613,201, filed Jul. 3, 2003, DeLuca et al.

Dame et al., "Monoclonal Antibodies to the Porcine Intestinal Receptor for 1,25-Dihydroxyvitamin $D_3$: Interaction with Distinct Receptor Domains," *Biochemistry*, vol. 25, pp. 4523-4534 (1986); American Chemical Society.

Daniewski, A. R. et al., "A Novel Silylcopper Catalyst for the Reductive Bromination of Hajos Cione. Improved Preparation of a CD Synthon for the Synthesis of Vitamin D," *J. Org. Chem.*, 66, pp. 626-628 (2001); American Chemical Society.

Green, H. et al., "An Established Pre-Adipose Cell Line and its Differentiation in Culture," *Cell*, 3, pp. 127-133 (1974); MIT.

Hanessian et al., "Total Synthesis of (-)-Reserpine Using the Chiron Approach," *J. Org. Chem.*, 62, pp. 465-473 (1997); American Chemical Society.

Kutner et al., "Novel Convergent Synthesis of Side-Chain-Modified Analogues of 1α,25- Dihydroxycholecalciferol and 1α,25-Dihydroxyergocalciferol," *J. Org. Chem.*, vol. 53, 3450-3457 (1988); American Chemical Society.

Lythgoe et al., "Calciferol and its Relatives. Part 22. A direct total Synthesis of Vitamin $D_2$ and Vitamin $D_3$", *J. Chem. Soc. Perkin Trans. I*, pp. 590-595 (1978).

Lythgoe, "Synthetic Approaches to Vitamin D and its Relatives," *Chem. Soc. Rev.*, vol. 9, 449-475 (1983).

Mackall, J. C. et al., "Induction of Lipogenesis during Differentiation in a 'Preadipocyte' Cell Line," *J. Biol. Chem.*, 251(20), pp. 6462-6464 (1976).

Mandrup, S. et al., "Regulating Adipogenesis," *J. Biol. Chem.*, 272(9), pp. 5367-5370 (1997); The American Society for Biochemistry and Molecular Biology, Inc.

Mascareñas et al., "Studies on the Synthesis of Side-Chain Hydroxylated Metabolites of Vitamin D. 3. Synthesis of 25-Ketovitamin $D_3$ and 25-Hydroxyvitamin $D_3$," *J. Org. Chem.*, vol. 51, 1269-1272 (1986); American Chemical Society.

Miyamoto et al., "Synthetic Studies of Vitamin D Analogues. XIV. Synthesis and Calcium Regulating Activity of Vitamin $D_3$ Analogues Bearing a Hydroxyalkoxy Group at the 2β-Position," *Chem. Pharm. Bull.*, vol. 41(6), pp. 1111-1113 (1993); Pharmaceutical Society of Japan.

Mincione et al., "Improved Conversion of Vitamin $D_2$ into the Windaus Ketone and its Regioselective Hydroxylation via Organoboranes at $C_{26}$," *Synth. Commun.*, vol. 19(5&6), pp. 723-735 (1989).

Nishii et al., "The Development of Vitamin $D_3$ Analogues for the Treatment of Osteoporosis," *Osteoporosis Int. Suppl.*, vol. 1, 190-193 (1993); European Foundation for Osteoporosis.

Ntambi, J. M. et al., "Loss of stearoyl-CoA desaturase-1 function protects mice against adiposity," *Proc. Natl. Acad. Sci. USA*, 99(17), pp. 11482-11486 (2002).

Okano et al., "Regulatory Activities of 2β-(3-Hydroxypropoxy)-1α,25-Dihydroxy-Vitamin $D_3$, a Novel Synthetic Vitamin $D_3$ Derivative, on Calcium Metabolism," *Biochem. Biophys. Res. Commun.*, vol. 163(3), 1444-1449 (1989); published by Academic Press, Inc.

Ostrem et al., "24- and 26-homo-1,25-dihydroxyvitamin $D_3$: Preferential activity in inducing differentiation of human leukemia cells HL-60 in vitro," *Proc. Natl. Acad. Sci. USA*, vol. 84, pp. 2610-2614 (1987).

Ostrem et al., "Induction of Monocytic Differentiation of HL-60 Cells by 1,25-Dihydroxyvitamin D Analogs," *J. Biol. Chem.*, vol. 262(29), pp. 14164-14171 (1987); The American Society for Biochemistry and Molecular Biology, Inc.

Peleg, S., *Chapter 60: Molecular Basis for Differential Action of Vitamin D Analogs, In: Vitamin D*, Feldman, Glorieux and Pike (eds.), pp. 1011-1025 (1977); Academic Press.

Perlman et al., "1α,25-Dihydroxy-19-Nor-Vitamin $D_3$, A Novel Vitamin D-Related Compound with Potential Therapeutic Activity," *Tetrahedron Lett.*, vol. 31(13), pp. 1823-1824 (1990); Pergamon Press, Great Britain.

Perlman et al., "Novel Synthesis of 19-Nor-Vitamin D Compounds," *Tetrahedron Lett.*, vol. 32(52), pp. 7663-7666 (1991); Pergamon Press, Great Britain.

Peterson et al., Studies of the Ketone Obtained from the Ozonolysis of Vitamin D. Molecular Mechanics Calculations for It and Related Hydrindanones,: *J. Org. Chem.*, vol. 51, pp. 1948-1954 (1986); American Chemical Society.

Plum, L. A. et al., "Biologically active noncalcemic analogs of 1α,25-dihydroxyvitamin D with an abbreviated side chain containing no hydroxyl," *Proc. Natl. Acad. Sci. USA*, 101(18), pp. 6900-6904 (2004).

Posner et al., Stereocontrolled Total Synthesis of Calcitriol Derivatives: 1,25-Dihydroxy-2(4'-hydroxybutyl)vitamin $D_3$ Analogs of an Osteoporosis Drug, *J. Org. Chem.*, vol. 59, pp. 7855-7861 (1994); American Chemical Society.

Posner et al., "2-Fluoroalkyl A-Ring Analogs of 1,25-Dihydroxyvitamin $D_3$ Stereocontrolled Total Synthesis via Intramolecular and Intermolecular Diels—Alder Cycloadditions. Preliminary Biological Testing," *J. Org. Chem.*, vol. 60, 4617-4628 (1995); American Chemical Society.

Qiu, Z. et al., "DNA Synthesis and Mitotic Clonal Expansion Is Not a Required Step for 3T3-L1 Preacipocyte Differentiation into Adipocytes," *J. Biol. Chem.*, 276(15), pp. 11988-11995 (2001); The American Society for Biochemistry and Molecular Biology, Inc.

Sardina et al., "Studies on the Synthesis of Side-Chain Hydroxylated Metabolites of Vitamin D. 2. Stereocontrolled Synthesis of 25-Hydroxyvitamin $D_2$," *J. Org. Chem.*, vol. 51, 1264-1269 (1986); American Chemical Society.

Sato, M. et al., "Demonstration of 1α,25-Dihydroxyvitamin $D_3$ Receptor-Like Molecule in ST 13 and 3T3 L1 Preadipocytes and its Inhibitory Effects on Preadipocyte Differentiation," *J. Cell. Phys.*, 135, pp. 545-550 (1988); Alan R. Liss, Inc.

Sicinski, R. R. et al., "New 1α,25-Dihydroxy-19-norvitamin $D_3$ Compounds of High Biological Activity: Synthesis and Biological Evaluation of 2-Hydroxymethyl, 2-Methyl, and 2-Methylene Analogues," *J. Med. Chem.*, 41, 4662-4674 (1998); American Chemical Society.

Sicinski, R. R. et al., "Synthesis and Biological Activity of 2-Hydroxy and 2-Alkoxy Analogs of 1α,25-Dihydroxy-19-norvitamin $D_3$," *J. Med. Chem.*, 37, pp. 3730-3738 (1994); American Chemical Society.

Suda, T. et al., Biological Activity of 25-Hydroxyergocalciferol in Rats, *J. Nutrition*, vol. 100, pp. 1049-1052 (1970).

Toh et al., "Studies on a Convergent Route to Side-Chain Analogues of Vitamin D: 25-Hydroxy-23-oxavitamin $D_3$," *J. Org. Chem.*, 48, pp. 1414-1417 (1983); American Chemical Society.

Yeh, W. et al., "Cascade regulation of terminal adipocyte differentiation by three members of the C/EBP family of leucine zipper proteins," *Genes & Dev.*, 9, pp. 168-181 (1995); Cold Spring Harbor Laboratory Press.

Gregoire, F. M. et al., "Understanding Adipocyte Differentiation," *Physio. Rev.* 78, pp. 783-809, Jul. 1998; published by the American Physiological Society.

Enerbäck, S. et al., "The Adipocyte: A Multifunctional Cell," 2006, NS 134; printed from the Web on Feb. 12, 2009 at http://nobelprize.org/cgi-bin/print?from=%2Fnobelfoundation%2Fsymposia%2Fmedicine, 4 pages.

Sakuma, T. et al., "Inhibition of peroxisome proliferator—activated receptor a signaling by vitamin D receptor," *Biochemical and Biophysical Research Communications*, Dec. 12, 2003, vol. 312, No. 2, pp. 513-519.

Supplementary European Search Report for EP 04812196, dated Feb. 4, 2009.

Examiners First Report issued in AU 2004293092 dated Jun. 30, 2009.

International Search Report for PCT/US04/39625 mailed Jun. 1, 2005.

* cited by examiner

*Primary Examiner* — Sabiha Qazi
(74) *Attorney, Agent, or Firm* — Foley & Lardner LLP

(57) ABSTRACT

Methods for treating and preventing obesity, inhibiting adipocyte differentiation, inhibiting increased SCD-1 gene transcription, and/or reducing body fat in a subject include administering at least one analog of 1α,25-dihydroxyvitamin $D_3$ or 1α,25-dihydroxyvitamin $D_2$ or a pharmaceutical composition that includes such an analog to a subject in need thereof. The analog may be a 19-nor vitamin D analog such as a compound of formula IA, a compound of formula IB, or a mixture thereof where the variables $R^1$, $R^2$, and $R^3$ have the values described herein.

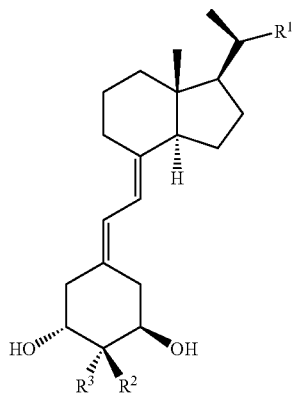

IA

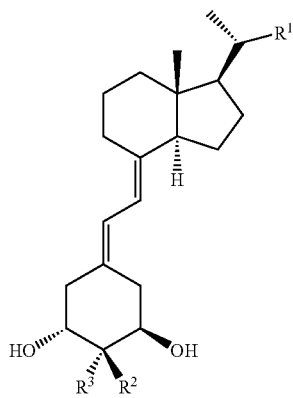

IB

14 Claims, 20 Drawing Sheets

FIG. 1A
No Inducer
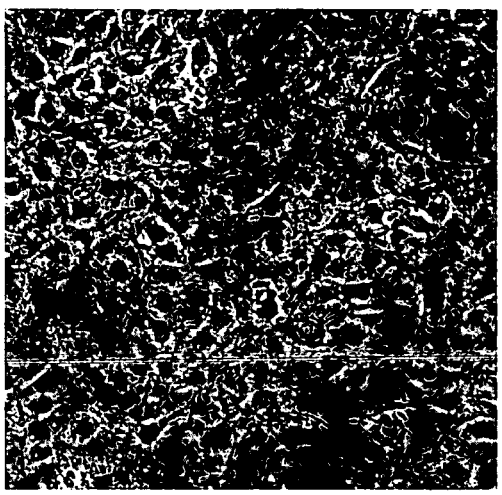
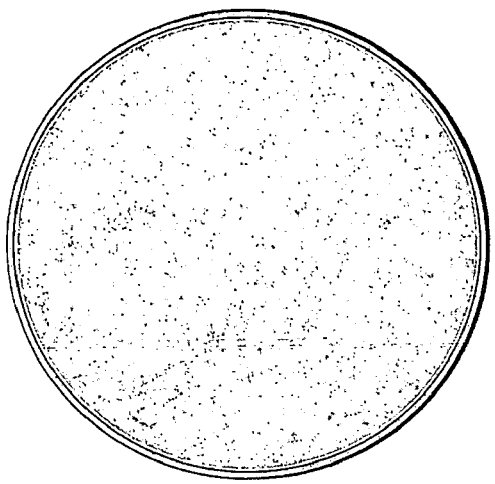
FIG. 1B
+ Inducer (MDI)
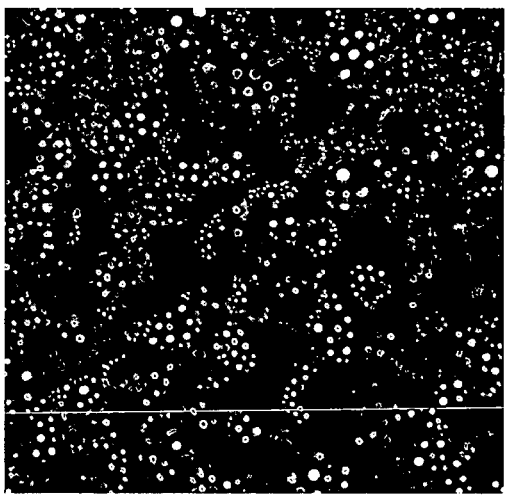
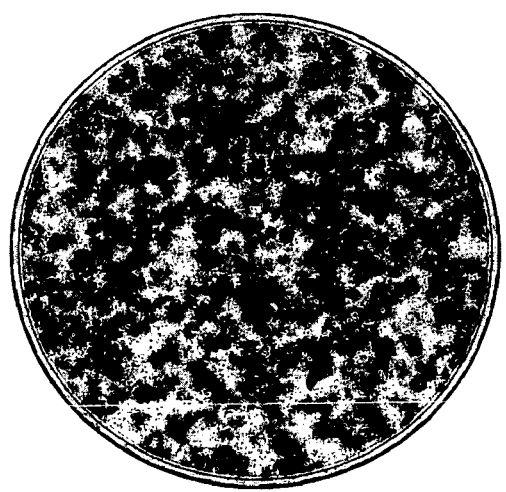

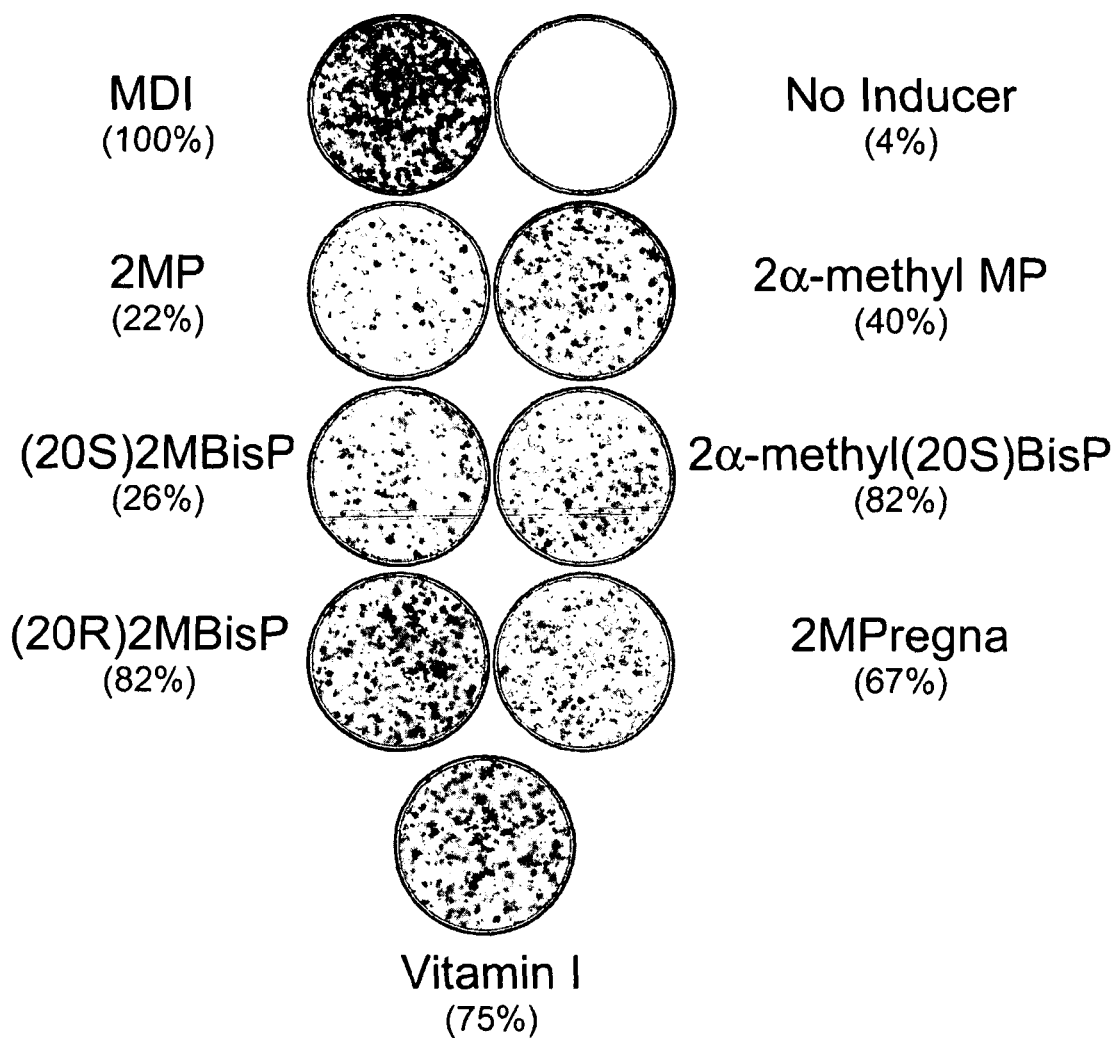

VITAMIN D ANALOGS FOR OBESITY PREVENTION AND TREATMENT

CROSS REFERENCES TO RELATED APPLICATIONS

This application claims priority to U.S. Provisional Application No. 60/524,798, filed Nov. 25, 2003, and U.S. Provisional Application No. 60/524,813, filed Nov. 25, 2003, the entire disclosure of which is hereby incorporated by reference in its entirety and for all purposes as if fully set forth herein.

FIELD OF THE INVENTION

This invention relates generally to vitamin D analogs, more particularly 19-nor vitamin D compounds, and to their use in preventing and treating obesity and their use in the preparation of pharmaceutical formulations for preventing and treating obesity. More particularly, the invention relates to methods of preventing and treating obesity, inhibiting an increase in PPARγ, C/EBPα, and SCD-1 gene transcription, inhibiting adipocyte differentiation, and/or reducing body fat that employ analogs of 1α,25-dihydroxyvitamin $D_3$ and 1α,25-dihydroxyvitamin $D_2$.

BACKGROUND OF THE INVENTION

Obesity is a disease that affects approximately one third of the population in the United States, and which has become a serious problem in many other countries. Over 60 percent of the American population may be characterized as being either overweight or obese. Obesity and the condition of being overweight both contribute substantially to the risk of morbidity from hypertension, dyslipidemia, type 2 diabetes, coronary heart disease, stroke, gallbladder disease, osteoarthritis, sleep apnea, respiratory problems and a wide range of cancers including endometrial, breast, prostrate, and colon cancer. Obesity is associated with increases in deaths from all causes.

Obesity is a complex disease with both genetic and environmental contributions. It increases steadily with age for both men and women, and the age groups with the highest prevalence are men aged 65 to 74 years and women aged 55 to 64 years. Obesity carries with it not only important health consequences, but it can also have a social impact on individuals who may experience stigmatization and discrimination in a variety of situations.

A wide variety of options currently exist for managing and treating obesity. Examples of such options include dietary therapy, increased physical activity, behavior therapy, surgery, and pharmacotherapy. The general goals of treatment include prevention of further weight gain, reduction of body weight, and maintenance of body weight over the long term. A number of drugs are currently approved for use in treating obesity in the United States. Examples of such drugs include those that act by blocking dietary fat absorption (e.g. Oristat) and those that suppress appetite (e.g. Phentermine, Sibutramine). The safety and effectiveness of such medications has not been established beyond one year. All prescription medications used to treat obesity with the exception of Oristat are considered controlled substances. There is a clear need for new classes of efficacious and safe drugs and medicaments for use in treating and preventing obesity.

Adipocytes are the major cellular component in adipose tissue. Adipocytes thus play a key role in the development of obesity. The increase in adipose tissue in obesity is believed to represent the expansion both in the size and number of adipocytes. The active hormonal form of vitamin D, 1α,25-dihydroxy-cholecalciferol (calcitriol) has been reported to inhibit the differentiation of cultured preadipocytes. Sato, M., et al., A. *J. Cell. Phys.*, 135, 545-550 (1988). The structure of calcitriol is shown below and includes the numbering scheme of the carbon atoms used in such compounds and related analogs.

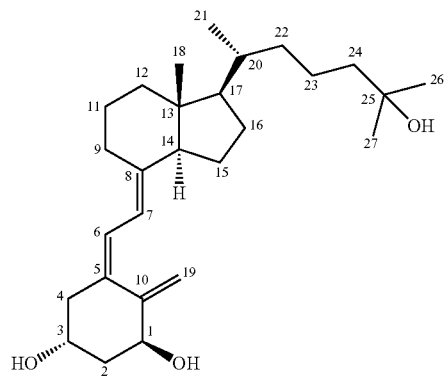

1α,25-Dihydroxyvitamin $D_3$=1α,25-Dihydroxycholecalciferol=Calcitriol

Recently, a new class of vitamin D analogs was discovered, the so-called 19-nor vitamin D compounds, which are characterized by the replacement of the A-ring exocyclic methylene group (carbon 19), typical of the vitamin D system, by two hydrogen atoms. Further substitution at the 2-position and/or modification of the side chain attached to carbon 17 of the five-membered ring has led to pharmacologically active compounds that are much less calcemic at physiologically active concentrations compared to the native hormone (Plum, L. A. et al., *Proc. Natl. Acad. Sci. USA* 101(18), 6900-9004 (2004)). Select analogs also exhibit tissue selectivity in their activity suggesting that they may have important therapeutic advantages over the native vitamin D hormone or other less-selective or non-selective analogs. Various methods of synthesizing 19-nor-vitamin D analogs have been disclosed (see Perlman et al., *Tetrahedron Lett.* 31, 1823 (1990); Perlman et al., *Tetrahedron Lett.* 32, 7663 25(1991), and DeLuca et al., U.S. Pat. No. 5,086,191). The synthesis of various intermediates for use in the preparation of various 19-nor vitamin D analogs is disclosed in U.S. Pat. No. 5,086,191 which is hereby incorporated by reference in its entirety and for all purposes as if fully set forth herein. The synthesis of various 19-nor vitamin D analogs including, but not limited to, (20R)-2-methylene-19-nor-1α,25-dihydroxyvitamin $D_3$, (20S)-2-methylene-19-nor-1α,25-dihydroxyvitamin $D_3$ (2-MD), (20S)-1α-hydroxy-2-methylene-19-nor-bishomopregnacalciferol (2-MbisP), and 1α-hydroxy-2-methylene-19-nor-homopregnacalciferol, is disclosed by DeLuca et al. in U.S. Pat. Nos. 5,843,928, 6,627,622, 5,945,410, and 6,579,861 which are all hereby incorporated by reference in their entireties and for all purposes as if fully set forth herein. The synthesis of (20S)-1α-hydroxy-2-methylene-19-nor-25-methylvitamin $D_3$ (TMM) is described in U.S. patent application Ser. No. 10/613,201 filed on Jul. 3, 2003, which is hereby incorporated by reference in its entirety and for all purposes as if fully set forth herein. The U.S. patent application titled, "Methods for Reducing Body Fat Using Vitamin D Compounds" and filed on Nov. 24, 2004, by DeLuca et al. is hereby incorporated by reference in its entirety and for all purpose as if fully set forth herein.

SUMMARY OF THE INVENTION

The invention provides methods for preventing and treating obesity, inhibiting adipocyte differentiation, inhibiting increased SCD-1 gene transcription, and/or reducing body fat in an animal using vitamin D analogs. The invention also provides the use of vitamin D analogs in preparing medicaments for use in preventing and treating obesity, inhibiting adipocyte differentiation, inhibiting an increase in SCD-1 gene transcription, and reducing body fat in an animal.

In one aspect, the invention provides methods for preventing and treating obesity, inhibiting adipocyte differentiation, inhibiting increased SCD-1 gene transcription, and reducing body fat in which at least one analog of 1α,25-dihydroxyvitamin $D_3$ and 1α,25-dihydroxyvitamin $D_2$ or a pharmaceutical composition that includes such an analog is administered in an effective amount to a subject, such as an obese or overweight animal subject, in need thereof. In some embodiments, the at least one analog is a 19-nor vitamin D compound. In some such embodiments, the 19-nor vitamin D analog is modified at the 2 position. In some such embodiments, the 19-nor vitamin D analog is a 2-alkylidene 19-nor vitamin D analog such as a 2-methylene 19-nor vitamin D analog. In some embodiments, the 19-nor vitamin D analog is a (20S) 19-nor vitamin D analog such as a (20S) 2-methylene 19-nor vitamin D analog whereas in other embodiments, the 19-nor vitamin D analog is a (20R) 19-nor vitamin D analog such as a (20R) 2-methylene 19-nor vitamin D analog. In some embodiments, the analog is a compound other than (20S)-2-methylene-19-nor-1α,25-dihydroxyvitamin $D_3$ (2-MD). In some embodiments, the analog is a 2-alkyl 19-nor vitamin D analog. In some such embodiments, the analog is a 2a-alkyl 19-nor vitamin D analog such as a 2α-methyl 19-nor vitamin D analog. In other embodiments, the analog is an 18,19-dinor vitamin D analog. In some such embodiments, the analog is a 2-alkylidene 18,19-dinor vitamin D analog such as a 2-methylene 18,19-dinor vitamin D analog. In other embodiments, the analog is a 2-alkyl 18,19-dinor vitamin D analog. In some such embodiments, the analog is a 2α-alkyl 18,19-dinor vitamin D analog such as a 2α-methyl 18,19-nor vitamin D analog In another aspect, the invention provides methods for inhibiting PPARγ and/or C/EBPα gene transcription in which at least one analog of 1α,25-dihydroxyvitamin $D_3$ or 1α,25-dihydroxyvitamin $D_2$ or a pharmaceutical composition that includes such an analog is administered in an effective amount to a subject, such as an obese or overweight animal subject, in need thereof. In some embodiments, the at least one analog is a 19-nor vitamin D compound. In some such embodiments, the 19-nor vitamin D analog is modified at the 2 position. In some such embodiments, the 19-nor vitamin D analog is a 2-alkylidene 19-nor vitamin D analog such as a 2-methylene 19-nor vitamin D analog. In some embodiments, the 19-nor vitamin D analog is a (20S) 19-nor vitamin D analog such as a (20S) 2-methylene 19-nor vitamin D analog whereas in other embodiments, the 19-nor vitamin D analog is a (20R) 19-nor vitamin D analog such as a (20R) 2-methylene 19-nor vitamin D analog. In some embodiments, the analog is a compound other than (20S)-2-methylene-19-nor-1α,25-dihydroxyvitamin $D_3$ (2-MD). In some embodiments, the analog is a 2-alkyl 19-nor vitamin D analog. In some such embodiments, the analog is a 2α-alkyl 19-nor vitamin D analog such as a 2α-methyl 19-nor vitamin D analog. In other embodiments, the analog is an 18,19-dinor vitamin D analog. In some such embodiments, the analog is a 2-alkylidene 18,19-dinor vitamin D analog such as a 2-methylene 18,19-dinor vitamin D analog. In other embodiments, the analog is a 2-alkyl 18,19-dinor vitamin D analog. In some such embodiments, the analog is a 2α-alkyl 18,19-dinor vitamin D analog such as a 2α-methyl 18,19-nor vitamin D analog.

In some embodiments, the animal subject is a mammal. In some such embodiments, the mammal is selected from a rodent, a primate, a bovine, an equine, a canine, a feline, an ursine, a porcine, a rabbit, or a guinea pig. In some such embodiments, the mammal is a rat or is a mouse. In some embodiments, the animal subject is a primate such as, in some embodiments, a human.

In some embodiments, the 19-nor vitamin D analog administered to the subject or used to prepare a pharmaceutical formulation is a compound of formula IA or IB, or is a mixture thereof. In some such embodiments, the analog is a compound of formula IA. In other embodiments, the vitamin D analog is a compound of formula IB.

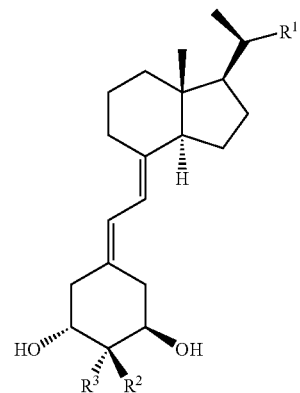

IA

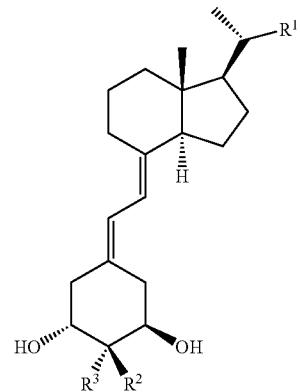

IB

In compounds of formula IA and IB, $R^1$ is selected from H, or straight or branched chain alkyl groups having from 1 to 8 carbon atoms, straight or branched chain alkenyl groups having from 2 to 8 carbon atoms, straight or branched chain hydroxy-substituted alkyl groups having from 1 to 8 carbon atoms, or straight and branched chain hydroxy-substituted alkenyl groups having from 2 to 8 carbon atoms. In some such embodiments, $R^1$ is selected from straight or branched chain alkyl groups having from 2 to 7 carbon atoms, straight or branched chain alkenyl groups having from 2 to 7 carbon atoms, straight or branched chain hydroxy-substituted alkyl groups having from 2 to 6 carbon atoms, or straight or branched chain hydroxy-substituted alkenyl groups having from 2 to 6 carbon atoms. In other such embodiments, $R^1$ is selected from straight or branched chain alkyl groups having from 2 to 7 carbon atoms, straight or branched chain alkenyl groups having from 2 to 7 carbon atoms, or straight or branched chain hydroxy-substituted alkenyl groups having from 2 to 6 carbon atoms.

In compounds of formula IA and IB, $R^2$ and $R^3$ are independently selected from H, straight or branched chain alkyl groups having from 1 to 8 carbon atoms, or straight or branched chain alkenyl groups having from 1 to 8 carbon atoms or $R^2$ and $R^3$ join together to form a group of formula IC

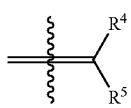

IC where the wavy line indicates the point of attachment to the carbon at the 2 position of the vitamin D analog and $R^4$ and $R^5$ are independently selected from H, straight or branched chain alkyl groups having from 1 to 8 carbon atoms, straight or branched chain hydroxyalkyl groups having from 1 to 8 carbon atoms, straight or branched chain hydroxyalkenyl groups having from 1 to 8 carbon atoms, straight or branched chain protected hydroxyalkyl groups having from 1 to 8 carbon atoms, straight or branched chain fluoroalkyl groups having from 1 to 8 carbon atoms, or straight or branched chain alkenyl groups having from 1 to 8 carbon atoms. In some embodiments, the analog is a compound of formula IA or IB and $R^3$ is H. In some such embodiments, $R^2$ is a straight chain alkyl group such as methyl, ethyl, or propyl. In other embodiments, $R^2$ and $R^3$ join together to form a group of formula IC in which $R^4$ and $R^5$ are both H. Examples of some such compounds include compounds of formula IIA and IIB.

In some embodiments, the 19-nor vitamin D analog administered to the subject or used to prepare a pharmaceutical formulation is a compound of formula IIA or IIB, or is a mixture thereof. In some such embodiments, the vitamin D analog is a compound of formula IIA. In other embodiments, the vitamin D analog is a compound of formula IIB.

IIA

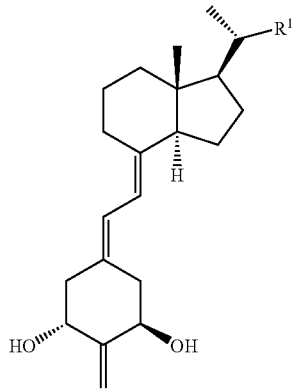

IIB

In compounds of formula IIA and IIB, $R^1$ has the same values as set forth above with respect to compounds of formula IA and IB. Thus, $R^1$ is selected from H, or straight or branched chain alkyl groups having from 1 to 8 carbon atoms, straight or branched chain alkenyl groups having from 2 to 8 carbon atoms, straight or branched chain hydroxy-substituted alkyl groups having from 1 to 8 carbon atoms, or straight or branched chain hydroxy-substituted alkenyl groups having from 2 to 8 carbon atoms. In some such embodiments, $R^1$ is selected from straight or branched chain alkyl groups having from 2 to 7 carbon atoms, straight or branched chain alkenyl groups having from 2 to 7 carbon atoms, straight or branched chain hydroxy-substituted alkyl groups having from 2 to 6 carbon atoms, or straight or branched chain hydroxy-substituted alkenyl groups having from 2 to 6 carbon atoms. In other such embodiments, $R^1$ is selected from straight or branched chain alkyl groups having from 2 to 7 carbon atoms, straight or branched chain alkenyl groups having from 2 to 7 carbon atoms, or straight or branched chain hydroxy-substituted alkenyl groups having from 2 to 6 carbon atoms. In some embodiments, the compound is a compound of formula IIA or IIB other than (20S)-2-methylene-19-nor-1α,25-dihydroxyvitamin $D_3$ (2-MD) or a compound of formula IIC.

In some embodiments, the compound of formula IA, IB, IIA, or IIB is a compound of formula IA, IB, IIA, or IIB where $R^1$ is selected from one of the following groups where the wavy line over a straight bond indicates the point of attachment to the rest of the molecule and a wavy line originating at a carbon indicates that both or either of the S or R configurations is contemplated at that position.

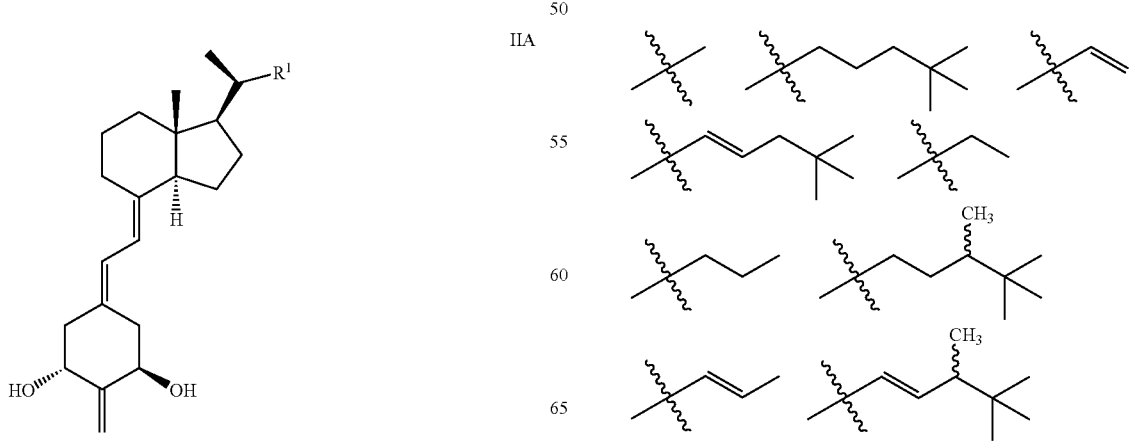

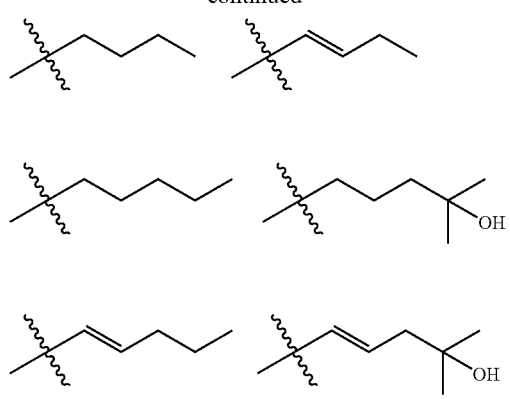

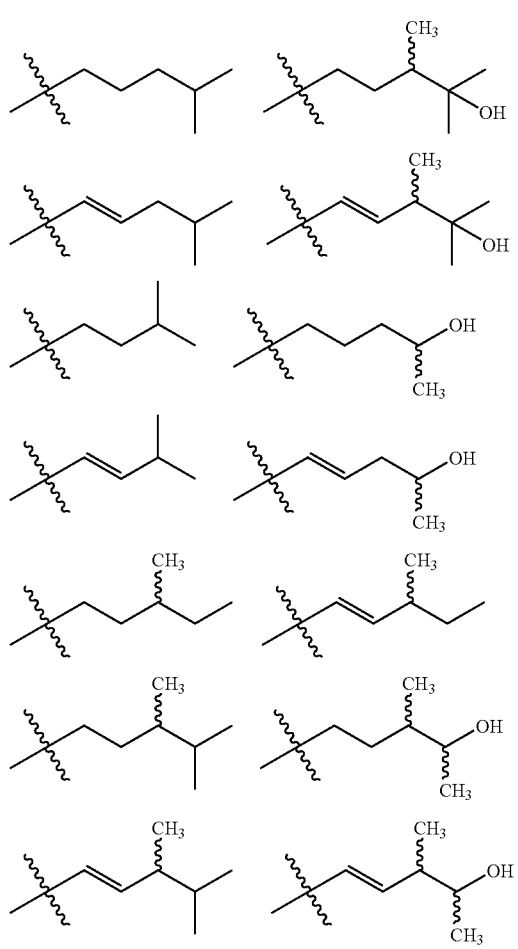

For the alkenyl groups shown above, it will be understood that with respect to the structures shown above, both the cis and trans (Z and E) isomers and mixtures thereof are contemplated.

In some embodiments, the 19-nor vitamin D analog administered to the subject or used to prepare a pharmaceutical formulation is a compound of formula IIC where $R^1$ is a hydroxy-substituted branched chain alkyl group having 6 carbon atoms (a $—CH_2CH_2CH_2C(CH_3)_2OH$ group), and the compound has the name (20S)-2-methylene-19-nor-1α,25-dihydroxyvitamin $D_3$ (2-MD).

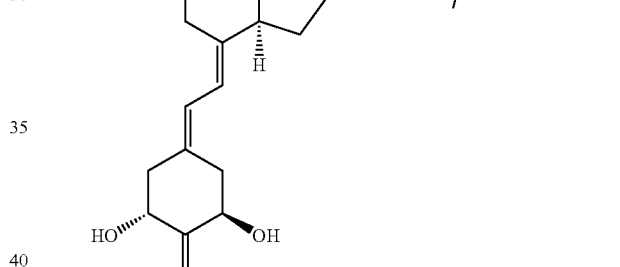

In some embodiments, the 19-nor vitamin D analog administered to the subject or used to prepare a pharmaceutical formulation is a compound of formula IID where $R^1$ is a branched chain alkyl group having 7 carbon atoms (a $—CH_2CH_2CH_2C(CH_3)_3$ group), and the compound has the name (20S)-1α-hydroxy-2-methylene-19-nor-25-methylvitamin $D_3$ (TMM).

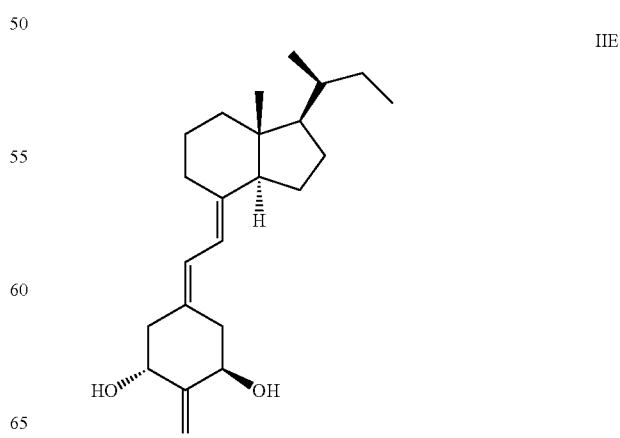

In some embodiments, the 19-nor vitamin D analog administered to the subject or used to prepare a pharmaceutical formulation is a compound of formula IIE where $R^1$ is a straight chain alkyl group having 2 carbon atoms (a $—CH_2CH_3$ group), and the compound has the name (20S)-1α-hydroxy-2-methylene-19-nor-bishomopregnacalciferol (2-MbisP).

In some embodiments, the 19-nor vitamin D analog administered to the subject or used to prepare a pharmaceutical formulation is a compound of formula IIF where $R^1$ is a straight chain alkyl group having 1 carbon atom (a —$CH_3$ group), and the compound has the name 1α-hydroxy-2-methylene-19-nor-homopregnacalciferol (2-MP).

IIF

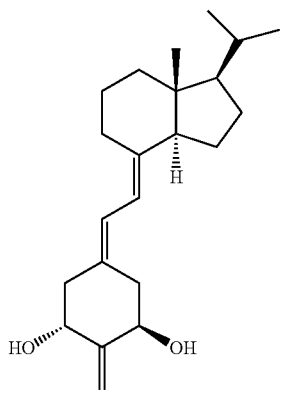

In some embodiments, the 19-nor vitamin D analog administered to the subject or used to prepare a pharmaceutical formulation is a compound of formula IIG where $R^1$ is a straight chain alkyl group having 2 carbon atoms (a —$CH_2CH_3$ group), and the compound has the name (20R)-1α-hydroxy-2-methylene-19-nor-bishomopregnacalciferol ((20R)2MbisP).

IIG

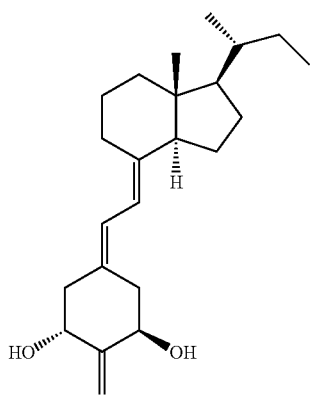

In some embodiments, the 19-nor vitamin D analog administered to the subject or used to prepare a pharmaceutical formulation is a compound of formula IIH where $R^1$ is a H, and the compound has the name 2-methylene-19-nor-1α-hydroxy-pregnacalciferol (2-Mpregna).

IIH

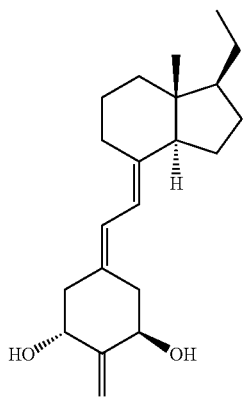

In some embodiments, the 19-nor vitamin D analog administered to the subject or used to prepare a pharmaceutical formulation is a compound of formula IIJ where $R^1$ is a straight chain alkyl group having 2 carbon atoms (a —$CH_2CH_3$ group), $R^2$ is a methyl group, and $R^3$ is H, and the compound has the name 2α-methyl-19-nor-(20S)-1α-hydroxy-bishomopregnacalciferol ((20S)2αMbisP).

IIJ

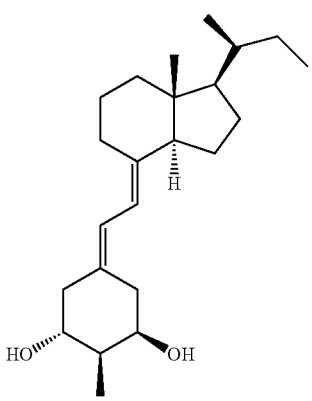

In some embodiments, the 19-nor vitamin D analog administered to the subject or used to prepare a pharmaceutical formulation is a compound of formula IIK where $R^1$ is a straight chain alkyl group having 1 carbon atoms (a —$CH_3$ group), $R^2$ is a methyl group, and $R^3$ is H, and the compound has the name 2α-methyl-19-nor-1α-hydroxy-homopregnacalciferol (2α-methyl MP).

IIK

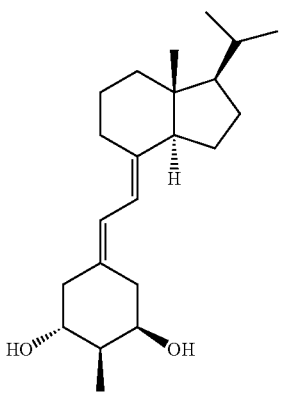

In some embodiments, the 19-nor vitamin D analog administered to the subject or used to prepare a pharmaceutical formulation is a compound of formula IIL where $R^1$ is a straight chain alkyl group having 3 carbon atoms (a —$CH_2CH_2CH_3$ group), and the compound has the name 2-methylene-19-nor-(20S)-1α-hydroxy-trishomopregnacalciferol (2MtrisP).

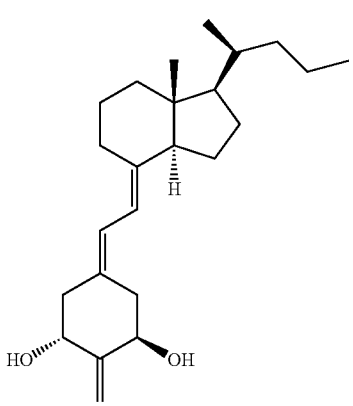

In some embodiments, the 19-nor vitamin D analog administered to the subject or used to prepare a pharmaceutical formulation is a compound of formula IIM where $R^1$ is a straight chain alkyl group having 4 carbon atoms (a —CH$_2$CH$_2$CH$_2$CH$_3$ group), and the compound has the name 2-methylene-19,26,27-trinor-(20S)-1α-hydroxyvitamin D$_3$ ((20S)OM).

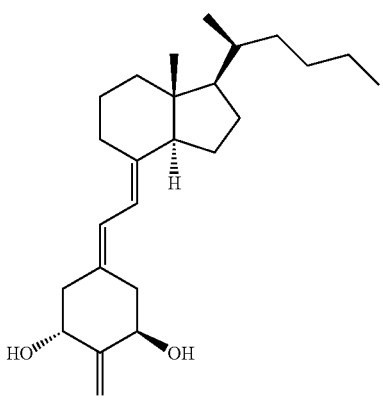

In some embodiments, the 19-nor vitamin D analog administered to the subject or used to prepare a pharmaceutical formulation is a compound of formula IIN where $R^1$ is a straight chain alkyl group having 4 carbon atoms (a —CH$_2$CH$_2$CH$_2$CH$_3$ group), $R^2$ is a methyl group, $R^3$ is H, and the compound has the name 2α-methyl-19,26,27-trinor-(20S)-1α-hydroxyvitamin D$_3$ (2α-methyl-19,26,27-trinor).

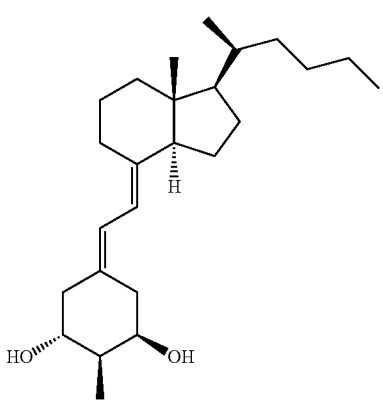

In some embodiments, the 19-nor vitamin D analog administered to the subject or used to prepare a pharmaceutical formulation is a compound of formula IIO where $R^1$ is a hydroxy-substituted branched chain alkyl group having 6 carbon atoms (a —CH$_2$CH$_2$CH$_2$C(CH$_3$)$_2$OH group), $R^2$ and $R^3$ are a group of formula IC, $R^4$ is H, $R^5$ is a hydroxypropyl group, and the compound has the name 2-(3'-hydroxypropylidene)-19-nor-(20S)-1α,25-dihydroxyvitamin D$_3$ (1AGS).

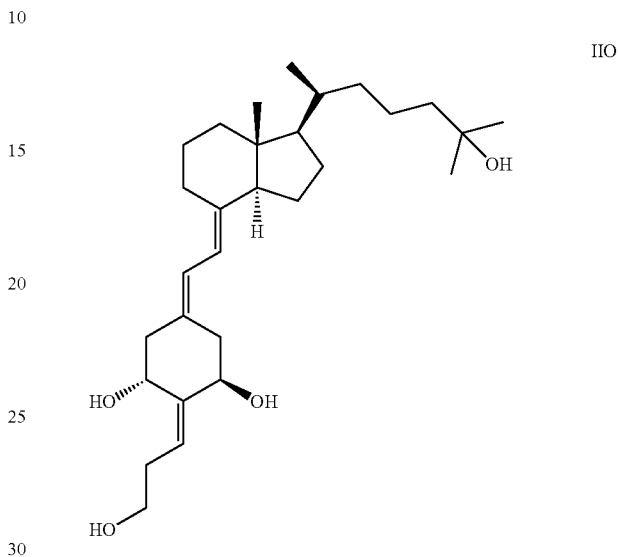

In some embodiments, the 19-nor vitamin D analog administered to the subject or used to prepare a pharmaceutical formulation is a compound of formula IIP where $R^1$ is a hydroxy-substituted branched chain alkyl group having 6 carbon atoms (a —CH$_2$CH$_2$CH$_2$C(CH$_3$)$_2$OH group), $R^2$ and $R^3$ are a group of formula IC, $R^4$ is H, $R^5$ is a hydroxypropyl group, and the compound has the name 2-(3'-hydroxypropylidene)-19-nor-1α,25-dihydroxyvitamin D$_3$ (1AGR).

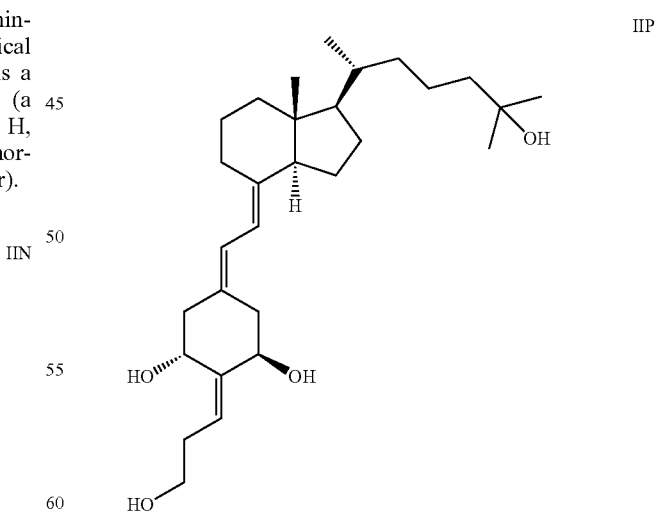

In some embodiments, the 19-nor vitamin D analog administered to the subject or used to prepare a pharmaceutical formulation is a compound of formula IIQ where $R^1$ is a hydroxy-substituted branched chain alkyl group having 6 carbon atoms (a —CH$_2$CH$_2$CH$_2$C(CH$_3$)$_2$OH group), $R^2$ and R³ are a group of formula IC, R⁴ is H, R⁵ is a —CH₂CH₂OCH₂OCH₃ group (a protected hydroxyalkyl group), and the compound has the name 2-[(3'-methoxymethoxy)-propylidene]-19-nor-1α,25-dihydroxyvitamin D₃ (F-Wit).

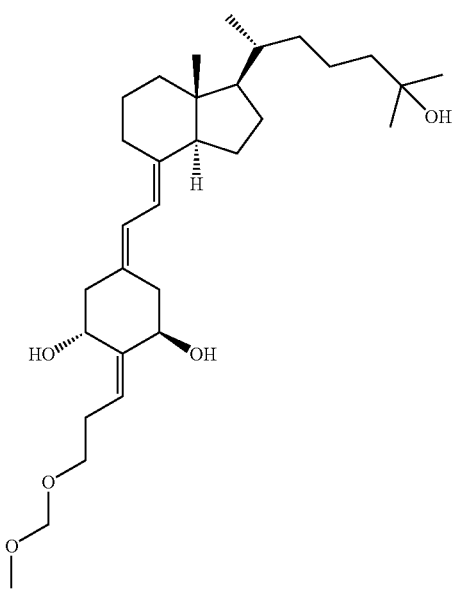

IIQ

In some embodiments, the 19-nor vitamin D analog administered to the subject or used to prepare a pharmaceutical formulation is a 19,21-dinor vitamin D₃ analog or is a 19,21-dinor vitamin D₂ analog having the name 2-methylene-19,21-dinor-1α-hydroxybishomopregnacalciferol (19,21-dinor) and having the formula IIR.

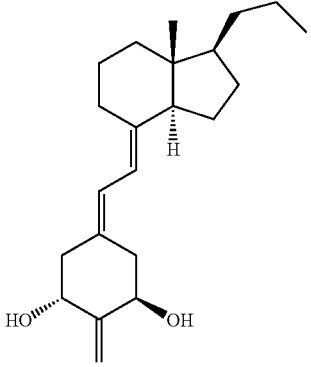

IIR

In some embodiments, the 19-nor vitamin D analog administered to the subject or used to prepare a pharmaceutical formulation is a 19-nor 17-ene vitamin D₃ analog or is a 19-nor 17-ene vitamin D₂ analog having the name 2-methylene-19-nor-1α-hydroxy-17-ene-homopregnacalciferol (Vitamin I or VIT-I) and having the formula IIS.

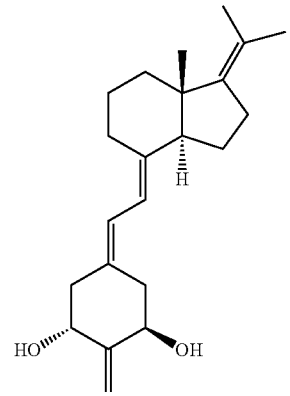

IIS

In some embodiments, the 19-nor vitamin D analog administered to the subject or used to prepare a pharmaceutical formulation is an 18,19-dinor vitamin D₃ analog or is an 18,19-dinor vitamin D₂ analog. In some such embodiments, the compound has the name 2-methylene-18,19-dinor-(20S)-1α,25-dihydroxyvitamin D₃ (VD-03) and has the formula IIT. In other such embodiments, the compound has the name 2-methylene-18,19-dinor-1α-hydroxyhomopregnacalciferol (18,19-dinor-2MP) and has the formula IIU.

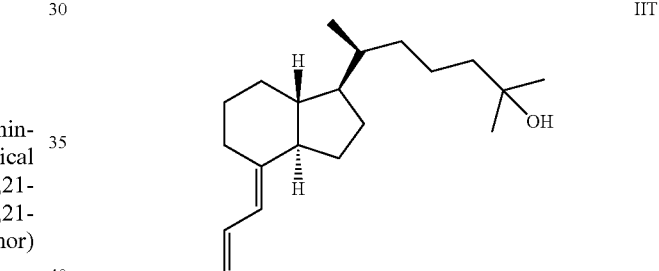

IIT

IIU

In some embodiments, the compound administered to the subject or used to prepare a pharmaceutical formulation is a 19-nor vitamin D₂ analog. In some such embodiments, the compound has the name 2-methylene-19-nor-24-epi-1α,25-dihydroxyvitamin D₂ ((24epi)D₂) and has the formula IIV. In other such embodiments, the compound has the name 19-nor- 1α,25-dihydroxyvitamin D$_2$ (1α,25(OH)$_2$(19nor)D$_2$ or Zemplar) and has the formula IIW.

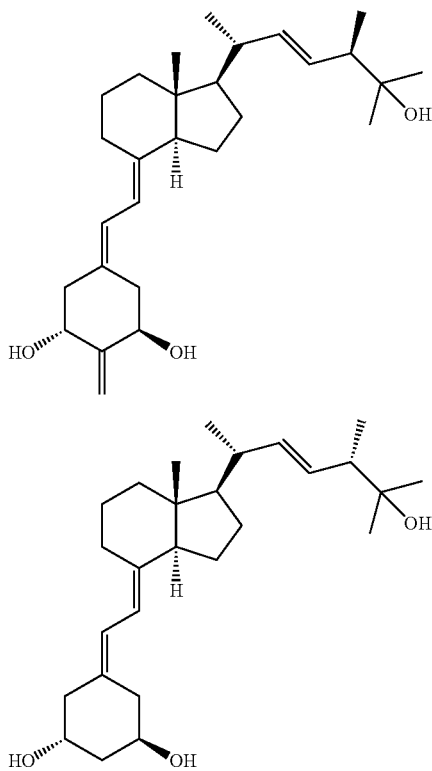

In various embodiments, the 19-nor vitamin D analog is administered orally, parenterally, transdermally, or topically. In some such embodiments, the 19-nor vitamin D analog is administered orally. In other embodiments, the 19-nor vitamin D analog is administered by injection or via suppository. In other embodiments, the 19-nor vitamin D analog is administered intravaginally.

The above compounds exhibit a desired, and highly advantageous, pattern of biological activity. Generally, the amount of vitamin D analog administered to the subject ranges from about 0.001 μg to about 100 mg per day and in some embodiments ranges from about 0.1 μg to about 1000 μg per day. In some such embodiments, the analogs are present in a pharmaceutical formulation or medicament that includes a carrier. In some such embodiments, the amount of compound administered to the subject ranges from about 0.001 μg to about 100 mg per day and in other embodiments ranges from about 0.1 μg to about 1000 μg per day and in other embodiments ranges from 0.1 μg to about 50 μg per day. In some compositions, the amount of the vitamin D analog in the composition ranges from about 0.01 μg/gram to about 1000 μg/gram, and in some such embodiments the amount of analog in the composition ranges from about 0.1 μg/gram to about 50 μg/gram. It will be understood that the dosage will be based on numerous factors set forth herein and on the specific activity of the given compound.

Further objects, features and advantages of the invention will be apparent from the following detailed description and drawings.

BRIEF DESCRIPTION OF THE DRAWINGS

FIGS. 1A and 1B are scanned images of murine 3T3-L1 cells showing that murine 3T3-L1 cells treated with inducer cocktail (FIG. 1B) differentiate into mature adipocytes after 10 days as assessed by Oil-Red-O staining whereas those treated with vehicle (FIG. 1A) do not. The figures on the left represent higher magnification views of the images on the right.

FIG. 9 is a scanned image showing that 2-MP, (20S)2MbisP, (20R)2MbisP, 2α-methyl MP, 2α-methyl(20S)bisP, 2-Mpregna, and Vitamin I are active in inhibiting the differentiation of MDI-treated 3T3-L1 cells into mature adipocytes, as assessed by inhibition of oil-red-O staining and SCD1 mRNA induction (the expression of SCD1 mRNA is expressed as a percentage of that found in cells treated with MDI alone and is shown in the parentheses). All compounds were tested at a concentration of $1 \times 10^{-8.5}$ M.

FIG. 14A is a scanned image showing 1α,25(OH)$_2$D$_3$ and (1αOH, 20S)2M-bisP inhibition of murine MDI-treated 3T3-L1 cells into mature adipocytes as assessed by oil-red-O staining after exposure to various concentrations of compounds ($10^{-7.0}$ M, $10^{-8.0}$ M, $10^{-9.0}$ M, $10^{-10.0}$ M, $10^{-11.0}$ M) and FIG. 14B shows inhibition of SCD1 mRNA expression by the analogs. In contrast, the (1βOH, 20S)2M-BisP compound is ineffective in producing inhibition of oil-red-O staining or SCD1 mRNA expression at any concentration tested.

DETAILED DESCRIPTION OF THE INVENTION

Figure 2:
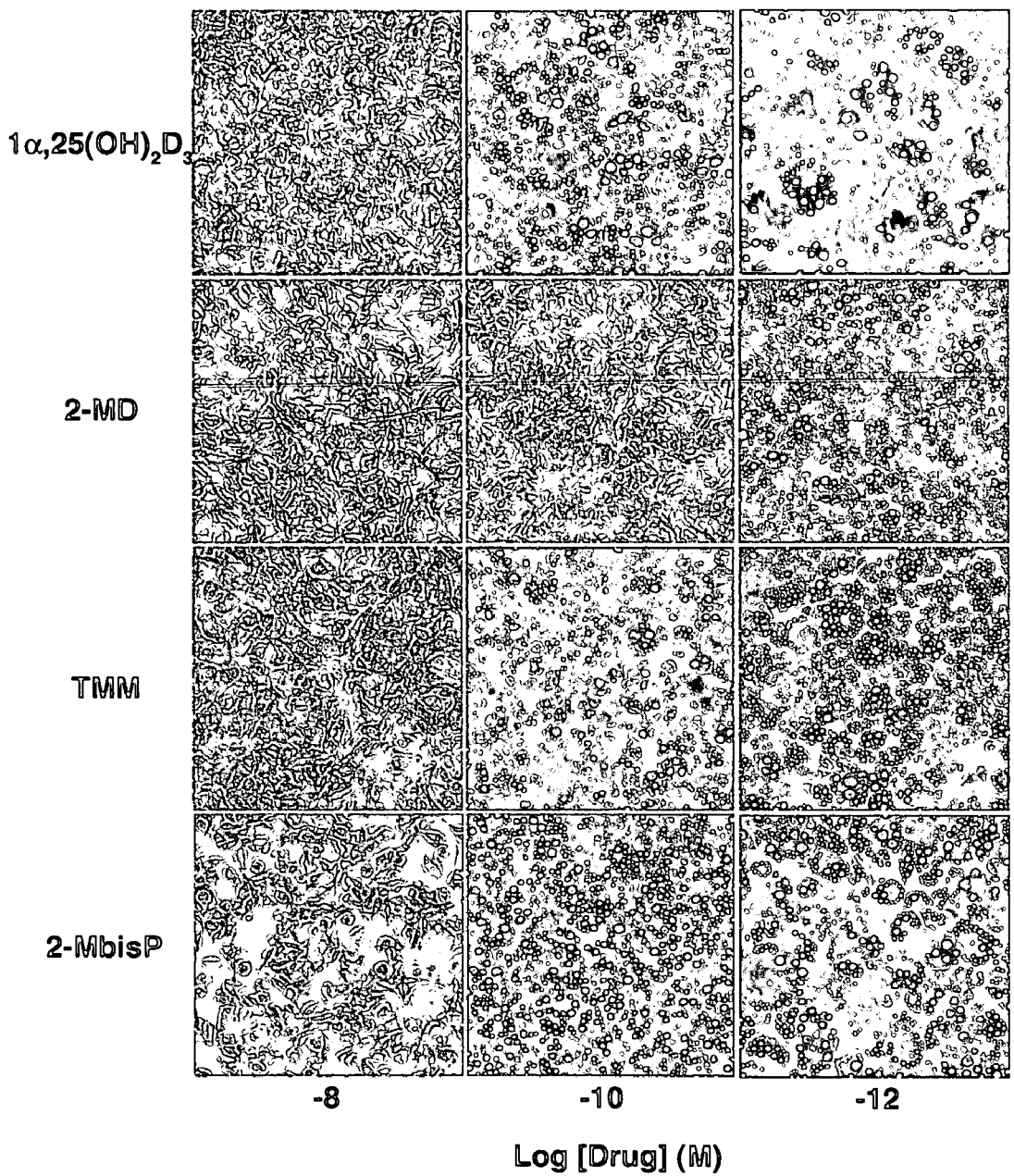
FIG. 2 is a scanned image showing that various vitamin D analogs (1α,25(OH)$_2$D$_3$, 2-MD, TMM, and 2-MbisP) inhibit the differentiation of murine 3T3-L1 cells into mature adipocytes as assessed by Oil-Red-O staining.

The following table shows the structure and names of compounds referred to using abbreviations throughout this document:

| Abbreviation | Name | Structure |
|---|---|---|
| 1α,25(OH)$_2$D$_3$ | 1α,25-dihydroxyvitamin D$_3$ | 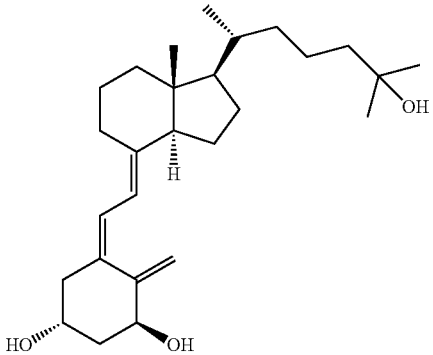 |
| 2-MD | (20S)-2-methylene-19-nor-1α,25-dihydroxyvitamin D$_3$ | 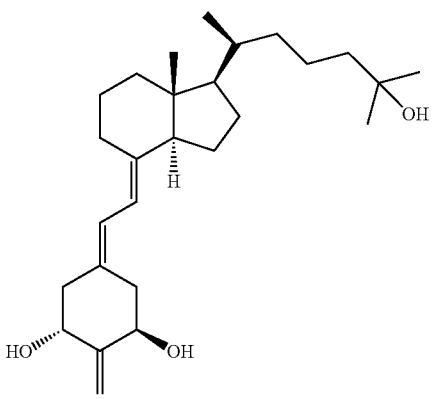 |

-continued

| Abbreviation | Name | Structure |
|---|---|---|
| TMM | (20S)-1α-hydroxy-2-methylene-19-nor-25-methylvitamin $D_3$ | 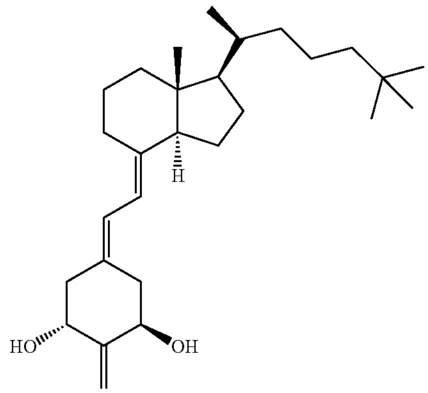 |
| 2-MbisP or (20S)2MbisP or (1α,20S)2MbisP | 2-methylene-19-nor-(20S)-1α-hydroxy-bishomo-pregnacalciferol | 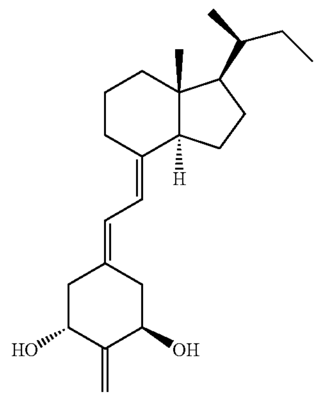 |
| 2-MP | 1α-hydroxy-2-methylene-19-nor-homopregnacalciferol | 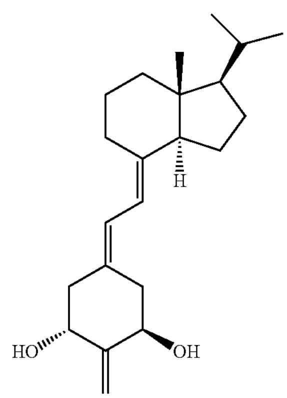 |
| (20R)2MbisP | (20R)-1α-hydroxy-2-methylene-19-nor-bishomo-pregnacalciferol | 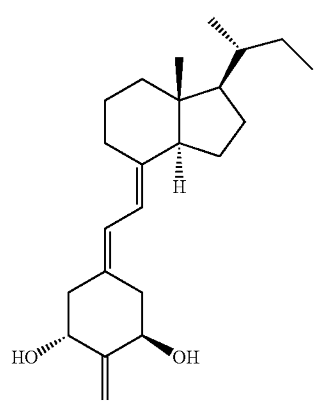 |

-continued

| Abbreviation | Name | Structure |
|---|---|---|
| 2-Mpregna | 2-methylene-19-nor-1α-hydroxy-pregnacalciferol | 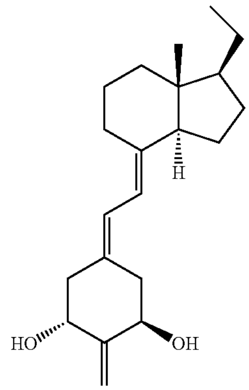 |
| (20S)2αMbisP or 2α-methyl(20S)bisP | 2α-methyl-19-nor-(20S)-1α-hydroxy-bishomopregna-calciferol | 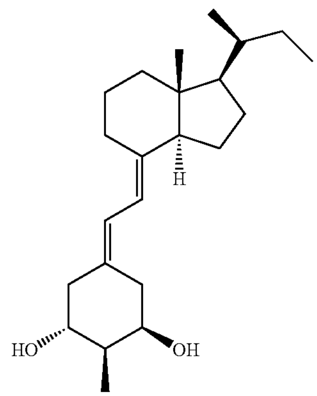 |
| 2α-methyl MP | 2α-methyl-19-nor-1α-hydroxy-homopregna-calciferol | 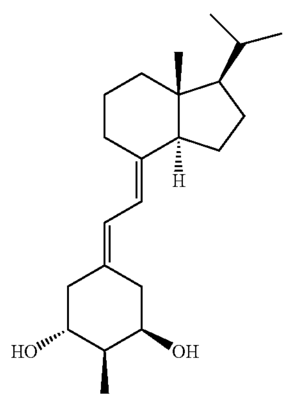 |
| (20S)2MtrisP or 2MtrisP | 2-methylene-19-nor-(20S)-1α-hydroxy-trishomopregna-calciferol | 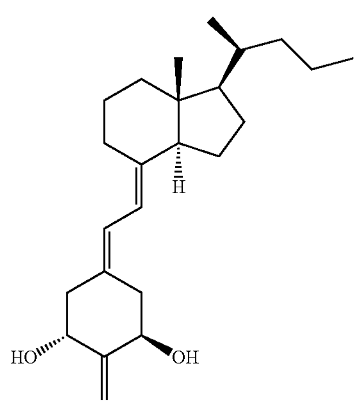 |

-continued

| Abbreviation | Name | Structure |
|---|---|---|
| (20S)OM or OM | 2-methylene-19,26,27-trinor-(20S)-1α-hydroxyvitamin D₃ | 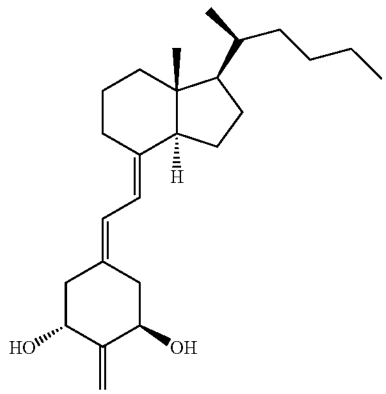 |
| 2α-methyl-19,26,27-trinor | 2α-methyl-19,26,27-trinor-(20S)-1α-hydroxyvitamin D₃ | 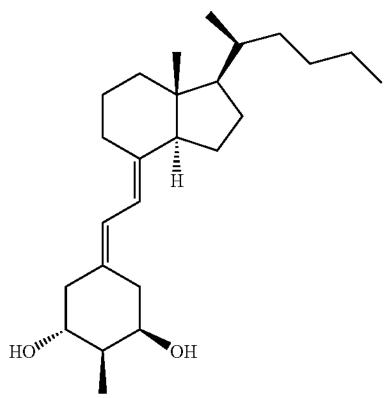 |
| 2β-methyl-19,26,27-trinor | 2β-methyl-19,26,27-trinor-(20S)-1α-hydroxyvitamin D₃ | 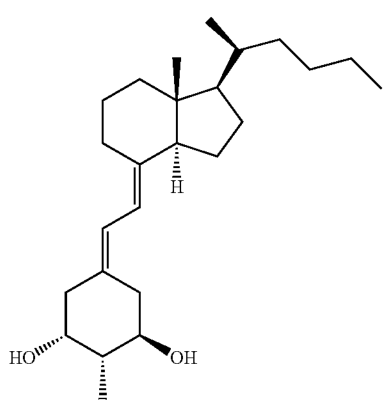 |

-continued

| Abbreviation | Name | Structure |
|---|---|---|
| 1AGS | 2-(3'-hydroxypropylidene)-19-nor-(20S)-1α,25-dihydroxyvitamin D₃ (E isomer) | 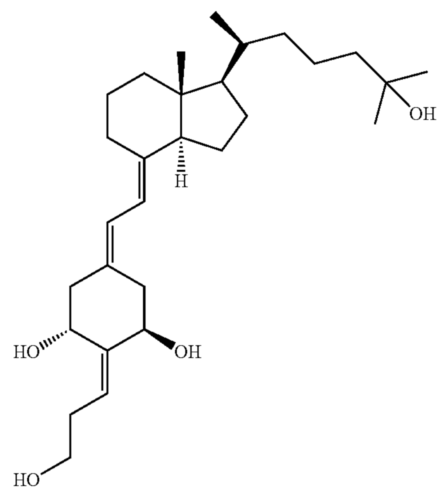 |
| 1AGR | 2-(3'-hydroxypropylidene)-19-nor-1α,25-dihydroxyvitamin D₃ (E isomer) | 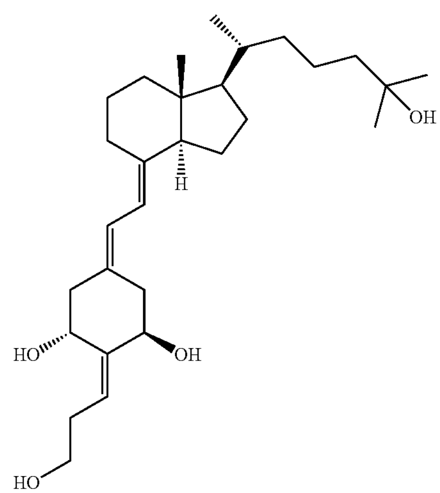 |
| F-Wit | 2-[(3'-methoxymethoxy)-propylidene]-19-nor-1α,25-dihydroxyvitamin D₃ | 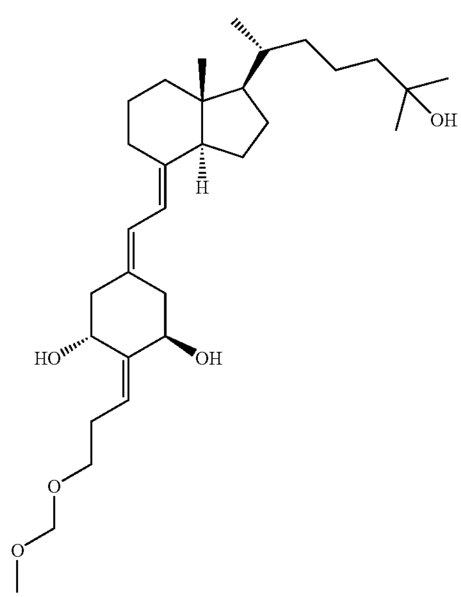 |

-continued

| Abbreviation | Name | Structure |
|---|---|---|
| 19,21-dinor | 2-methylene-19,21-dinor-1α-hydroxy-bishomopregna-calciferol | 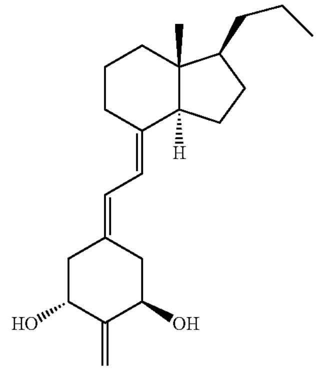 |
| Vitamin I or VIT-I | 2-methylene-19-nor-1α-hydroxy-17-ene-homopregnacalciferol | 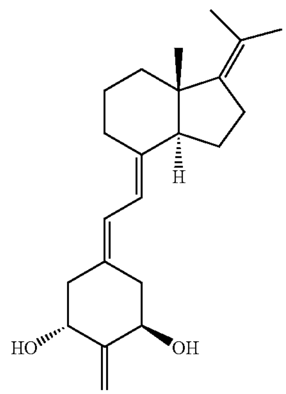 |
| VD-03 or DP035 | 2-methylene-18,19-dinor-(20S)-1α,25-dihydroxyvitamin $D_3$ | 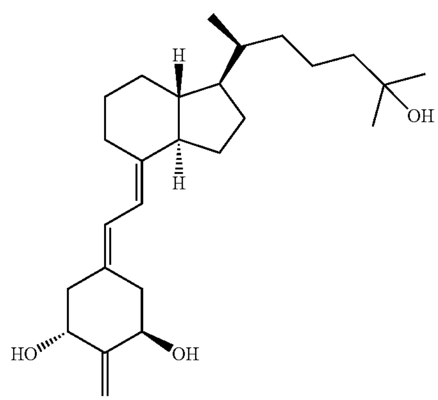 |
| 18,19-dinor-2MP | 2-methylene-18,19-dinor-1α-hydroxyhomopregnacalciferol | 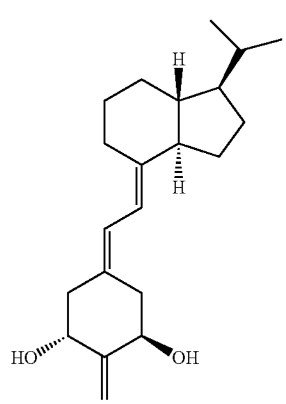 |

| Abbreviation | Name | Structure |
|---|---|---|
| (24epi)D$_2$ | 2-methylene-19-nor-24-epi-1α,25-dihydroxyvitamin D$_2$ | 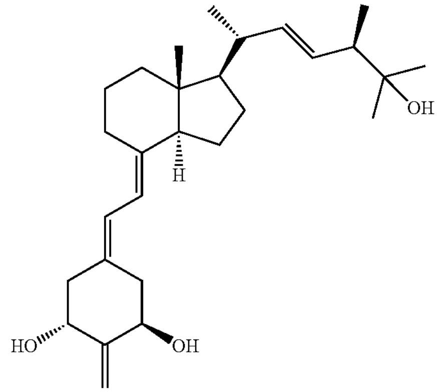 |
| 1α,25(OH)$_2$(19nor)D$_2$ or Zemplar | 19-nor-1α,25-dihydroxyvitamin D$_2$ | 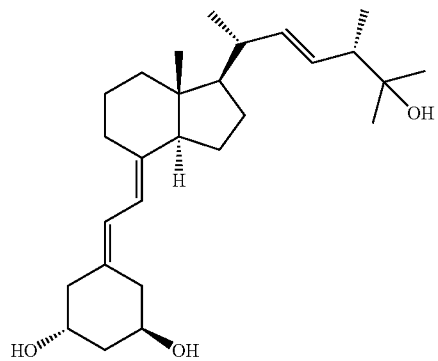 |
| (1β,20S)2MbisP | (20S)-1β-hydroxy-2-methylene-19-nor-bishomo-pregnacalciferol | 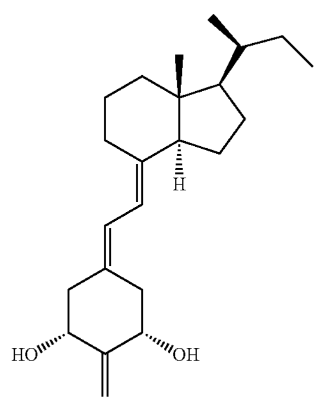 |

Various analogs of 1α,25-dihydroxyvitamin D$_3$ and 1α,25-dihydroxyvitamin D$_2$ including 19-nor vitamin D analogs were or are tested as described herein and found to inhibit the differentiation of preadipocytes into mature adipocytes, to reduce body fat, to inhibit an increase in PPARγ, C/EBPα, and/or SCD-1 gene transcription and to be useful in treating and preventing obesity both in vivo and in vitro as described below.

As used herein, the phrase "straight and branched chain alkyl groups" refers to groups that include carbon and hydrogen atoms that only include carbon-carbon single bonds and carbon-hydrogen single bonds. These groups do not include any heteroatoms (atoms other than H or C). Thus, the phrase "straight and branched chain alkyl groups" includes straight chain alkyl groups such as methyl, ethyl, propyl, butyl, pentyl, hexyl, heptyl, and octyl groups and branched chain isomers of straight chain alkyl groups, including but not limited to, the following which are provided by way of example only: —CH(CH$_3$)$_2$, —CH(CH$_3$)(CH$_2$CH$_3$), —CH(CH$_2$CH$_3$)$_2$, —C(CH$_3$)$_3$, —C(CH$_2$CH$_3$)$_3$, —CH$_2$CH(CH$_3$)$_2$, —CH$_2$CH(CH$_3$)(CH$_2$CH$_3$), —CH$_2$CH(CH$_2$CH$_3$)$_2$, —CH$_2$C(CH$_3$)$_3$, —CH$_2$C(CH$_2$CH$_3$)$_3$, —CH(CH$_3$)CH(CH$_3$)(CH$_2$CH$_3$), —CH$_2$CH$_2$CH(CH$_3$)$_2$, —CH$_2$CH$_2$CH(CH$_3$)(CH$_2$CH$_3$), —CH$_2$CH$_2$CH(CH$_2$CH$_3$)$_2$, —CH$_2$CH$_2$C(CH$_3$)$_3$, —CH(CH$_3$)CH$_2$CH(CH$_3$)$_2$, —CH(CH$_3$)CH(CH$_3$)CH(CH$_3$)$_2$, —CH$_2$CH$_2$CH$_2$C(CH$_3$)$_3$, —CH$_2$CH$_2$CH$_2$CH(CH$_3$)$_2$, —CH$_2$CH$_2$CH(CH$_3$)C(CH$_3$)$_3$, —CH$_2$CH$_2$CH(CH$_3$)CH(CH$_3$)$_2$, and the like.

As used herein, the phrase "hydroxy-substituted alkyl groups" refers to "straight and branched chain alkyl groups" as defined above in which a bond to a carbon or a hydrogen atom is replaced by a bond to a hydroxyl (—OH) group.

As used herein, the phrase "straight and branched chain alkenyl groups" refers to "straight and branched chain alkyl groups" as defined above, except that at least one double bond exists between two of the carbon atoms. Examples include, but are not limited to the cis and trans (Z and E) isomers of —CH=CH$_2$, —CH=C(H)(CH$_3$), —CH=C(CH$_3$)$_2$, —C(CH$_3$)=C(H)$_2$, —C(CH$_3$)=C(H)(CH$_3$), —C(CH$_2$CH$_3$)=CH$_2$, —C(H)=C(H)CH$_2$CH(CH$_3$)$_2$, —C(H)=C(H)CH(CH$_3$)CH(CH$_3$)$_2$, —C(H)=C(H)CH$_2$C(CH$_3$)$_3$, —C(H)=C(H)CH(CH$_3$)C(CH$_3$)$_3$, and the like.

As used herein, the phrase "hydroxy-substituted alkenyl groups" has the same meaning with respect to "straight and branched chain alkenyl groups" that "hydroxy-substituted alkyl groups" had with respect to "straight and branched chain alkyl groups". Therefore, "hydroxy-substituted alkenyl groups" are "straight and branched chain alkenyl groups" in which a bond to a hydrogen atom or carbon atom that is not double-bonded to another carbon atom is replaced by a bond to a hydroxyl (—OH) group.

As used herein, the term "hydroxy-protecting group" signifies any group commonly used for the temporary protection of the hydroxy (—OH) functional group, such as, but not limited to, alkoxycarbonyl, acyl, alkylsilyl or alkylarylsilyl groups (hereinafter referred to simply as "silyl" groups), and alkoxyalkyl groups. Alkoxycarbonyl protecting groups are alkyl-O—CO— groups such as methoxycarbonyl, ethoxycarbonyl, propoxycarbonyl, isopropoxycarbonyl, butoxycarbonyl, isobutoxycarbonyl, tert-butoxycarbonyl, benzyloxycarbonyl or allyloxycarbonyl. The term "acyl" signifies an alkanoyl group of 1 to 6 carbons, in all of its isomeric forms, or a carboxyalkanoyl group of 1 to 6 carbons, such as an oxalyl, malonyl, succinyl, glutaryl group, or an aromatic acyl group such as benzoyl, or a halo, nitro or alkyl substituted benzoyl group. Alkoxyalkyl protecting groups are groupings such as methoxymethyl, ethoxymethyl, methoxyethoxymethyl, or tetrahydrofuranyl and tetrahydropyranyl. Preferred silyl-protecting groups are trimethylsilyl, triethylsilyl, t-butyldimethylsilyl, dibutylmethylsilyl, diphenylmethylsilyl, phenyldimethylsilyl, diphenyl-t-butylsilyl and analogous alkylated silyl radicals. The term "aryl" specifies a phenyl-, or an alkyl-, nitro- or halo-substituted phenyl group. An extensive list of protecting groups for the hydroxy functionality may be found in Protective Groups in Organic Synthesis, Greene, T. W.; Wuts, P. G. M., John Wiley & Sons, New York, N.Y., (3rd Edition, 1999) which can be added or removed using the procedures set forth therein and which is hereby incorporated by reference in its entirety and for all purposes as if fully set forth herein.

A "protected hydroxy" group is a hydroxy group derivatized or protected by any of the above groups commonly used for the temporary or permanent protection of hydroxy functional groups, e.g., the silyl, alkoxyalkyl, acyl or alkoxycarbonyl groups, as previously defined.

Various analogs of 1α,25-dihydroxyvitamin D$_3$ and 1α,25-dihydroxyvitamin D$_2$ such as 19-nor vitamin D analogs are useful in inhibiting adipocyte differentiation, inhibiting an increase in PPARγ, C/EBPα, and/or SCD-1 gene transcription, and reducing body fat and are thus useful in treating and preventing obesity in animal subjects or treating overweight animal subjects that include mammals such as, but not limited to, rodents, primates, bovines, equines, canines, felines, ursines, porcines, rabbits, and guinea pigs. In some embodiments, the animal subject is a mammal such as a rat or a mouse whereas in other embodiments, the animal subject is a primate such as a monkey or a human. In some embodiments, the subject is a human male and in other embodiments, the subject is a human female. Various analogs of 1α,25-dihydroxyvitamin D$_3$ and 1α,25-dihydroxyvitamin D$_2$ may be used in accordance with the invention including 19-nor vitamin D analogs which are modified in the 2 carbon position (do not include a CH$_2$ group as C-2). Examples of such C-2 modified compounds include, but are not limited to 2-alkylidene 19-nor vitamin D compounds such as, but not limited to 2-methylene-19-nor vitamin D compounds including, but not limited to, (20S) 2-methylene-19-nor vitamin D compounds and (20R) 2-methylene-19-nor vitamin D compounds. The compounds of the invention are preferably 1α-hydroxy compounds that bind to the vitamin D receptor.

As noted above, various 19-nor vitamin D analogs may be used in accordance with the invention. In one embodiment, the 19-nor vitamin D analog administered to the subject is a compound of formula IA or IB, or is a mixture thereof. In some such embodiments, the analog is a compound of formula IA. In other embodiments, the vitamin D analog is a compound of formula IB.

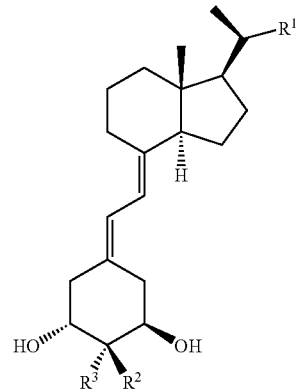

IA

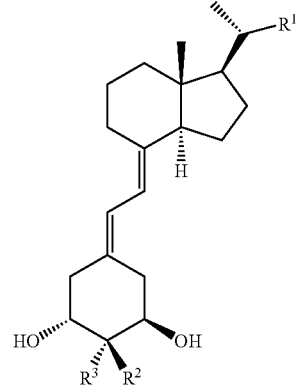

IB

In compounds of formula IA and IB, R$^1$ is selected from H, or straight and branched chain alkyl groups having from 1 to 8 carbon atoms, straight and branched chain alkenyl groups having from 2 to 8 carbon atoms, straight and branched chain hydroxy-substituted alkyl groups having from 1 to 8 carbon atoms, or straight and branched chain hydroxy-substituted alkenyl groups having from 2 to 8 carbon atoms. In some such embodiments, R$^1$ is selected from straight and branched chain alkyl groups having from 2 to 7 carbon atoms, straight and branched chain alkenyl groups having from 2 to 7 carbon atoms, straight and branched chain hydroxy-substituted alkyl groups having from 2 to 6 carbon atoms, or straight and branched chain hydroxy-substituted alkenyl groups having from 2 to 6 carbon atoms. In other such embodiments, R$^1$ is selected from straight and branched chain alkyl groups having from 2 to 7 carbon atoms, straight and branched chain alkenyl groups having from 2 to 7 carbon atoms, or straight and branched chain hydroxy-substituted alkenyl groups having from 2 to 6 carbon atoms.

In compounds of formula IA and IB, $R^2$ and $R^3$ are independently selected from H, straight or branched chain alkyl groups having from 1 to 8 carbon atoms, or straight or branched chain alkenyl groups having from 1 to 8 carbon atoms or $R^2$ and $R^3$ join together to form a group of formula IC

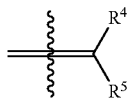

IC where the wavy line indicates the point of attachment to the carbon at the 2 position of the vitamin D analog and $R^4$ and $R^5$ are independently selected from H, straight or branched chain alkyl groups having from 1 to 8 carbon atoms, straight or branched chain hydroxyalkyl groups having from 1 to 8 carbon atoms, straight or branched chain protected hydroxyalkyl groups having from 1 to 8 carbon atoms, straight or branched chain hydroxyalkenyl groups having from 1 to 8 carbon atoms, straight or branched chain fluoroalkyl groups having from 1 to 8 carbon atoms, or straight or branched chain alkenyl groups having from 1 to 8 carbon atoms. In some embodiments, the analog is a compound of formula IA or IB and $R^3$ is H. In some such embodiments, $R^2$ is a straight chain alkyl group such as methyl, ethyl, or propyl. In other embodiments, $R^2$ and $R^3$ join together to form a group of formula IC in which $R^4$ and $R^5$ are both H. Examples of some such compounds include compounds of formula IIA and IIB described below.

As noted above, various 19-nor vitamin D analogs may be used in accordance With the invention. In some embodiments, the 19-nor vitamin D analog is a compound of formula IIA or IIB

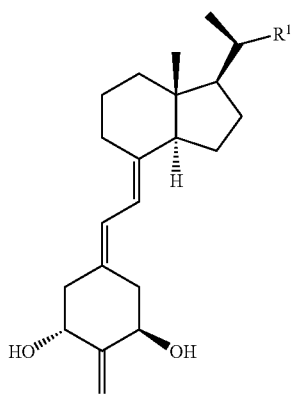

IIA

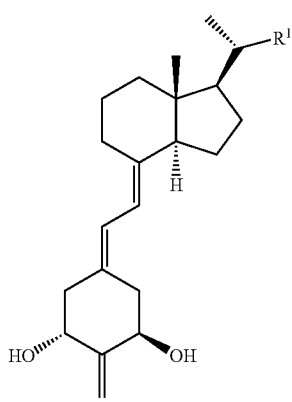

IIB where $R^1$ is selected from H, or straight and branched chain alkyl groups having from 1 to 8 carbon atoms, straight and branched chain alkenyl groups having from 2 to 8 carbon atoms, straight and branched chain hydroxy-substituted alkyl groups having from 1 to 8 carbon atoms, or straight and branched chain hydroxy-substituted alkenyl groups having from 2 to 8 carbon atoms. In some such embodiments, $R^1$ is selected from straight and branched chain alkyl groups having from 2 to 7 carbon atoms, straight and branched chain alkenyl groups having from 2 to 7 carbon atoms, straight and branched chain hydroxy-substituted alkyl groups having from 2 to 6 carbon atoms, or straight and branched chain hydroxy-substituted alkenyl groups having from 2 to 6 carbon atoms. In other such embodiments, $R^1$ is selected from straight and branched chain alkyl groups having from 2 to 7 carbon atoms, straight and branched chain alkenyl groups having from 2 to 7 carbon atoms, or straight and branched chain hydroxy-substituted alkenyl groups having from 2 to 6 carbon atoms. In some embodiments, the compound of formula IIA or IIB is a compound other than (20S)-2-methylene-19-nor-1α,25-dihydroxyvitamin $D_3$ (2-MD).

An example of just one 19-nor vitamin D analog that may be administered to a subject or used to prepare a medicament in accordance with the methods of the invention is a compound of formula IIC where $R^1$ is a hydroxy-substituted branched chain alkyl group having 6 carbon atoms (a —$CH_2CH_2CH_2C(CH_3)_2OH$ group). The compound has the name (20S)-2-methylene-19-nor-1α,25-dihydroxyvitamin $D_3$ (2-MD).

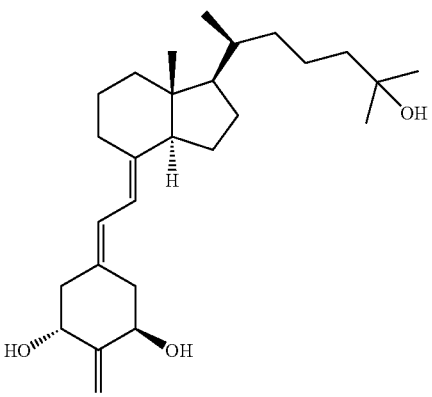

IIC

An example of another 19-nor vitamin D analog that may be administered to a subject or used to prepare a medicament in accordance with the methods of the invention is a compound of formula IID where $R^1$ is a branched chain alkyl group having 7 carbon atoms (a —$CH_2CH_2CH_2C(CH_3)_3$ group). The compound has the name (20S)-1α-hydroxy-2-methylene-19-nor-25-methylvitamin $D_3$ (TMM).

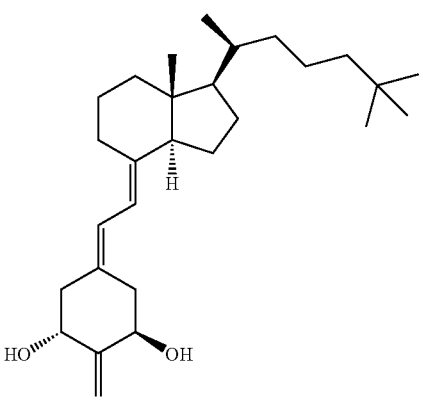

IID

An example of another 19-nor vitamin D analog that may be administered to a subject or used to prepare a medicament in accordance with the methods of the invention is a compound of formula IIE where $R^1$ is a straight chain alkyl group having 2 carbon atoms (a —CH$_2$CH$_3$ group). The compound has the name (20S)-1α-hydroxy-2-methylene-19-nor-bishomopregnacalciferol (2-MbisP).

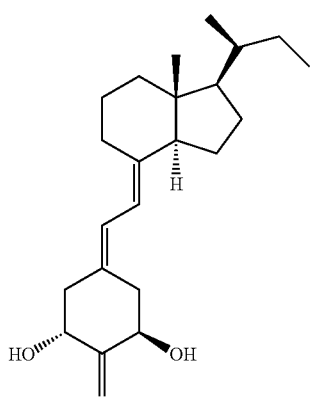

IIE

An example of yet another 19-nor vitamin D analog that may be administered to a subject or used to prepare a medicament in accordance with the methods of the invention is a compound of formula IIF where $R^1$ is a straight chain alkyl group having 1 carbon atoms (a —CH$_3$ group). The compound has the name 1α-hydroxy-2-methylene-19-nor-homopregnacalciferol.

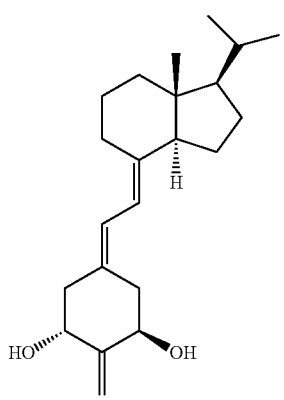

IIF

An example of yet another 19-nor vitamin D analog that may be administered to a subject or used to prepare a medicament in accordance with the methods of the invention is a compound of formula IIG where $R^1$ is a straight chain alkyl group having 2 carbon atoms (a —CH$_2$CH$_3$ group), and the compound has the name (20R)-1α-hydroxy-2-methylene-19-nor-bishomopregnacalciferol ((20R)2MbisP).

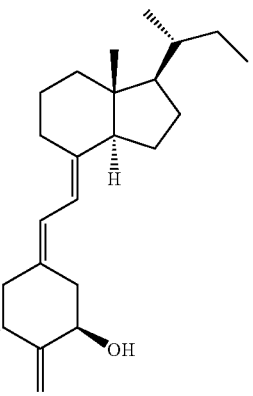

IIG

An example of yet another 19-nor vitamin D analog that may be administered to the subject or used to prepare a medicament in accordance with the methods of the invention is a compound of formula IIH where $R^1$ is a H, and the compound has the name 2-methylene-19-nor-1α-hydroxy-pregnacalciferol (2-Mpregna).

IIH

An example of yet another 19-nor vitamin D analog that may be administered to the subject or used to prepare a medicament in accordance with the methods of the invention is a compound of formula IIJ where $R^1$ is a straight chain alkyl group having 2 carbon atoms (a —CH$_2$CH$_3$ group), $R^2$ is a methyl group, and $R^3$ is H, and the compound has the name 2α-methyl-19-nor-(20S)-1α-hydroxy-bishomopregnacalciferol ((20S)2αMbisP).

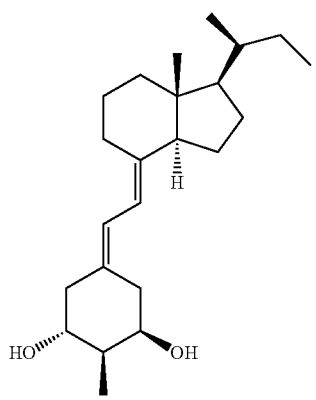

IIJ

An example of yet another 19-nor vitamin D analog that may be administered to the subject or used to prepare a medicament in accordance with the methods of the invention is a compound of formula IIK where $R^1$ is a straight chain alkyl group having 1 carbon atoms (a —$CH_3$ group), $R^2$ is a methyl group, and $R^3$ is H, and the compound has the name 2α-methyl-19-nor-1α-hydroxy-homopregnacalciferol (2α-methyl MP).

IIK

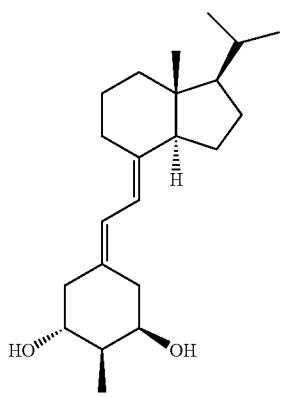

An example of yet another 19-nor vitamin D analog that may be administered to the subject or used to prepare a medicament in accordance with the methods of the invention is a compound of formula IIL where $R^1$ is a straight chain alkyl group having 3 carbon atoms (a —$CH_2CH_2CH_3$ group), and the compound has the name 2-methylene-19-nor-(20S)-1α-hydroxy-trishomopregnacalciferol (2MtrisP).

IIL

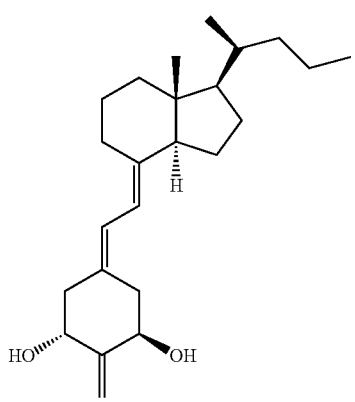

An example of yet another 19-nor vitamin D analog that may be administered to the subject or used to prepare a medicament in accordance with the methods of the invention is a compound of formula IIM where $R^1$ is a straight chain alkyl group having 4 carbon atoms (a —$CH_2CH_2CH_2CH_3$ group), and the compound has the name 2-methylene-19,26,27-trinor-(20S)-1α-hydroxyvitamin $D_3$ ((20S)OM).

IIM

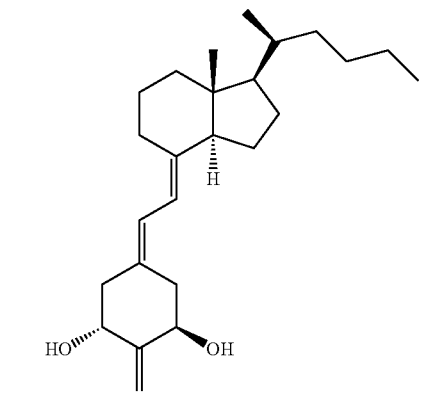

An example of yet another 19-nor vitamin D analog that may be administered to the subject or used to prepare a medicament in accordance with the methods of the invention is a compound of formula IIN where $R^1$ is a straight chain alkyl group having 4 carbon atoms (a —$CH_2CH_2CH_2CH_3$ group), $R^2$ is a methyl group, $R^3$ is H, and the compound has the name 2α-methyl-19,26,27-trinor-(20S)-1α-hydroxyvitamin $D_3$ (2α-methyl-19,26,27-trinor).

IIN

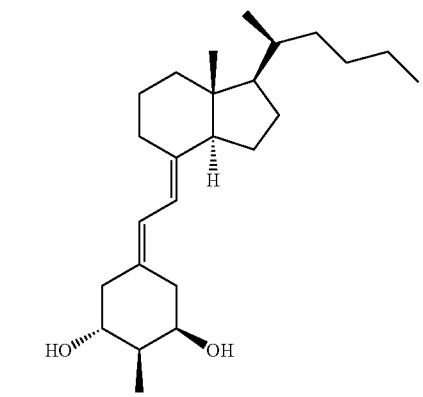

An example of yet another 19-nor vitamin D analog that may be administered to the subject or used to prepare a medicament in accordance with the methods of the invention is a compound of formula IIO where $R^1$ is a hydroxy-substituted branched chain alkyl group having 6 carbon atoms (a —$CH_2CH_2CH_2C(CH_3)_2OH$ group), $R^2$ and $R^3$ are a group of formula IC, $R^4$ is H, $R^5$ is a hydroxypropyl group, and the compound has the name 2-(3'-hydroxypropylidene)-19-nor-(20S)-1α,25-dihydroxyvitamin $D_3$ (1AGS).

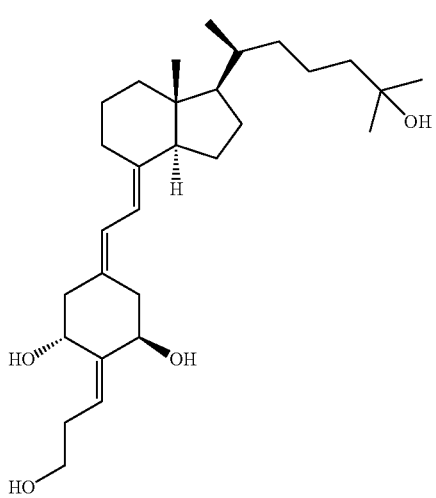

IIO

An example of yet another 19-nor vitamin D analog that may be administered to the subject or used to prepare a medicament in accordance with the methods of the invention is a compound of formula IIP where $R^1$ is a hydroxy-substituted branched chain alkyl group having 6 carbon atoms (a —$CH_2CH_2CH_2C(CH_3)_2OH$ group), $R^2$ and $R^3$ are a group of formula IC, $R^4$ is H, $R^5$ is a hydroxypropyl group, and the compound has the name 2-(3'-hydroxypropylidene)-19-nor-1α,25-dihydroxyvitamin $D_3$ (1AGR).

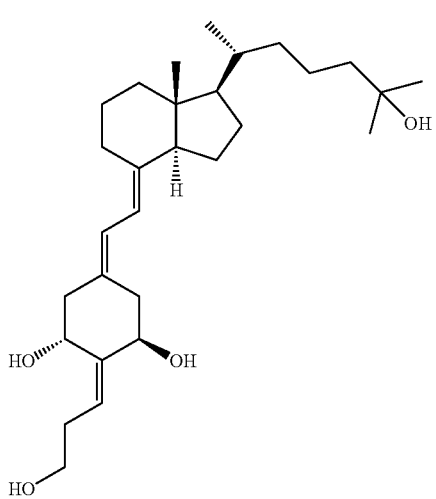

IIP

An example of yet another 19-nor vitamin D analog that may be administered to the subject or used to prepare a medicament in accordance with the methods of the invention is a compound of formula IIQ where $R^1$ is a hydroxy-substituted branched chain alkyl group having 6 carbon atoms (a —$CH_2CH_2CH_2C(CH_3)_2OH$ group), $R^2$ and $R^3$ are a group of formula IC, $R^4$ is H, $R^5$ is a —$CH_2CH_2OCH_2OCH_3$ group (a protected hydroxyalkyl group), and the compound has the name 2-[(3'-methoxymethoxy)-propylidene]-19-nor-1α,25-dihydroxyvitamin $D_3$ (F-Wit).

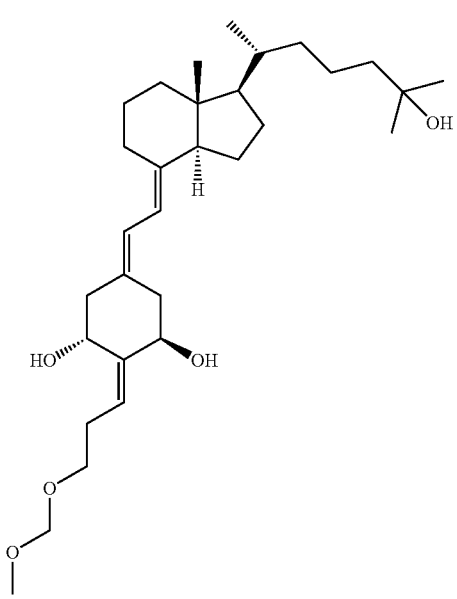

IIQ

An example of yet another 19-nor vitamin D analog that may be administered to the subject or used to prepare a medicament in accordance with the methods of the invention is a compound of formula IIR, a 19,21-dinor vitamin $D_3$ analog, having the name 2-methylene-19,21-dinor-1α-hydroxybishomopregnacalciferol (19,21-dinor) and having the formula IIR.

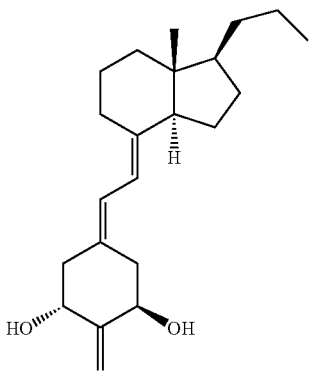

IIR

An example of yet another 19-nor vitamin D analog that may be administered to the subject or used to prepare a medicament in accordance with the methods of the invention is a compound of formula IIS, a 19-nor 17-ene vitamin D analog, having the name 2-methylene-19-nor-1α-hydroxy-17-ene-homopregnacalciferol (Vitamin I or VIT-I) and having the formula IIS.

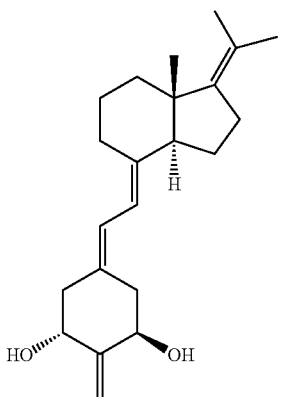

IIS

Examples of other 19-nor vitamin D analogs that may be administered to the subject or used to prepare a medicament in accordance with the methods of the invention are 18,19-dinor vitamin D analogs such as compounds of formula IIT and IIU. In some such embodiments, the compound has the name 2-methylene-18,19-dinor-(20S)-1α,25-dihydroxyvitamin D$_3$ (VD-03) and has the formula IIT. In other such embodiments, the compound has the name 2-methylene-18,19-dinor-1α-hydroxyhomopregnacalciferol (18,19-dinor-2MP) and has the formula IIU.

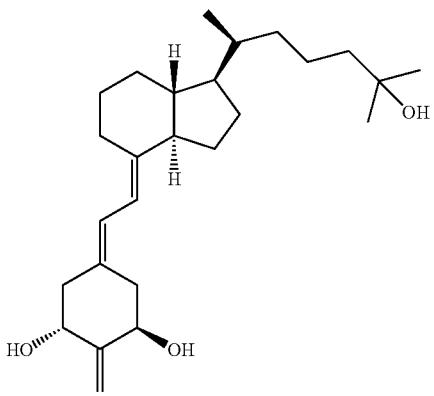

IIT

IIU

Examples of other 19-nor vitamin D analogs that may be administered to the subject or used to prepare a medicament in accordance with the methods of the invention are 19-dinor vitamin D$_2$ analogs such as compounds of formula IIV and IIW. In some such embodiments, the compound has the name 2-methylene-19-nor-24-epi-1α,25-dihydroxyvitamin D$_2$ ((24epi)D$_2$) and has the formula IIV. In other such embodiments, the compound has the name 19-nor-1α,25-dihydroxyvitamin D$_2$ (1α,25(OH)$_2$(19nor)D$_2$ or Zemplar) and has the formula IIW.

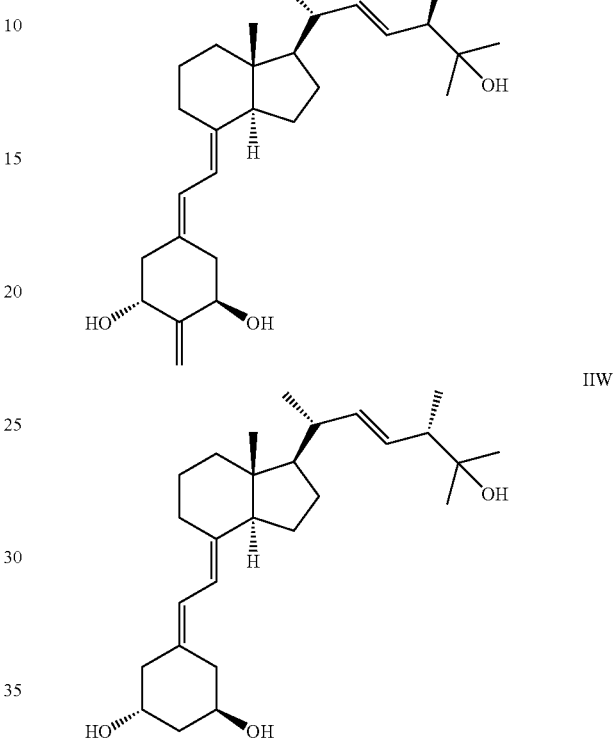

IIV

IIW

For treatment purposes, the compounds for use in accordance with the invention such as, but not limited to, those defined by formula IA, for formula IB, formula IIA, formula IIB, and formulas IIC-IIW may be formulated for pharmaceutical applications as a solution in innocuous solvents, or as an emulsion, suspension or dispersion in suitable solvents or carriers, or as pills, tablets or capsules, together with solid carriers, according to conventional methods known in the art. Any such formulations may also contain other pharmaceutically acceptable and non-toxic excipients such as stabilizers, anti-oxidants, binders, coloring agents or emulsifying or taste-modifying agents. Pharmaceutically acceptable excipients and carriers are generally known to those skilled in the art and are thus included in the instant invention. Such excipients and carriers are described, for example, in "Remingtons Pharmaceutical Sciences" Mack Pub. Co., New Jersey (1991), which is hereby incorporated by reference in its entirety and for all purposes as if fully set forth herein.

The compounds may be administered orally, topically, parenterally, or transdermally. The compounds are advantageously administered by injection or by intravenous infusion or suitable sterile solutions, or in the form of liquid or solid doses via the alimentary canal, or in the form of creams, ointments, patches, or similar vehicles suitable for transdermal applications. In some embodiments, doses of from 0.001 μg to about 100 mg per day of the compound are appropriate for treatment purposes. In some such embodiments an appropriate and effective dose may range from 0.01 μg to 1000 μg per day of the compounds, such doses being adjusted according to the degree of obesity to be treated, the activity of the specific compound to be administered, the severity of the disease, and the response of the subject as is well understood in the art. Since the compounds exhibit specificity of action, each may be suitably administered alone, or together with graded doses of another active vitamin D compound. In some embodiments a compound such as 2-MD may be administered to the subject in a dose of 0.001 µg to 1 µg per day. In other embodiments, a compound such as 2-MbisP or 2-MP may be administered to a subject in a dose ranging from 0.1 mg to 100 mg per day. In still other embodiments, a compound such as TMM may be administered to a subject in a dose ranging from 5 ng to 10 µg per day. In some embodiments, a compound of formula IA or formula IB in which $R^2$ and $R^3$ form a group of formula IC in which one of $R^4$ or $R^5$ is a hydroxyalkyl, hydroxyalkenyl, a protected hydroxyalkyl, or a protected hydroxyalkenyl group, the compound may be administered in a dose ranging from 0.1 ng to 10 ng per day.

Compositions for use in treating and preventing obesity, inhibiting adipocyte differentiation, inhibiting increased SCD-1 gene transcription, and/or reducing body fat comprise an effective amount of the 19-nor vitamin D analog as the active ingredient, and a suitable carrier. An effective amount of such compounds for use in accordance with some embodiments of the invention will generally be a dosage amount such as that described herein, and may be administered topically, transdermally, orally, or parenterally.

The compound may be formulated as creams, lotions, ointments, topical patches, pills, capsules or tablets, or in liquid form as solutions, emulsions, dispersions, or suspensions in pharmaceutically innocuous and acceptable solvent or oils, and such preparations may contain, in addition, other pharmaceutically innocuous or beneficial components, such as stabilizers, antioxidants, emulsifiers, coloring agents, binders or taste-modifying agents.

In some embodiments, the compound is advantageously administered in amounts sufficient to prevent or inhibit the differentiation of cells into adipocytes. Dosages, as described above, are suitable, it being understood that the amounts given are to be adjusted in accordance with the severity of the disease, and the condition and response of the subject as is well understood in the art.

The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof.

Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion.

Formulations for rectal administration may be in the form of a suppository incorporating the active ingredient and carrier such as cocoa butter, or in the form of an enema.

Formulations suitable for parenteral administration conveniently comprise a sterile oily or aqueous preparation of the active ingredient which is preferably isotonic with the blood of the recipient.

Formulations suitable for topical administration include liquid or semi-liquid preparations such as liniments, lotions, applicants, oil-in-water or water-in-oil emulsions such as creams, ointments or pastes; or solutions or suspensions such as drops; or as sprays.

The formulations may conveniently be presented in dosage unit form and may be prepared by any of the methods well known in the art of pharmacy. By the term "dosage unit" is meant a unitary, i.e., a single dose which is capable of being administered to a patient as a physically and chemically stable unit dose comprising either the active ingredient as such or a mixture of it with solid or liquid pharmaceutical diluents or carriers.

Synthesis of Compounds

Preparation of 19-nor vitamin D compounds such as those having the basic structure IA and IB can be accomplished utilizing the same common general method, i.e., the condensation of an appropriate bicyclic Windaus-Grundmann type ketone (IIIA or IIIB) with the allylic phosphine oxide IV followed by deprotection (removal of the $Y_1$ and $Y_2$ groups).

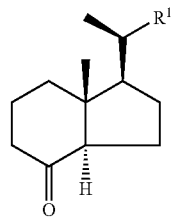

IIIA

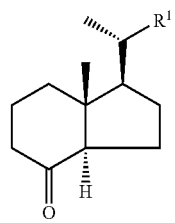

IIIB

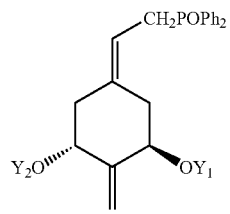

IV

In the structures IIIA, IIIB, and IV, $R^1$ represents groups as defined above, and $Y_1$ and $Y_2$ are preferably hydroxy-protecting groups such as silyl protecting groups, it being also understood that any functionalities in $R^1$ that might be sensitive, or that interfere with the condensation reaction, be suitably protected as is well-known in the art. For example, a hydroxyl functionality in an $R^1$ group is suitably protected with a trialkylsilyl group such as a triethylsilyl group during the reaction of the compound of formula IIIA or IIIB with the compound of formula IV. The process described above represents an application of the convergent synthesis concept, which has been applied effectively to the preparation of numerous vitamin D compounds (see Lythgoe et al., *J. Chem. Soc. Perkin Trans. I,* 590 (1978); Lythgoe, *Chem. Soc. Rev.* 9, 449 (1983); Toh et al., *J. Org. Chem.* 48, 1414 (1983); Baggiolini et al., *J. Org. Chem.* 51, 3098 (1986); Sardina et al., *J. Org. Chem.* 51, 1264 (1986); *J. Org. Chem.* 51, 1269 (1986); DeLuca et al., U.S. Pat. No. 5,086,191; DeLuca et al., U.S. Pat. No. 5,536,713; and DeLuca et al., U.S. Pat. No. 5,843,928 all of which are hereby incorporated by reference in their entirety and for all purposes as if fully set forth herein).

2-Methylene phosphine oxide IV is a convenient reagent that can be used to prepare a large number of 19-nor vitamin D compounds and which may be prepared according to the procedures described by Sicinski et al., *J. Med. Chem.*, 41, 4662 (1998), and DeLuca et al., U.S. Pat. No. 5,843,928.

Hydraindanones of the general structure IIIA and IIIB are known, or can be prepared by known methods or adapted methods as will be readily apparent to one of skill in the art. Specific important examples of bicyclic ketones are Grundmann's ketone analogs (a, b, and c) (see Mincione et al., *Synth. Commun* 19, 723, 1989; Peterson et al., *J. Org. Chem.* 51, 1948, (1986)).

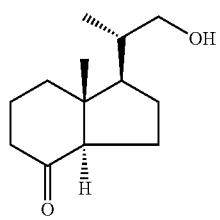

a

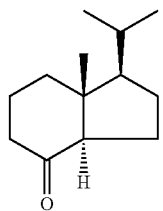

b

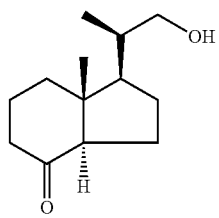

c

The synthesis of compounds of formula IIA and IIB in which $R^1$ is a hydroxy-substituted alkenyl group or $R^1$ is a straight or branched chain alkenyl group may be readily prepared using the procedure described below and depicted in Scheme I and Scheme II.

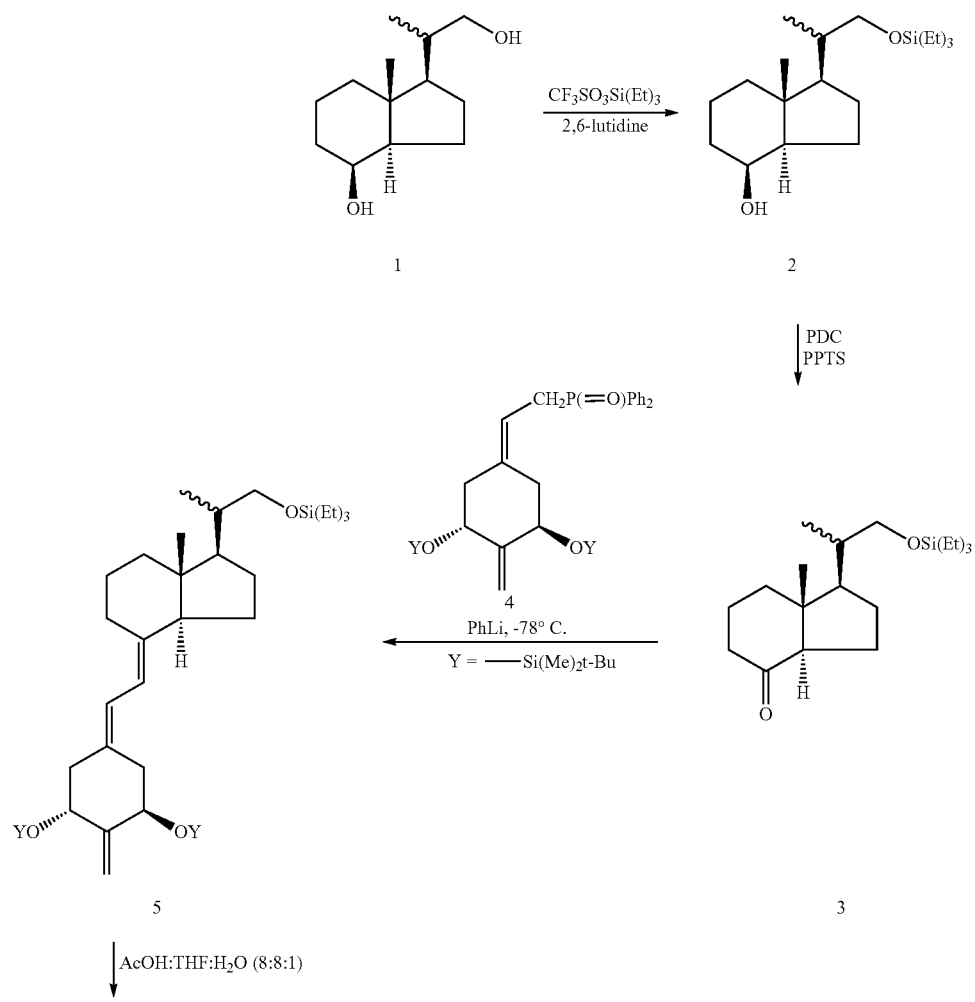

-continued
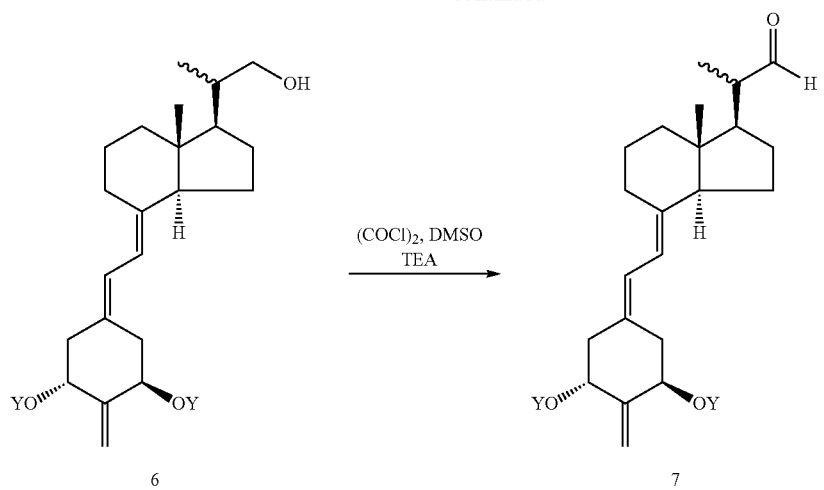
Scheme II
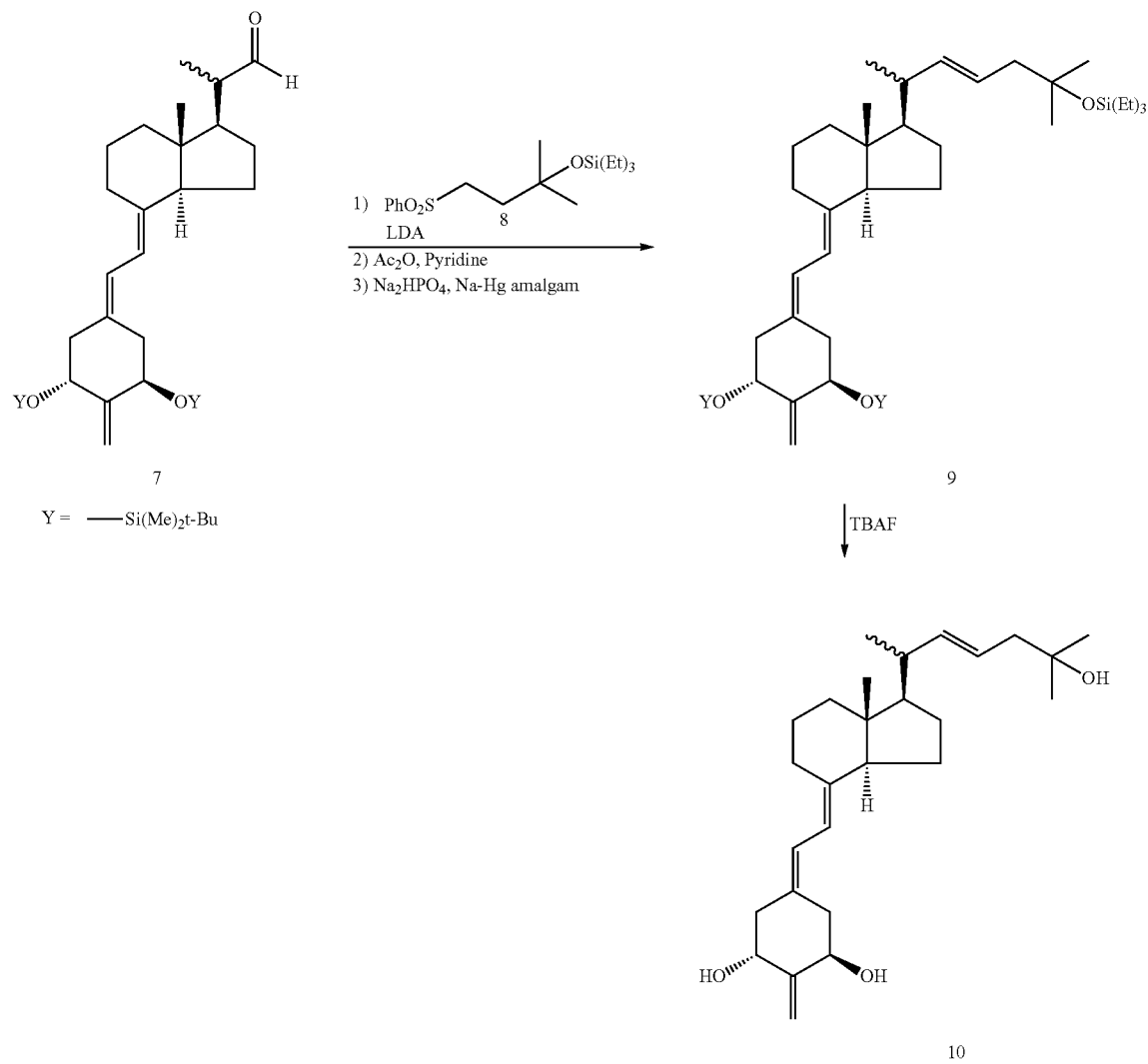
Y = —Si(Me)₂t-Bu

As shown in Scheme I, a diol 1, which may be obtained by the ozonolysis of vitamin $D_2$, may be selectively protected as the mono triethylsilyl ether 2, and the secondary hydroxyl at C-8 may be oxidized with PDC to afford the Grundmann's ketone 3. Wittig-Horner coupling of the conjugate base of phosphine oxide 4, produced by deprotonation with a lithium reagent such as phenyllithium, with the protected Grundmann's ketone 3 affords the expected protected 19-nor-pregnacalciferol 5 in high yields. The triethylsilyl protecting group of compound 5 is selectively cleaved using an 8:8:1 mixture of $AcOH:THF:H_2O$. The hydroxy vitamin D analog may then be oxidized to the aldehyde derivative 7 under Swern oxidation conditions using $(COCl)_2$, DMSO and TEA. Aldehyde 7 may be utilized to prepare a large number of compounds of formula IIA and IIB. For example, compounds of formula IIA and IIB in which $R^1$ includes a hydroxy-substituted alkenyl group or a straight or branched chain alkenyl groups may be prepared using aldehyde 7 and Julia olefination conditions as shown in Scheme II. As shown in Scheme II, Julia olefination of aldehyde 7 with a sulfone such as, for example, compound 8 followed by desulfonylation provides the protected analog 9. Deprotection of the silyl protecting groups may be readily accomplished with tetrabutylammonium fluoride to yield the 2-methylene 19-nor vitamin D compounds of formula IIA and IIB, such as compound 10. A wide range of sulfones may be used in accordance with the procedure described in Scheme II providing access to a large variety of compounds of formula IIA and IIB. For example, sulfones such as, but not limited to, $PhO_2SCH_2CH_2CH_2CH_3$, $PhO_2SCH_2CH_2CH(CH_3)_2$, $PhO_2SCH_2CH(CH_3)CH(CH_3)_2$, $PhO_2SCH_2CH_2C(CH_3)_3$ and the like may be used to prepare various compounds of formula IIA and IIB. Various sulfones and hydroxy-protected sulfones may be prepared using known procedures such as that described by Kutner et al., *J. Org. Chem.* 53, 3450 (1988). Alcohols such as compound 6 of Scheme I may also be used to prepare a large number of compounds of formula IIA and IIB. For example, alcohol 6 may be reacted with TsCl using the conditions set forth in Scheme IV. Reaction of the tosylate with a copper reagent formed from a Grignard reagent as shown in Scheme IV and described below with respect to the synthesis of the Grundmann's ketone and synthesis of TMM allows the synthesis of a wide array of the compounds of the invention.

EXAMPLES

Synthesis of Specific 19-nor Vitamin D Analogs

The synthesis and characteristics of various 19-nor vitamin D analogs is described in numerous United States patents including U.S. Pat. Nos. 5,843,928, 6,627,622, 6,579,861, 5,086,191, 5,585,369, and 6,537,981. Each of the above-described references is hereby incorporated by reference in its entirety and for all purposes as if fully set forth herein. The natural hormone, $1\alpha,25$-dihydroxyvitamin $D_3$, is commercially available and was obtained from Sigma-Aldrich (Milwaukee, Wis.). 19-nor-$1\alpha,25$-dihydroxyvitamin $D_2$ was prepared as described in U.S. Pat. Nos. 5,246,925 and 5,587,497 which are hereby incorporated by reference in their entireties and for all purposes as if fully set forth herein. 2-methylene-19-nor-24-epi-$1\alpha,25$-dihydroxyvitamin $D_2$ ((24epi)$D_2$) was prepared as described in U.S. Pat. No. 5,936,133 which is hereby incorporated by reference in its entirety and for all purposes as if fully set forth herein.

Synthesis of (20S)-$1\alpha$-Hydroxy-2-methylene-19-nor-bishomopregnacalciferol (2-MbisP)

The preparation of (20S)-$1\alpha$-hydroxy-2-methylene-19-nor-bishomopregnacalciferol (2-MbisP) was accomplished as described in U.S. Pat. No. 6,627,622, hereby incorporated by reference in its entirety and for all purposes as if fully set forth in its entirety, using a general method, i.e. the condensation of a bicyclic Windaus-Grundmann type ketone V with an allylic phosphine oxide VI to provide the corresponding protected 2-methylene-19-nor-vitamin D analog VII which, upon deprotection at C-1 and C-3, afforded the title compound.

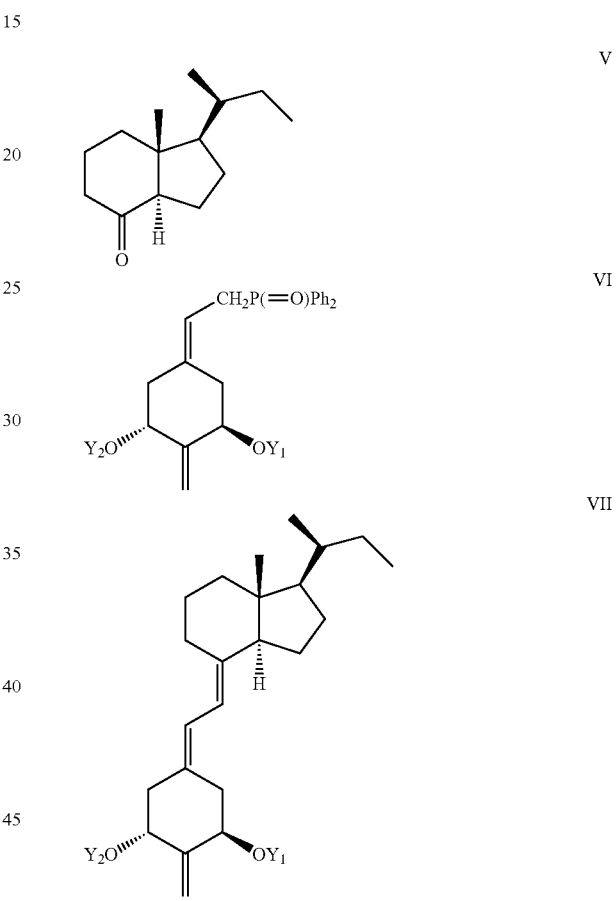

In the structures, VI and VII, $Y_1$ and $Y_2$ are hydroxy-protecting groups, it being understood that any functionalities that might be sensitive, or that interfere with the condensation reaction, be suitably protected as is well-known in the art. The process described above represents an application of the convergent synthesis concept and is set forth in U.S. Pat. No. 6,627,622 hereby incorporated by reference in its entirety and for all purposes as if fully set forth herein, which has been applied effectively for the preparation of vitamin D compounds (e.g. Lythgoe et al., *J. Chem Soc. Perkins Trans. I,* 590 (1978); Lythgoe, *Chem. Soc. Rev.* 9, 449 (1983); Toh et al., *J. Org. Chem.* 48, 1414 (1983); Baggiolini et al., *J. Org. Chem.* 51, 3098 (1986); Baggiolini et al., *J. Org. Chem.* 51, 1269 (1986); DeLuca et al., U.S. Pat. No. 5,086,191 hereby incorporated by reference in its entirety and for all purposes as if fully set forth herein; DeLuca et al., U.S. Pat. No. 5,536,713 hereby incorporated by reference in its entirety and for all purposes as if fully set forth herein). Hydraindanones of the general structure V are known, or can be prepared by methods known to those skilled in the art. For the preparation of the required phosphine oxides of general structure VI, a synthetic route has been developed starting from a methyl quinicate derivative which is easily obtained from commercial (1R,3R, 4S,5R)-(−)-quinic acid as described by Perlman et al., *Tetrahedron Lett.* 32, 7663 (1991) and DeLuca et al., U.S. Pat. No. 5,086,191 incorporated herein by reference in its entirety. The overall process for the synthesis of (20S)-1α-hydroxy-2-methylene-19-nor-bishomopregnacalciferol (2-MbisP) is illustrated and described in U.S. Pat. No. 5,843,928 which is hereby incorporated by reference in its entirety and for all purposes as if fully set forth herein.

Synthesis of (20S)-2-Methylene-19-nor-1α,25-dihydroxyvitamin $D_3$ (2-MD)

The synthesis of the title compound is described in U.S. Pat. No. 5,843,928 (see columns 14 and 15) which is hereby incorporated by reference in its entirety and for all purposes as if fully set forth herein. The preparation of (20S)-2-methylene-19-nor-1α,25-dihydroxyvitamin $D_3$ (2-MD) was accomplished using the same general method described above for the synthesis of 2-MbisP using the bicyclic Windaus-Grundmann type ketone VIII protected with the triethylsilyl protecting group in place of bicyclic Windaus-Grundmann ketone V.

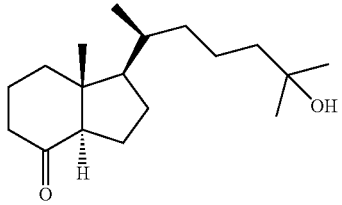

VIII

Synthesis of 1α-Hydroxy-2-methylene-19-nor-homopregnacalciferol (2-MP)

The synthesis of the title compound is described in U.S. patent Publication No. 2004/0220418 which is hereby incorporated by reference in its entirety and for all purposes as if fully set forth herein. The preparation of 1α-hydroxy-2-methylene-19-nor-homopregnacalciferol (2-MP) was accomplished using the same general method described above for the synthesis of 2-MbisP using the bicyclic Windaus-Grundmann type ketone IX in place of bicyclic Windaus-Grundmann V.

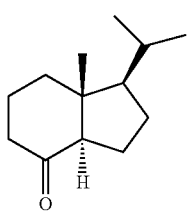

IX

Synthesis of (20S)-1α-Hydroxy-2-methylene-19-nor-25-methylvitamin $D_3$ (TMM)

The synthesis of (20S)-1α-hydroxy-2-methylene-19-nor-25-methylvitamin $D_3$ (TMM) is readily accomplished using the procedure described above for the synthesis of 2-MbisP using the bicyclic Windaus-Grundmann type ketone X in place of bicyclic Windaus-Grundmann ketone V. This procedure is set forth in U.S. patent application Ser. No. 10/613,201 filed on Jul. 3, 2003 and hereby incorporated by reference in its entirety and for all purposes as if fully set forth herein. The procedure is shown in Schemes III, IV, and V. Scheme III shows a method that may be generally used to prepare a wide variety of 20S and 20R vitamin D analogs from vitamin $D_2$. As set forth in Scheme III, aldehyde 3 may be treated with n-$Bu_4$NOH to provide a mixture of 3 and its 20-epimer which may be used to synthesize a wide array of 20S vitamin D analogs as will be understood by those skilled in the art. For example, alkyl chlorides or bromides, alkenyl chlorides and bromides, hydroxy-protected hydroxyalkyl chlorides and bromides, and hydroxy-protected hydroxyalkenyl chlorides and bromides may be used to prepare a wide variety of Grignard reagents which may be used in place of Grignard reagent 7 of Scheme IV to synthesize a plethora of vitamin D analogs using the procedures in Schemes IV and V.

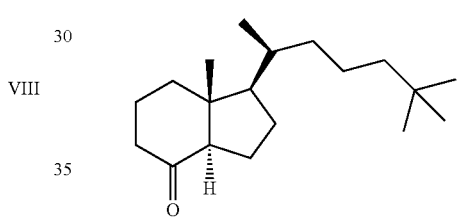

X

Scheme VI shows the general procedure outlined in U.S. Pat. No. 5,843,928 which is hereby incorporated by reference in its entirety as if fully set forth herein. Modification of the method shown in Scheme VI may be used to produce a large number of vitamin D analogs for use in the present invention as will be apparent to those skilled in the art. For example, a wide variety of phosphonium compounds may be used in place of the $MePh_3P^+Br^-$ used to convert ketone B to alkene C. Examples of such compounds include $EtPh_3P^+Br^-$, $PrPh_3P^+Br^-$, and compounds generally prepared by reaction of triphenylphosphine with an alkyl halide, an alkenyl halide, a protected-hydroxyalkyl halide, and a protected hydroxyalkenyl halide. Alkenes prepared using this procedure may then be carried through to prepare a phosphine oxide in analogous manner to that used to prepare phosphine oxide H in Scheme VI. Alternatively, an alkene analogous to compound C of Scheme VI or indeed a compound of formula IIA or IIB may be reduced with $(Ph_3P)_3RhCl$ and $H_2$ to provide compounds of formula IA and IB in which one of $R^2$ and $R^3$ is H and the other is an alkyl group. See U.S. Pat. No. 5,945,410 and Sicinski, R. R. et al., *J. Med. Chem.*, 41, 4662-4674 (1998) both of which are hereby incorporated by reference in their entireties and for all purposes. Therefore, the procedure for forming the phosphine oxide shown in Scheme VI may be used to prepare a wide variety of compounds of the present invention.

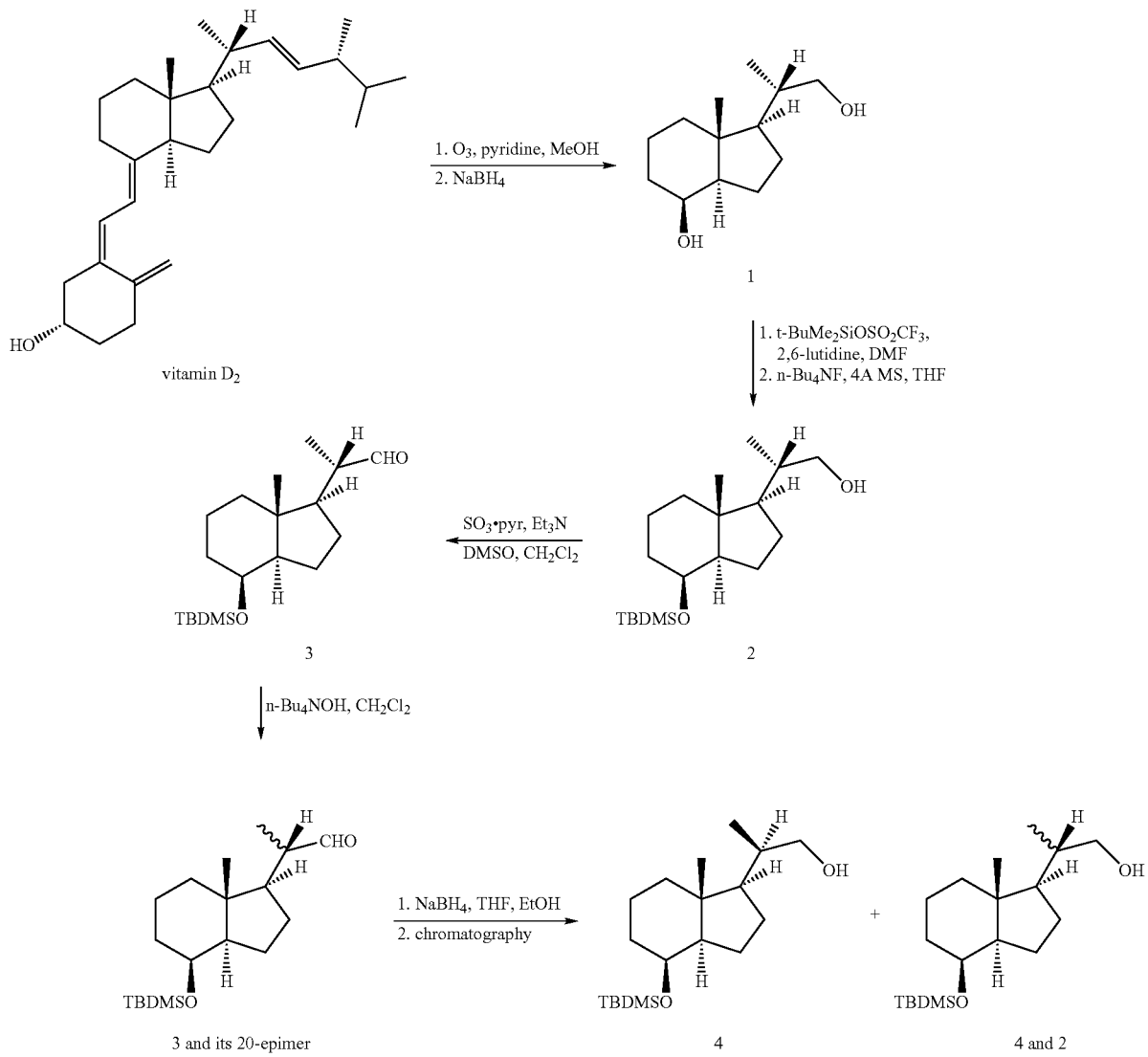
Scheme III
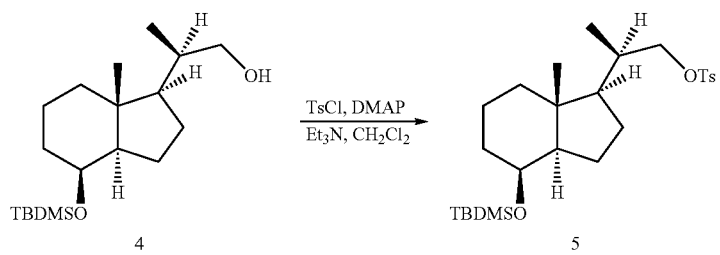
Scheme IV
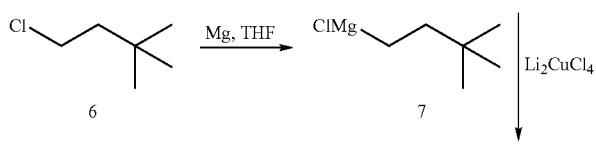

-continued
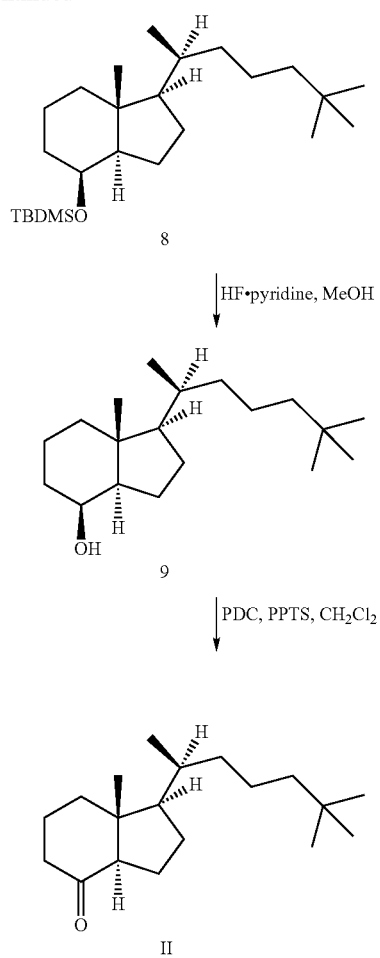
Scheme V
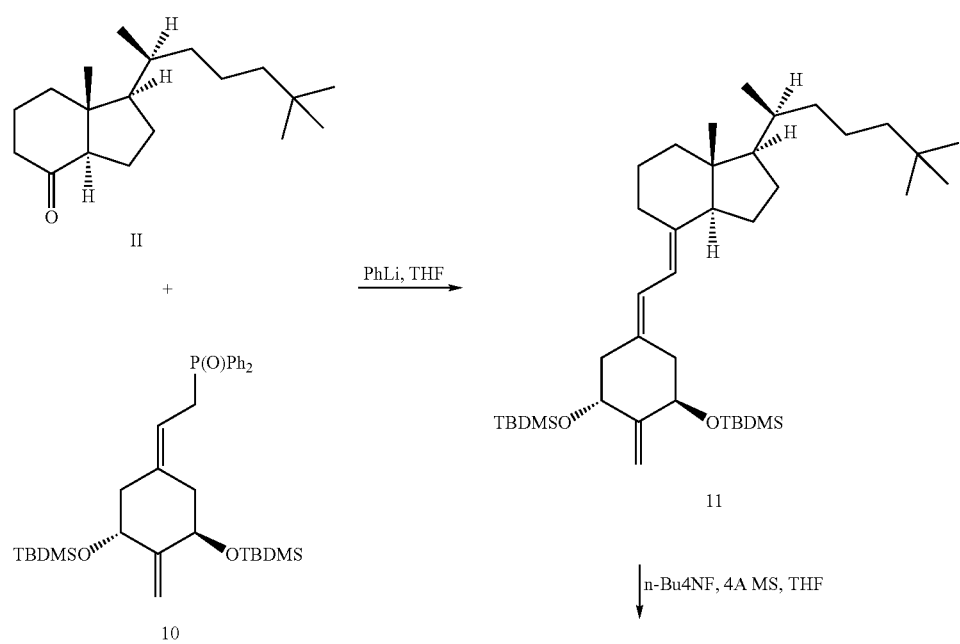

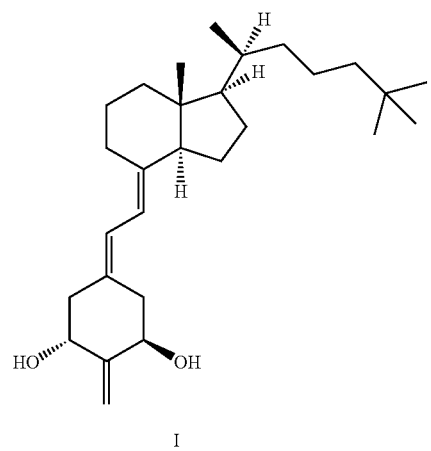
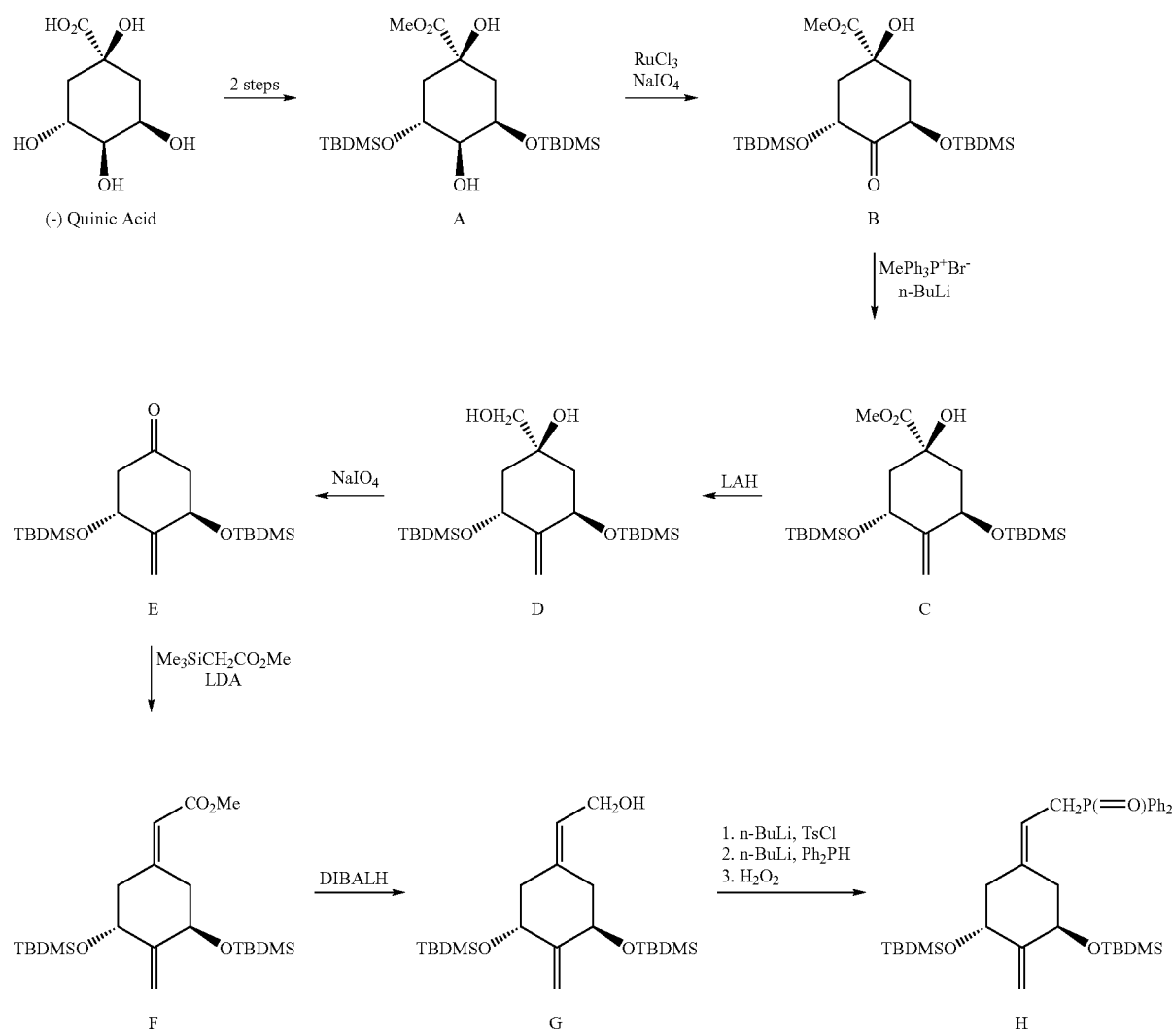

Synthesis of 2-Methylene-19-nor-1α-hydroxypregnacalciferol (2-Mpregna)

The synthesis of the title compound is described in U.S. Pat. No. 6,566,352 which is hereby incorporated by reference in its entirety and for all purposes as if fully set forth herein. The preparation of 2-methylene-19-nor-1α-hydroxypregnacalciferol (2-Mpregna) was accomplished using the same general method described above for the synthesis of 2-MbisP using the bicyclic Windaus-Grundmann type ketone XI in place of bicyclic Windaus-Grundmann V.

XI

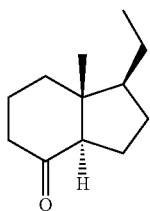

Synthesis of 2-Methylene-19,21-dinor-1α-hydroxy-bishomopregnacalciferol (19,21-dinor)

2-Methylene-19,21-dinor-1α-hydroxy-bishomopregnacalciferol (19,21-dinor) was prepared using the methods shown in Schemes VI and VII. The starting material, compound 1, was prepared using the procedure set forth by Andrzej R. Daniewski and Wen Liu (*J. Org. Chem.* 66, 626-628 (2001) using $Ph_3P^+Pr\ Br^-$ in place of $Ph_3P^+Et\ Br^-$ in the step for converting compound 7 to compound 8 in Scheme I of the article which is hereby incorporated by reference in its entirety and for all purposes as if fully set forth herein. Starting material 1 was then hydrogenated using palladium on carbon as a catalyst to yield the saturated compound 2 having a molecular weight of 196. The reaction was followed using thin layer chromatography (TLC) using a 20% ethyl acetate in a hexane solvent system. Compound 2 was then oxidized with pyridinium chlorochromate as described in U.S. patent Publication No. 2004/0220418, published on Nov. 4, 2004 (U.S. patent application Ser. No.10/847,040), hereby incorporated by reference in its entirety and for all purposes as if fully set forth herein, to yield 3 as followed by TLC using the same solvent system. The Ring-A phosphine oxide compound 4 was synthesized as shown in Scheme VI. The condensation was carried out again as described in the above-referenced patent documents with n-butyl lithium and was followed by TLC using a solvent of 5% ethyl acetate in hexane to yield compound 5. The t-butyldimethylsilyl protecting groups were removed using tetrabutylammonium fluoride as described in U.S. patent Publication No. 2004/0220418 to yield compound 6 (2-methylene-19,21-dinor-1α-hydroxy-bishomopregnacalciferol). TLC was used to follow completion of the reaction using the solvent system described above. The final product was fully characterized as described below.

Scheme VII

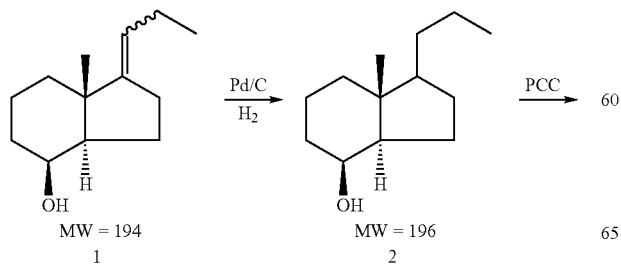

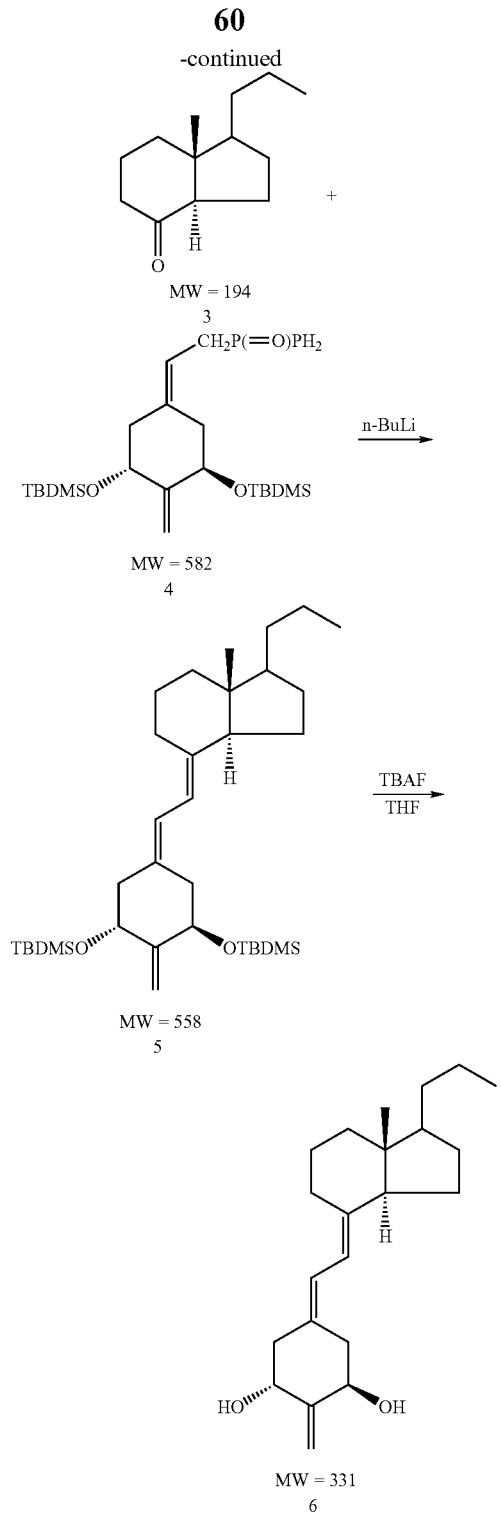

2-Methylene-19,21-dinor-1α-hydroxy-bishomopregnacalciferol (19,21-dinor)

UV (in EtOH) $\lambda_{max}$ 244, 252, 262 nm; $^1$H NMR (CDCl$_3$), 0.451 (3H, s, 18-H$_3$), 0.898 (3H, t, J=6.8 Hz, 23-H$_3$), 1.8-2.05 (2H, m), 2.29 (1H, dd, J=13.2, 8.7 Hz, 10α-H), 2.33 (1H, dd, J=13.5, 5.7 Hz, 4β-H), 2.58 (1H, dd, J=13.5, 3.8 Hz, 4α-H), ca. 2.84 (1H, overlapped with 10β-H, 9β-H), 2.86 (1H, dd, J=13.2, 4.5 Hz, 10β-H), 4.49 (2H, m, 1β- and 3α-H), 5.10 and 5.11 (1H and 1H, each s, =CH$_2$), 5.89 and 6.37 (1H and 1H, each d, J=11.4 Hz, 7- and 6-H); MS (APCl) m/z (relative intensity) 331 ([M+H]+, 7), 313 ([M+H]+-H$_2$O, 100), 295 ([M+H]+-2.H$_2$O, 92).

Synthesis of 2-Methylene-19-nor-(20R)-1α-hydroxy-bishomopregnacalciferol ((20R)2MbisP)

2-Methylene-19-nor-(20R)-1α-hydroxy-bishomopregnacalciferol ((20R)2MbisP) was prepared using the methods shown in Schemes VI, VIIIA, and VIIIB. Compound 1 is obtained by ozonolysis of ergocalciferol or vitamin D$_2$ as described by Sicinski et al. (*J. Med. Chem.* 41, 4662-4672, 1998). Compound 1 is reduced with sodium borohydride to produce the dialcohol compound 2. These reactions can be followed by thin layer chromatography (TLC) using a solvent system of 10% ethyl acetate in hexane. Treatment of 2 with acetic anhydride in pyridine provides the acetate compound 3. Compound 3 is then treated with triethylsilyl trifluoromethane sulfonate followed by base hydrolysis to yield compound 4. Again, these reactions are followed by the same TLC system as above. Compound 4 is then iodinated using iodine dissolved in potassium iodide and catalyzed with imidazole and tetraphenyl-21H/23H porphine to yield compound 5. Reaction of compound 5 with methyl magnesium bromide provides compound 6, and these reactions are followed using TLC with a solvent of 20% ethyl acetate in hexane. Compound 6 is hydrolyzed with a mild acid, pyridinium paratoluene sulfonate (PPTS), to give the free alcohol 7. Alcohol 7 is then oxidized to compound 8 using pyridinium chlorochromate as described in U.S. patent Publication No. 2004/0220418, published on Nov. 4, 2004 (U.S. patent application Ser. No. 10/847,040), hereby incorporated by reference in its entirety and for all purposes as if fully set forth herein. TLC using 20% ethyl acetate in hexane is used to follow these reactions. The Ring-A phosphine oxide compound 9 was synthesized as shown in Scheme VI as previously described. Compound 8 was then coupled with the A-ring phosphonium salt using n-butyl lithium as set forth in the above-referenced patent documents to produce compound 10, the t-butyldimethylsilyl (TBDMS) protected vitamin derivative. Removal of the protecting groups from compound 10 with tetrabutylammonium fluoride (TBAF) in tetrahydrofuran (THF) provided the desired product compound 11 and is detected using TLC using 5% methanol in dichloromethane. This product was fully characterized as described below.

Scheme VIIIA

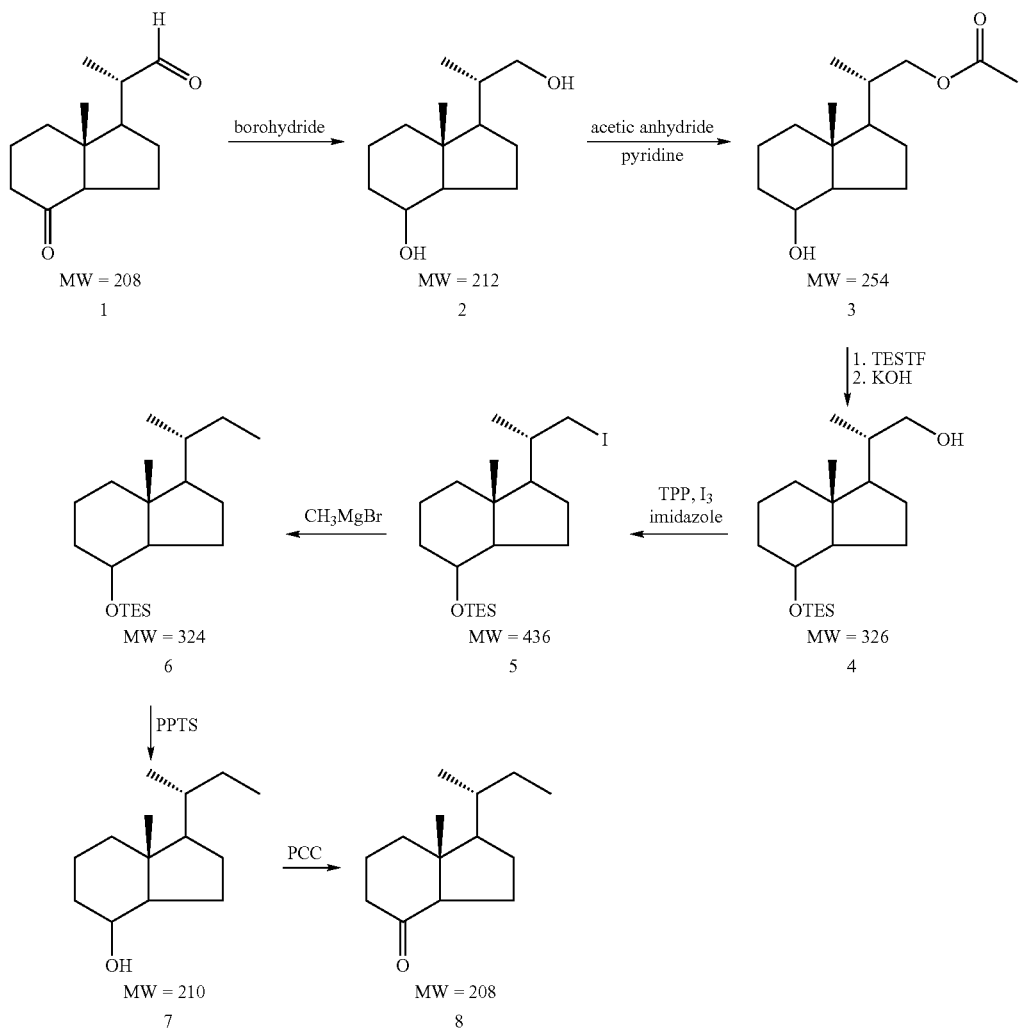

Scheme VIIIB

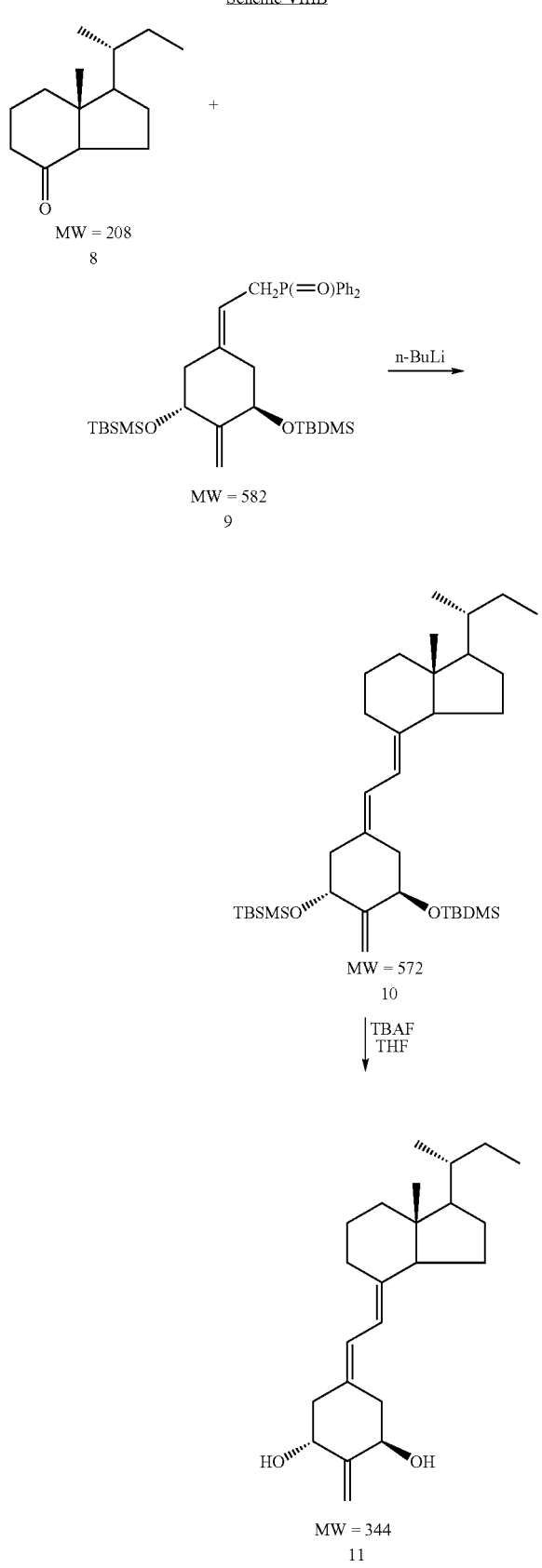

2-Methylene-19-nor-(20R)-1α-hydroxy-bishomopregnacalciferol ((20R)2MbisP)

$^1$H NMR (CDCl$_3$), 0.551 (3H, s, 18-H$_3$), 0.837 (3H, t, J=7.4 Hz, 23-H$_3$), 0.918 (3H, d, J=5.7 Hz, 21-H$_3$), 1.90 (1H, m), 2.01 (2H, m), 2.29 (1H, dd, J=13.0, 8.7 Hz, 10α-H), 2.33 (1H, dd, J=13.3, 6.3 Hz, 4β-H), 2.58 (1H, dd, J=13.3, 3.8 Hz, 4α-H), 2.81 (1H, dd, J=12.3, 3.8 Hz, 9β-H), 2.86 (1H, dd, J=13.0, 4.5 Hz, 10β-H), 4.49 (2H, m, 1β- and 3α-H), 5.09 and 5.11 (1H and 1H, each s, =CH$_2$), 5.89 and 6.37 (1H and 1H, each d, J=11.2 Hz, 7- and 6-H); MS (APCl) m/z (relative intensity) no M+, 327 ([M+H]+-H$_2$O, 76), 309 ([M+H]+-2.H$_2$O, 100).

Synthesis of 2-Methylene-19-nor-(20S)-1α-hydroxy-trishomopregnacalciferol (2MtrisP)

2-Methylene-19-nor-(20S)-1α-hydroxy-trishomopregnacalciferol (2MtrisP) was prepared using the methods shown in Schemes VI, IXA, and IXB. Compound 1 was obtained by ozonolysis of ergocalciferol or vitamin D$_2$ as described by Sicinski et al. (J. Med. Chem. 41, 4662-4672, 1998). Compound 1 is reduced with sodium borohydride to produce the dihydroxy compound 2. These reactions can be followed by thin layer chromatography (TLC) using a solvent system of 10% ethyl acetate in hexane. Treatment of 2 with acetic anhydride in pyridine provides the acetate compound 3. Compound 3 is then treated with triethylsilyl trifluoromethane sulfonate followed by base hydrolysis (heating with KOH in methanol) to yield compound 4. Again, these reactions are followed by the same TLC system as above. Compound 4 is oxidized with sulfur trioxide in pyridine, dimethylsulfoxide and triethylamine to provide 5. The reaction is followed by TLC using 10% in acetic acid. Treatment of 5 with sodium bicarbonate to epimerize the compound followed by reduction with sodium borohydride in methanol provides alcohol 6 and is detected by TLC with 20% ethyl acetate in hexane. Compound 6 is then tosylated with p-toluene sulfonyl chloride in triethylamine to produce compound 7 which is in turn treated with sodium cyanide in DMSO to produce the cyano derivative compound 8. Again, TLC with 20% ethyl acetate is used to follow the reaction. Treatment of 8 with acid in H$_2$O followed by reaction with diisobutylaluminium hydride provides compound 9. The reactions were followed by 10% ethyl acetate in hexane using TLC. Compound 9 is then reacted with n-butyl lithium and methyltriphenylphosphonium bromide to produce compound 10. Reduction of 10 using hydrogen and palladium on carbon as the catalyst produced compound 11. These products were detected by TLC using 5% ethyl acetate in hexane. The triethylsilyl (TES) protecting group was removed using tetrabutylammonium fluoride (TBAF) to provide compound 12 which was detected with 20% ethyl acetate in hexane using TLC. Oxidation of 12 with pyridinium chlorochromate produced ketone 13. The Ring-A phosphine oxide compound 14 was synthesized as shown in Scheme VI as previously described. Compound 13 was then coupled with the A-ring phosphonium salt using n-butyl lithium as set forth in the above-referenced patent documents to produce compound 15, the t-butyidimethylsilyl (TBDMS) protected vitamin derivative. The TBDMS protecting groups were then removed using TBAF in tetrahydrofuran to provide the final compound 16 again detected by TLC using 5% ethyl acetate in hexane. This product was fully characterized as described below.

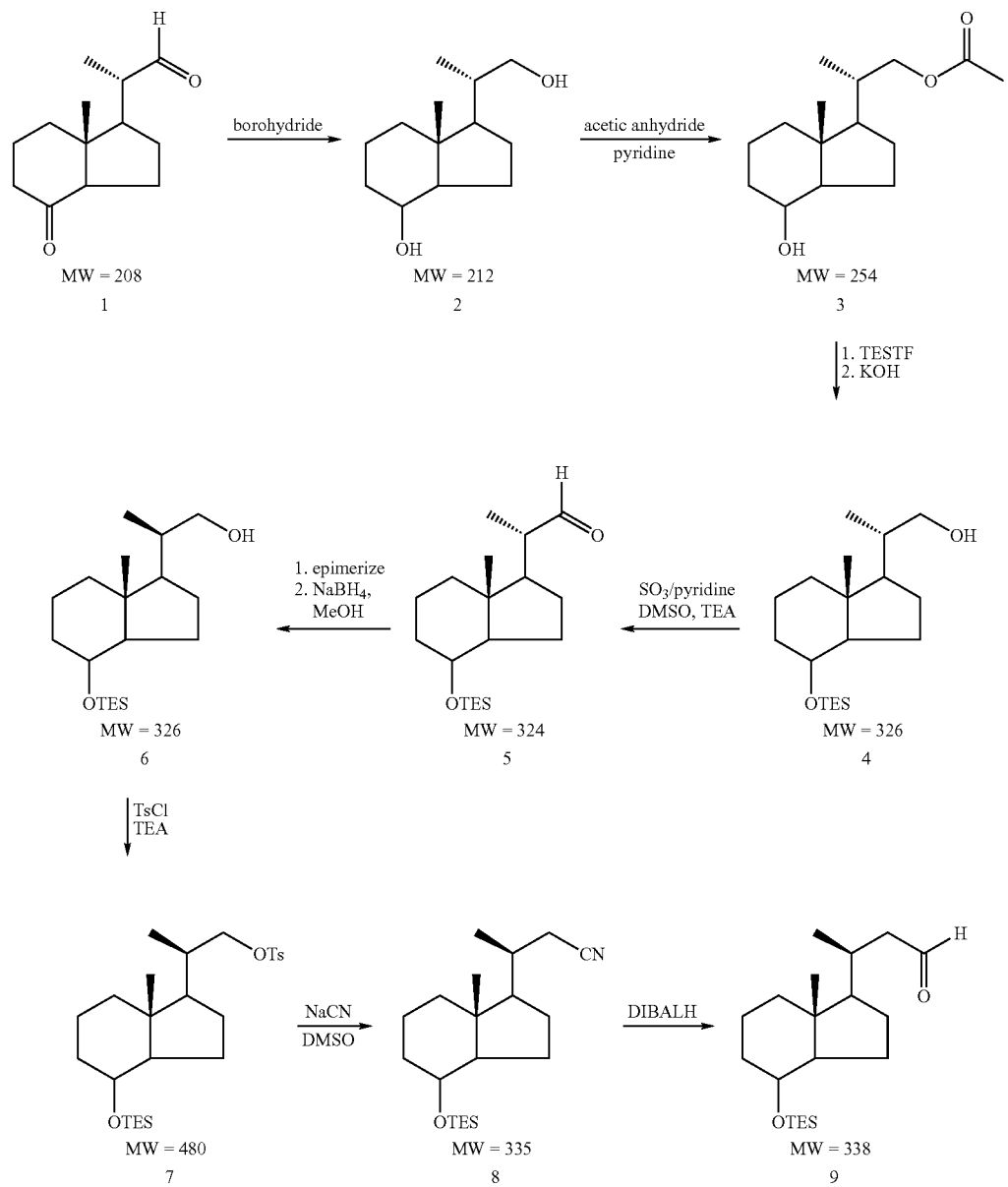
Scheme IXA
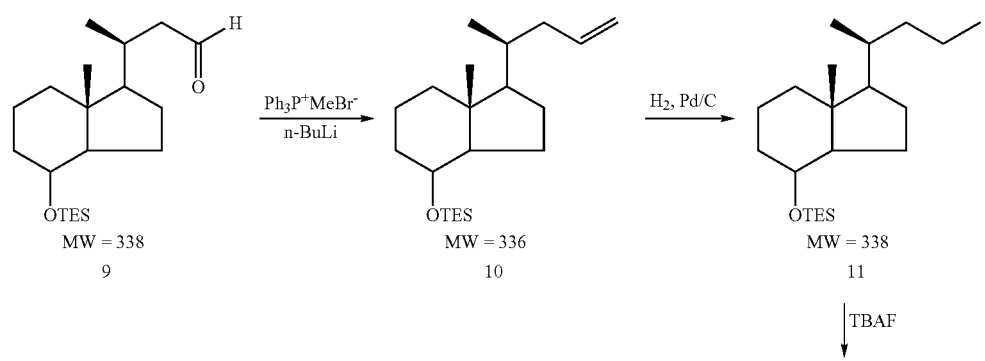
Scheme IXB

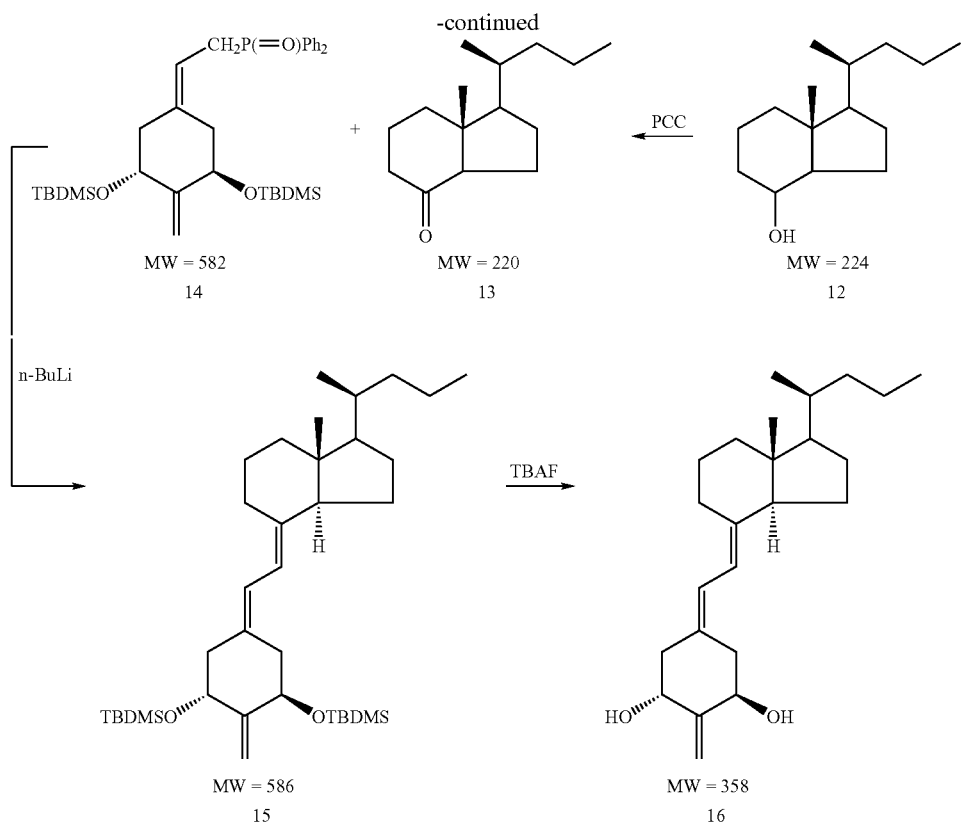

2-Methylene-19-nor-(20s)-1α-hydroxy-trishomopregnacalciferol (2MtrisP)

UV (in EtOH) λ$_{max}$ 244, 253, 262 nm; $^1$H NMR (CDCl$_3$), 0.550 (3H, s, 18-H$_3$), 0.835 (3H, d, J=6.9 Hz, 21-H$_3$), 0.869 (3H, t, J=7.5 Hz, 24-H$_3$), 1.87 (1H, m), 2.01 (2H, m), 2.29 (1H, dd, J=13.2, 8.7 Hz, 10α-H), 2.33 (1H, dd, J=13.2, 6.3 Hz, 4β-H), 2.58 (1H, dd, J=13.2, 4.2 Hz, 4α-H), 2.82 (1H, dd, J=12.0, 3.9 Hz, 9β-H), 2.86 (1H, dd, J=13.2, 4.8 Hz, 10β-H), 4.49 (2H, m, 1β- and 3α-H), 5.09 and 5.11 (1H and 1H, each s, =CH$_2$), 5.89 and 6.36 (1H and 1H, each d, J=11.1 Hz, 7- and 6-H); MS (APCI) m/z (relative intensity) 359 ([M+H]+, 13), 341 ([M+H]+-H$_2$O, 100), 323 ([M+H]+-2.H$_2$O, 97)).

Synthesis of 2α-Methyl-19-nor-(20S)-1α-hydroxy-bishomopregnacalciferol ((20S)2αMbisP)

2α-Methyl-19-nor-(20S)-1α-hydroxy-bishomopregnacalciferol ((20S)2αMbisP) was prepared by hydrogenating 2MbisP as shown in Scheme X. Tris(triphenylphosphine)rhodium (I) chloride (29.0 mg, 31.3 μmol) was added to dry benzene (30 mL) presaturated with hydrogen for 20 minutes. The mixture was stirred at room temperature until a homogeneous solution was formed (about 50 minutes). A solution of 2MbisP 1 (10 mg, 29.0 μmol) in dry benzene (4 mL) was then added, and the reaction was allowed to proceed under a continuous stream of hydrogen for 3.5 hours. Benzene was removed under vacuum, and the residue was redissolved in hexane/ethyl acetate (7:3) and applied on Waters silica Sep-Pak (Vac 20 mL). Less polar impurities were eluted with the same solvent system (30 mL), and a mixture of 2-methyl vitamins was eluted with hexane/ethyl acetate (65:35, 10 mL) and hexane/ethyl acetate (6:4, 20 mL). The combined fractions were evaporated to give crude products (about 11 mg) which were further purified by HPLC (10 mm×25 cm Zorbax-Sil column, 4 mL/min) using hexane/2-propanol (90:10) solvent system. The mixture (ca. 1:1) of both 2α-and 2β-methyl-19-norvitamins 2 and 3 (6.85 mg, 69%) gave a single peak at R$_V$ 28 mL (2MbisP 1 was eluted at R$_V$ 26 mL in the same system). Separation of both epimers was achieved by reverse-phase HPLC (6.2 mm×25 cm Zorbax-ODS column, 2 mL/min) using methanol/water (90:10) solvent system. 2β-Methyl vitamin 3 (2.99 mg, 30%) was collected at R$_V$ 24 mL and its 2α-epimer 2 (3.46 mg, 34%) at R$_V$ 28 mL (2MbisP 1 was eluted at R$_V$ 27 mL in the same system).

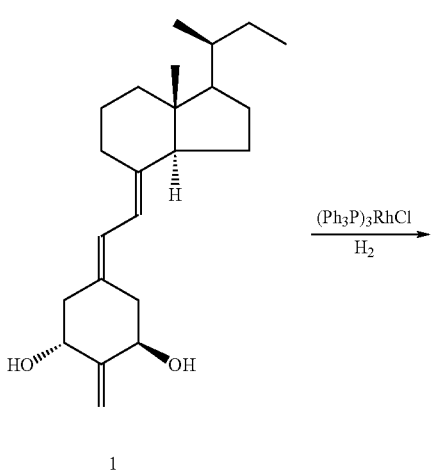

Scheme X

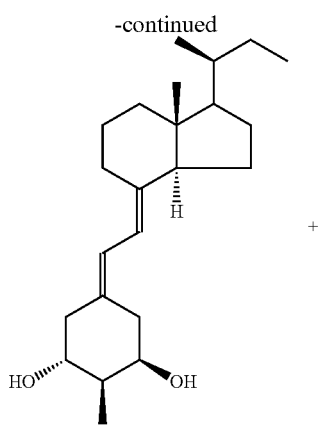

2

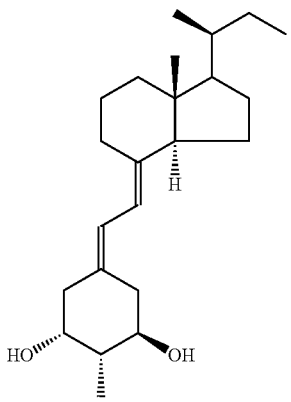

3

2α-Methyl-19-nor-(20S)-1α-hydroxy-bishomopreg-nacalciferol ((20S)2αMbisP)

UV (in EtOH) $\lambda_{max}$ 242.0, 250.0, 260.0 nm; $^1$H NMR (CDCl$_3$) δ 0.531 (3H, s, 18-H$_3$), 0.827 (3H, d, J~5.5 Hz, 21-H$_3$), 0.834 (3H, t, J=7.2 Hz, 23-H$_3$), 1.134 (3H, d, J=6.9 Hz, 2α-CH$_3$), 2.13 (1H, ~t, J~11 Hz, 4β-H), 2.22 (1H, br d, J~13 Hz, 10β-H), 2.60 (1H, dd, J=12.7, 4.2 Hz, 4α-H), 2.80 (2H, m, 9β- and 10α-H), 3.61 (1H, m, w/2=25 Hz, 3α-H), 3.96 (1 H, m, w/2=12 Hz, 1β-H), 5.82 and 6.37 (1H and 1H, each d, J=11.2 Hz, 7- and 6-H); MS m/z (relative intensity) 346 (M$^+$, 100), 317 (16), 289 (39), 253 (18), 229 (35), 191 (56), 135 (59), 91 (64); exact mass calcd for C$_{23}$H$_{38}$O$_2$ 346.2872, found 346.2857.

Synthesis of 2α-Methyl-19-nor-(20S)-1α-hydroxy-homopregnacaiciferol (2α-methyl MP)

2α-Methyl-19-nor-(20S)-1α-hydroxy-homopregnacalciferol (2α-methyl MP) was prepared by hydrogenating 2-MP as shown in Scheme XI. Tris(triphenylphosphine)rhodium (I) chloride (32.0 mg, 34.6 μmol) was added to dry benzene (35 mL) presaturated with hydrogen for 20 minutes. The mixture was stirred at room temperature until a homogeneous solution was formed (about 70 minutes). A solution of 2-MP 1 (11 mg, 33.3 μmol) in dry benzene (6 mL) was then added and the reaction was allowed to proceed under a continuous stream of hydrogen for 3.5 hours. Benzene was removed under vacuum, and the residue was redissolved in hexane/ethyl acetate (7:3) and applied on Waters silica Sep-Pak (Vac 12 mL). The crude 2-methyl vitamins (about 11 mg) were eluted with the same solvent system (35 mL). The combined fractions were evaporated, and they were further purified by HPLC (10 mm×25 cm Zorbax-Sil column, 4 mL/min) using a hexane/2-propanol (90:10) solvent system. The mixture (ca. 1:1) of both 2α-and 2β-methyl-19-nor vitamins 2 and 3 (53:47 ratio; 6.37 mg, 58%) gave a single peak at R$_V$ 29 mL. Separation of both epimers was achieved by reverse-phase HPLC (6.2 mm×25 cm Zorbax-ODS column, 2 mL/min) using a methanol/water (90:10) solvent system. 2β-Methyl vitamin 3 was collected at R$_V$ 17 mL and its 2α-epimer 2 at R$_V$ 19 mL.

Scheme XI

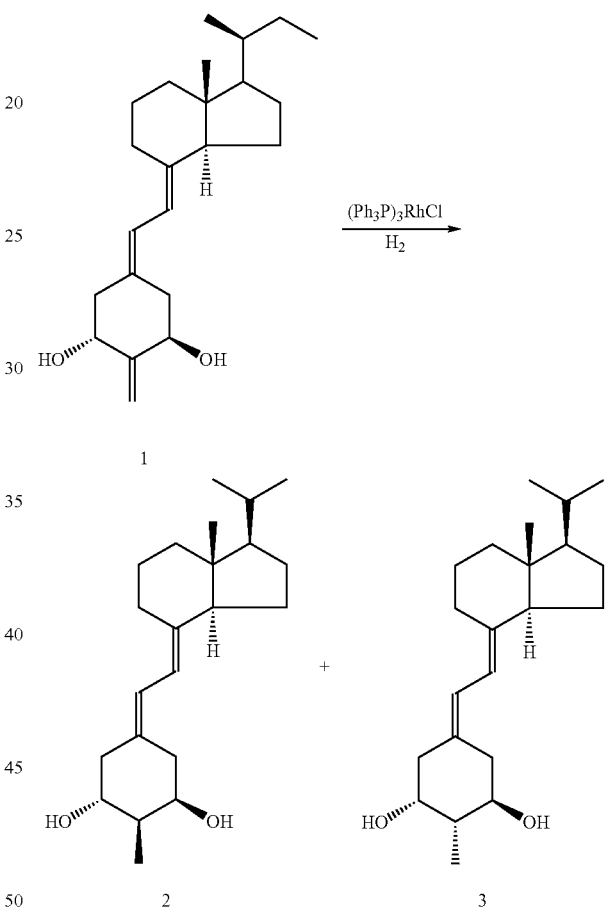

2α-Methyl-19-nor-(20S)-1α-hydroxy-homopregna-calciferol (2α-methyl MP)

UV (in EtOH) $\lambda_{max}$ 242.0, 250.0, 260.0 nm; $^1$H NMR (CDCl$_3$) δ 0.531 (3H, s, 18-H$_3$), 0.860 and 0.940 (3H and 3H, each d, J=6.5 Hz, 21- and 22-H$_3$), 1.134 (3H, d, J=6.8 Hz, 2 α-CH$_3$), 2.13 (1H, ~t, J~11 Hz, 4β-H), 2.22 (1H, br d, J~13 Hz, 10β-H), 2.60 (1H, dd, J=12.9, 4.1 Hz, 4α-H), 2.80 (2H, m, 9β- and 10α-H), 3.61 (1H, m, w/2=23 Hz, 3α-H), 3.96 (1H, m, w/2=14 Hz, 1β-H), 5.82 and 6.37 (1H and 1H, each d, J=11.2 Hz, 7- and 6-H); MS m/z (relative intensity) 332 (M$^+$, 100), 289 (37), 253 (21), 177 (67), 135 (76), 91 (78); exact mass calcd for C$_{22}$H$_{36}$O$_2$ 332.2715, found 332.2712.

Synthesis of 2-Methylene-19,26,27-trinor-(20S)-1α-hydroxyvitamin D$_3$ (OM)

2-Methylene-19,26,27-trinor-(20S)-1α-hydroxyvitamin D$_3$ (OM) was prepared as shown in Schemes IV, XIIA, and XIIB and described below.

A. (20S)-de-A,B-8β-(tert-butyldimethylsilyl)oxy-20-(hydroxymethyl)-pregnane (2)

Ozone was passed through a solution of vitamin D$_2$ (3 g, 7.6 mmol) in methanol (250 mL) and pyridine (2.44 g, 2.5 mL, 31 mmol) for 50 minutes at −78° C. The reaction mixture was then flushed with oxygen for 15 min to remove the residual ozone, and the solution was treated with NaBH$_4$ (0.75 g, 20 mmol). After 20 minutes, the second portion of NaBH$_4$ (0.75 g, 20 mmol) was added, and the mixture was allowed to warm to room temperature. The third portion of NaBH$_4$ (0.75 g, 20 mmol) was then added and the reaction mixture was stirred for 18 hours. The reaction was quenched with water (40 mL), and the solution was concentrated under reduced pressure. The residue was extracted with ethyl acetate (3×80 mL), and the combined organic phases were washed with 1M aq. HCl, saturated aq. NaHCO$_3$, dried (Na$_2$SO$_4$) and concentrated under reduced pressure. The residue was chromatographed on silica gel with hexane/ethyl acetate (75:25) to give (20S)-de-A,B-20-(hydroxymethyl)pregnan-8β-ol 1 (1.21 g, 75% yield) as white crystals.

tert-Butyldimethylsilyl trifluoromethanesulfonate (3.24 mL, 3.72 g, 14.1 mmol) was added to a solution of the 8β,20-diol 1 (1 g, 4.7 mmol) and 2,6-lutidine (1.64 mL, 1.51 g, 14.1 mmol) in anhydrous DMF (15 mL) at 0° C. The mixture was stirred under argon at 0° C. for 1 hour and then at room temperature for 18 hours. The reaction was quenched with water (50 mL) and extracted with ethyl acetate (3×30 mL). The combined organic phases were washed with brine, dried (Na$_2$SO$_4$) and concentrated under reduced pressure. The residue was dissolved in anhydrous THF (8 mL), triethylamine (3 mL, 2.17 g, 21.5 mmol) and a solution of tetrabutylammonium fluoride (1 M in THF, 6.5 mL, 6.5 mmol) were added, followed by freshly activated molecular sieves 4A (3 g). The reaction mixture was stirred under argon at room temperature for 4 hours, filtered through a short layer of Celite, and evaporated. The residue was dissolved in ethyl acetate (30 mL), washed with brine, water, dried (Na$_2$SO$_4$) and concentrated under reduced pressure. The pure alcohol 2 (1.42 g, 93% yield) was isolated by chromatography on silica gel with hexane/ethyl acetate (97.5:2.5 to 95:5), as a colorless oil: $^1$H NMR (500 MHz, CDCl$_3$) δ 4.00 (1H, d, J=2.4 Hz, 8α-H), 3.63 (1H, dd, J=10.5, 3.2 Hz, 22-H), 3.39 (1H, dd, J=10.5, 6.8 Hz, 22-H), 1.94 (1H, br.d, J=12.5 Hz), 1.02 (3H, d, J=6.6 Hz, 21-H3), 0.924 (3H, s, 18-H$_3$), 0.882 (9H, s, Si-t-Bu), 0.005 and −0.010 (each 3H, each s, each Si-Me); $^{13}$C NMR (125 MHz) δ 69.29 (d, C-8), 67.94 (t, C-22), 53.06 (d), 52.80 (d), 42.12 (s, C-13), 40.54 (t), 38.27 (d), 34.39 (t), 26.79 (t), 25.79 (q, SiMe$_3$), 23.08 (t), 18.00 (s, SiCMe3), 17.61 (t), 16.65 (q, C-21), $\overline{13.75}$ (q, C-18), −4.81 and $\overline{-5.18}$ (each q, each SiMe.

B. 20S -de-A,B-8β-tert-butyldimethylsilyl)oxy-20-formylpregnane (3)

Sulfur trioxide pyridine complex (1.32 g, 8.28 mmol) was added to a solution of the alcohol 2 (451 mg, 1.38 mmol), triethylamine (960 µL, 697 mg, 6.9 mmol) in anhydrous methylene chloride (20 mL) and anhydrous DMSO (5 mL) at 0° C. The reaction mixture was stirred under argon at 0° C. for 20 minutes and then concentrated. The residue was purified by column chromatography on silica gel with hexane/ethyl acetate (95:5) to give the aldehyde 3 (364 mg, 81% yield) as an oil: $^1$H NMR (500 MHz, CDCl$_3$) δ 9.55 (1H, d, J=3.1 Hz, CHO), 4.00 (1H, s, 8α-H), 2.33 (1H, m, 20-H), 1.89 (1H, dm, J=12.4 Hz), 1.07 (3H, d, J=6.8 Hz, 21-H$_3$), 0.939 (3H, s, 18-H$_3$),0.862 (9H, s, Si-t-Bu), −0.009 and −0.026 (each 3H, each s, each SiMe); $^{13}$C NMR (125 MHz) δ 205.37 (d, CHO), 68.99 (d, C-8), 52.28 (d), 51.58 (d), 49.15 (d), 42.58 (s, C-13), 40.35 (t), 34.29 (t), 26.16 (t), 25.74 (q, SiMe$_3$, 23.27 (t), 17.96 (s, SiCMe$_3$), 17.52 (t), 14.04 (q, C-21), $\overline{13.28}$ (q, C-18), −4.85 and $\overline{-5.23}$ (each q, each SiMe.

C. (20R)-de-A,B-8β-(tert-butyldimethylsilyl)oxy-20-(hydroxymethyl)-pregnane (4)

The aldehyde 3 (364 mg, 1.12 mmol) was dissolved in methylene chloride (15 mL) and a 40% aq. n-Bu$_4$NOH solution (1.47 mL, 1.45 g, 2.24 mmol) was added. The resulting mixture was stirred under argon at room temperature for 16 hours, diluted with methylene chloride (20 mL), washed with water, dried (Na$_2$SO$_4$) and concentrated under reduced pressure. A residue was chromatographed on silica gel with hexane/ethyl acetate (95:5) to afford a mixture of aldehyde 3 and its 20-epimer (292 mg, 80% yield) in about a 1:2 ratio as determined by $^1$H NMR.

The mixture of aldehydes (292 mg, 0.9 mmol) was dissolved in THF (5 mL) and NaBH$_4$ (64 mg, 1.7 mmol) was added, followed by a dropwise addition of ethanol (5 mL). The reaction mixture was stirred at room temperature for 30 minutes and it was quenched with a saturated aq. NH$_4$Cl solution. The mixture was extracted with ether (3×20 mL) and the combined organic phase was washed with water, dried (Na$_2$SO$_4$) and concentrated under reduced pressure. The residue was chromatographed on silica gel with hexane/ethyl acetate (96:4 to 80:20) to give the desired, pure (20R)-alcohol 4 (160 mg, 55% yield) as an oil and a mixture of 4 and its 20-epimer 2 (126 mg, 43% yield) in about a 1:3 ratio (by 1H NMR). 4: [α]$_D$ +40.8° (c 1.09, CHCl$_3$); $^1$H NMR (500 MHz, CDCl$_3$) δ 4.00 (1H, d, J=1.9 Hz, 8α-H), 3.70 (1H, dd, J=10.6, 3.2 Hz, 22-H), 3.43 (1H, dd, J=10.6, 7.0 Hz, 22-H), 0.94 (3H, d, J=6.7 Hz, 21-H$_3$), 0.927 (3H, s, 18-H$_3$), 0.884 (9H, s, Si-t-Bu), 0.007 and −0.006 (each 3H, each s, SiMe$_2$);$^{13}$C NMR (125 MHz) δ 69.30 (d, C-8), 66.83 (t, C-22), 53.02 (d), 52.96 (d), 41.91 (s, C-13), 40.12 (t), 37.48 (d), 34.38 (t), 26.71 (t), 25.79 (q, SiCMe$_3$), 22.85 (t), 18.01 (s, SiCMe$_3$), 17.64 (t), 16.58 (q, C-21),$\overline{14.07}$ (q, C-18), −4.81 and −5.18 (each q, each SiMe).

D. (20R)-de-A,B-8β-(tert-butyldimethylsilyl)oxy-20-(iodomethyl)-pregnane (5)

A solution of iodine (471 mg, 1.84 mmol) in methylene chloride (30 mL) was slowly added to a solution of triphenylphosphine (482 mg, 1.84 mmol) and imidazole (250 mg, 3.68 mmol) in methylene chloride (15 mL) at 0° C. After 15 minutes, a solution of alcohol 4 (149 mg, 0.46 mmol) in methylene chloride (3 mL) was added to the mixture. After stirring for 20 minutes at 0° C., followed by 18 hours at room temperature, the reaction mixture was washed with water, dried (Na$_2$SO$_4$) and concentrated under reduced pressure. The residue was chromatographed on silica gel with hexane/ ethyl acetate (97:3) to give the desired iodide 5 (201 mg, 100%): [α]$_D$ −0.3° (c 0.97, CHCl$_3$); $^1$H NMR (500 MHz, CDCl$_3$) δ 3.99 (1H, s, 8α-H), 3.46 (1 H, dd, J=9.5, 2.9 Hz, 22-H), 3.18 (1H, dd, J=9.5, 6.4 Hz), 1.88-1.74 (3H, m), 1.67 (1H, dm, J=13.9 Hz), 0.95 (3H, d, J=6.4 Hz, 21-H$_3$), 0.918 (3H, s, 18-H$_3$), 0.882 (9H, s, Si-t-Bu), 0.008 and −0.008 (each, 3H, each s, SiMe$_2$); $^{13}$C NMR (125 MHz) δ 69.27 (d, C-8), 55.19 (d), 52.69 (d), 41.99 (s, C-13), 40.48 (t), 36.15 (d), 34.24 (t), 26.90 (t), 25.80 (q, SiCMe$_3$), 22.81 (t), 21.38 (q, C-21), 19.58 (t), 18.02 (s, SiCMe$_3$),$\overline{17.63}$ (t), 14.12 (q, C-18), −4.79 and −5.17 (each q, each SiMe); MS (EI) m/z 436 (15, M$^+$), 421(8, M$^+$-CH$_3$), 393 (9, M$^+$-C$_3$H$_7$), 379 (98, M$^+$-t-Bu), 303 (65, M⁺-t-BuMe₂SiOH—H), 177 (70), 135 (70), 95 (55), 75 (100); exact mass calculated for $C_{19}H_{37}OSi1$ (M⁺) 436.1658, found 436.1672.

E. (20S)-de-A,B-8β-(tert-butyldimethylsilyl)oxy-20-(3-isopropoxy-carbonyl)propyl-pregnane (6)

A mixture of zinc powder (124 mg, 1.9 mmol), anhydrous pyridine (4 mL) and isopropyl acrylate (235 μL, 217 mg, 1.9 mmol) was warmed to 50° C., then nickel(II) chloride hexahydrate (109 mg, 0.46 mmol) was added. The resulting mixture was warmed to 65° C. and stirred for 2 hours until its green color turned to reddish brown. After cooling to 0° C., a solution of iodide 5 (222 mg, 0.51 mmol) in anhydrous pyridine (3 mL) was added and the reaction mixture was stirred for 4 hours at room temperature. The mixture was diluted with ethyl acetate (20 mL) and the resulting precipitate was filtered off through a pad of Celite. The filtrate was washed with 5% aq. HCl and brine, dried (Na₂SO₄) and concentrated under reduced pressure. The residue was chromatographed on silica gel with hexane and hexane/ethyl acetate (95:5) to give the ester 6 (177 mg, 82%): [α]$_D$ +19.7° (c 1.13, CHCl₃); ¹H NMR (400 MHz, CDCl₃) δ 5.00 (1 H, sep, J=6.3 Hz, OCHMe₂), 3.99 (1H, d, J=2.2 Hz, 8α-H, 2.23 (1H, dd, J=7.4, 2.5 Hz, 24-H), 2.21 (1H, dd, J=6.8, 1.9 Hz, 24-H), 1.90 (1H, dm, J=12.2 Hz), 1.22 (6H, d, J=6.3 Hz, OCHMe₂), 0.895 (3H, s, 18-H₃), 0.881 (9H, s, Si-t-Bu), 0.82 (3H, d, J=6.6 Hz, 21-H₃), 0.001 and −0.012 (each, 3H, each s, SiMe2); ¹³C NMR (100 MHz) δ 173.48 (s, COO-iPr), 69.45 (d, C-8), 67.31 (d, COO CHMe2), 56.29 (d), 53.08 (d), 42.16 (s, C-13), 40.64 (t), 35.05 (t), 34.71 (t), 34.51 (d), 34.44 (t), 27.16 (t), 25.80 (q, SiCMe₃), 22.93 (t), 21.92 (t), 21.86 (q,-12-COOCHMe₂), 18.48 (q, C-21), 18.02 (t), 17.69 (s, SiCMe₃), 14.01 (q, C-18), −4.79 and −5.16 (each q, each SiMe); MS (EI) m/z 424 (5, M⁺), 409 (15, M⁺-CH₃), 381 (35, M⁺-C₃H₇), 367 (89, M⁺-t-Bu), 321 (39, M⁺-CH₃COOCHMe₂-H), 307 (85, M⁺-CH₃CH₂COOCHMe₂-H), 283 (65), 265 (41), 249 (45), 233 (60), 215 (73), 189 (70), 163 (78), 135 (86), 109 (70), 95 (79), 75 (100); exact mass calculated for $C_{25}H_{48}O_3Si$ (M⁺) 424.3373, found 424.3371.

F. (20S)-de-A,B-8β-(tert-butyldimethylsilyl)oxy-20-(3-hydroxy)propyl-pregnane (7)

Lithium aluminum hydride (20 mg, 0.53 mmol) was added to a solution of ester 6 (188 mg, 0.28 mmol) in anhydrous THF (5 mL) at 0° C. The reaction mixture was stirred for 30 minutes at 0° C., then the cooling bath was removed and the stirring was continued for an additional 19 hours at room temperature. The excess hydride was quenched by careful, successive addition of sat. aq. NH₄Cl. Methylene chloride (15 mL) and Celite (0.5 g) were added and the slurry was stirred for 20 minutes. The aluminum salts were separated by vacuum filtering the slurry through a Celite pad. The salts were repeatedly washed with methylene chloride. The filtrate was dried (Na₂SO₄) and concentrated under reduced pressure. The residue was chromatographed on silica gel with hexane/ethyl acetate (90:10) to afford the alcohol 7 (96 mg, 93% yield) as a colorless oil: [α]$_D$+25.5° (c 1.0, CHCl₃); ¹H NMR (400 MHz, CDCl₃) δ 3.99 (1H, d, J=2.1 Hz, 8α-H), 3.64 (2H, t, J=6.6 Hz, CH₂OH), 1.92 (1H, dm, J=12.3 Hz), 0.907 (3H, s, 18-H₃), 0.886 (9H, s, Si-t-Bu), 0.81 (3H, d, J=6.6 Hz, 21-H₃), 0.007 and −0.006 (each, 3H, each s, SiMe₂);¹³C NMR (100 MHz) δ 69.43 (d, C-8),63.18 (t, C-25), 56.31 (d), 53.10 (d), 42.17 (s, C-13), 40.65 (t), 35.05 (t), 34.70 (d), 34.45 (t), 33.20 (t), 27.17 (t), 25.79 (q, SiCMe₃), 22.94 (t), 22.35 (t), 18.53 (q, C-21), 18.02 (s, SiCMe₃), 17.71 (t), 14.03 (q, C-18), −4.81 and −5.17 (each q, each SiMe; MS (EI) m/z no M⁺, 325 (3, M⁺-C₃H₇), 311 (9, M⁺-C₄H₉), 269 (6, M⁺-C₆H₁₁O) 251 (1,6, M⁺-H-t-BuSiMe₂H), 235 (25, M⁺-H-t-BuSiMe2OH), 219 (29), 163 (46), 135 (78), 109 (62), 75 (100); exact mass calculated for $C_{18}H_{35}O_2Si$ (M⁺-C₄H₉) 311.2406, found 311.2397.

G. (20S)-de-A,B-8β-(tert-butyldimethylsilyl)oxy-20-butyl-pregnane (8)

To a stirred solution of the alcohol 7 (95 mg, 0.26 mmol), 4-dimethylaminopyridine (5 mg, 0.04 mmol) and triethylamine (145 μL, 105 mg, 1.04 mmol) in anhydrous methylene chloride (5 mL), was added p-toluenesulfonyl chloride (68 mg, 0.36 mmol) at 0° C. The cooling bath was removed and stirring was continued for 22 hours. Methylene chloride (20 mL) was added, and the mixture was washed with a saturated aq. NaHCO₃ solution, dried (Na₂SO₄) and concentrated under reduced pressure. The residue was dissolved in anhydrous THF (5 mL) and lithium aluminum hydride (32 mg, 0.84 mmol) was added to the solution at 0° C. The cooling bath was removed, and the mixture was stored for 18 hours at room temperature. The excess hydride was quenched by careful, successive addition of sat. aq. NH₄Cl. Methylene chloride (15 mL) and Celite (0.5 g) were added and the slurry was stirred for 20 minutes. The aluminum salts were separated by vacuum-filtering the slurry through a Celite pad. The salts were repeatedly washed with methylene chloride. The filtrate was dried (Na₂SO₄) and concentrated under reduced pressure. The residue was chromatographed on silica gel with hexane/ethyl acetate (97:3) to give the product 8 (85 mg, 93% yield): [α]$_D$+25.3° (c 1.26, CHCl₃); ¹H NMR (400 MHz, CDCl₃) δ 4.00 (1H, d, J=2.1 Hz, 8α-H), 1.95 (1H, dm, J=12.4 Hz), 0.914 (3H, s, 18-H₃), 0.893 (9H, s, Si-t-Bu), 0.81 (3H, d, J=6.6 Hz, 21-H₃), 0.013 and 0.000 (each 3H, each s, each SiMe);¹³C NMR (100 MHz) δ 69.52 (d, C-8), 56.47 (d), 53.15 (d), 42.19 (s, C-13), 40.68 (t), 35.02 (t), 34.79 (d), 34.52 (t), 28.56 (t), 27.21 (t), 25.81 (q, SiCMe₃, 23.09 (t), 22.99 (t), 18.62 (q, C-21), 18.05 (s, SiCMe₃), 17.75 (t), 14.26 (q, C-25), 14.02 (q, C-18), −4.79 and −5.16 (each q, each SiMe; MS (EI) m/z 352 (2, M⁺), 337 (4, M⁺-CH₃), 295 (81, M⁺-t-Bu), 253 (13, M⁺-C₆H₁₁O), 219 (71, M⁺-H-t-BuSiMe2OH), 177 (10), 135 (22), 75 (100); exact mass calculated for $C_{18}H_{35}OSi$ (M⁺-C₄H₉) 295.2457, found 295.2454.

H. (20S)-de-A,B-20-butyl-pregnan-8β-ol (9)

The protected alcohol 8 (84 mg, 0.24 mmol) was dissolved in anhydrous THF (5 mL) and anhydrous methanol (5 mL). Hydrogen fluoride-pyridine complex (4 mL) was added followed at room temperature and the mixture was stored for 19 h. Ethyl acetate (20 mL) was added and the organic phase was washed with brine and water, dried (Na₂SO₄) and concentrated under reduced pressure. The residue was diluted with hexane and chromatographed on silica gel with hexane to give the product 9 (17 mg, 30% yield) as a colorless oil: ¹H NMR (500 MHz, CDCl₃) δ 4.07 (1H, d, J=2.5 Hz, 8α-H), 1.98 (1H, dm, J=13.1 Hz), 1.88-1.76 (3H, m), 0.927 (3H, s, 18-H₃), 0.89 (3H; t; J=7.1 Hz, 25-H₃); 0.81 (3H, d: J=6.6 Hz, 21-H₃);¹³C NMR (125 MHz) δ 69.46 (d, C-8), 56.32 (d), 52.67 (d), 41.90 (s, C-13), 40.32 (t), 34.97 (t), 34.76 (d), 33.59 (t), 28.52 (t), 27.05 (t), 23.08 (t), 22.42 (t), 18.56 (q, C-21), 17.49 (t), 14.23 (q, C-25), 13.77 (q, C-18).

I. (20S)-de-A,B-20-butyl-pregnan-8-one (II)

Pyridinium dichromate (118 mg, 314 μmol) was added to a solution of the alcohol 9 (15 mg, 63 μmol) and pyridinium p-toluenesulfonate (2 mg, 8 μmol) in anhydrous methylene chloride (5 mL). The resulting suspension was stirred at room temperature for 2 hours. The reaction mixture was filtered through a Waters silica Sep-Pak cartridge (5 g) that was further washed with hexane/ethyl acetate (95:5). After removal of solvents, the ketone II (12 mg, 81% yield) was obtained as a colorless oil: $^1$H NMR (400 MHz, CDCl$_3$) δ 2.45 (1H, dd, J=11.5, 7.6 Hz), 2.32-2.16 (2H, m), 0.90 (3H, t, J=6.9 Hz, 25-H3), 0.85 (3H, d, J=6.1 Hz, 21-H$_3$), 0.634 (3H, s, 18-H$_3$); $^{13}$C NMR (100 MHz) δ 212.14 (C-8), 62.01 (C-14), 56.24, 49.96 (C-13), 40.96, 38.86, 35.18, 34.87, 28.43, 27.15, 24.06, 23.03, 18.94 (C-21), 18.51, 14.19 (C-25), 12.72 (C-18).

J. 2-Methylene-19,26,27-trinor-(20S)-1α-hydroxyvitamin D$_3$ (OM) (I)

To a solution of phosphine oxide 11 (60 mg, 103 μmol) in anhydrous THF (600 μL) at −20° C. was slowly added PhLi (1.8 M in cyclohexane-ether, 60 μL, 108 μmol) under argon with stirring. The solution turned deep orange. After 30 minutes, the mixture was cooled to −78° C. and a precooled (−78° C.) solution of ketone II (12 mg, 51 μmol) in anhydrous THF (200 μL) was slowly added. The mixture was stirred under argon at −78° C. for 3 hours and at 0° C. for 18 hours. Ethyl acetate was added, and the organic phase was washed with brine, dried (Na$_2$SO$_4$) and evaporated. The residue was dissolved in hexane and applied on a Waters silica Sep-Pak cartridge (2 g). The cartridge was washed with hexane and hexane/ethyl acetate (99.5:0.5) to give TBDMS (or TBS) protected 19-norvitamin derivative 12 (13 mg). The Sep-Pak was then washed with hexane/ethyl acetate (96:4) to recover the unchanged ketone II (6 mg, 25 μmol), and with ethyl acetate to recover diphenylphosphine oxide 11 (56 mg). The TBDMS protected vitamin 12 was further purified by HPLC (9.4×250 mm Zorbax-Silica column, 4 mL/min) using a hexane/2-propanol (99.9:0.1) solvent system. Pure compound 12 (8.3 mg, 53% yield) was eluted at R$_f$=3.2 minutes as a colorless oil: MS (EI) m/z 600 (14, M$^+$), 585 (4, M$^+$-Me), 543 (11, M$^+$-C$_4$H$_9$), 468 (100, M$^+$-t-BuMe$_2$SiOH), 366 (43), 323 (9), 257 (13), 234 (16), 147 (24), 73 (97); exact mass calculated for C$_{37}$H$_{68}$O$_2$Si$_2$ (M$^+$) 600.4758, found 600.4742.

Protected vitamin 12 (8 mg, 13 μmol) was dissolved in anhydrous THF (4 mL) and a solution of tetrabutylammonium fluoride (1 M in THF, 100 μL, 100 μmol) was added, followed by freshly activated molecular sieves 4A (300 mg). The mixture was stirred under argon at room temperature for 4 hours, and was then diluted with 2 mL of hexane/ethyl acetate (9:1) and applied on a Waters silica Sep-Pak cartridge (2 g). Elution with the same solvent system gave the crude product I that was further purified by HPLC (9.4×250 mm Zorbax-Silica column, 4 mL/min) using a hexane/2-propanol (9:1) solvent system. Analytically pure 2-methylene-19,26,27-trinor-(20S)-1α-hydroxyvitamin D$_3$ (OM) I (3.59 mg, 74% yield) was collected at R$_f$=6.4 minutes as a colorless oil: UV (in EtOH) λ$_{max}$ 261, 251, 243 nm; $^1$H NMR (750 MHz, CDCl$_3$) δ 6.36 and 5.89 (1H and 1H, each d, J=11.2 Hz, 6- and 7-H), 5.11 and 5.09 (each 1H, each s, =CH$_2$), 4.47 (2H, m, 1β- and 3α-H), 2.84 (1 H, dd, J=13.3, 4.4 Hz, 10β-H), 2.82 (1H, br d, J=12.3 Hz, 9β-H), 2.58 (1H, dd, J=13.3, 3.4 Hz, 4α-H), 2.32 (1H, dd, J=13.3, 6.1 Hz, 4β-H), 2.30 (1H, dd, J=13.3, 8.4 Hz, 10α-H), 2.05-1.95 (2H, m), 1.90-1.82 (1H, m), 0.89 (3H, t, J=7.11-17, 25-H$_3$), 0.84 (3H, d, J=6.5 Hz, 21-H$_3$), 0.552 (3H, s, 18-H$_3$); $^{13}$C NMR (100 MHz) δ 151.97 (s, C-2), 143.55 (s, C-8), 130.29 (s, C-5), 124.30 (d, C-6), 115.24 (d, C-7), 107.71 (t, =CH$_2$), 71.82 and 70.70 (each d, C-1 and C-3), 56.36 (d), 56.22 (d), 45.84 (s, C-13), 45.79 (t), 40.34 (t), 38.16 (t), 35.45 (d), 35.29 (t), 28.98 (t), 28.55 (t), 27.29 (t), 23.51 (t), 23.08 (t), 22.17 (t), 18.59 (q, C-21), 14.23 (q, C-25), 12.33 (q, C-18); MS (EI) m/z 372 (100, M$^+$), 354 (4, M$^+$-H$_2$O), 324 (15, M$^+$-H$_2$O—C$_2$H$_6$), 287 (60, M$^{30}$ -C$_6$H$_{13}$), 269 (22, M$^+$-C$_6$H$_{13}$—H$_2$O), 251 (18, M$^+$-C$_6$H$_{13}$-2H$_2$O), 2.31 (22), 219 (35), 147 (46), 135(76), 119 (27), 107 (61); exact mass calculated for C$_{25}$H$_{40}$O$_2$ (M$^+$) 372.3028 found 372.3039.

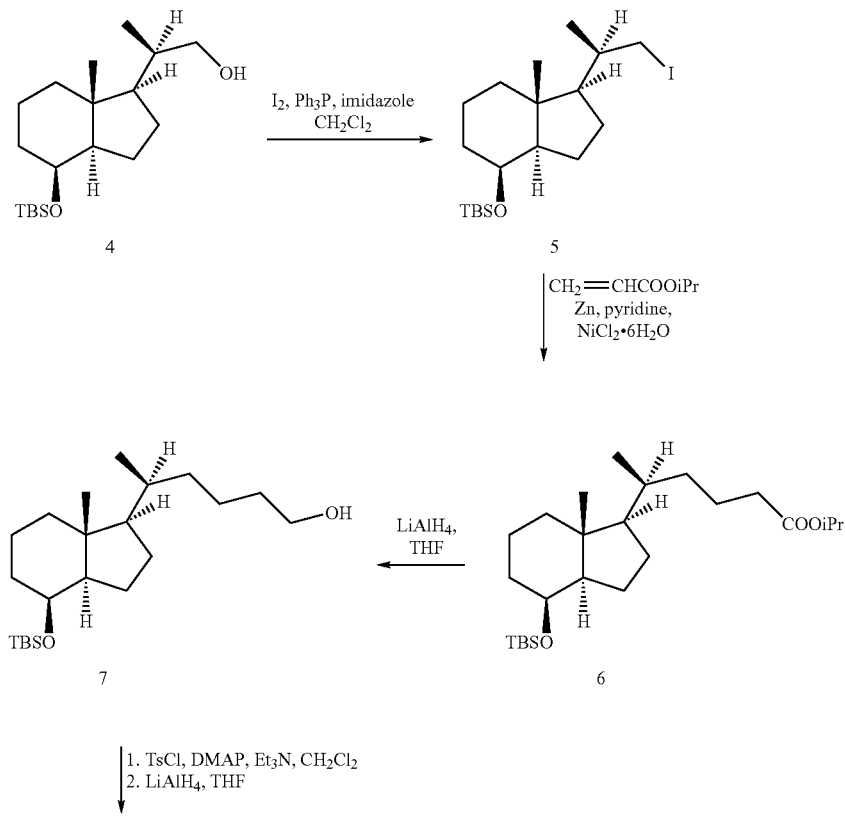

Scheme XIIA

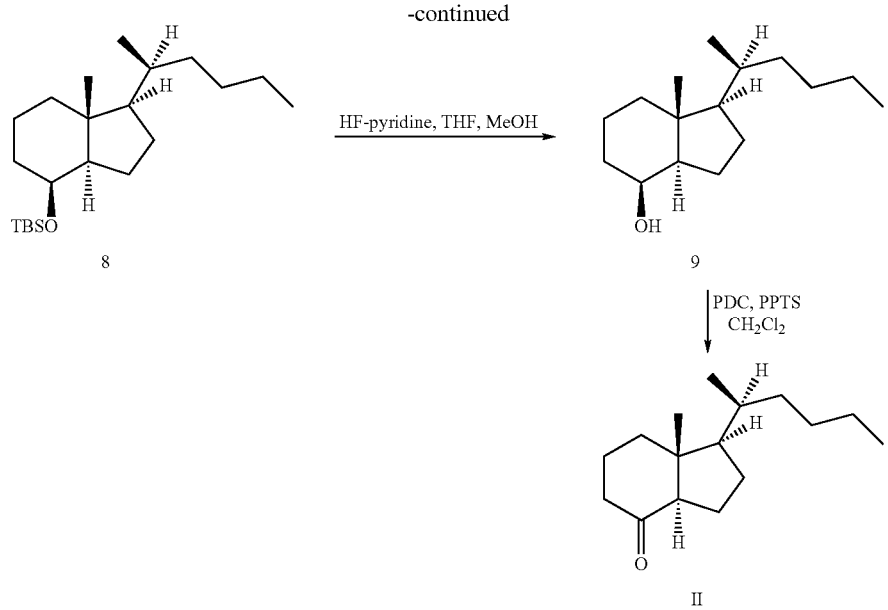

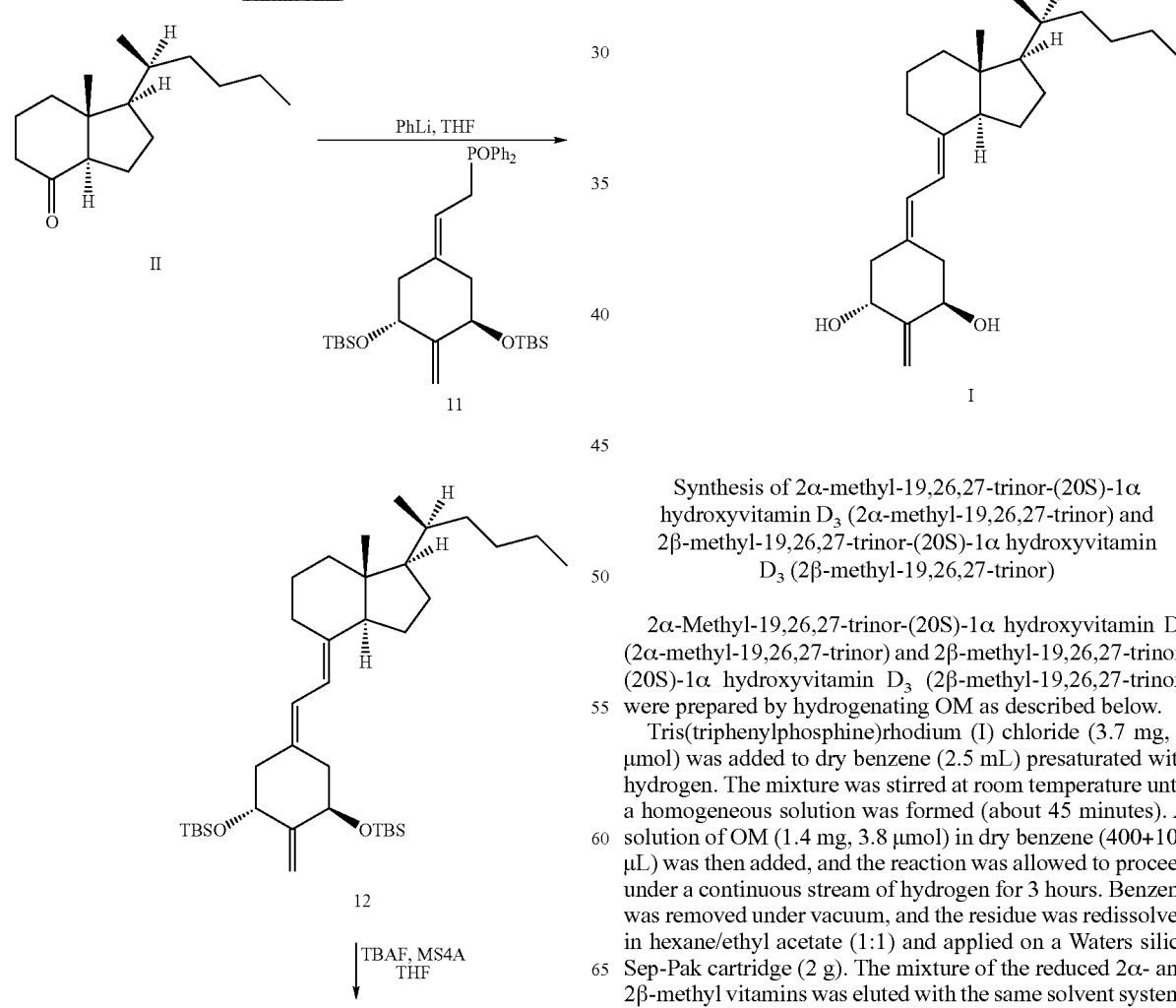

Synthesis of 2α-methyl-19,26,27-trinor-(20S)-1α hydroxyvitamin $D_3$ (2α-methyl-19,26,27-trinor) and 2β-methyl-19,26,27-trinor-(20S)-1α hydroxyvitamin $D_3$ (2β-methyl-19,26,27-trinor)

2α-Methyl-19,26,27-trinor-(20S)-1α hydroxyvitamin $D_3$ (2α-methyl-19,26,27-trinor) and 2β-methyl-19,26,27-trinor-(20S)-1α hydroxyvitamin $D_3$ (2β-methyl-19,26,27-trinor) were prepared by hydrogenating OM as described below.

Tris(triphenylphosphine)rhodium (I) chloride (3.7 mg, 4 μmol) was added to dry benzene (2.5 mL) presaturated with hydrogen. The mixture was stirred at room temperature until a homogeneous solution was formed (about 45 minutes). A solution of OM (1.4 mg, 3.8 μmol) in dry benzene (400+100 μL) was then added, and the reaction was allowed to proceed under a continuous stream of hydrogen for 3 hours. Benzene was removed under vacuum, and the residue was redissolved in hexane/ethyl acetate (1:1) and applied on a Waters silica Sep-Pak cartridge (2 g). The mixture of the reduced 2α- and 2β-methyl vitamins was eluted with the same solvent system. The compounds were further purified by HPLC (9.4×250 mm Zorbax-Silica column, 4 mL/min) using a hexane/2-propanol (9:1) solvent system. The mixture of 2α- and 2β-methyl vitamins gave a single peak at $R_f$=7.0 minutes. Separation of both epimers was achieved by reverse-phase HPLC (9.4×250 mm Zorbax Eclipse XDB-C18 column, 3 mL/min) using methanol/water (9:1) solvent system. 2β-Methyl vitamin (266 μg, 19% yield) was collected at $R_t$=15.9 minutes and its 2α-epimer (398 μg, 28% yield) was collected at $R_t$=18.2 minutes.

2α-Methyl-19,26,27-trinor-(20S)-1α hydroxyvitamin $D_3$ (2α-methyl-19,26,27-trinor): UV (in EtOH))$\lambda_{max}$ 260, 250, 242 nm; $^1$H NMR (500 MHz, $CDCl_3$) δ 6.37 and 5.82 (1H and 1H, each d, J=11.3 Hz, 6- and 7-H), 3.96 (1H, m, w/2=14 Hz, 1β-H), 3.61 (1H, m, w/2=21 Hz, 3α-H), 2.80 (2H, br m, 9β- and 10α-H), 2.60 (1H, dd, J=13.2, 4.4 Hz, 4α-H), 2.22 (1H, br d, J=12.7 Hz, 10β-H), 2.13 (1H, ~t, J~12.0 Hz, 4β-H), 1.133 (3H, d, J=6.8 Hz, 2α-$CH_3$), 0.887 (3H; t, J=7.1 Hz, 25-$H_3$), 0.829 (3H, d, J=6.5 Hz, 21-$H_3$),0.529 (3H, s, 18-$H_3$); MS (EI) m/z 374 (100, M$^+$), 317 (15, M$^+$-$C_4H_9$), 289 (40, M$^+$-$C_6H_{13}$), 271 (17, M$^+$-$C_6H_{13}$—$H_2O$), 253 (17, M$^+$-$C_6H_{13}$-$2H_2O$), 231 (29), 219 (47), 147 (31), 129 (42); exact mass calculated for $C_{25}H_{42}O_2$ (M$^+$) 374.3185 found 374.3186.

2β-methyl-19,26,27-trinor-(20S)-1α hydroxyvitamin $D_3$ (2β-methyl-19,26,27-trinor): UV (in EtOH) $\lambda_{max}$ 260, 250, 242 nm; $^1$H NMR (500 MHz, $CDCl_3$) δ 6.26 and 5.87 (1H and 1H, each d, J=11.1 Hz, 6-H and 7-H), 3.90 (1H, m, w/2=15 Hz, 3α-H), 3.50 (1H, m, w/2=26 Hz, 1β-H), 3.08 (1H, dd, J=12.4, 4.6 Hz, 10β-H), 2.80 (1H, dd, J=12.4, 4.1 Hz, 9β-H), 2.43 (1H, br d, J=ca. 14 Hz, 4α-H), 2.34 (1H, dd, J=14.0, 2.8 Hz, 4β-H), 1.142 (3H, d, J=6.8 Hz, 2β-$CH_3$), 0.997 (3H, t, J=7.1 Hz, 25-$H_3$),0.833 (3H, d, J=6.5 Hz, 21-$H_3$), 0.541 (3H, s, 18-$H_3$); MS (EI) m/z 374 (75, M$^+$), 317 (12, M$^+$-$C_4H_9$), 289 (28, M$^+$-$C_6H_{13}$), 271 (13, M$^+$-$C_6H_{13}$—$H_2O$), 253 (12, M$^+$-$C_6H_{13}$-$2H_2O$), 219 (32), 149 (45), 135 (38), 81 (52), 69 (100); exact mass calculated for $C_{25}H_{42}O_2$ (M$^+$) 374.3185, found 374.3172.

Synthesis of 2-Methylene-18,19-dinor-1α-hydroxy-homopregnacalciferol (18,19-dinor-2MP)

2-Methylene-18,19-dinor-1α-hydroxy-homopregnacalciferol (18,19-dinor-2MP) was prepared as shown in Scheme XIII and described below.

A. Des-A,B-23,24-dinorcholane-8β,22-diol (1)

A solution of vitamin $D_2$ (5 g, 12.7 mmol) in methanol (400 mL) and pyridine (5 mL) was cooled to −78° C. while purging with argon. The argon stream was stopped and a stream of ozone was passed until a blue color appeared. The solution was purged with oxygen until the blue color disappeared and treated with $NaBH_4$ (1.2 g, 32 mmol). After 20 minutes, the second portion of $NaBH_4$ (1.2 g, 32 mmol) was added and reaction was allowed to warm to room temperature. The third portion of $NaBH_4$ (1.2 g, 32 mmol) was added and the reaction mixture was stirred at room temperature overnight. The reaction was quenched with 70 mL of water and concentrated under vacuum. The residue was extracted with methylene chloride (3×100 mL). The organic phase was washed with 1M aqueous solution of HCl (2×100 mL), saturated aqueous solution of $NaHCO_3$ (100 mL), dried over anhydrous $MgSO_4$ and concentrated under vacuum. The residue was purified by flash chromatography (25% ethyl acetate/hexane) to yield 2.05 g (9.69 mmol, 76% yield) of diol 1 as white crystals. $[\alpha]_D$+56.0 (c 0.95, $CHCl_3$); mp 110-111° C.; $^1$H NMR (400 MHz, $CDCl_3$) δ 0.96 (3H, s), 1.03 (3H, d, J=6.6 Hz), 3.38 (1H, dd, J=10.5 Hz, J=6.8 Hz), 3.64 (1H, dd, J=10.5 Hz, J=3.2 Hz), 4.09 (1H, d, J=2.3 Hz); $^{13}$C NMR (100 MHz, $CDCl_3$) δ 13.6, 16.6, 17.4, 22.6, 26.6, 33.5, 38.2, 40.2, 41.3, 52.3, 52.9, 67.8, 69.2; MS (EI) m/z 212 (2, M$^+$), 194 (17), 179 (18), 163 (10), 135 (19), 125 (34), 111 (100); exact mass calculated for $C_{13}H_{22}O$ ([M−$H_2O$]$^+$) 194.1671, found 194.1665.

B. Des A,B-23,24-dinor-22-(tosyloxy)cholane-8β-ol (2)

To a stirred solution of 1 (450 mg, 2.12 mmol), triethylamine (975 μl, 708 mg, 7.00 mmol) and DMAP (20 mg, 0.16 mmol) in anhydrous methylene dichloride (20 mL) tosyl chloride was added at 0° C. The reaction mixture was kept at 4° C. overnight. Then, methylene dichloride (30 mL) was added and the reaction mixture was washed with saturated aqueous solution of $NaHCO_3$ (2×30 mL), dried over anhydrous $Na_2SO_4$ and concentrated under reduced pressure. The residue was purified by column chromatography (25-30% ethyl acetate/hexane) to give 754 mg (2.06 mmol, 97% yield) of 2. $[\alpha]_D$+21.0 (c 1.10, $CHCl_3$); $^1$H NMR (500 MHz, $CDCl_3$) δ 0.89 (3H, s),0.96 (3H, d, J=6.7 Hz), 2.45 (3H, s), 3.81 (1H, dd, J=9.2 Hz, J=6.2 Hz), 3.95 (2H, dd, J=9.2 Hz, J=3.0 Hz), 4.07 (1H, br d), 7.34 (2H, d, J=8.2 Hz), 7.78 (2H, d, J=8.2 Hz); $^{13}$C NMR (125 MHz, $CDCl_3$) δ 13.4, 16.8, 17.3, 21.6, 22.4, 26.4, 33.5, 35.7, 40.0, 41.8, 52.2, 69.0, 75.6, 127.9, 129.8, 133.1, 144.6; MS (EI) m/z 366 (7, M$^+$, 348 (5), 194 (16), 179 (19), 161 (11), 155 (19), 150 (16), 135 (15), 125 (37), 1 1 1 (100); exact mass calculated for $C_{20}H_{30}O_4S$ 366.1865, found 366.1876.

C. Des A,B-23,24-dinorcholane-8β-ol (3)

To a stirred slurry of $LiAlH_4$ (290 mg, 7.65 mmol) in diethyl ether (30 mL) a solution of 2 (700 mg, 1.91 mmol) in diethyl ether (20 mL) was added dropwise via cannula. The reaction mixture was stirred for 1 hour under argon. Then several drops of ethyl acetate, 5% aqueous solution of HCl (25 mL, at 0° C.) and water (30 mL) were added and the mixture was extracted with diethyl ether (3×40 mL). Organic phase was dried over anhydrous $Na_2SO_4$, concentrated under reduced pressure and the residue was purified by column chromatography (5-10% ethyl acetate/hexane) to give 320 mg (1.60 mmol, 85% yield) of 3. $[\alpha]_D$+23.5 (c 0.90, $CHCl_3$); $^1$H NMR (400 MHz, $CDCl_3$) δ 0.84 (3H, d, J=6.6 Hz), 0.91- 0.93 (6H, m), 4.07 (1H, br d, J=2.2 Hz); $^{13}$C NMR (100 MHz, $CDCl_3$) δ 13.6, 17.4, 22.4, 22.5, 23.0, 27.4, 30.5, 33.5, 40.3, 41.8, 52.6, 58.7, 69.4; MS (EI) m/z 196 (15, M$^+$), 181 (16), 135 (13), 125 (16), 111 (100); exact mass calculated for $C_{13}H_{24}O$ 196.1827, found 196.1828.

D. Des-A,B-23,24-dinorcholane-8β-yl nitrite (4)

To a stirred solution of 3 (285 mg, 1.53 mmol) in chloroform (8 mL) tert-butyl nitrite (2.2 mL) was added dropwise in darkness. After 1 hour, benzene was added and solvents were removed under reduced pressure.

E. (18E)-18-(Hydroxyimino)-des A,B-23,24-dinor-cholane-8β-ol (5)

Crude nitrite 4 was dissolved in anhydrous benzene (150 mL) and irradiated in an apparatus consisting of a Pyrex vessel with a watercooled immersion well and Hanovia high-pressure mercury arc lamp equipped with Pyrex filter. A slow stream of argon was passed through solution and temperature was maintained at about 10° C. A reaction progress was monitored by TLC. After 45 min. reaction was completed.

Benzene was removed under reduced pressure and the residue was dissolved in 2-propanol (5 mL) and kept overnight to accomplish isomerisation of a nitroso compound to an oxime. The solvent was evaporated and the residue was purified on Waters silica gel Sep-Pack cartridge (15-25% ethyl acetate/hexane) to give 230 mg (1.02 mmol, 67% yield starting from 3) of 5. $[\alpha]_D$+45:7 (c 0.90, $CHCl_3$); mp. 144° C.; $^1$H NMR (400 MHz, $CDCl_3$) δ 0.88 (3 H, d, J=6.5 Hz), 1.02 (3H, d, J=6.5 Hz), 2.20 (1H, d, J=13.2 Hz), 4.04 (1H, s), 6.78 (1H, s), 7.34 (1H, s), 10.94 (1H, s); $^{13}$C NMR (100 MHz, $CDCl_3$) δ 17.4, 21.9, 22.3, 23.1, 27.7, 30.9, 34.2, 36.5, 49.5, 52.5, 58.9, 67.5, 151.9; MS (EI) m/z 225 (20, M$^+$), 208 (92), 190 (70), 183 (78), 175 (40), 164 (43), 136 (66), 121 (51), 87 (100); exact mass (ESI) calculated for $C_{13}H_{23}NO_2Na$ ([M+Na]$^+$) 248.1626, found 248.1620.

F. 8β-(Acetoxy)-des A,B-23,24-dinorcholane-18-nitrile (6)

A solution of 5 (220 mg, 0.98 mmol) in acetic anhydride (15 mL) was refluxed for 1.5 hours. The reaction mixture was cooled, poured carefully into ice and extracted with benzene (3×60 mL). The combined organic phases were washed with saturated aqueous solution of $NaHCO_3$ (2×50 mL), water (30 mL), dried over anhydrous $Na_2SO_4$ and evaporated. The residue was purified on Waters silica gel Sep-Pack cartridge (8-10% ethyl acetate/hexane) to give 239 mg (0.96 mmol, 98% yield) of 6. $[\alpha]_D$-5.2 (c 0.95, $CHCl_3$); mp. 40° C.; $^1$H NMR (400 MHz, $CDCl_3$) δ 0.94 (3H, d, J=6.6 Hz), 1.05 (3H, d, J=6.6 Hz), 2.14 (3H, s), 2.49 (1H, br d, J=13.8 Hz), 5.20 (1H, s); $^{13}$C NMR (100 MHz, $CDCl_3$) δ 18.7, 20.9, 22.3, 23.4, 27.4, 29.8, 32.1, 36.2, 45.7, 51.9, 56.2, 68.6, 121.1, 170.9; MS (EI) m/z 249 (2, M$^+$), 224 (9), 207 (66), 189 (43), 183 (100); exact mass calculated for $C_{15}H_{23}NO_2$ 249.1729, found 249.1733.

G. Des-A,B-23,24-dinorcholane-18-nitrile-8β-ol (7)

6 (225 mg, 0.90 mmol) was dissolved in methanol (10 mL) and treated with 10% solution of NaOMe in methanol (10 mL) for 2 hours. After that solvent was removed under reduced-pressure, the residue was treated water (20 mL) and saturated aqueous solution of $NH_4Cl$ (15 mL) and extracted with methylene dichloride (3×50 mL). Organic phase was dried over anhydrous $Na_2SO_4$ and evaporated. The residue was purified on Waters silica gel Sep-Pack cartridge (20-30% ethyl acetate/hexane) to give 180 mg (0.87 mmol, 97% yield) of 7. $[\alpha]_D$+20.6 (c 1.15, $CHCl_3$); $^1$H NMR (500 MHz, $CDCl_3$) δ 0.94 (3H, d, J=6.6 Hz), 1.04 (3H, d, J=6.6 Hz), 2.46 (1H, br d, J=13.0 Hz), 4.11 (1H, m); $^{13}$C NMR (125 MHz, $CDCl_3$) δ 18.0, 22.2, 22.2, 23.0, 27.5, 32.0, 32.7, 36.3, 44.9, 53.4, 56.2; 67.4, 122.3; MS (EI) m/z 207 (14, M$^+$), 180 (16), 174 (26), 162 (39), 147 (20), 136 (39), 121 (100); exact mass calculated for $C_{13}H_{21}NO$ 207.1623, found 207.1618.

H. Des-A,B-18,23,24-trinorcholane-8β-ol (8)

To a stirred mixture of potassium (270 mg, 6.75 mmol) in HMPA (950 μL, 979 mg, 5.46 mmol) and diethyl ether (2 mL) a solution of 7 (185 mg, 0.89 mmol) in tert-butyl alcohol (220 μl) and diethyl ether (850 μl) was added dropwise at 0° C. under argon. The mixture was allowed to warm up to room temperature and stirred overnight. Remaining potassium was removed, a few drops of 2-propanol and benzene (40 mL) were added. Organic phase was washed with water (10 mL), dried over anhydrous $Na_2SO_4$ and concentrated under reduced pressure. The residue was purified on Waters silica gel Sep-Pack cartridge (5-10% ethyl acetate/hexane) to give 112 mg (0.62 mmol, 69% yield) of 8. $[\alpha]_D$+54.9 (c 0.85, $CHCl_3$); $^1$H NMR (500 MHz, $CDCl_3$) δ 0.82 (3H, d, J=6.8Hz), 0.90 (3H, d, J=6.8Hz), 1.83 (1H, br dd, J=13.4 Hz, J=2.3 Hz), 1.92 (1H, br dd, J=12.5 Hz, J=2.3Hz), 4.07 (1H, s); $^{13}$C NMR (125 MHz, $CDCl_3$) δ 18.1, 20.1, 21.8, 24.0, 24.6, 29.4, 31.1, 33.2, 40.1, 50.1, 50.3, 67.9; MS (EI) m/z 163 (4), 149 (3), 139 (12), 121 (100); exact mass calculated for $C_9H_{15}O$ ([M−$C_3H_7$]$^+$) 139.1123, found 139.1124.

I. Des-A,B-18,23,24-trinorcholane-8β-one (9)

To a stirred solution of 8 (15 mg, 82 μmol) and PPTS (2 crystals) in methylene dichloride (4 mL) PDC (110 mg, 290 μmol) was added at 0° C. After 5 min. cooling bath was removed and the reaction mixture was stirred for 6 h. Then solvent was removed under reduced pressure and the residue was purified on Waters silica gel Sep-Pack cartridge (2-5% ethyl acetate/hexane) to give 12 mg (67 μmol, 81% yield) of 9. $^1$H NMR (400 MHz, $CDCl_3$) δ 0.82 (3H, d, J=6.8 Hz), 0.92 (3H, d, J=6.8 Hz); $^{13}$C NMR (100 MHz, $CDCl_3$) δ 18.0, 21.4, 21.6, 24.1, 27.8, 29.3, 30.3, 41.5, 51.3, 51.6, 58.3, 212.0; MS (EI) m/z 180 (40, M$^+$), 137 (100); exact mass calculated for $C_{12}H_{20}O$ 180.1514, found 180.1520.

J. 2-Methylene-18,19-dinor-1α-hydroxyhomopregnacalciferol (18,19-dinor-2MP) (12)

To a stirred solution of phosphine oxide 10 (45 mg, 77 μmol) in anhydrous THF (600 μl) a 1.5 M solution of phenyl lithium in THF (75 μl, 105 μmol) was added at −20° C. under argon. The mixture was stirred for 20 min. and then cooled to −78° C. A precooled solution of 9 (6 mg, 33 μmol) in anhydrous THF (200 μl) was added via cannula and the reaction mixture was stirred for 3 h at −78° C. After that the reaction mixture was stirred at 4° C. overnight. Then ethyl acetate was added and organic phase was washed with brine, dried over anhydrous $Na_2SO_4$ and concentrated under reduced pressure. The residue was purified on Waters silica gel Sep-Pack cartridge (hexane to 3% ethyl acetate/hexane) and then on HPLC (0.03% 2-propanol/hexane, 4 mL/min., Zorbax-silica 10×250 mm) to give 11.4 mg (21 mmol, 64% yield) of 11 at $R_t$=7.08 min. UV (hexane) $\lambda_{max}$=242, 250, 261 nm; $^1$H NMR (400 MHz, $CDCl_3$) δ 0.03 (3H, s), 0.04 (3H, s), 0.07 (3H, s), 0.08 (3H, s), 0.80 (3H, d, J=6.8 Hz), 0.86 (9H, s), 0.89 (9H, s), 2.18 (1H, dd, J=12.4 Hz, J=7.7 Hz), 2.86 (1H, br d, J=13.8 Hz), 4.42 (1H, m), 4.93 (1H, s), 4.96 (1H, s), 5.93 (1H, d, J=11.2 Hz), 6.20 (1H, d, J=11.2 Hz); $^{13}$C NMR (100 MHz, $CDCl_3$) δ −5.1, −4.9, −4.8, 18.2, 18,2, 18.3, 21.6, 24.6, 25.8, 25.8, 27.8, 28.9, 29.8, 31.9, 38.7, 47.5, 50.7, 50.8, 52.7, 71:9, 72.3, 106.3, 113.7, 122.4, 132.9, 143.7, 153.0; MS (EI) m/z 544 (3, M$^+$), 448 (9), 412 (36), 366 (14), 313 (11), 290 (100); exact mass calculated for $C_{33}H_{60}O_2Si_2$ 544.4132, found 544.4131.

To a stirred solution of 11 (11 mg, 20 μmol) in anhydrous n-butanol (1 mL) (1S)-(+)=10-camphorsulfonic acid (7 mg, 30 −mol) was added at 0° C. Then cooling bath was removed and the reaction mixture was stirred for 4 days. After that saturated aqueous solution of $NaHCO_3$ (1 mL) and water (3 mL) were added and the mixture was extracted with ethyl acetate (3×7 mL). Organic phase was dried over anhydrous $Na_2SO_4$, concentrated under reduced pressure and the residue was purified on Waters silica gel Sep-Pack cartridge (20-30% ethyl acetate/hexane). Crude vitamin was repurified on HPLC (10% 2-propanol/hexane, 4 mL/min., Zorbax-silica 10×250 mm) to give 6 mg (19 μmol, 93% yield) of 12 at $R_t$=7.78 min. UV (EtOH) $\lambda_{max}$=242, 250, 260 nm; $^1$H NMR (400 MHz, $CDCl_3$) δ 0.80 (3H, d, J=6.8 Hz), 0.88 (3H, d, J=6.8 Hz), 2.58 (1H, dd, J=13.2 Hz, J=3.8 Hz), 4.48 (1H, br s), 5.09 (1H, s), 5.10 (1H, s), 5.97 (1H, d, J=11.3Hz), 6.35 (1H, d, J=11.3 Hz); $^{13}$C NMR (100 MHx, $CDCl_3$) δ 18.3, 21.7, 24.5, 25.8, 27.8, 29.1, 29.8, 31.7, 38.0, 45.9, 50.7, 50.9, 52.7, 70.9, 71.7, 107.7, 112.9, 124.3, 130.7, 146.0, 152.0; MS (EI) m/z 316 (14, M$^+$), 298 (10), 280 (15), 237 (19), 84 (71) 66 (100); exact mass calculated for $C_{21}H_{32}O_2$ 316.2402, found 316.2387.

Scheme XIII

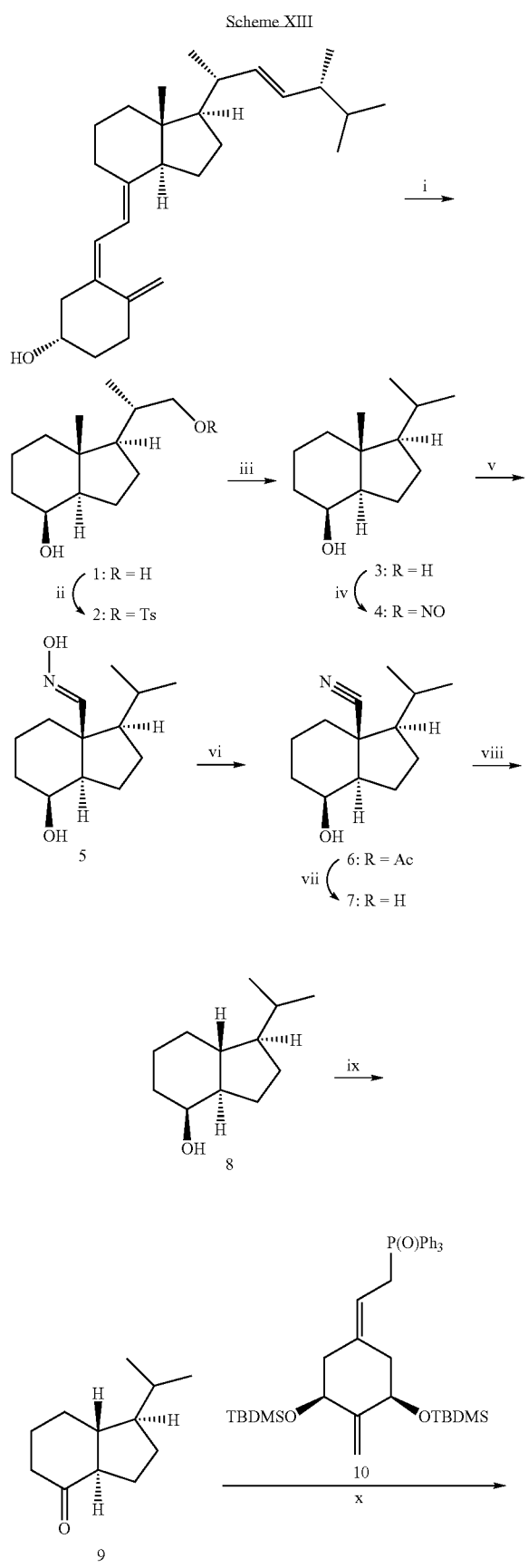

(i) O₃, MeOH, py; NaBH₄, 76%.
(ii) TsCl, Et₃N, DMAP, CH₂Cl₂, 97%.
(iii) LiAlH₄, Et₂O, 85%.
(iv) t-BuONO, CHCl₃.
(v) hv, C₆H₆; i-PrOH, 67% (from 3).
(vi) Ac₂O, 98%.
(vii) MeONa/MeOH, 97%.
(viii) K, HMPA, t-BuOH, Et₂O, 69%.
(ix) PDC, PPTS, CH₂Cl₂, 81%.
(x) 10, PhLi, THF, 64%.
(xi) CSA, n-BuOH, 93%.

Synthesis of 2-Methylene-19-dinor-1α-hydroxy-17-ene-homopregnacalciferol (Vitamin I or VIT-I)

2-Methylene-19-dinor-1α-hydroxy-17-ene-homopregnacalciferol (Vitamin I or VIT-I) was prepared as shown in Scheme XIV and described below.

A. Des-A,B-23,24-dinorcholane-8β,22-diol (2)

A flame dried 1000 ml, two necked flask was charged with ergocalciferol 1 (5 g, 12.6 mmol), pyridine (5 mL), and anhydrous MeOH (400 mL). The solution was cooled to −78° C. in an argon atmosphere. O₃ was bubbled through the solution until a deep blue color developed and persisted (about 1 hour). The solution was then treated with O₂ until the blue color faded (15 minutes). Then NaBH₄ (1.5 g, 39.7 mmol) was added. After 15 minutes, a second portion of NaBH₄ (1.5 g, 39.7 mmol) was added and the reaction was allowed to warm to room temperature. A third portion of NaBH₄ (1.5 g, 39.7 mmol) was then added, and the reaction was left over night. The reaction was quenched by adding water (50 mL) drop wise. Methanol was evaporated in vacuo, and the residue was dissolved in ethyl acetate. The organic phase was washed with 1 N aqueous solution of HCl (100 mL), saturated NaHCO₃ solution (100 mL) and brine (100 mL). The organic phase was dried (Na₂SO₄), filtered and evaporated. Purification by silica gel chromatography (25% ethyl acetate/hexane) afforded 2.18 g (10.3 mmol, 81%) of diol 2 as a white solid. Mp 110-111° C.; $^1$H NMR (400 MHz, CDCl₃) δ:4.09 (1H, m), 3.64 (1H, dd, J=10.5 and 3.2 Hz), 3.38 (1H, dd, J=10.5 and 6.7 Hz), 1.03 (3H, d, J=6.6 Hz), 0.96 (3H, s); $^{13}$C NMR (100 MHz, CDCl₃) δ: 69.2, 67.8, 52.9, 52.4, 41.8, 40.2, 38.2, 33.6, 26.6, 22.6, 17.4, 16.6, 13.6; MS m/z (relative integration): 212 (M⁺, 2), 194 (15), 179 (18), 125 (43), 111 (100); exact mass calculated for C₁₃H₂₂O ([M−H₂O]⁺) is 194.1671, found 194.1665.

B. Des A,B-22-(p-toluensulfonyloxy)-23,24-dinorcholane-8β-ol (3)

A solution of diol 2 (1 g, 4.71 mmol) in anhydrous pyridine (12 mL) was cooled to −25° C. and a precooled solution of p-toluenesulfonyl chloride (1.08 g, 5.66 mmol) in anhydrous pyridine (2 mL) was added dropwise. The reaction mixture was stirred at that temperature for 4 hours and allowed to warm to 0° C. and stirred at that temperature for an additional 20 hours. The mixture was diluted with $CH_2Cl_2$ (50 mL) and washed with saturated $CuSO_4$ solution (30 mL), 1 N HCl (30 mL), and water (50 mL). The organic phase was dried ($Na_2SO_4$), filtered, and concentrated. Purification by silica gel chromatography (25% ethyl acetate/hexane) yielded 1.7 g (4.64 mmol, 99%) of 3. $^1$H NMR (400 MHz, $CDCl_3$) δ: 7.78 (2H, d, J=8.2 Hz), 7.35 (2H, d, J=8.2 Hz), 4.06 (1H, m), 3.95 (1H, dd, J=9.2 and 3.0 Hz), 3.8 (1H, dd, J=9.2 and 6.2 Hz), 2.45 (3H, s), 0.96 (3H, d, J=6.6 Hz), 0.89 (3H, s); $^{13}$C NMR (100 MHz, $CDCl_3$) δ:144.7, 133.0,129.8, 127.9, 75.6, 69.0, 60.4, 52.2, 41.9, 40.1, 35.7, 33.5, 26.4, 22.4, 21.6, 17.3, 16.7, 13.4; MS m/z (relative integration): 366 ($M^+$, 6), 194(14), 179(16), 125(30), 111(100).

C. Des A,B-8β-(triethylsilyloxy)-22-(p-toluenesulfonyloxy)-23,24-dinorcholane (4)

To a −50° C. cooled solution of hydroxyl tosylate 3 (1.7 g, 4.64 mmol) in anhydrous $CH_2Cl_2$ (20 mL) was added 2,6-lutidine (0.64 mL, 5.57 mmol) followed by TESOTf (1.26 mL, 1.47 g, 5.57 mmol). The solution was stirred at 0° C. for 15 minutes and water (10 mL) was added. The mixture was extracted with $CH_2Cl_2$ (3×40 mL), and the combined organic phases were washed with 1N aqueous solution of NaOH (40 mL) dried ($Na_2SO_4$), filtered, and concentrated. The residue was purified by silica gel column chromatography (5% ethyl acetate/hexane) to give 1.87 g (3.89 mmol, 84%) of O-silylated tosylate 4. $^1$H NMR (400 MHz, $CDCl_3$) δ: 7.77 (2H, d, J=8.2 Hz), 7.33 (2H, d, J=8.2 Hz), 4.01(1H, m), 3.95(1H, dd, J=9.2 and 3.0 Hz), 3.78 (1H, dd, J=9.2 and 6.4 Hz), 2.43 (3H, s), 0.94 (3H, d, J=7.0 Hz), 0.93 (9H, t, J=7.9 Hz), 0.85 (3H, s), 0.53 (6H, q, J=7.9 Hz); $^{13}$C NMR (100 MHz, $CDCl_3$) δ: 144.5, 133.1, 129.7, 127.9, 75.7, 69.1, 52.7, 52.4, 42.1, 40.4, 35.7, 34.5, 26.5, 22.9, 21.6, 17.5, 16.7, 13.4, 6.9, 4.9; MS m/z (relative integration): 480 ($M^+$, 30), 437 (50), 279 (49), 257 (49), 257 (84), 177 (100); exact mass calculated for $C_{26}H_{44}O_4SSi$ ($M^+$) is 480.2730, found 480.2741.

D. Des A,B-8β-(triethylsilyloxy)-23,24-dinorcholane-22-al (5)

A solution of O-silylated tosylate 4 (1.8 g, 3.75 mmol) in DMSO (5 mL) was added to a suspension of $NaHCO_3$ (1.42 g, 16.8 mmol) in DMSO (20 mL) at room temperature. The mixture was heated to 150° C. under argon for 15 minutes and cooled to room temperature. Water (50 mL) followed by ethyl acetate (50 mL) were added, and the aqueous phase was extracted with ethyl acetate (3×30 mL). The combined organic phases were dried ($Na_2SO_4$), filtered, and concentrated. The residue was purified by column chromatography (2% ethyl acetate/hexane) to afford 0.92 g (2.83 mmol, 76%) of O silylated aldehyde 5. $^1$H NMR (500 MHz, $CDCl_3$) δ: 9.58 (1H, d, J=3.2 Hz), 4.06 (1H, m), 2.35 (1H, m), 1.09 (3H, d, J=6.8 Hz), 0.96 (3H, s), 0.95 (9H, t, J=8.1Hz), 0.55 (6H, q, J=8.1Hz); $^{13}$C NMR (100 MHz, $CDCl_3$) δ: 205.5, 69.0, 52.3, 51.7, 49.2, 42.6, 40.5, 34.5, 26.2, 23.3, 17.6, 13.9, 13.3, 6.9, 4.9; MS m/z (relative integration): no $M^+$, 295 ($M^+$-$C_2H_5$, 41), 163 (100), 135 (35), 103 (72); exact mass calculated for $C_{17}H_{31}O_2Si$ ($[M-C_2H_5]^+$) is 295.2093, found 295.2095.

E. Des A,B-8β-(triethylsilyloxy)-pregnan-20-one (6)

A flame dried flask was charged with KO-t-Bu (1.55 g, 13.9 mmol) and anhydrous t-BuOH (30 mL). $O_2$ was bubbled through the solution for 15 minutes. A solution of O-silylated aldehyde 5 (0.9 g, 2.78 mmol) in anhydrous t-BuOH (15 mL) was added to the reaction mixture and $O_2$ was bubbled through the solution for an additional 10 minutes. The solution was quenched with water (15 ml) and extracted with ether (3×30 mL). The combined organic phases were dried ($Na_2SO_4$), filtered and concentrated. The residue was purified by-column chromatography (3% ethyl acetate/hexane) to give 0.53 g (1.7 mmol, 62%) of the O-silylated 20-ketone 6. $^1$H NMR (500 MHz, $CDCl_3$) δ:4.07 (1H, m), 2.46 (1H, t, J=9.0 Hz), 2.09 (3H, s), 0.94 (9H, t, J=8.0 Hz), 0.85 (3H, 3), 0.55 (6H, q, J=8.0 Hz); $^{13}$C NMR (100 MHz, $CDCl_3$) δ: 209.6, 68.9, 64.5, 53.2, 43.7, 39.9, 34.4, 31.5, 23.1, 21.8, 17.6, 15.3, 6.9, 4.9; MS m/z (relative intensity): 310 ($M^+$, 12), 281 (100), 267 (59), 103 (98); exact mass calculated for $C_{18}H_{34}O_2Si$ ($M^+$) is 310.2328, found 310.2325.

F. Des A,B-20-methyl-8β-(triethylsilyloxy)-pregnan-20-ol (7)

To a solution of ketone 6 (0.5 g, 1.61 mmol) in dry THF (10 mL) was added a 3 M solution of methylmagnesium bromide in diethyl ether (1.3 mL, 0.48 g, 4.03 mmol) at 0° C. under argon atmosphere. The reaction was allowed to come to room temperature and stirred at that temperature for 2 hours. The reaction was then quenched with saturated ammonium chloride solution. The mixture was extracted with ethyl acetate (3×20 mL). The combined organic extracts were washed with water (30 mL) and brine solution (30 mL). The organic phase was then dried ($Na_2SO_4$), filtered, and concentrated. The residue was purified by column chromatography (10% ethyl acetate/hexane) to give 0.428 (1.29 mmol, 80%) of the tertiary alcohol 7. $^1$H NMR (400 MHz,. $CDCl_3$) δ: 4.05 (1H, m), 2.05 (1H, m), 1.29 (3H, s), 1.17 (3H, s), 1.10 (3H, s), 0.95 (9H, t, J=7.9 Hz), 0.55 (6H, q, J=7.9 Hz); $^{13}$C NMR (100 MHz, $CDCl_3$) δ: 73.1, 69.0, 60.1, 52.6, 42.5, 40.7, 34.1, 29.5, 22.3, 21.7, 17.2, 14.9, 6.5, 4.5; MS m/z (relative intensity):326 ($M^+$, 2), 311 (4), 297 (31), 279 (100); exact mass calculated for $C_{17}H_{33}O_2Si$ ($[M-C_2H_5]^+$) is 297.2250, found 297.2246.

G. Des A,B-20-methyl-pregnan-17(20)-ene-8β-ol (8)

A mixture of compound 7 (0.150 g, 0.46 mmol), 2M hydrochloric acid (5 mL) and THF (5 mL) was refluxed at 70° C. for 1 hour. THF was evaporated in vacuo and the aqueous phase was made basic using 2.5 M NaOH solution. The aqueous phase was extracted with ethyl acetate (3×30 mL). The combined organic phases were washed with water (50 mL) and brine (30 mL). The organic phase was dried ($Na_2SO_4$), filtered, and concentrated. The residue was purified by column chromatography (12% ethyl acetate/hexane) followed by HPLC (6.2 mm×25 cm Zorbax-sil column, 4 mL/min) using a hexane/ethyl acetate (95.5:0.5) solvent system to give 0.041 g (0.21 mmol, 46%) the alcohol 8. $^1$H NMR (500 MHz, $CDCl_3$) δ: 4.16 (1H, m), 2.28 (2H, m), 2.18 (1H, m), 1.70 (3H, s), 1.55 (3H, s), 1.10 (3H, s).

H. Des A,B-20-methyl-pregnan-17(20)-ene-8-one (9)

To a solution of alcohol 8 (0.020 g, 0.10 mmol) in anhydrous $CH_2Cl_2$ (5 mL) was added PDC (0.054 g, 0.14 mmol) at room temperature. After stirring the reaction for 3 hours under an argon atmosphere, the solution was passed through a pad of celite with ethyl acetate. The filtrate was concentrated and applied on a Sep-Pak cartridge and eluted with ethyl acetate/hexane (6%) to give ketone 9 as a colorless oil. The ketone was purified on HPLC (6.2 mm×25 cm Zorbax-sil column, 4 mL/min) using a 4% ethyl acetate/hexane solvent system. Pure ketone 9 (15.4 mg, 0.08 mmol, 78%) was eluted at $R_v$=42 mL as a colorless oil. $^1$H NMR (500 MHz, CDCl$_3$) δ: 2.57 (1H, m), 1.74 (3H, s), 1.59 (3H, m), 1.56 (3H, s), MS m/z (relative intensity): 192 (M$^+$, 98), 177 (88), 159 (100), 149 (91), 107 (89); exact mass calculated for $C_{13}H_{20}O$ ([M−$C_2H_5$]$^+$) is 192.1514, found 192.1521.

I. 2-Methylene-19-dinor-1α-hydroxy-17-ene-homopregnacalciferol (VIT-I) (12)

To a solution of phosphine oxide 10 (0.030 g, 0.05 mmol) in anhydrous THF (500 μL) at −25° C. was slowly added PhLi (34 μL, 5 mg, 0.061 mmol) under argon with stirring. The solution turned deep orange. The mixture was stirred at that temperature for 20 minutes and then cooled to −78° C. A precooled (−78° C.) solution of ketone 9 (0.004 g, 0.02 mmol) in anhydrous THF (100 μL) was added slowly. The mixture was stirred under argon atmosphere at −78° C. for 3 hours and at 0° C. for 18 hours. Ethyl acetate was added, and the organic phase was washed with brine, dried (Na$_2$SO$_4$) and evaporated. The residue was applied on a Sep-Pak cartridge, and eluted with 1% ethyl acetate/hexane to give the TBDMS-protected vitamin derivative (1 mg of unreacted ketone was recovered). The protected compound was further purified by HPLC (6.2 mm×25 cm zorbax-sil column, 4 mL/min) using a hexane/ethyl acetate (99.05:0.05) solvent system. Pure compound 11, (3.6 mg, 0.0067 mmol, 41%) was eluted at $R_v$=28 mL as a colorless oil. UV (in hexane): $\lambda_{max}$ 244, 252, 262 nm; $^1$H NMR (500 MHz, CDCl$_3$) δ: 6.21 and 5.87 (1H and 1H, each d, J=11.4 Hz), 4.97 and 4.92 (2H, each s), .4.43 (2H, m), 2.80 (1H, m), 2.53 (1H, dd, J=13.8 and 5.6 Hz), 2.452 (1H, dd, J=8.2 and 5.6 Hz), 1.71 (3H. s), 1.58 (3H, s), 0.90, 0.84 (9H and 9H, each s), 0.74 (3H, s), 0.027, 0.050, 0.068, 0.081 (Each 3H, each s).

The TBDMS-protected vitamin 11 (0.0036 g, 0.0067 mmol) was dissolved in anhydrous THF (500 μL) and treated with TBAF (66 μL, 18 mg, 0.067 mmol) and stirred at room temperature in the dark overnight. The solvent was removed in vacuo, and the residue was applied on a Sep-Pak cartridge, and eluted with 30% ethyl acetate/hexane to obtain the deprotected vitamin. The vitamin was further purified by HPLC (6.2 mm×25 cm zorbax-sil column, 4mL/min) using hexane/IPA (90/10) as solvent system. Pure vitamin 12 (1.3 mg, 0.0036 mmol, 61%) was eluted at $R_v$=26 mL. UV (in ethanol): $\lambda_{max}$ 243, 251, 261 nm; $^1$H NMR (500 MHz, CDCl$_3$) δ: 6.35 and 5.92 (1H and 1H, each d, J=11.3 Hz), 5.10 and 5.13 (1H and 1H, each s), 4.48 (2H, m), 2.88 (1H, dd, J=13.3 and 4.5 Hz), 2.78 (1H, dd, J=12.6 and 3.6 Hz), 2.58 (1H, dd, J=12.7 and 3.6 Hz), 2.13 (1H, m), 1.71 (3H, s), 1.25 (3H, s), 0.739 (3H, s); MS m/z (relative intensity):328 (M$^+$, 100), 313 (23), 310 (15), 295 (11), 277 (8), 243 (35), 229 (41), 149 (83); exact mass calculated for $C_{22}H_{32}O_2Na$ ([MNa]$^+$) is 351.2300, found 351.2304.

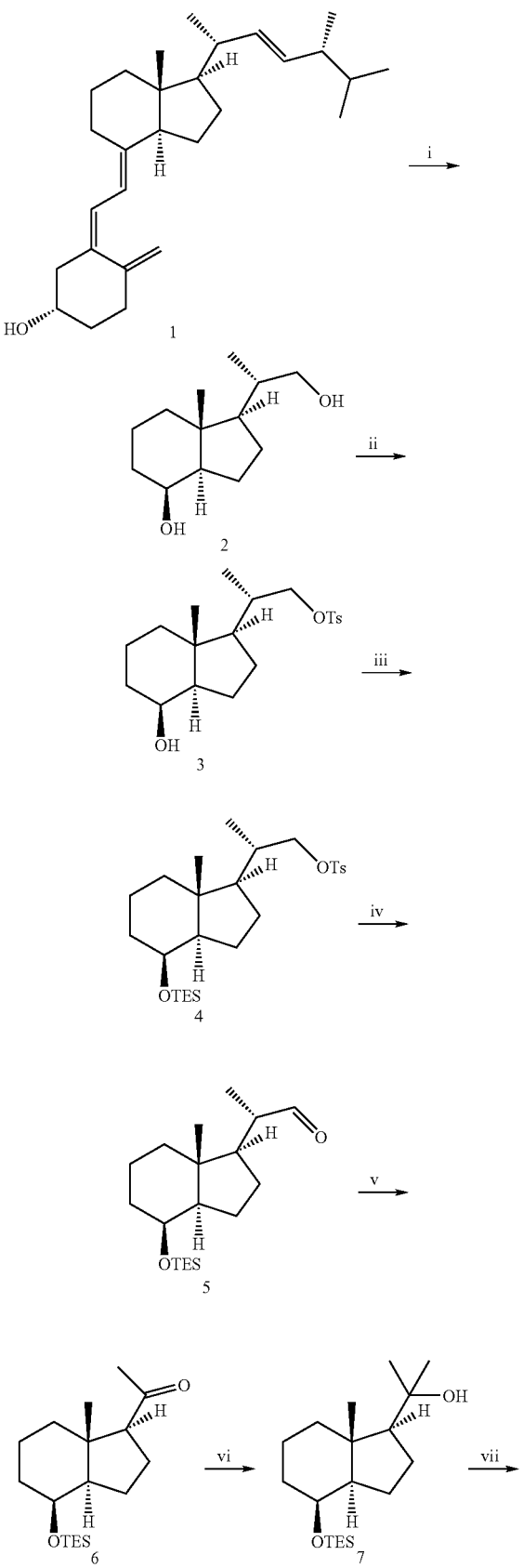

Scheme XIV

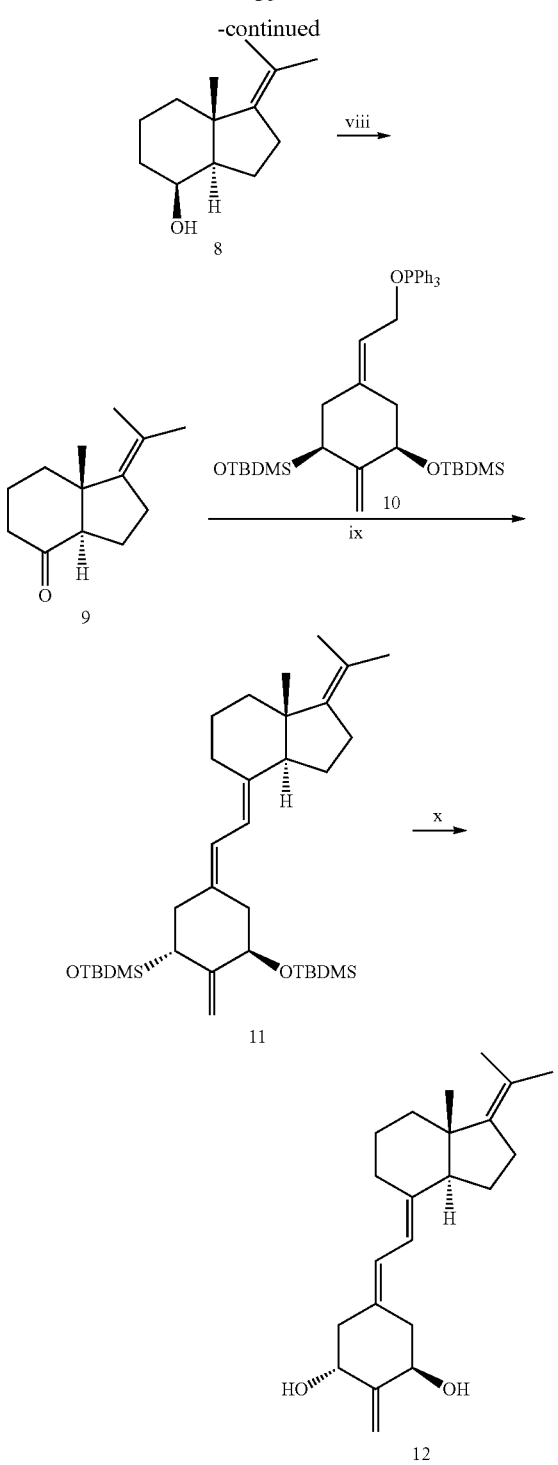

(i) O₃, C₅H₆N, MeOH; NaBH₄, 81%.
(ii) TsCl, C₅H₅N, 98%.
(iii) TESOTf, 2,6-lutidine, CH₂Cl₂, 84%.
(iv) NaHCO₃, DMSO, 76%.
(v) t-BuOK, t-BuOH, O₂, 62%.
(vi) MeMgBr, THF, 82%.
(vii) 2M HCl:THF (1:1), 46%.
(viii) PDC, CH₂Cl₂ 82%,
(ix) 10, PhLi, THF 41%,
(x) TBAF, THF, 61%

(i)O₃, C₅H₅N, MeOH: NaBH₄, 81%. (ii) TsCl, C₅H₅N, 98%.
(iii) TESOTf, 2,6-lutidine, CH₂Cl₂84%. (iv) NaHCO₃, DMSO, 76%. (v) t-BuOK t-BuOH, O₂, 62%. (vi) MeMgBr, THF, 82%. (vii) 2M HCl:THF (1:1). 46%. (viii) PDC, CH₂Cl₂ 82%, (ix) 10, PhLi, THF 41%, (x) TBAF, THF, 61%

Synthesis of 2-Methylene-18,19-dinor-(20S)-1α,25-dihydroxyvitamin D₃ (VD-03 or DP035)

2-Methyiene-18,19-dinor-(20S)-1α,25-dihydroxyvitamin D₃ (VD-03) was prepared as shown in Scheme XV and described below.

A. Des-A,B-23,24-dinorcholane-83,22-diol (1)

A solution of vitamin D₂ (5 g, 12.7 mmol) in methanol (400 mL) and pyridine (5 mL) was cooled to −78° C. while purging with argon. The argon stream was stopped and a stream of ozone was passed until a blue color appeared. The solution was purged with oxygen until the blue color disappeared, and the reaction was then treated with NaBH₄ (1.2 g, 32 mmol). After 20 minutes, a second portion of NaBH₄ (1.2 g, 32 mmol) was added and the reaction was allowed to warm to room temperature. A third portion of NaBH₄ (1.2 g, 32 mmol) was added, and the reaction mixture was stirred overnight at room temperature. The reaction was quenched with 70 mL of water and concentrated under vacuum. The residue was extracted with methylene chloride (3×100 mL). The organic phase was washed with 1M aqueous solution of HCl (2×100 mL), saturated aqueous solution of NaHCO₃ (100 mL), dried over anhydrous MgSO₄ and concentrated under vacuum. The residue was purified by flash chromatography (25% ethyl acetate/hexane) to yield 1.875 g (8.84 mmol, 70% yield) of diol 1 as white crystals. $[\alpha]_D$+56.0°(c 0.95, CHCl₃); mp 110-111° C.; ¹H NMR (400 MHz, CDCl₃) δ0.96 (3H, s), 1.03 (3H, d, J=6.6 Hz), 3.38 (1H, dd, J=10.5 Hz, J=6.8 Hz), 3.64 (1H, dd, J=10.5 Hz, J=3.2 Hz), 4.09 (1H, d, J=2.3 Hz); ¹³C NMR (100 MHz, CDCl₃) δ13.6, 16.6, 17.4, 22.6, 26.6, 33.5, 38.2, 40.2, 41.3, 52.3, 52.9, 67.8, 69.2; MS (EI) m/z 212 (2, M⁺), 194 (17), 179 (18), 163 (10), 135 (19), 125 (34), 111 (100); exact mass calculated for C₁₃H₂₂O ([M−H₂O]⁺) 194.1671, found 194.1665.

B. Des-A,B-80-(benzoyloxy)-23,24-dinorcholane-22-ol (2)

Diol 1 (1.85 g, 8.79 mmol) was dissolved in pyridine (30 mL) and DMAP (45 mg, 0.3 mmol) was added. The solution was cooled to 0° C. and then benzoyl chloride (3 mL, 3.6 g, 25 mmol) was added dropwise. The reaction mixture was kept at 5° C. for 24 hours. Methylene chloride (100 mL) was added, and the resulting mixture was washed with 5% aqueous solution of HCl (100 mL), saturated aqueous solution of CuSO₄ (2×80 mL), saturated aqueous solution of NaHCO₃ (80 mL) and water (100 mL). The extract was dried over anhydrous MgSO₄. Removal of the solvent in vacuo afforded a crude dibenzoate.

The crude dibenzoate (5.05 g) was added at room temperature to a solution of KOH (87%, 1.5 g, 23.3 mmol) in absolute ethanol (30 mL). The resulting reaction mixture was stirred at room temperature for 3 hours and 20 minutes. The reaction mixture was then quenched with ice and neutralized with 5% aqueous solution of HCl. The reaction mixture was extracted with methylene chloride (3×60 mL). The combined organic phases were washed with saturated aqueous solution of NaHCO₃ (50 mL) and dried over anhydrous MgSO₄. The drying agent was removed, and solvent was evaporated in vacuo. Pure product was obtained by column chromatography (25% ethyl acetate/hexane) to give 2.58 g (8.16 mmol, 93% yield from diol 1) of monobenzoate 2. $[\alpha]_D$+65.2° (c 1.15, CHCl$_3$); $^1$H NMR (400 MHz, CDCl$_3$) δ3.39 (1H, dd, J=10.4 Hz, J=6.8 Hz), 3.65 (1H, dd, J=10.5 Hz, J=3.2 Hz), 5.42 (1H, br d, J=22.2 Hz), 7.45 (2H, m), 7.56 (1H, m), 8.05 (2H, m); $^{13}$C NMR (100 MHz, CDCl$_3$) δ13.6, 16.6, 18.0, 22.7, 26.6, 30.5, 38.4, 39.8, 41.9, 51.4, 52.7, 67.7, 72.1, 128.3, 129.5, 130.8, 166.5; MS (EI) m/z 211 (4), 194 (52), 179 (11), 135 (41), 108 (23), 105 (100); exact mass (ESI) calculated for C$_{20}$H$_{28}$O$_3$Na ([M+Na]$^+$) 339.1936, found 339.1941.

C. Des-A,B-8β-(benzoyloxy)-23,24-dinorcholane-22-al (3)

Sulfur trioxide pyridine complex (7.02 g, 44.1 mmol) was added to a solution of alcohol 2 (2.32 g, 7.34 mmol) and triethylamine (5.15 mL, 3.71 g, 36.7 mmol) in anhydrous methylene chloride (30 mL) and DMSO (8 mL) at 0° C. The reaction mixture was stirred under argon for 20 minutes at 0° C. and then concentrated in vacuo. The residue was purified by column chromatography (5% ethyl acetate/hexane) to give 2.05 g (6.53 mmol, 90% yield) of aldehyde 3. $[\alpha]_D$+67.4° (c 0.95, CHCl$_3$); $^1$H NMR (400 MHz, CDCl$_3$) δ1.10 (3H, s), 1.15 (3H, d, J=6.8Hz), 5.44 (1H, brd, J=2.2Hz), 7.45 (2H, m), 7.56 (1H, m), 8.05 (2H, m), 9.60 (1H, d, J=3.2 Hz); $^{13}$C NMR (100 MHz, CDCl$_3$) δ13.6, 14.1, 18.1, 23.1, 26.2, 30.7, 39.8, 42.6, 49.2, 51.2, 51.5, 128.6, 129.7, 130.9, 133.0, 205.0; MS (EI) m/z 285 (3), 216 (3), 208 (9), 180 (17), 162 (47), 147 (21), 135 (46), 122 (16), 105 (100), 95 (22), 77 (49); exact mass (ESI) calculated for C$_{19}$H$_{25}$O$_2$ ([M–CHO]$^+$) 285.1855, found 285.1848.

D. (20R)-Des-A,B-8β-(benzoyloxy)-23,24-dinorcholane-22-ol (4)

To a solution of aldehyde 3 (2.05 g, 6.53 mmol) in methylene dichloride (25 mL), a 40% aqueous solution of n-Bu$_4$NOH (8.4 mL, 12.9 mmol) was added. The resulting reaction mixture was vigorously stirred overnight. Methylene dichloride (30 mL) was then added, and the mixture was washed with water (20 mL), dried over anhydrous MgSO$_4$ and concentrated under reduced pressure. The residue was purified by column chromatography (5% ethyl acetate/hexane) to give 1.50 g (4.78 mmol) of the mixture of diastereoisomeric aldehydes.

The mixture of aldehydes was dissolved in ethanol (15 mL) and NaBH$_4$ (350 mg, 9.2 mmol) was added. The resulting mixture was stirred for 30 minutes. The reaction mixture was quenched with saturated aqueous solution of NH$_4$Cl (30 mL). The mixture was extracted with methylene chloride (3×40 mL) and the combined organic phases were washed with water (30 mL), dried over anhydrous MgSO$_4$ and concentrated under reduced pressure. The residue was purified by column chromatography (5% ethyl acetate/hexane) to give 870 mg (2.75 mmol, 42% yield) of 4 and 437 mg (1.38 mmol, 21% yield) of 2. $[\alpha]_D$+50.00 (c 1.10, CHCl$_3$); $^1$H NMR (500 MHz, CDCl$_3$) δ0.97 (3H, d, J=6.7 Hz), 1.07 (3H, s), 3.48 (1H, dd, J=10.5 Hz, J=7.1Hz), 3.76 (1H, dd, J=10.6 Hz, J=3.5 Hz), 5.42 (1H, s), 7.45 (2H, m), 7.55 (1H, m), 8.05 (2H, m); $^{13}$C NMR (125 MHz, CDCl$_3$) δ13.9, 16.5, 18.0, 22.5, 26.4, 30.5, 37.5, 39.3, 41.7, 51.5, 52.7, 66.9, 72.0, 128.3, 129.5, 130.8, 166.5; MS (EI) m/z 316 (16, M$^+$), 301 (5), 285 (9), 242 (11), 194 (60), 147 (71), 105 (100); exact mass (ESI) calculated for C$_{20}$H$_{28}$O$_3$Na ([M+Na]$^+$) 339.1936, found 339.1948.

E. (20R)-Des-A,B-8β-(bzenzoyloxy)-23,24-dinor-22-(tosyloxy)cholane (5)

To a mixture of alcohol 4 (870 mg, 2.75 mmol), triethylamine (1.5 mL, 10.8 mmol) and DMAP (20 mg) in anhydrous methylene chloride (20 mL), was added tosyl chloride (710 mg, 3.73 mmol) at 0° C. The reaction mixture was allowed to stand at room temperature for 16 hours. Methylene chloride (100 mL) was then added, and the mixture was washed with saturated aqueous solution of NaHCO$_3$ (2×50 mL), dried over anhydrous MgSO$_4$, and concentrated under reduced pressure. The residue was purified by column chromatography (5% ethyl acetate/hexane) to give 1162 mg (2.47 mmol, 90% yield) of 5. $[\alpha]_D$+14.20 (c 0.95, CHCl$_3$); mp. 100-102° C.; $^1$H NMR (500 MHz, CDCl$_3$) δ0.90 (3H, d, J=6.6 Hz), 0.98 (3H, s), 2.46 (3H, s), 3.83 (1H, dd, J=9.2 Hz, J=7.2 Hz), 4.15 (1H, dd, J=9.3 Hz, J=3.3 Hz), 7.35 (2H, d, J=8.1Hz), 7.44 (2H, m), 7.55 (1H, m), 7.80 (2H, d, J=8.1 Hz), 8.02 (2H, m); $^{13}$C NMR (125 MHz, CDCl$_3$) δ13.9, 16.6, 17.9, 21.6, 22.3, 26.3, 30.4, 34.8, 39.1, 41.6, 71.8, 74.0, 127.9, 128.4, 129.5, 129.7, 130.7, 132.8, 133.1, 144.6, 166.7; MS (EI) m/z 365 (12), 348 (61), 193 (9), 176 (32), 161 (13), 134 (19), 105 (100), 91 (17), 77 (20); exact mass (ESI) calculated for C$_{27}$H$_{34}$O$_5$SNa ([M+Na]$^+$) 493.2025, found 493.2032.

F. (20S)-Des-A,B-cholestan-8β-ol (7)

Magnesium turnings (4.41 g, 184 mmol) were stirred with a magnetic stir bar overnight under argon. Anhydrous THF (50 mL) and 1-chloro-3-methylbutane (11 mL, 90.8 mmol) were then added. The mixture was refluxed for 6 hours. The resulting solution of Grignard reagent 6 was then added via cannula to a stirred solution of 5 in anhydrous THF (15 mL) at –78° C. followed by addition of a solution of dilithium tetrachlorocuprate (620 mg, 2.73 mmol) in anhydrous THF (27 mL). The cooling bath was removed, and the reaction mixture was stirred overnight. The reaction mixture was poured into a stirred mixture of ice (15 mL) and a saturated aqueous solution of NH$_4$Cl (40 mL). The mixture was then extracted with ethyl acetate (3×100 mL), washed with water and dried over anhydrous Na$_2$SO$_4$. The residue was purified by column chromatography (5 to 25% ethyl acetate/hexane) to give 389 mg (1.46 mmol, 58% yield) of 7. $[\alpha]_D$+9.60 (c 1.15, CHCl$_3$); $^1$H NMR (500 MHz, CDCl$_3$) δ0.82 (3H, d, J=6.6 Hz), 0.87 (6H, d, J=6.6 Hz), 0.93 (3H, s), 4.07 (1H, s); $^{13}$C NMR (125 MHz, CDCl$_3$) μ13.8, 17.5, 18.5, 22.4, 22.5, 22.6, 22.7, 24.0, 27.1, 28.0, 29.7, 33.6, 34.8, 35.5, 39.4, 40.3, 41.9, 52.7, 56.3, 69.5; MS (EI) m/z266 (45, M$^+$), 251 (19), 233 (8), 177 (9), 163 (11), 152 (20), 135 (30), 125 (37), 111 (100); exact mass calculated for C$_{18}$H$_{34}$O 266.26310, found 266.2623.

G. (20S)-Des-A,B-cholestan-8β-yl nitrite (8)

A solution of 7 (185 mg, 0.69 mmol) in chloroform (5 mL) was treated with tert-butyl nitrite (1 mL) for 1 hour in darkness. Benzene (10 mL) was then added and solvents were removed under reduced pressure, protecting the mixture from light. $^1$H NMR (500 MHz, CDCl$_3$) δ0.76 (3H, s), 0.81 (3H, d, J=6.5 Hz), 0.87 (6H, d, J=6.6 Hz), 5.78 (1H, s); $^{13}$C NMR (125 MHz, CDCl$_3$) δ13.1, 17.9, 18.5, 22.2, 22.6, 22.7, 23.9, 27.1, 28.0, 31.5, 34.9, 35.3, 39.3, 39.7, 41.9, 51.9, 56.0.

H. (18E)-(20S)-18-(Hydroxyimino)-des-A,B-cholestan-8β-ol (9)

Crude nitrite 8 was dissolved in anhydrous benzene (150 mL) and irradiated in an apparatus consisting of a Pyrex vessel with a watercooled immersion well and Hanovia high-pressure mercury arc lamp equipped with Pyrex filter. A slow stream of argon was passed through the solution and the temperature was maintained at about 10° C. Reaction progress was monitored by TLC. After 30 minutes, reaction was complete. Benzene was removed under reduced pressure, and the residue was dissolved in 2-propanol (5 mL) and refluxed for 2 hours, cooled, and allowed to stand overnight to accomplish isomerization of a nitroso compound to an oxime. The solvent was then evaporated, and the residue was purified on Waters silica gel Sep-Pack cartridge (25% ethyl acetate/hexane) to give 102 mg (0.35 mmol, 51% yield from 7) of the oxime 9. $[\alpha]_D$+8.2° (c 0.80, $CHCl_3$); $^1H$ NMR (400 MHz, $CDCl_3$) δ0.84 (3H, d, J=6.3 Hz), 0.87 (6H, d, J=6.6 Hz), 2.20 (1H, br d, J=13.1Hz), 4.04 (1H, br d, J=2.6 Hz), 7.33 (1H, s), 10.8 (1H, br s); $^{13}C$ NMR (100 MHz, $CDCl_3$) δ17.5, 18.6, 21.8, 22.6, 22.7, 24.1, 27.2, 28.0, 34.3, 35.0, 35.6, 39.3, 49.5, 52.6, 56.7, 67.6, 152.2; MS (EI) m/z 295 (2, $M^+$), 278 (28), 260 (20), 245 (8), 206 (19), 183 (38), 165 (13), 148 (15), 121 (100); exact mass calculated for $C_{18}H_{33}NO_2Na$ ($[M+Na]^+$) 318.2409, found 318.2412.

I. (20S)-8β-(Acetoxy)-des-A,B-cholestan-18-nitrile (10)

A solution of 9 (100 mg, 0.34 mmol) in acetic anhydride (5 mL) was refluxed for 1.5 hours. The reaction mixture was cooled, poured carefully into ice and extracted with benzene (3×40 mL). The combined organic phases were washed with saturated aqueous solution of $NaHCO_3$ (2×40 mL), water (30 mL), dried over anhydrous $Na_2SO_4$, and evaporated. The residue was purified on a Waters silica gel Sep-Pack cartridge (5% ethyl acetate/hexane) to give 91 mg (0.28 mmol, 84% yield) of 9. $[\alpha]_D$−26.4° (c 0.75, $CHCl_3$); IR ($CHCl_3$) 2228, 1741, 1241; $^1H$ NMR (500 MHz, $CDCl_3$) δ0.87 (6H, d, J=6.6 Hz), 0.91 (3H, d, J=6.6 Hz), 2.15 (3H, s), 2.46 (1H, br d, J=3.2 Hz), 5.20 (1H, s); $^{13}C$ NMR (125 MHz, $CDCl_3$) δ17.9, 18.8, 22.6, 22.7, 23.3, 23.8, 27.1, 28.0, 29.9, 35.6, 36.2, 36.3, 39.1, 45.6, 51.9, 54.1, 68.7, 121.2, 171.0; MS (EI) m/z 319 (18, $M^+$), 304 (10), 290 (3), 277 (84), 259 (100), 244 (54), 234 (27), 216 (40), 202 (33), 188 (60), 174 (47), 147 (39), 134 (34), 121 (95); exact mass (ESI) calculated for $C_{20}H_{33}NO_2Na$ ($[M+Na]^+$) 342.2409, found 342.2413.

J. (20S)-Des-A,B-cholestan-18-nitrile-8β-ol (11)

Compound 10 (90 mg, 0.28 mmol) was dissolved in methanol (3 mL) and treated with 5% solution of NaOMe in methanol (3 mL) for 2 hours. The reaction mixture was quenched with a saturated aqueous solution of $NH_4Cl$ (5 mL), water (10 mL), extracted with methylene chloride (5×40 mL), dried over anhydrous $Na_2SO_4$, and evaporated. The residue was purified on a Waters silica gel Sep-Pack cartridge (20% ethyl acetate/hexane) to give 73 mg (0.26 mmol, 94% yield) of 10. $[\alpha]_D$−6.1 (c 0.75, $CHCl_3$); IR ($CHCl_3$) 3486, 2228; $^1H$ NMR (500 MHz, $CDCl_3$) δ0.87 (6H, d, J=6.6 Hz), 0.92 (3H, d, J=6.7 Hz), 2.43 (1H, br d, J=3.1 Hz), 4.10 (1H, s); $^{13}C$ NMR (125 MHz, $CDCl_3$) δ17.9, 22.6, 22.7, 22.9, 23.9, 27.1, 28.0, 32.8, 35.7, 36.2, 36.3, 44.7, 53.4, 54.2, 122.5; MS (EI) m/z 277 (28, $M^+$), 262 (34), 259 (18), 248 (16), 244 (24), 220 (30), 216 (18), 206 (100); exact mass calculated for $C_{18}H_{31}NO$ 277.2496, found 277.2395.

K. (20S)-Des-A,B-18-norcholestan-8β-ol (12)

To a stirred mixture of potassium (110 mg, 2.82 mmol) in HMPA (280 μL, 1.62 mmol) and diethyl ether (700 μL) a solution of 11 (70 mg, 0.25 mmol) in tert-butyl alcohol (65 μL) and diethyl ether (250 μL) was added dropwise at 0° C. under argon. The mixture was allowed to warm to room temperature and stirred for 5 hours. The remaining potassium was removed, and a few drops of 2-propanol and benzene (20 mL) were added. The organic phase was washed with water (10 mL), dried over anhydrous $Na_2SO_4$ and concentrated under reduced pressure. The residue was purified on Waters silica gel Sep-Pack cartridge (10% ethyl acetate/hexane) to give 54 mg (0.21 mmol, 85% yield) of 12. $[\alpha]_D$+32.6 (c 0.90, $CHCl_3$); $^1H$ NMR (500 MHz, $CDCl_3$) δ0.78 (3H, d, J=6.8 Hz), 0.87 (6H, d, J=6.6 Hz), 4.06 (1H, s); $^{13}C$ NMR (125 MHz, $CDCl_3$) δ14.7, 20.2, 22.7, 22.9, 24.7, 25.3, 28.0, 30.8, 33.1, 33.5, 36.3, 39.3, 39.7, 48.6, 50.3, 67.9; MS (EI) m/z 252 (6, $M^+$), 234 (21), 219 (23), 209 (26), 191 (8), 179 (4), 167 (13), 149 (89), 139 (47), 122 (90), 107 (35), 95 (80), 79 (87), 67 (88), 58 (100); exact mass calculated for $C_{17}H_{32}O$ 252.2453, found 252.2448.

L. (20S)-Des-A,B-25-hydroxy-18-norcholestane-8-one (13)

To a stirred solution of $RuCl_3 \times H_2O$ (10 mg, 0.05 mmol) and $NaIO_4$ (227 mg, 1.06 mmol) in water (1 mL), was added a solution of 12 (74 mg, 0.29 mmol) in tetrachloromethane (0.75 mL) and acetonitrile (0.75 mL). The reaction mixture was vigorously stirred for 3 days. A few drops of 2-propanol and water (10 mL) were then added. Reaction products were extracted with methylene chloride (3×20 mL). The organic phase was dried over anhydrous $Na_2SO_4$ and concentrated under reduced pressure. The residue was purified on a Waters silica gel Sep-Pack cartridge (10 to 30% ethyl acetate/hexane) to give 13 mg (0.05 mmol, 17% yield) of 13. $^1H$ NMR (400 MHz, $CDCl_3$) δ0.78 (3H, d, J=6.7 Hz), 1.22 (6H, s), 2.01 (1H, br d, J=12.3 Hz); $^{13}C$ NMR (100 MHz, $CDCl_3$) δ14.3, 21.3, 22.2, 22.6, 27.8, 29.3, 29.7, 33.0, 36.5, 41.6, 44.1, 49.6, 51.0, 58.0, 71.0, 212.0; MS (EI) m/z 264 (3), 248 (57), 233 (19), 215 (4), 208 (15), 163 (29), 137 (100); exact mass (ESI) calculated for $C_{17}H_{30}O_2Na$ ($[M+Na]^+$) 289.2144, found 289.2136.

M. (20S)-25-[(Triethylsilyl)oxy]-des-A,B-18-norcholestane-8-one (14)

To a stirred solution of 13 (12 mg, 45 μmol) and 2,6-lutidine (13 μl, 100 μmol) in anhydrous methylene dichloride (250 μl) triethylsilyl trifluoromethanesulfonate was added dropwise at −50° C. under argon. After 20 minutes, a few drops of wet methylene chloride and water (7 mL) were added. The reaction mixture was extracted with methylene chloride (3×7 mL). The organic phase was dried over anhydrous $Na_2SO_4$ and concentrated under reduced pressure. The residue was purified on a Waters silica gel Sep-Pack cartridge (3% ethyl acetate/hexane) and on HPLC (5% ethyl acetate/hexane, 4 mL/min., Zorbax-silica 10×250 mm) to give 13 mg (34 μmol, 76% yield) of 14. $^1H$ NMR (500 MHz, $CDCl_3$) δ0.56 (6H, q, J=7.9 Hz), 0.77 (3H, d, J=6.8 Hz), 0.94 (9H, t, J=7.9 Hz), 1.19 (6H, s); $^{13}C$ NMR (125 MHz, $CDCl_3$) δ6.8, 7.1, 14.3, 21.4, 22.2, 22.7, 27.8, 29.7, 29.8, 29.9, 32.9, 36.4, 41.6, 45.2, 49.6, 51.1, 58.0, 73.4, 212.1; MS (EI) m/z 365 (8), 351 (100), 322 (6), 239 (2), 231 (25), 220 (4), 205 (15), 189 (4), 173 (92); exact mass (ESI) calculated for $C_{23}H_{44}O_2SiNa$ ($[M+Na]^+$) 403.3008, found 403.2995.

N. 2-Methylene-18,19-dinor-(20S)-1α,25-dihydroxyvitamin $D_3$ (VD-03 or DP035) (17)

To a stirred solution of phosphine oxide 15 (46 mg, 79 μmol) in anhydrous THF (600 μL), was added a 1.5 M solution of phenyl lithium in THF (63 μl, 95 μmol) at −20° C. under argon. The mixture was stirred for 20 minutes and then cooled to −78° C. A precooled solution of 14 (13 mg, 34 μmol) in anhydrous THF (300 μl) was added via cannula and the reaction mixture was stirred for 3 hours at −78° C. The reaction mixture was then stirred at 4° C. overnight. Ethyl acetate was then added and the organic phase was washed with brine, dried over anhydrous Na$_2$SO$_4$, and concentrated under reduced pressure. The residue was purified on a Waters silica gel Sep-Pack cartridge (hexane to 2% ethyl acetate/hexane) and then on HPLC (0.05% 2-propanol/hexane, 4 mL/min., Zorbax-silica 10×250 mm) to give 13.5 mg (18 μmol, 53% yield) of TBDMS-protected vitamin D$_3$ 16. UV (hexane) λ$_{max}$=242, 251, 261 nm; $^1$H NMR (500 MHz, CDCl$_3$) δ0.06 (3H, s), 0.11 (3H, s), 0.17 (3H, s), 0.19 (3H, s), 0.56 (6H, q, J=8.0 Hz), 0.76 (3H, d, J=6.7 Hz), 0.94 (9H, t, J=8.0 Hz), 2.18 (1H, dd, J=12.5 Hz, J=8.1 Hz), 2.86 (1H, brd, J=13.8 Hz), 4.42 (2H, m), 4.93 (1H, s), 4.96 (1H, s), 5.92 (1H, d, J=11.1 Hz), 6.19 (1H, d, J=11.1 Hz); $^{13}$C NMR (125 MHz, CDCl$_3$) δ-5.1,-4.9,-4.9,-4.8, 6.8, 7.1, 18.2, 18.2, 22.3, 23.1, 25.8, 25.8, 27.8, 29.0, 29.7, 29.8, 29.9, 31.3, 33.6, 36.5, 38.7, 45.3, 47.5, 49.0, 50.2, 52.3, 71.9, 72.3, 73.4, 106.3, 113.7, 122.4, 132.9, 143.8, 152.9; MS (EI) m/z 687 (6), 628 (2), 612 (100), 583 (6), 555 (4), 480 (29), 366 (44); exact mass calculated for C$_{40}$H$_{75}$O$_3$Si$_3$ ([M−t-Bu]$^+$) 687.5024, found 687.5028.

16 (13 mg, 17 μmol) was dissolved in anhydrous THF (5 mL). A 1M solution of tetrabutylammonium fluoride in THF (260 μl, 260 μmol) was then added dropwise followed by addition of activated molecular sieves 4A (200 mg). The reaction mixture was stirred under argon for 2 hours. The solvent was then removed under reduced pressure and the residue was purified on a Waters silica gel Sep-Pack cartridge (40 to 50% ethyl acetate/hexane). Crude 17 was then purified on HPLC (20% 2-propanol/hexane, 4 mL/min., Zorbax-silica 10×250 mm) to give 3.8 mg (9.5 pmol, 56% yield) of 17 at Rt=5.58 minutes; UV (EtOH) λ$_{max}$=242, 250, 260 nm; $^1$H NMR (500 MHz, CDCl$_3$) δ0.77 (3H, d, J=6.6 Hz), 1.21 (6H, s), 2.58 (1H, dd, J=13.2 Hz, J=3.9 Hz), 2.81 (1H, dd, J=13.3 Hz, J=4.4 Hz), 2.87 (1H, brd, J=13.9 Hz), 4.48 (2H, m), 5.10 (1H, s), 5.11 (1H, s), 5.97 (1H, d, J=11.3 Hz), 6.35 (1H, d, J=11.3 Hz); MS (EI) m/z 402 (39, M$^{+}$), 384 (41), 366 (14), 351 (11), 299 (58), 231 (36), 142 (58), 69 (100); exact mass calculated for C$_{26}$H$_{42}$O$_3$ 402.3134, found 402.3121.

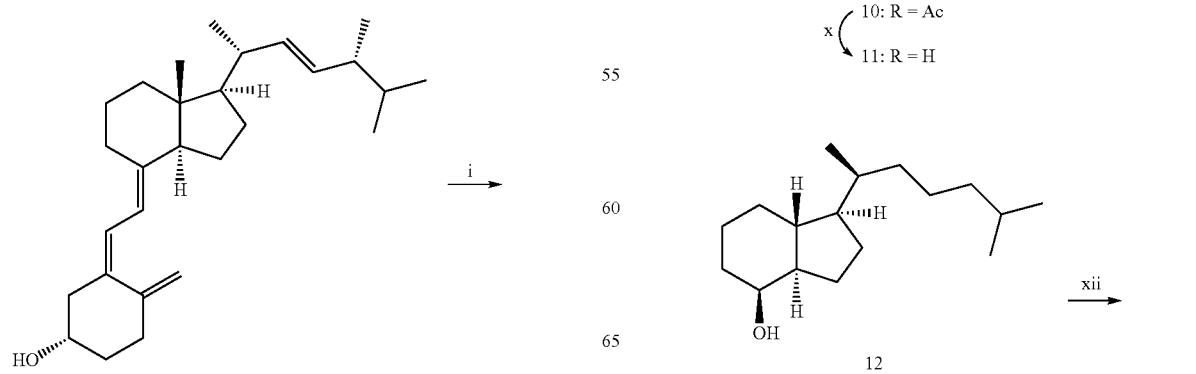

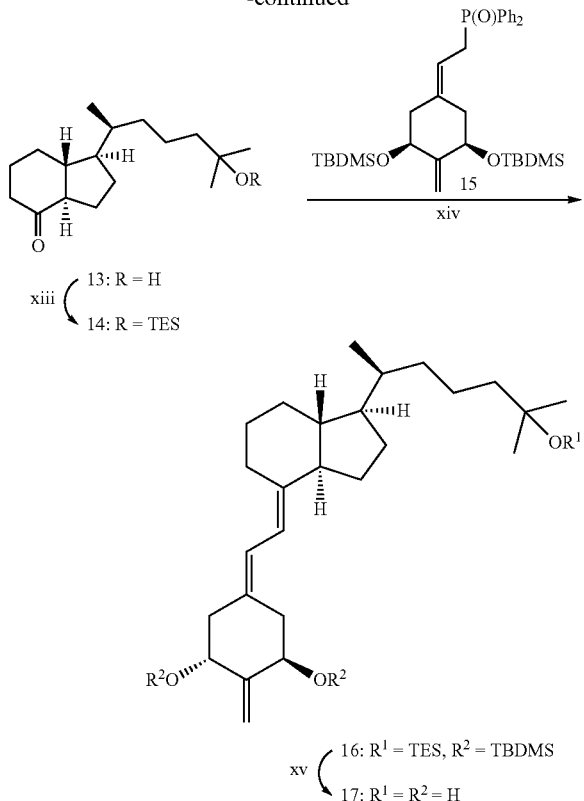

(i) O₃, MeOH, py; NaBH₄, 70%.
(ii) BzCl, DMAP, py; KOH/EtOH, 93%.
(iii) SO₃/py, DMSO, Et₃N, CH₂Cl₂, 90%.
(iv) 40% aq. n-Bu₄NOH, CH₂Cl₂; NaBH₄, EtOH, 42%.
(v) TsCl, Et₃N, DMAP, CH₂Cl₂, 90%.
(vi) 6, Li₂CuCl₄, THF, 58%.
(vii) t-BuONO, CHCl₃.
(viii) hv, C₆H₆; i-PrOH, 51% (from 7).
(ix) Ac₂O, 94%.
(x) MeONa/MeOH, 91%.
(xi) K, HMPA, t-BuOH, 78%.
(xii) RuCl₃·H₂O, NaIO₄, CCl₄, CH₃CN, H₂O, 17%.
(xiii) TESOTf, 2,6-lutidine, CH₂Cl₂, 83%.
(xiv) 15, PhLi, THF, 53%.
(xv) TBAF, molecular sieves 4A, THF, 56%.

Synthesis of 1AGR, 1AGS, and F-Wit

1AGR, 1AGS, and F-Wit were prepared using a modified phosphine oxide as shown in Schemes XVIA, XVIB, and XVIC and described below. Referring first to Scheme XVIA, the starting bicyclic lactone 1 was obtained from commercial (−)-quinic acid as described previously by Hanessian et al., *J. Org. Chem.* 62, 465 (1997).

Synthesis of F-Wit

A. (1R,3R,4S,5R)-1,4-Dihydroxy-3-[(tert-butyldimethylsilyl)oxy]-6-oxa-bicyclo[3.2.1]octan-7-one (2)

To a stirred solution of lactone 1 (1.80 g, 10.34 mmol) and imidazole (2.63 g, 38.2 mmol) in anhydrous DMF (14 mL) was added t-butyldimethylsilyl chloride (1.80 g, 11.9 mmol) at 0° C. The mixture was stirred at 0° C. for 30 minutes and 1 hour at room temperature, poured into water, and extracted with ethyl acetate and ether. The organic layer was washed several times with water, dried (MgSO₄), and evaporated to give a colorless crystalline residue which was crystallized from hexane/ethyl acetate to give 2.12 g of pure 2. The mother liquors were evaporated and purified by flash chromatography. Elution with hexane/ethyl acetate (8:2) gave additional quantity of crystalline monoether 2 (0.14 g, overall yield 76%) and some quantity of crystalline isomeric (3-OH, 4-OTBDMS) ether (0.10 g, 3%). 2: m.p. 90-94° C. (from hexane); $[\alpha]^{24}_D$ −440 (c 1.00 CHCl₃); ¹H NMR (500 MHz, CDCl₃) δ0.095 (6H, s, 2×SiCH₃), 0.901 (9H, s, Si-t-Bu), ca. 2.0 (2H, br m, 2α- and 2β-H), 2.29 (1H, ddd, J=11.6, 6.0, 2.6 Hz, 8β-H), 2.63 (1H, d, J=11.6 Hz, 8α-H), 3.89 (1H, ddd, J=10.4, 7.0,4.5 Hz, 3β-H), 3.98 (1H, t, J=4.6 Hz, 4β-H), 4.88 (1H, dd, J=6.0, 4.8 Hz, 5α-H); ¹³C NMR (125 MHz) δ−5.0 (Si—CH₃), −4.7 (Si—CH₃), 17.9 [C(CH₃)₃], 25.6 [C(CH₃)₃], 36.4 (C₈), 40.2 (C₂), 65.8 (C₄), 67.0 (C₃), 71.9 (C₁), 76.3 (C₅), 177.9 (C=O), MS (EI) m/z (relative intensity) 288(M⁺, 1), 231 (41), 213 (21), 185 (85), 75 (100); HRMS (ESI), exact mass calcd for C₁₃H₂₄O₅SiNa (M⁺+Na) 311.1291, measured 311.1287; Anal. Calcd for C₁₃H₂₄O₅Si: C, 54.14, H, 8.39. Found: C, 53.94, H, 8.36.

B. (1R,3R,5R)-3-[(tert-Butyldimethylsilyl)oxy]-1-hydroxy-6-oxa-bicyclo[3.2.1]octane-4,7-dione (3)

To a stirred suspension of Dess-Martin periodinane reagent (6.60 g, 15.5 mmol) in anhydrous CH₂Cl₂ (100 mL) was added compound 2 (3.86 g, 13.4 mmol). The mixture was stirred at room temperature for 18 hours, poured into water, and extracted with ethyl acetate. The organic layer was washed several times with water, dried (MgSO₄), and evaporated to give an oily residue which slowly crystallized on cooling (3.67 g, 95%). TLC indicated high purity of the obtained ketone 3 which could be used in the next step without further purification. Analytical sample was obtained by recrystallization from hexane. 3: m.p. 92-95° C.; ¹H NMR (400 MHz, CDCl₃) δ0.040 and 0.133 (3H and 3H, each s, 2×SiCH₃), 0.895 (9H, s, Si-t-Bu), 2.15 (1H, dd, J=12.4, 10.4 Hz, 2α-H), 2.42 (1H, d, J=12.5 Hz, 8α-H), 2.54 (1H, ddd, J=12.4, 9.0, 3.9 Hz, 2β-H), 2.86 (1H, ddd, J=12.5, 6.7, 3.9 Hz, 8β-H), 4.54 (1H, dd, J=10.4, 9.0 Hz, 3β-H), 4.73 (1H, d, J=6.7 Hz, 5α-H); ¹³C NMR (125 MHz) δ−5.6 (Si—CH₃), −4.8 (Si—CH₃), 18.2 [C(CH₃)₃], 25.6 [C(CH₃)₃], 42.3 (C₈), 43.0 (C₂), 70.3 (C₃), 71.8 (C₁), 78.7 (C₅), 177.1 (C=O), 202.4 (C₄); MS (EI) m/z (relative intensity) no M⁺, 271 (M⁺−CH₃, 4), 229 (92), 201 (28), 157 (100); HRMS (ESI) exact mass calcd for C₉H₁₃O₅Si (M⁺−t-Bu) 229.0532, measured 229.0539; Anal. Calcd for C₁₃H₂₂O₅Si×H₂O: C, 51.29, H, 7.95. Found: C, 51.09, H, 7.90.

C. (1R,3R,5R)-1-Acetoxy-3-[(tert-butyldimethylsilyl)oxy]-6-oxa-bicyclo[3.2.1]octane-4,7-dione (4)

A solution of hydroxy ketone 3 (1.64 g, 5.8 mmol) in anhydrous pyridine (12 mL) and acetic anhydride (5.5 mL) was stirred for 3 hours at room temperature. The reaction mixture was then poured into water and extracted with ethyl acetate. The organic layer was washed with saturated NaHCO₃, saturated CuSO₄ and water, dried (MgSO₄), and evaporated to give an oily residue which was dissolved in hexane/ethyl acetate (8:2) and filtered through short path of silica gel. Evaporation of solvents gave pure crystalline acetate 4 (1.51 g, 81%). Analytical sample was obtained by recrystallization from hexane/ethyl acetate. 4: m.p. 134-7° C.; $[\alpha]^{24}_D$ −78° (c 1.00 CHCl₃); ¹H NMR (400 MHz, CDCl₃) δ0.046 and 0.141 (3H and 3H, each s, 2×SiCH₃), 0.901 (9H, s, Si-t-Bu), 2.17 (3H, s, CH₃CO), 2.28 (1H, dd, J=12.2, 10.4 Hz, 2α-H), 2.32 (1H, d, J=12.1 Hz, 8α-H), 2.65 (1H, ddd, J=12.2, 8.8, 3.9 Hz, 2β-H), 3.56 (1H, ddd, J=12.1, 6.9, 3.9 Hz, 8β-H), 4.58 (1H, dd, J=10.4, 8.8 Hz, 3β-H), 4.80 (1H, d, J=6.9 Hz, 5α-H); $^{13}$C NMR (125 MHz) δ-5.8 (Si—CH$_3$), -4.9 (Si—CH$_3$), 18.2 [C(CH$_3$)$_3$], 20.9 (CH$_3$—C═O), 25.6 [C(CH$_3$)$_3$], 38.3 (C$_8$), 40.3 (C$_2$), 70.4 (C$_3$), 75.3 (C$_1$), 78.4 (C$_5$), 169.1 (CH$_3$—C═O), 171.5 (C═O), 201.8 (C$_4$); MS (EI) m/z (relative intensity) 328 (M$^+$, 6), 271 (100), 256 (38), 229 (54), 211 (53); HRMS (ESI) exact mass calcd for C$_{11}$H$_{15}$O$_6$Si (M$^+$-t-Bu) 271.0638, measured 271.0646; Anal. Calcd for C$_{15}$H$_{24}$O$_6$Si: C, 54.86, H, 7.37. Found: C, 54.88, H, 7.37.

D. [3-(Methoxymethoxy)propyl]triphenylphosphonium bromide (A)

To a solution of bromomethyl methyl ether (1.3 mL, 16 mmol) and N,N-diisopropylethylamine (4.5 mL, 27.7 mmol) in anhydrous CH$_2$Cl$_2$ (50 mL) at 0° C. was added 3-bromo-1-propanol (1.0 mL, 11 mmol), and the mixture was stirred at 0° C. for 1 hour and then at room temperature for 20 hours. The reaction mixture was poured into 1N HCl (150 mL), and the organic phase was separated and the water phase was extracted with CH$_2$Cl$_2$. The combined organic phases were washed with water and dilute NaHCO$_3$, dried (MgSO$_4$), and evaporated to give a yellowish oil. The residue was purified by flash chromatography. Elution with hexane/ethyl acetate (95:5) afforded pure oily 1-bromo-3-(methoxymethoxy)propane (1.12 g, 55%): $^1$H NMR (400 MHz, CDCl$_3$) δ2.13 (2H, m, CH$_2$—CH$_2$—CH$_2$), 3.37 (3H, s, O—CH$_3$), 3.53 (2H, br t, J=6.5 Hz, Br—CH$_2$), 3.67 (2H, br t, J=5.8 Hz, CH$_2$—CH$_2$—O), 4.63 (2H, s, O—CH$_2$—O).

To a solution of 1-bromo-3-(methoxymethoxy)propane (0.46 g, 2.5 mmol) in anhydrous toluene (1.5 mL) was added triphenylphosphine (0.71 g, 2.7 mmol) under argon with stirring. The mixture was heated at 100° C. for 20 hours and cooled to room temperature. The liquid was decanted and the solid residue was grounded with spatula, filtered and washed several times with ether. After drying overnight in a vacuum dessicator, colorless crystals of phosphonium salt A (0.98 g, 88%) could be used in the Wittig reaction without further purification. A: $^1$H NMR (500 MHz, CDCl$_3$) δ1.96 (2H, m, CH$_2$—CH$_2$—CH$_2$), 3.31 (3H, s, O—CH$_3$), 3.85 (2H, br t, J=5.6 Hz, CH$_2$—CH$_2$—O), 4.00 (2H, m, P—CH$_2$), 4.60 (2H, s, O—CH$_2$—O), 7.70, 7.79 and 7.86 (6H, 3H and 6H, each m, Ar—H); Anal. Calcd for C$_{23}$H$_{26}$O$_2$PBr: C, 62.03, H, 5.88, Br, 17.94. Found: C, 61.87, H, 5.77, Br, 17.89.

E. [(E)- and (Z)-(1R,3R,5R)-1-Acetoxy-3-[(tert-butyldimethylsilyl)oxy]-6-oxa-4-[3'-(methoxymethoxy)propylidene]bicylo[3.2.1]octan-7-one (5a and 5b)

To the phosphonium bromide A (420 mg, 0.94 mmol) in anhydrous THF (5 mL) at 0° C. was added dropwise n-BuLi (1.6 M in hexanes, 1.12 mL, 1.8 mmol) under argon with stirring. After 5 minutes, another portion of A was added (420 mg, 0.94 mmol), and the solution was stirred at 0° C. for 10 minutes and then at room temperature for 20 minutes. The orange-red mixture was cooled to –78 ° C. and siphoned in 2 equal portions (30 minute interval) to a solution of keto lactone 4 (300 mg, 0.91 mmol) in anhydrous THF (8 mL). The reaction mixture was stirred at –78° C. and stopped by addition of brine containing 1% HCl (3 hours after addition of the first portion of the Wittig reagent). Ethyl acetate (9 mL), benzene (6 mL), ether (3 mL), sat. NaHCO$_3$ (3 mL), and water (3 ml) were added, and the mixture was vigorously stirred at room temperature for 18 hours. The organic phase was separated, washed with brine, dried (MgSO$_4$), and evaporated. The oily residue (consisting mainly with isomeric 5a and 5b in the ratio of ca. 5:1) was separated by flash chromatography on silica. Elution with hexane/ethyl acetate (85:15) resulted in partial separation of products: 29 mg of 5b, mixture of 5a and 5b (85 mg) and pure 5a (176 mg; total yield 77%). Rechromatography of the mixed fractions resulted in almost complete separation of the products.

5a: [α]$^{24}_D$ –63° (c 0.60 CHCl$_3$); $^1$H NMR (500 MHz, CDCl$_3$) δ0.074 (6H, s, 2×SiCH$_3$), 0.914 (9H, s, Si-t-Bu), 2.13 (3H, s, OCH$_3$), 2.00 (1H, br t, J=11.2, Hz, 2α-H), 2.10 (1H, d, J=10.8Hz, 8α-H), 2.34 (1H, ddd, J=11.7, 7.0, 2.9 Hz, 2β-H), 2.38 and 2.43 (1H and 1H, each m, ═C—CH$_2$), 3.31 (1H, ddd, J=10.8, 6.5, 2.9 Hz, 8β-H), 3.35 (3H, s, O—CH$_3$), 3.54 and 3.60 (1H and 1H, each m, CH$_2$—CH$_2$—O), 4.41 (1H, t, J=8.2 Hz, 3β-H), 4.60 (2H, s, O—CH$_2$—O), 5.52 (1H, d, J=6.5 Hz, 5α-H), 5.71 (1H, br t, J=7.1 Hz, ═CH); $^{13}$C NMR (125 MHz) δ–5.1 (Si—CH$_3$), -4.9 (Si—CH$_3$), 18.1 [C(CH$_3$)$_3$], 21.1 CH$_3$—C═O), 25.7 [C(CH$_3$)$_3$], 27.5 (CH$_2$—CH$_2$—C═), 40.5 (C$_8$), 41.5 (C$_2$), 55.2 (O—CH$_3$), 66.7 (O—CH$_2$—CH$_2$), 66.8 (C$_3$), 77.1 (C$_1$), 73.9 (C$_5$), 96.3 (O—CH$_2$—O), 121.9 (═C—CH$_2$), 136.8 (C$_4$), 169.1 (CH$_3$—C═O), 172.9 (C═O); MS (EI) m/z (relative intensity), no M$^+$, 383 (M$^+$-OCH$_3$, 3), 357 (10), 325 (44), 297 (12), 267 (15), 265 (40), 237 (89), 75 (100); HRMS (ESI) exact mass calcd for C$_{20}$H$_{34}$O$_7$SiNa (M$^+$+Na) 437.1972, measured 437.1975.

5b: $^1$H NMR (500 MHz, CDCl$_3$) δ0.108 and 0.125 (3H and 3H, each s, 2×SiCH$_3$), 0.912 (9H, s, Si-t-Bu), 2.13 (3H, s, OCH$_3$), 2.15 (1H, dd, J=12.6, 8.3 Hz, 2α-H), 2.31 (1H, d, J=10.8 Hz, 8α-H), 2.33 (1H, 2β-H overlapped with 8α-H), 2.67 and 2.73 (1H and 1H, each m, ═C—CH$_2$), 3.25 (1H, ddd, J=10.8, 6.3, 2.8 Hz, 8β-H), 3.36 (3H, s, O—CH$_3$), 3.55 (2H, m, CH$_2$—CH$_2$—O), 4.61 (2H, s, O—CH$_2$—O), 4.71 (1H, br t, J~7 Hz, 3β-H), 4.94 (1H, d, J=6.3 Hz, 5α-H), 5.64 (1H, dt, J=1.7, 7.1 Hz, ═CH); $^{13}$C NMR (125 MHz) δ–4.6 (Si—CH$_3$), -4.5 (Si—CH$_3$), 17.9 [C(CH$_3$)$_3$], 21.1 (CH$_3$—C═O), 25.7 [C(CH$_3$)$_3$], 27.8 (CH$_2$—CH$_2$—C═), 38.9 (C$_8$), 41.2 (C$_2$), 55.3 (O—CH$_3$), 67.1 (O—CH$_2$—CH$_2$), 67.2 (C$_3$), 77.1 (C$_1$), 81.8 (C$_5$), 96.4 (O—CH$_2$—O), 128.9 (═C—CH$_2$), 134.8 (C$_4$), 169.1 (CH$_3$—C═O), 173.0 (C═O); MS (EI) m/z (relative intensity), no M$^+$, 383 (M$^+$-OCH$_3$, 2), 357 (2), 325 (22), 297 (17), 267 (35), 265 (14), 237 (96), 75 (100); HRMS (ESI) exact mass calcd for C$_{20}$H$_{34}$O$_7$SiNa (M$^+$+Na) 437.1972, measured 437.1974.

F. [(E)-(1'R,3'R,5'R)-3-[(tert-Butyldimethylsilyl)oxy]-1',5-dihydroxy-4'-[3''-(methoxymethoxy)propylidene]cyclohexyl]methanol (7)

(a) To a stirred solution of compound 5a (165 mg, 0.40 mmol) in anhydrous ethanol (5 mL) at 0° C. was added NaBH$_4$ (151 mg, 4.0 mmol) and the mixture was stirred at 0° C. for 1 hour, then for 10 hours at 6° C., and then for 2 hours at room temperature. The saturated NH$_4$Cl was added and the mixture was poured into brine and extracted several times with ether and methylene chloride. The extracts were washed with brine, combined, dried (MgSO$_4$), and evaporated. The oily residue was purified by flash chromatography. Elution with hexane/ethyl acetate (2:8) gave pure triol 7 as a colorless oil (115 mg, 79%). 7: [α]$^{24}_D$ –59° (c 1.40 CHCl$_3$); $^1$H NMR (400 MHz, CDCl$_3$) δ0.087 and 0.110 (3H and 3H, each s, 2×SiCH$_3$), 0.895 (9H, s, Si-t-Bu), 1.66 (1H, dd, J=13.0, 9.1 Hz, 6β-H), 1.69 (1H, dd, J=13.8, 3.1 Hz, 2β-H), 1.84 (1H, s, OH), 1.96 (1H, ddd, J=13.8, 5.0, 1.7 Hz, 2α-H), 2.04 (1H, ddd, J=13.0, 4.6, 1.7 Hz, 6α-H), 2.54 (1H, s, OH), 2.63 (2H, m, ═C—CH$_2$), 3.34 (3H, s, O—CH$_3$), 3.39 and 3.50 (1H and 1H, after D$_2$O: each d, J=11.0 Hz, CH$_2$—OH), 3.50 (1H, s, OH), 3.58 (2H, m, CH$_2$—CH$_2$—O), 4.19 (1H, s, OH), 4.47

(1H, m, w/2=10 Hz, 3β-H), 4.63 (2H, s, —O—CH$_2$—O), 4.89 (1H, m; after D$_2$O: dd, J=9.1, 4.6 Hz, 5α-H), 5.51 (1H, t, J=8.3 Hz, =CH); $^{13}$C NMR (125 MHz δ-5.2 (Si—CH$_3$), -4.7 (Si—CH$_3$), 18.0 [C(CH$_3$)$_3$], 25.7 [C(CH$_3$)$_3$], 27.2 (CH$_2$—CH$_2$—C=), 41.3 (C$_2$), 44.1 (C$_6$), 55.4 (O—CH$_3$), 66.4 (C$_5$), 66.7 (O—CH$_2$—CH$_2$), 70.3 (CH$_2$—OH), 73.7 (C$_1$), 75.9 (C$_3$), 96.4 (O—CH$_2$—O), 122.0 (=C—CH$_2$), 144.2 (C$_4$); MS (EI) m/z (relative intensity), no M$^+$, 358 (M$^+$-H$_2$O, 2), 327 (3), 297 (3), 239 (17), 75 (100); HRMS (ESI) exact mass calcd for C$_{18}$H$_{36}$O$_6$SiNa (M$^+$+Na) 399.2179, measured 399.2198.

(b) To a solution of compound 5a (186 mg, 0.45 mmol) in anhydrous THF (17 mL) at 0° C. was added LiAlH$_4$ (128 mg, 3.42 mmol), and the mixture was stirred at 0° C. for 1 hour and then for 3 hours at room temperature. The mixture was carefully poured into the saturated solution of Na$_2$SO$_4$ and extracted several times with ethyl acetate and ether. The organic layer was washed with brine, dried (MgSO$_4$), and evaporated. The oily residue was purified by flash chromatography. Elution with hexane/ethyl acetate (2:8) gave pure triol 8 as a a colorless oil (100 mg, 59%).

G. [(E)-(3R,5R)-3-[(tert-Butyldimethylsilyl)oxy]-5-hydroxy-4-[3'-(methoxymethoxy)propylidene]]cyclohexanone (9)

Sodium periodate-saturated water (1.2 mL) was added to a solution of the triol 7 (79 mg, 0.21 mmol) in methanol (5 mL) at 0° C. The solution was stirred at 0° C. for 1 hour, poured into brine, and extracted with ethyl acetate and ether. The extract was washed with brine, dried (MgSO$_4$), and evaporated. An oily residue was redissolved in hexane/CH$_2$Cl$_2$ and applied on a Sep-Pak cartridge. Pure hydroxy ketone 9 (64 mg, 88%) was eluted with hexane/ethyl acetate (7:3) as an oil slowly crystallizing in the refrigerator. 9: [α]$^{24}_D$+41° (c 1.45 CHCl$_3$); $^1$H NMR (500 MHz, CDCl$_3$) δ0.048 and 0.076 (3H and 3H, each s, 2×SiCH$_3$), 0.863 (9H, s, Si-t-Bu), 2.34 (1H, m, one of =C—CH$_2$), 2.50 (1H, dd, J=16.0, 6.0 Hz, 2α-H), 2.62 (1H, m, dd, J=16.1, 3.2 Hz, one of 6-H), 2.65 (1H, m, =C—CH$_2$), 2.70 (1H, dd, J=16.0, 3.4 Hz, 2β-H), 2.75 (1H, dd, J=16.1, 3.4 Hz, one of 6-H), 3.33 (3H, s, O—CH$_3$), 3.53 and 3.74 (1H and 1H, each m, CH$_2$—CH$_2$—O), 4.62 (3H, br m, 3β-H and O—CH$_2$—O), 4.95 (1H, t, J~3.3 Hz, 5α-H), 5.73 (1H, dd, J=10.2, 6.3 Hz, =CH); $^{13}$C NMR (125 MHz) δ-4.9 (Si—CH$_3$), -4.7 (Si—CH$_3$), 18.0 [C(CH$_3$)$_3$], 25.6 [C(CH$_3$)$_3$], 28.0 (CH$_2$—CH$_2$—C=), 45.3 (C$_2$), 48.3 (C$_6$), 55.4 (O—CH$_3$), 63.1 (C$_5$), 65.7 (O—CH$_2$—CH$_2$), 70.3 (C$_3$), 96.3 (O—CH$_2$—O), 126.7 (=C—CH$_2$), 142.5 (C$_4$), 208.7 (C$_1$); MS m/z (relative intensity), no M$^+$, 313 (M$^+$-OCH$_3$, 3), 287 (15), 269 (7), 255 (21), 237 (11), 227 (68), 225 (91), 213 (17), 195 (57), 75 (100); HRMS (ESI) exact mass calcd for C$_{13}$H$_{21}$O$_5$Si (M$^+$-t-Bu) 287.1315, measured 287.1312.

H. [(3R,5R)-3,5-Bis[(tert-Butyldimethylsilyl)oxy]-4-[3'-(methoxy-methoxy)propylidene]cyclohexanone (11)

To a solution of hydroxy ketone 9 (40 mg, 117 µmol) in anhydrous CH$_2$Cl$_2$ (0.4 mL) at -50° C. was added 2,6-lutidine (32 µL, 274 µmol) and t-butyldimethylsilyl triflate (56 µL, 240 µmol). The mixture was stirred for 5 minutes at -50° C., then it was allowed to warm to -1 5° C. and stirred at this temperature for an additional 30 minutes. Benzene and water were added, and the mixture was poured into water and extracted with benzene. The extract was washed with saturated CuSO$_4$ and water, dried (MgSO$_4$), and evaporated. The oily residue was redissolved in hexane, and purified by flash chromatography on silica. Elution with hexane/ethyl acetate (95:5) gave pure protected ketone 11 as a colorless oil (30 mg, 57%; 66% based on recovered substrate) and unreacted 9 (6 mg). 11: [α]$^{24}_D$-26° (c 0.30 CHCl$_3$); $^1$H NMR (400 MHz, CDCl$_3$) δ0.019 and 0.065 (3H and 9H, each s, 4×SiCH$_3$), 0.838 and 0.912 (9H and 9H, each s, 2×Si-t-Bu), 2.32 (1H, dd, J=14.1, 10.4 Hz, 2α-H), 2.45 (3H, br m, =C—CH$_2$ and 6α-H), 2.53 (1H, ddd, J=14.4, 3.2, 2.1 Hz, 6β-H), 2.75 (1H, ddd, J=14.1, 5.6, 2.1 Hz, 2β-H), 3.36 (3H, s, O—CH$_3$), 3.58 (2H, m, CH$_2$—CH$_2$—O), 4.62 (2H, s, O—CH$_2$—O), 4.75 (1H, ddd, J=10.4, 5.6, 1.4 Hz, 3β-H), 5.01 (1H, t, J~3.2 Hz, 5α-H), 5.70 (1H, dt, J=1.7, 7.8 Hz, =CH); $^{13}$C NMR (125 MHz) δ-5.08 (Si—CH$_3$), -5.06 (Si—CH$_3$), -5.05 (Si—CH$_3$), -5.00 (Si—CH$_3$), 17.9 [C(CH$_3$)$_3$], 25.5 [C(CH$_3$)$_3$], 27.7 (CH$_2$—CH$_2$—C=), 50.2 (C$_6$), 52.4 (C$_2$), 55.2 (O—CH$_3$), 65.8 (C$_3$), 67.1 (O—CH$_2$—CH$_2$), 67.8 (C$_5$), 96.4 (O—CH$_2$—O), 118.5 (=C—CH$_2$), 141.5 (C$_4$), 207.5 (C$_1$); MS (EI) m/z (relative intensity) 443 (M$^+$+H, 2), 427 (M$^+$-CH$_3$, 5), 401 (55), 371 (15), 339 (20), 75 (100); exact mass calcd for C$_{12}$H$_{43}$O$_4$Si$_2$ (M$^+$-CH$_3$) 427.2700, measured 427.2701.

I. [(E)- and (Z)-(3'R,5'R)-3',5'-Bis[(tert-butyldimethylsilyl)oxy]-4'-[3"-(methoxymethoxy)propylidene]cyclohexylidene]acetic Acid Methyl Esters (13a and 13b)

To a solution of diisopropylamine (25 µL, 0.18 mmol) in anhydrous THF (0.15 mL) was added n-BuLi (2.5 M in hexanes, 72 µL, 0.18 mmol) under argon at -78° C. with stirring, and methyl(trimethylsilyl)acetate (30 µL, 0.18 mmol) was then added. After 15 minutes, the ketone 11 (38.4 mg, 84 µmol) in anhydrous THF (0.2 mL) was added. The solution was stirred at -78° C. for an additional 2 hours and the reaction mixture was quenched with wet ether, poured into brine and extracted with ether and benzene. The combined extracts were washed with brine, dried (MgSO$_4$), and evaporated. An oily residue was redissolved in hexane and applied on a Sep-Pak cartridge. Pure allylic esters 13a and 13b (37.2 mg, 86%; isomer ratio of 13a 13b=ca. 7:1) were eluted with hexane/ethyl acetate (97:3). Separation of the products was achieved by HPLC (10 mm×25 cm Zorbax-Sil column, 4 mL/min) using the hexane/ethyl acetate (95:5) solvent system. Pure compounds 13a and 13b were eluted at R$_V$ 41 mL and 44 mL, respectively, as colorless oils.

13a: $^1$H NMR (500 MHz, CDCl$_3$) δ-0.006, 0.056, 0.078, 0.107 (each 3H, each s, 4×SiCH$_3$), 0.832 and 0.923 (9H and 9H, each s, 2×Si-t-Bu), 1.87 (1H, t, J=11.8 Hz, 2α-H), 2.28 (1H, brd, J=13.2 Hz, 6α-H), 2.34 (1H, br d, J=13.2 Hz, 6β-H), 2.42 (2H, q, J~7 Hz, =C—CH$_2$), 3.36 (3H, s, CH$_2$—O—CH$_3$), 3.55 (2H, m, CH$_2$—CH$_2$—O), 3.70 (3H, s, CO—O—CH$_3$), 4.14 (1H, dd, J=12.8, 3.8 Hz, 2β-H), 4.45 (1H, br m, 3β-H), 4.62 (2H, s, O—CH$_2$—O), 4.88 (1H, narr m, 5α-H), 5.55 (1H, br t, J=7.5 Hz, =CH—CH$_2$), 5.65 (1H, br s, =CH—CO); MS (EI) m/z (relative intensity) no M$^+$, 499 (M$^+$-CH$_3$, 2), 482 (11), 469 (31), 457 (65), 425 (63), 351 (70), 293 (76), 89 (100); HRMS (ESI) exact mass calculated for C$_{26}$H$_{50}$O$_6$Si$_2$Na 537.3044, measured 537.3018.

13b: $^1$H NMR (500 MHz, CDCl$_3$) δ-0.008, 0.048, 0.057 and 0.063 (each 3H, each s, 4×SiCH$_3$), 0.804 and 0.915 (9H and 9H, each s, 2×Si-t-Bu), 1.95 (1H, brd, J=13.8 Hz, 2β-H), 2.17 (1H, t, J~11.6 Hz, 6β-H), 2.42 (2H, m, =C—CH$_2$), 2.55 (1H, ddd, J~12.4, ~5.0, ~1.2 Hz, 6α-H), 3.36 (3H, s, CH$_2$—O—CH$_3$), 3.55 (2H, m, CH$_2$—CH$_2$—O), 3.67 (3H, s, CO—O—CH$_3$), 3.96 (1H, br d, J=13.8 Hz, 2α-H), 4.51 (1H, br m, 5α-H), 4.62 (2H, s, O—CH$_2$—O), 4.89 (1H, narr m, 3β-H), 5.50 (1H, br t, J=7.5 Hz, =CH—CH$_2$), 5.80 (1H, br s, =CH—CO); MS m/z (relative intensity) no M$^+$, 499 (M$^+$–CH$_3$, 4), 482 (14), 469 (34), 457 (82), 425 (69), 351 (58), 293 (59), 89 (100); HRMS (ESI) exact mass calcd for C$_{26}$H$_{50}$O$_6$Si$_2$Na 537.3044, measured 537.3053.

J. 2-[(E)- and (Z)-(3'R,5'R)-3',5'-Bis[(tert-butyldimethylsilyl)oxy]-4'-[3''-(methoxymethoxy)propylidene]-cyclohexylidene]ethanol (15a and 15b)

Diisobutylaluminum hydride (1.0 M in toluene, 0.35 mL, 0.35 mmol) was slowly added to a stirred solution of the allylic esters 13a and 13b (37.2 mg, 74 µmol) in toluene/methylene chloride (2:1, 1.5 mL) at −78° C. under argon. Stirring was continued at −78° C. for 1 hour, then the mixture was quenched by addition of potassium sodium tartrate (2 N, 2 mL), aq. HCl (2 N, 2 mL) and H$_2$O (24 mL), and then diluted with ether and benzene. The organic layer was washed with diluted NaHCO$_3$ and brine, dried (MgSO$_4$), and evaporated. The residue was purified by flash chromatography. Elution with hexane/ethyl acetate (95:5) resulted in partial separation of products: 16 mg of 15a, mixture of 15a and 15b (15 mg) and pure 15b (3 mg; total yield 97%). Rechromatography of the mixed fractions resulted in almost complete separation of the products.

15a (major): $^1$H NMR (500 MHz, CDCl$_3$) δ−0.007, 0.057, and 0.067 (3H, 6H and 3H, each s, 4×SiCH$_3$), 0.839 and 0.916 (9H and 9H, each s, 2×Si-t-Bu), 1.81 (1H, t, J=11.7 Hz, 2α-H), 2.17 (1H, d, J=13.4 Hz, 6α-H), 2.26 (1H, br d, J=13.4 Hz, 6α-H), 2.41 (2H, q, J=7 Hz, =C—CH$_2$—CH$_2$), 2.86 (1H, dd, J=12.5, 3.8 Hz, 2β-H), 3.36 (3H, s, O—CH$_3$), 3.54 (2H, m, CH$_2$—CH$_2$—O), 4.38 (1H, dd, J=10.6, 3.8 Hz, 3β-H), 4.17 (2H, t, J~6 Hz; after D$_2$O: d, J=6.9 Hz, CH$_2$—OH), 4.62 (2H, s, O—CH$_2$—O), 4.81 (1H, narr m, 5α-H), 5.48 (2H, m, 2×=CH); MS (EI) m/z (relative intensity) 486 (M$^+$, 3), 468 (30), 454 (17), 441 (32), 429 (24), 423 (34), 89 (100); HRMS (ESI) exact mass calcd for C$_{25}$H$_{50}$O$_5$Si$_2$Na 509.3095, measured 509.3111.

15b (minor): $^1$H NMR (500 MHz, CDCl$_3$) δ0.011, 0.054, 0.069 (3H, 3H and 6H, each s, 4×SiCH$_3$), 0.850 and 0.917 (9H and 9H, each s, 2×Si-t-Bu), 1.88 (1H, br d, J=13.4 Hz, 2β-H), 2.03 (1H, t, J=11.4 Hz, 6β-H), 2.42 (2H, m, =C—CH$_2$), 2.51 (1H, ddd, J=12.0, 4.8, 1.2 Hz, 6α-H), 2.75 (1H, br d, J=13.4 Hz, 2α-H), 3.36 (3H, s, O—CH$_3$), 3.55 (2H, m, CH$_2$—CH$_2$—O), 4.02 and 4.15 (1H and 1H, each m; after D$_2$O: each dd, J=11.8, 7.2 Hz, CH$_2$—OH), 4.40 (1H, br m, 5α-H), 4.62 (2H, s, O—CH$_2$—O), 4.90 (1H, narr m, 3β-H), 5.53 (1H, br t, J=7.4 Hz, =CH—CH$_2$), 5.71 (1H, t, J=7.2 Hz, =CH—CH$_2$—OH); MS (EI) m/z (relative intensity) 486 (M$^+$, 5), 468 (27), 454 (11), 441 (22), 429 (30), 423 (29), 89 (100); HRMS (ESI) exact mass calc. for C$_{25}$H$_{50}$O$_5$Si$_2$Na 509.3095, measured 509.3108.

K. [2-[(E)- and (Z)-(3'R,5'R)-3',5'-Bis[(tert-butyldimethylsilyl)oxy]-4'-[3''-(methoxymethoxy)propylidene]cyclohexylidene]ethyl]-diphenylphosphine Oxides (17a and 17b)

To the allylic alcohols 15a and 15b (ca. 7:1, 34 mg, 70 µmol) in anhydrous THF (0.8 mL) was added n-BuLi (2.5 M in hexanes, 28 µL, 70 µmol) under argon at 0° C. with stirring. Freshly recrystallized tosyl chloride (14.0 mg, 73 µmol) was dissolved in anhydrous THF (190 µL) and added to the allylic alcohol-BuLi solution. The mixture was stirred at 0° C. for 5 minutes and set aside at 0° C. In another dry flask with air replaced by argon, n-BuLi (2.5 M in hexanes, 140 µL, 0.35 mmol) was added to Ph$_2$PH (62 µL, 0.34 mmol) in anhydrous THF (420 µL) at 0° C. with stirring. The red solution was siphoned under argon pressure to the solution of tosylate until the orange color persisted (ca. ¼ of the solution was added). The resulting mixture was stirred an additional 40 minutes at 0° C., and quenched by addition of H$_2$O (40 µL). Solvents were evaporated under reduced pressure and the residue was redissolved in methylene chloride (1.0 mL) and stirred with 10% H$_2$O$_2$ (0.5 mL) at 0° C. for 1 hour. The organic layer was separated, washed with cold aq. sodium sulfite and H$_2$O, dried (MgSO$_4$), and evaporated. The residue was subjected to flash chromatography. Elution with hexane/ethyl acetate (85:15) gave unchanged allylic alcohols (3.9 mg). Subsequent elution with benzene/ethyl acetate (7:3) resulted in partial separation of products: 27.6 mg of 17a, mixture of 17a and 17b (2 mg) and pure 17b (2 mg; total yield 68%). Analytical samples of both isomers were obtained after HPLC (10 mm×25 cm Zorbax-Sil column, 4 mL/min) purification using hexane/2-propanol (9:1) solvent system. Pure oily compounds 17a and 17b were eluted at R$_V$ 41 mL and 44 mL, respectively.

17a: $^1$H NMR (500 MHz, CDCl$_3$) δ−0.031, −0.013, 0.017, and 0.024 (each 3H, each s, 4×SiCH$_3$), 0.795 and 0.899 (9H and 9H, each s, 2×Si-t-Bu), 1.47 (1H, br t, J~11Hz, 2α-H), 2.06 (1H, br m, 6α-H), 2.23 (1H, d, J=13.5 Hz, 6β-H), 2.37 (2H, q, J=7.0, =C—CH$_2$—CH$_2$), 2.62 (1H, dd, J=12.8, 4.5 Hz, 2β-H), 3.34 (3H, s, O—CH$_3$), 3.51 (2H, m, CH$_2$—CH$_2$—O), 4.33 (1H, dd, J=10.6, 4.5 Hz, 3β-H), 3.15 (2H, dd, J=15.2, 7.6 Hz, CH$_2$—PO), 4.60 (2H, s, O—CH$_2$—O), 4.74 (1H, narr m, 5α-H), 5.28 (1H, m, =CH—CH$_2$—PO), 5.44 (1H, t, J~7 Hz, =CH—CH$_2$—CH$_2$), 7.45, 7.52 and 7.73 (4H, 2H and 4H, each m, Ar—H); MS (EI) m/z (relative intensity) no M$^+$, 613 (100), 538 (9), 481 (31), 449 (22); HRMS (ESI) exact mass calcd for C$_{37}$H$_{59}$O$_5$Si$_2$PNa 693.3536, measured 693.3506.

17b: $^1$H NMR (500 MHz, CDCl$_3$) δ−0.035, 0.018, 0.022, and 0.030 (each 3H, each s, 4×SiCH$_3$), 0.822 and 0.885 (9H and 9H, each s, 2×Si-t-Bu), 1.47 (1H, br d, J=12.9 Hz, 2β-H), 1.93 (1H, m, 6β-H), 2.36 (2H, q, J=7.2 Hz, =C—CH$_2$), 2.46 (2H, br m, 2α- and 6α-H), 3.03 and 3.17 (1H and 1H, each m, CH$_2$—PO), 3.35 (3H, s, O—CH$_3$), 3.50 (2H, m, CH$_2$—CH$_2$—O), 4.36 (1H, dd, J=10.6, 4.0 Hz, 5α-H), 4.60 (2H, s, O—CH$_2$—O), 4.75 (1H, narr m, 3β-H), 5.39 (1H, m, =CH—CH$_2$—PO), 5.44 (1H, br t, J=7.3 Hz, =CH—CH$_2$), 7.4-7.75 (10H, br m, Ar—H); MS (EI) m/z (relative intensity) no M$^+$, 613 (100), 538 (28), 481 (90), 449 (80); HRMS (ESI) exact mass calcd for C$_{37}$H$_{59}$O$_5$Si$_2$PNa 693.3536, measured 693.3538.

L. 1α-[(tert-Butyldimethylsilyl)oxy]-2-[3'-(methoxymethoxy)-propylidene]-25-[(triethylsilyl)oxy]-19-norvitamin D$_3$ tert-Butyldimethylsilyl Ether (20)

To a solution of phosphine oxide 17a (15.5 mg, 23 µmol) in anhydrous THF (0.25 mL) at −78° C. was slowly added phenyllithium (1.8 M in cyclohexane/ether, 13 µL, 23 µmol) under argon with stirring. The solution turned deep orange. The mixture was stirred at −78° C. for 20 minutes and a precooled (−78° C.) solution of protected hydroxy ketone 19a (19 mg, 48 µmol), prepared according to published procedure [Sicinski et al., J. Med. Chem. 37, 3730 (1994)], in anhydrous THF (0.25 mL) was slowly added. The mixture was stirred under argon at −78° C. for 3 hours and at 6° C. for 16 hours. Ethyl acetate and water were added, and the organic phase was washed with brine, dried (MgSO$_4$), and evaporated. The residue was dissolved in hexane, applied on a silica Sep-Pak cartridge, and washed with hexane/ethyl acetate (98:2, 10 mL) to give 19-norvitamin derivative 20 (9.5 mg, 48%). The Sep-Pak was then washed with hexane/ethyl acetate (96:4, 10 mL) to recover some unchanged C,D-ring ketone 19a (10 mg), and with ethyl acetate (10 mL) to recover diphenylphosphine oxide 17a (1 mg). 20: UV (in hexane) $\lambda_{max}$ 244.0, 252.5, 262.5 nm; $^1$H NMR (500 MHz, CDCl$_3$) δ −0.015, 0.056, 0.061, and 0.069 (each 3H, each s, 4×SiCH$_3$), 0.556 (3H, s, 18-H$_3$), 0.565 (6H, q, J=7.9 Hz, 3×SiCH$_2$), 0.821 and 0.921 (9H and 9H, each s, 2×Si-t-Bu), 0.930 (3H, d, J~7 Hz, 21-H$_3$), 0.947 (9H, t, J=7.9 Hz, 3×SiCH$_2$CH$_3$), 1.191 (6H, s, 26- and 27-H$_3$), 1.79 (1H, t, J=12.2 Hz, 10α-H), 1.90 (1H, m), 2.00 (2H, m), 2.20 (1H, brd, J=13.2 Hz, 4β-H), 2.29 (1H, brd, J=13.2 Hz, 4α-H), 2.41 (2H, q, J~7 Hz, =CH—CH$_2$) 2.79 (1H, brd, J=12.6 Hz, 9β-H), 3.04 (1H, dd, J=12.4, 4.5 Hz, 10β-H), 3.36 (3H, s, O—CH$_3$), 3.54 (2H, m, CH$_2$—CH$_2$—O), 4.35 (1H, m, w/2=21 Hz, 1β-H), 4.62 (2H, s, O—CH$_2$—O), 4.81 (1H, t, J~2.7 Hz, 3α-H), 5.47 (1H, dt, J=1.5, 7.6 Hz, HC=C—CH$_2$), 5.87 and 6.12 (1H and 1H, each d, J=11.0 Hz, 7- and 6-H).

M. 2-[(3'-methoxymethoxy)propylidene]-19-nor-1α, 25-dihydroxy-vitamin D$_3$ (F-Wit) (21)

To a solution of the protected 19-norvitamin D$_3$ 20 (3.0 mg, 3.5 µmol) in anhydrous THF (200 µL), was added tetrabutylammonium fluoride (1.0 M in THF, 210 µL, 210 µmol). The mixture was stirred under argon at room temperature for 18 hours, poured into brine, and extracted with ethyl acetate. The organic extracts were washed with brine. dried (MgSO$_4$), and evaporated. The residue was purified by HPLC (10 mm×25 cm Zorbax-Sil column, 4 mL/min) using a hexane/2-propanol (75:25) solvent system. Analytically pure 19-norvitamin 21 (1.27 mg, 71%) was collected at R$_V$ 26 mL. The compound gave also a single peak on reverse-phase HPLC (6.2 mm×25 cm Zorbax-ODS column, 2 mL/min) using a methanol/water (8:2) solvent system; it was collected at R$_V$ 35 mL. 21: UV (in EtOH) $\lambda_{max}$ 243.5, 252.0, 262.0 nm; $^1$H NMR (500 MHz, CDCl$_3$) δ 0.549 (3H, s, 18-H$_3$), 0.940 (3H, d, J=6.4 Hz, 21-H$_3$), 1.220 (6H, s, 26- and 27-H$_3$), 2.38 (1H, m, one of =CH—CH$_2$), 2.47 (2H, narr m, 4α- and 4β-H), 2.59 (1H, m, one of =CH—CH$_2$), 2.82 (1H, br d, J=12.8 Hz, 9β-H), 3.14 (1H, dd, J=13.1, 4.9 Hz, 10β-H), 3.34 (3H, s, O—CH$_3$), 3.55 and 3.63 (1H and 1H, each m, CH$_2$—CH$_2$—O), 4.44 (1H, m, w/2=20 Hz, 1β-H), 4.62 (2H, s, O—CH$_2$—O), 4.84 (1H, m, w/2=10 Hz, 3α-H), 5.68 (1H, t, J=7.4 Hz, HC=C—CH$_2$), 5.88 and 6.31 (1H and 1H, each d, J=11.2 Hz, 7- and 6-H); HRMS (ESI) exact mass calcd for C$_{31}$H$_{52}$O$_5$Na 527.3712, measured 527.3702.

Synthesis of 1AGR and 1AGS

Referring first to Scheme XVIA, the keto lactone 4 was obtained from commercial (−)-quinic acid as described in the synthesis of F-Wit Steps (A-C).

A. [3-[(tert-Butyldimethylsilyl)oxy]propyl]triphenylphosphonium bromide (B)

To a solution of 1-bromo-3-[(tert-butyldimethylsilyl)oxy]propane (2.18 g, 8.56 mmol) in anhydrous benzene (1.6 mL) was added triphenylphosphine (2.64 g, 10.2 mmol) under argon with stirring. The mixture was heated at 85° C. for 18 hours and cooled to room temperature. The liquid was decanted and the solid residue was grounded with spatula, filtered, and washed several times with ether. Colorless crystals of phosphonium salt B (3.7 g) were purified by silica column chromatography. Pure salt B (3.04 g, 69%) was eluted with chloroform/methanol (96:4). B: $^1$H NMR (500 MHz, CDCl$_3$) δ 0.039 (6H, s, 2×SiCH$_3$), 0.857 (9H, s, Si-t-Bu), 1.93 (2H, m, CH$_2$—CH$_2$—CH$_2$), 3.86-3.94 (4H, br m, CH$_2$—CH$_2$—O and P—CH$_2$), 7.70, 7.79 and 7.85 (6H, 3H and 6H, each m, Ar—H).

B. [(E)- and (Z)-(1R,3R,5R)-1-Acetoxy-3-[(tert-butyldimethylsilyl)oxy]-6-oxa-4-[3'-((tert-butyldimethylsilyl)oxy)propylidene]-bicyclo[3.2.1]octan-7-one (6a and 6b)

To the phosphonium bromide B (1.55 g, 3.04 mmol) in anhydrous THF (42 mL) at −20° C. was added dropwise n-BuLi (2.0 M in cyclohexane, 1.50 mL, 3.00 mmol) under argon with stirring, and the solution was stirred at −20° C. for 15 minutes. The orange-red mixture was cooled to −45° C. and siphoned during 15 minutes to a solution of keto acetate 4 (700 mg, 2.13 mmol) in anhydrous THF (24 mL). The reaction mixture was stirred at −40° C. for 2 hours and stopped by addition of brine containing 1% HCl. Ethyl acetate (30 mL), benzene (20 mL), ether (10 mL), saturated NaHCO$_3$ (10 mL), and water (10 ml) were added, and the mixture was vigorously stirred at room temperature for 18 hours. The organic phase was then separated, washed with brine, dried (MgSO$_4$), and evaporated. The residue (consisting mainly with isomeric 6a and 6b in the ratio of ca. 3:2) was purified by flash chromatography on silica. Elution with hexane/ethyl acetate (9:1) gave the mixture of products 6a and 6b (905 mg, 87%). Analytical samples of both isomers were obtained after HPLC (10 mm×25 cm Zorbax-Sil column, 4 mL/min) separation using hexane/ ethyl acetate (9:1) solvent system. Pure oily compounds 6a and 6b were eluted at R$_V$ 28 mL and 29 mL, respectively.

6a: $^1$H NMR (500 MHz, CDCl$_3$) δ 0.049 and 0.073 (6H and 6H, each s, 4×SiCH$_3$), 0.889 and 0.914 (9H and 9H, each s, 2×Si-t-Bu), 2.01 (1H, brt, J=11.0 Hz, 2α-H), 2.07 (1H, d, J=10.5 Hz, 8α-H), 2.13 (3H, s, OAc), 2.26-2.36 (3H, m, 2β-H overlapped with =C—CH$_2$), 3.29 (1H, ddd, J=10.5, 6.4, 2.8 Hz, 8β-H), 3.65 (2H, m, CH$_2$—CH$_2$—O), 4.40 (1H, ~t, J=8.5 Hz, 3β-H), 5.50 (1H, d, J=6.4 Hz, 5α-H), 5.71 (1H, t, J=7.3 Hz, =CH), MS (EI) m/z (relative intensity) no M$^+$, 469 (M$^+$−Me, 1), 427 (64), 367 (13), 337 (26), 73 (100); HRMS (ESI) exact mass calcd for C$_{24}$H$_{44}$O$_6$Si$_2$Na (M$^+$+Na) 507.2574, measured 507.2575.

6b: $^1$H NMR (500 MHz, CDCl$_3$) δ 0.042 (6H, s, 2×SiCH$_3$), 0.098 and 0.117 (3H and 3H, each s, 2×SiCH$_3$), 0.885 and 0.907 (9H and 9H, each s, 2×Si-t-Bu), 2.13 (3H, s, OAc), 2.14 (1H, m, 2α-H), 2.31 (1H, 2β-H overlapped with 8α-H), 2.32 (1H, d, J=11.0 Hz, 8α-H), 2.51 and 2.64 (1H and 1H, each m, =C—CH$_2$), 3.24 (1H, m, 8β-H), 3.62 (2H, m, CH$_2$—CH$_2$—O), 4.69 (1H, ~t, J=7.2 Hz, 3β-H), 4.93 (1H, d, J=6.3 Hz, 5α-H), 5.63 (1H, t, J=7.0 Hz, =CH), MS (EI) m/z (relative intensity) no M$^+$, 469 (M$^+$−Me, 1), 427 (32), 367 (13), 337 (40), 73 (100); HRMS (ESI) exact mass calcd for C$_{24}$H$_{44}$O$_6$Si$_2$Na (M$^+$+Na) 507.2574, measured 507.2560.

C. [(E)- and (Z)-(1'R,3'R,5'R)-3-[(tert-Butyldimethylsilyl)oxy]-1',5-dihydroxy-4'-[3"-[((tert-butyldimethylsilyl)oxy)propylidene]-cyclohexyl]methanol (8a and 8b)

To a stirred solution of compounds 6a and 6b (150 mg, 0.309 mmol) in anhydrous ethanol (4 mL) at 0° C., was added NaBH$_4$ (116 mg, 3.09 mmol), and the mixture was stirred at room temperature for 21 hours. The mixture was poured to a saturated NH$_4$Cl solution and extracted several times with ethyl acetate. The organic layer was washed with brine, dried (MgSO$_4$), and evaporated. The oily residue was purified by silica chromatography. Elution with hexane/ethyl acetate (4:6) gave a semicrystalline mixture of triols 8a and 8b (136 mg, 98%).

8a (major): $[\alpha]^{24}_D$ −53° (c 1.00 CHCl$_3$); $^1$H NMR (500 MHz, CDCl$_3$) δ0.077, 0.082, 0.084 and 0.110 (4×3H, each s, 4×SiCH$_3$), 0.887 and 0.902 (9H and 9H, 2×s, 2×Si-t-Bu), 1.58 (1H, dd, J=12.8, 10.2 Hz, 6'β-H), 1.62 (1H, dd, J=14.0, 2.8 Hz, 2'β-H), 2.03 (1H, ddd, J=14.0, 3.9, 1.9 Hz, 2'α-H), 2.11 (1H, ddd, J=12.8, 4.5, 1.9 Hz, 6'α-H), 2.46 and 2.66 (1H and 1H, each m, =C—CH$_2$), 3.35 and 3.47 (1H and 1H, after D$_2$O: 2×d, J=10.8 Hz, 1-H$_2$), 3.68 (2H, m, CH$_2$—CH$_2$—O), 4.46 (1H, ~t, J=3.3 Hz, 3'β-H), 4.88 (1H, after D$_2$O: dd, J=10.2, 4.5 Hz, 5'α-H), 5.45 (1H, ~t, J=8.6 Hz, =CH); $^{13}$C NMR (125 MHz) δ−5.6 (Si—CH$_3$), −5.38 (Si—CH$_3$), −5.36 (Si—CH$_3$), −4.5 (Si—CH$_3$), 17.9 [$\underline{C}$(CH$_3$)$_3$], 18.4 [$\underline{C}$(CH$_3$)$_3$], 25.7 [C(CH$_3$)$_3$], 26.0 [C($\underline{CH_3}$)$_3$], 29.2 (CH$_2$—C$\underline{H}_2$—CH=), 40.4 ($\overline{C}_{2'}$), 44.1 (C$_{6'}$), $\overline{62.2}$ (O—CH$_2$—CH$_2$), $\overline{66.2}$ (C$_{5'}$), 70.3 (C$_1$), 73.8 (C$_{1'}$), 74.1 (C$_{3'}$), 121.9 (=C—CH$_2$), 145.0 (C$_{4'}$), HRMS (ESI) exact mass calcd for $\overline{C}_{22}$H$_{46}$O$_5$Si$_2$Na (M$^+$+Na) 469.2824, measured 469.2781.

D. [(E)- and (Z)-(3R,5R)-3-[(tert-Butyldimethylsilyl)oxy]-5-hydroxy-4-[3'-[((tert-butyldimethylsilyl)oxy)propylidene]]cyclohexanone (10a and 10b)

Sodium periodate-saturated water (1.6 mL) was added to a solution of the triols 8a and 8b (104 mg, 0.233 mmol) in methanol (8 mL) at 0° C. The solution was stirred at 0° C. for 1 hour, poured into brine, and extracted with ethyl acetate and ether. The extract was washed with brine, dried (MgSO$_4$), and evaporated. An oily residue was dissolved in hexane/CH$_2$Cl$_2$ and applied on a Sep-Pak cartridge. Hydroxy ketones 10a and 10b (85 mg, 88%) were eluted with hexane/ethyl acetate (8:2) as an oil slowly crystallizing in the refrigerator.

10a (major): $[\alpha]^{24}_D$ +550 (c 1.17 CHCl$_3$); $^1$H NMR (400 MHz, CDCl$_3$) δ0.042, 0.065 and 0.074 (3H, 6H and 3H, each s, 4×SiCH$_3$), 0.849 and 0.880 (9H and 9H, each s, 2×Si-t-Bu), 2.28 (1H, m, one of =C—CH$_2$), 2.50 (1H, dd, J=16.2, 5.4 Hz, 2α-H), 2.55-2.70 (3H, m, 2β-H overlapped with one of 6-H and =C—CH$_2$), 2.77 (1H, dd, J=16.2, 2.5 Hz, one of 6-H), 3.62 (1H, dt, J=2.6, 10.2 Hz, one of CH$_2$—CH$_2$—O), 3.85 (1H, m, one of CH$_2$—CH$_2$—O), 4.60 (1H, m, 3β-H), 4.90 (1H, narr m, 5α-H), 5.66 (1H, dd, J=10.5, 6.0 Hz, =CH); $^{13}$C NMR (125 MHz) δ−5.6 (Si—CH$_3$), −5.4 (Si—CH$_3$), −4.9 (Si—CH$_3$), −4.6 (Si—CH$_3$), 18.0 [C(CH$_3$)$_3$], 18.5 [C(CH$_3$)$_3$], 25.7 [C(CH$_3$)$_3$], 26.0 [C($\underline{CH_3}$)$_3$], 30.7 (CH$_2$—C$\underline{H}_2$—C=), 45.1 ($\overline{C}_2$), 47.9(C$_6$), $\overline{63.0}$ (C$_5$), 61.8 (O—$\overline{CH_2}$—CH$_2$), 70.8 (C$_3$), 127.5 (=C—CH$_2$), 142.9 (C$_4$), 208.9 ($\overline{C}_1$); MS m/z (relative intensity) no M$^+$, 399 (M$^+$-Me, 2), 357 (69), 339 (12), 327 (41), 299 (9), 265 (10), 225 (81), 73 (100); HRMS (ESI) exact mass calcd for C$_{21}$H$_{42}$O$_4$Si$_2$Na (M$^+$+Na) 437.2519, measured 437.2537.

E. [(3R,5R)-3,5-Bis[(tert-Butyldimethylsilyl)oxy]-4-[3'-[((tert-butyldimethylsilyl)oxy)propylidene]cyclohexanone (12)

To a solution of hydroxy ketones 10a and 10b (22 mg, 53 µmol) in anhydrous CH$_2$Cl$_2$ (0.2 mL) at −50° C. was added 2,6-lutidine (14.5 µL, 124 µmol) and t-butyldimethylsilyl triflate (25 µL, 106 µmol). The mixture was stirred at −50° C. for 50 minutes. Cold and wet CH$_2$Cl$_2$ was added and the mixture was poured into water and extracted with CH$_2$Cl$_2$. The extract was washed with saturated CuSO$_4$ and water, dried (MgSO$_4$), and evaporated. The oily residue was redissolved in hexane, and purified by flash chromatography on silica. Elution with hexane/ethyl acetate (95:5) gave pure protected ketone 12 as a colorless oil (18 mg, 64%; 74% based on recovered substrates) and a mixture of unreacted 10a and 10b (3 mg).

12: $[\alpha]^{24}_D$ −17° (c 1.35 CHCl$_3$); $^1$H NMR (500 MHz, CDCl$_3$) δ0.008 (3H, s, SiCH$_3$), 0.061 (15H, s, 5×SiCH$_3$), 0.833, 0.900 and 0.910 (3×9H, each s, 3×Si-t-Bu), 2.32 (1H, dd, J=14.2, 10.4 Hz, 2α-H), 2.32-2.43 (2H, br m, =C—CH$_2$), 2.43 (1H, dd, J=14.4, 2.8 Hz, 6α-H), 2.52 (1H, ddd, J=14.4, 3.4, 2.2 Hz, 6β-H), 2.75 (1H, ddd, J=14.2, 5.6, 2.2 Hz, 2β-H), 3.65 and 3.71 (each 1H, each m, CH$_2$—CH$_2$—O), 4.76 (1H, ddd, J=10.4, 5.6, 1.7 Hz, 3β-H), 5.01 (1H, ~t, J=3.2 Hz, 5α-H), 5.70 (1H, dt, J=1.7, 7.6 Hz, =CH); $^{13}$C NMR (125 MHz) δ−5.27 (Si—CH$_3$), −5.25 (Si—CH$_3$), −5.01 (Si—CH$_3$), −5.00 (Si—CH$_3$), −4.95 (Si—CH$_3$), −4.89 (Si—CH$_3$), 17.9 [$\underline{C}$(CH$_3$)$_3$], 18.3 [$\underline{C}$(CH$_3$)$_3$], 18.4 [$\underline{C}$(CH$_3$)$_3$], 25.6 [C(CH$_3$)$_3$], $\overline{25.8}$ [C($\underline{CH_3}$)$_3$], 26.0 [C($\underline{CH_3}$)$_3$], 29.7 (CH$_2$—$\underline{CH_2}$—C=), 50.4 ($\overline{C}_6$), 52.5 (C$_2$), $\overline{62.8}$ (O—CH$_2$—$\underline{CH_2}$), 65.9 (C$_3$), 67.9 (C$_5$), 119.1 (=C—CH$_2$), 141.1 ($\overline{C}_4$), 207.5 (C$_1$); MS (EI) m/z (relative intensity) no M$^+$, 513 (M$^+$-Me, 2), 471 (74), 381 (5), 339 (63), 73 (100); exact mass calcd for C$_{27}$H$_{56}$O$_4$Si$_3$ (M$^+$-C$_4$H$_9$) 471.2782, measured 471.2796.

F. [(E)- and (Z)-(3'R,5'R)-3',5'-Bis[(tert-butyldimethylsilyl)oxy]-4'-[3''-[((tert-butyldimethylsilyl)oxy)propylidene]cyclohexylidene]acetic Acid Methyl Esters (14a and 14b)

To a solution of diisopropylamine (49 µL, 0.363 mmol) in anhydrous THF (0.37 mL) was added n-BuLi (2.5 M in hexanes, 146 µL, 0.365 mmol) under argon at −78° C. with stirring, and methyl(trimethylsilyl)acetate (60.5 µL, 0.366 mmol) was then added. After 15 minutes, the ketone 12 (76.5 mg, 0.145 µmol) in anhydrous THF (0.45 mL) was added. The solution was stirred at −78° C. for an additional 70 minutes, and the reaction mixture was quenched with wet ether, poured into brine, and extracted with ether and benzene. The combined extracts were washed with brine, dried (MgSO$_4$), and evaporated. The oily residue was redissolved in hexane and applied on a Sep-Pak cartridge. Pure allylic esters 14a and 14b (60 mg, 68%; isomer ratio of 14a:14b=ca. 6:1) were eluted with hexane/ethyl acetate (98.5:1.5.

14a (major): $[\alpha]^{24}_D$: −33 (c 0.48 CHCl$_3$); $^1$H NMR (500 MHz, CDCl$_3$) δ−0.014, 0.054, 0.059, 0.070, 0.080 and 0.109 (each 3H, each s, 6×SiCH$_3$), 0.830, 0.845 and 0.926 (each 9H, each s, 3×Si-t-Bu), 1.87 (1H, ~t, J=12 Hz, 2'α-H), 2.26 (1H, brd, J=13.2 Hz, 6'α-H), 2.33 (1H, brd, J=13.2 Hz, 6'β-H), 2.3-2.4 (2H, m, =C—CH$_2$), 3.6-3.7 (2H, m, CH$_2$—CH$_2$—O), 3.71 (3H, s, COOCH$_3$), 4.15 (1H, ddd, J=12.7, 4.9, 1.5 Hz, 2'β-H), 4.46 (1H, dd, J=10.7, 4.9Hz, 3'β-H), 4.88 (1H, ~t, J=3 Hz, 5'α-H), 5.54 (1H, dt, J=1.5, 7.3 Hz, =CH), 5.65 (1H, br s, 2-H); $^{13}$C NMR (125 MHz) δ−5.26 (Si—CH$_3$), −5.22 (Si—CH$_3$), −5.14 (Si—CH$_3$), −4.92 (Si—CH$_3$), −4.87 (Si—CH$_3$), −4.77 (Si—CH$_3$), 17.95[$\underline{C}$(CH$_3$)$_3$], 18.38 [$\underline{C}$(CH$_3$)$_3$], 18.41 [$\underline{C}$(CH$_3$)$_3$], 25.6 [C($\underline{CH_3}$)$_3$], 25.9 [C(CH$_3$)$_3$], 26.0 [C(CH$_3$)$_3$], 30.8 (CH$_2$—CH$_2$—C=), 40.7 (C$_{6'}$), 46.5 (C$_{2'}$), 50.9 (CH$_3$CO), 63.1 (O—CH$_2$—CH$_2$), 66.5 (C$_{5'}$), 69.6 (C$_{3'}$), 117.0(=C—CH$_2$), 116.9($\overline{C}_2$), 142.7 (C$_{4'}$), 156.0 (C$_1$), 166.6 (C$_1$); minor isomer (Z) selected: 5.50 (1H, dt, J=1.5, 7.3 Hz, =CH), 5.80 (1H, br s, 2-H).

G. 2-[(E)- and (Z)-(3'R,5'R)-3',5'-Bis[(tert-butyldimethylsilyl)oxy]-4'-[3''-[((tert-butyldimethylsilyl)oxy)propylidene]-cyclohexylidene]ethanol (16a and 16b)

Diisobutylaluminum hydride (1.0 M in hexane, 616 µL, 616 µmol) was slowly added to a stirred solution of the allylic esters 14a and 14b (6:1, 60 mg, 103 µmol) in toluene/methylene chloride (2:1, 2.25 mL) at −78° C. under argon. Stirring was continued at −78° C. for 1 hour and then the mixture was quenched by addition of potassium sodium tartrate (2 N, 2 mL), aq. HCl (2 N, 2 mL) and H$_2$O (24 mL), and then diluted with ether and benzene. The organic layer was washed with diluted NaHCO$_3$ and brine, dried (MgSO$_4$), and evaporated.

The residue was purified by flash chromatography. Elution with hexane/ethyl acetate (95:5) resulted in 49 mg of mixture of products 16a and 16b, yield 86%). Analytical samples of both isomers were obtained after HPLC (10 mm×25 cm Zorbax-Sil column, 4 mL/min) using hexane/ethyl acetate (9:1) solvent system. Pure oily compounds 16a and 16b were eluted at $R_V$ 28 mL and 29 mL, respectively.

16a (major): $^1$H NMR (500 MHz, CDCl$_3$) δ −0.016, 0.055, 0.059, and 0.068 (3H, 6H, 6H and 3H, each s, 6×SiCH$_3$), 0.831, 0.888 and 0.911 (each 9H, each s, 3×Si-t-Bu), 1.80 (1H, t, J=11.8 Hz, 2'α-H), 2.16 (1H, br d, J=13.2 Hz, 6'α-H), 2.26 (1H, br d, J=13.2 Hz, 6'β-H), 2.34 (2H, m, =C—CH$_2$—CH$_2$), 2.86 (1H, ddd, J=12.4, 4.4, 1.5 Hz, 2'β-H), 3.62 (2H, m, CH$_2$—CH$_2$—O), 4.19 (2H, t, J~6 Hz; after D$_2$O: d, J=7.0 Hz, 1-H), 4.37 (1H, after D$_2$O: dm, J=10.4 Hz, 3'β-H), 4.80 (1H, ~t, J=3 Hz, 5'α-H), 5.47 (2H, m, 2×=CH); $^{13}$C NMR (125 MHz) δ −5.28 (2×Si—CH$_3$), −5.06 (Si—CH$_3$), −5.00 (Si—CH$_3$), −4.85 (Si—CH$_3$), −4.79 (Si—CH$_3$), 18.0 [C(CH$_3$)$_3$], 18.4 [2×C(CH$_3$)$_3$], 25.6 [C(CH$_3$)$_3$], 25.9 [C(CH$_3$)$_3$], 26.0 [C(CH$_3$)$_3$], 30.8 (CH$_2$—CH$_2$=C=), 40.0 (C$_{2'}$), 45.5 (C$_{6'}$), 58.7 (C$_1$), 63.2 (O—CH$_2$—CH$_2$), 66.5 (C$_{5'}$), 70.0 (C$_{3'}$), 116.6 (=C—CH$_2$), 125.4 (C$_2$), 137.2 (C$_{1'}$), 143.4 (C$_{4'}$); MS (EI) m/z (relative intensity) no M$^+$, 538 (M$^+$−H$_2$O, 9), 499 (12), 471 (7), 424 (39), 407 (11), 349 (23), 73 (100), HRMS (ESI) exact mass calcd for C$_{29}$H$_{60}$O$_4$Si$_3$Na (M$^+$+Na) 579.3697, measured 579.3704.

16b (minor): $^1$H NMR (500 MHz, CDCl$_3$) δ 0.029, 0.055, 0.060, 0.064 and 0.069 (3H, 6H, 3H, 3H and 3H, each s, 6×SiCH$_3$), 0.849, 0.898 and 0.918 (each 9H, each s, 3×Si-t-Bu), 1.87 (1H, br d, J=13.8 Hz, 2'β-H), 2.03 (1H, br t, J=11.5 Hz, 6'β-H), 2.34 (2H, m, =C—CH$_2$), 2.51 (1H, ddd, J=12.0, 5.0, 1.6 Hz, 6'α-H), 2.76 (1H, br d, J=13.8 Hz, 2'α-H), 3.64 (2H, m, CH$_2$—CH$_2$—O), 4.02 and 4.13 (1H and 1H, each m; after D$_2$O: each dd, J=11.8, 7.2 Hz, CH$_2$—OH), 4.39 (1H, dm, J=10.6 Hz, 5'α-H), 4.89 (1H, br s, 3β-H), 5.52 (1H, dt, J=1.3, 7.5 Hz, =CH—CH$_2$), 5.71 (1H, t, J=7.2 Hz, =CH—CH$_2$—OH); MS (EI) m/z (relative intensity) no M$^+$, 538 (M$^+$−H$_2$O, 4), 499 (6), 471 (4), 424 (12), 407 (6), 349 (11), 73 (100); HRMS (ESI) exact mass calcd for C$_{29}$H$_{60}$O$_4$Si$_3$ (M$^+$−H$_2$O) 538.3694, measured 538.3689.

H. [2-[(E)- and (Z)-(3'R,5'R)-3',5'-Bis[((tert-butyldimethylsilyl)oxy]-4'-[3''-[((tert-butyldimethylsilyl)oxy)propylidene]-cyclohexylidene]ethyl]-diphenylphosphine Oxides (18a and 18b)

To the allylic alcohols 16a and 16b (5.5:1, 40.5 mg, 70.2 μmol) in anhydrous THF (0.8 mL), was added n-BuLi (2.5 M in hexanes, 35 μL, 87.5 μmol) under argon at 0° C. with stirring. Freshly recrystallized tosyl chloride (14.0 mg, 73 μmol) was dissolved in anhydrous THF (190 μL) and added to the allylic alcohol-BuLi solution. The mixture was stirred at 0° C. for 5 minutes and set aside at 0° C. In another dry flask with air replaced by argon, n-BuLi (2.5 M in hexanes, 140 μL, 0.35 mmol) was added to Ph$_2$PH (62 μL, 0.34 mmol) in anhydrous THF (420 μL) at 0° C. with stirring. The red solution was siphoned under argon pressure into the solution of tosylate until the orange color persisted (ca. ¼ of the solution was added). The resulting mixture was stirred an additional 40 minutes at 0° C., and quenched by addition of H$_2$O (40 μl). Solvents were evaporated under reduced pressure, and the residue was dissolved in methylene chloride (1.0 mL) and stirred with 10% H$_2$O$_2$ (0.5 mL) at 0° C. for 1 hour. The organic layer was separated, washed with cold aq. sodium sulfite and H$_2$O, dried (MgSO$_4$), and evaporated. The residue was subjected to flash chromatography. Elution with hexane/ethyl acetate (95:5) gave unchanged allylic alcohols (16.3 mg). Subsequent elution with hexane/ethyl acetate (7:3) resulted in mixture of products: 18a and 18b (25 mg, 49%; 81% based on recovered substrates 16a,b).

18a (major isomer): $^1$H NMR (500 MHz, CDCl$_3$) δ −0.044, −0.022, 0.011, 0.020, 0.030, and 0.035 (each 3H, each s, 6×SiCH$_3$), 0.787, 0.878 and 0.894 (each 9H, each s, 3×Si-t-Bu), 1.47 (1H, br t, J~11Hz, 2'α-H), 2.04 (1H, m, 6'α-H), 2.22 (1H, d, J=13.7 Hz, 6'β-H), 2.28 (2H, m, =C—CH$_2$—CH$_2$), 2.62 (1H, dd, J=12.8, 4.2 Hz, 2'β-H), 3.58 (2H, m, CH$_2$—CH$_2$—O), 4.32 (1H, dm, J~10 Hz, 3'β-H), 3.17 (2H, dd, J=15.2, 7.6 Hz, CH$_2$—PO), 4.73 (1H, br s, 5'α-H), 5.27 (1H, m, =CH—CH$_2$—CH$_2$), 5.43 (1H, br t, J~7 Hz, =CH—CH$_2$—PO), 7.46, 7.51 and 7.72 (4H, 2H and 4H, each m, Ar—H); HRMS (ESI) exact mass calcd for C$_{41}$H$_{69}$O$_4$Si$_3$PNa (M$^+$+Na) 763.4139, measured 763.4157.

I. 1α-[(tert-Butyldimethylsilyl)oxy]-2-[3'-[((tert-butyldimethylsilyl)oxy)propylidene]-25-[(triethylsilyl)oxy]-19-norvitamin D$_3$ tert-Butyldimethylsilyl Ethers (22a and 22b)

To a solution of phosphine oxides 18a and 18b (6:1, 20.3 mg, 27.6 μmol) in anhydrous THF (0.3 mL) at −78° C. was slowly added phenyllithium (1.56 M in cyclohexane, 19 μL, 30 μmol) under argon with stirring. The solution turned deep orange. The mixture was stirred at −78° C. for 20 minutes and a precooled (−78° C.) solution of protected hydroxy ketone 19a (15.4 mg, 39 μmol), prepared according to published procedure [Sicinski et al., J. Med. Chem. 37, 3730 (1994)], in anhydrous THF (80 μL) was slowly added. The mixture was stirred under argon at −78° C. for 3 hours and at 6° C. for 19 hours. Ethyl acetate, benzene and water were added, and the organic phase was washed with brine, dried (MgSO$_4$), and evaporated. The residue was redissolved in hexane and applied on a silica column. Elution with hexane/ethyl acetate (99.5:0.5) yielded 19-norvitamin derivatives 22a and 22b (8.6 mg, 47% based on recovered substrates). The column was then washed with hexane/ethyl acetate (96:4) to recover some unchanged C,D-ring ketone 19a (7 mg), and with ethyl acetate to recover unreacted diphenylphosphine oxide (5.5 mg). Analytical sample of the main product 22a was obtained by HPLC (10 mm×25 cm Zorbax-Sil column, 4 mL/min) purification using hexane/ethyl acetate (99.8:0.2) solvent system. Pure compound 22a was eluted at $R_V$ 28 mL as a colorless oil. 22a: UV (in EtOH) λ$_{max}$ 244.0, 252.5, 262.5 nm; $^1$H NMR (500 MHz, CDCl$_3$) δ −0.023, 0.052, 0.056, 0.061, 0.063, and 0.070 (each 3H, each s, 6×SiCH$_3$), 0.555 (3H, s, 18-H$_3$), 0.565 (6H, q, J=7.9 Hz, 3×SiCH$_2$), 0.819, 0.897, and 0.923 (9H and 9H, each s, 3×Si-t-Bu), 0.878 (3H, d, J=7.1 Hz, 21-H$_3$), 0.947 (9H, t, J=7.9 Hz, 3×SiCH$_2$CH$_3$), 1.190 and 1.191 (3H and 3H, each s, 26- and 27-H$_3$), 1.79 (1H, t, J=11.6 Hz, 10α-H), 1.90 (1H, m), 2.00 (2H, m), 2.19 (1H, br d, J~14 Hz, 4β-H), 2.27 (1H, br d, J~14 Hz, 4α-H), 2.33 (2H, m, =CH—CH$_2$), 2.79 (1H, brd, J~13 Hz, 9β-H), 3.05 (1H, dd, J=12.0, 4.0 Hz, 10β-H), 3.62 (2H, m, CH$_2$—CH$_2$—O), 4.34 (1H, m, w/2=20 Hz, 1β-H), 4.81 (1H, t, J~2.8 Hz, 3α-H), 5.47 (1H, dt, J~1.5, ~7.5 Hz, HC=C—CH$_2$), 5.88 and 6.12 (1H and 1H, each d, J=11.0 Hz, 7- and 6-H); HRMS (ESI) exact mass calcd for C$_{53}$H$_{104}$O$_4$Si$_4$Na (M$^+$+Na) 939.6909, measured 939.6900.

J. (20S)-1α-[(tert-Butyldimethylsilyl)oxy]-2-[3'-[((tert-butyldimethylsilyl)oxy)propylidene]-25-[(triethylsilyl)oxy]-19-norvitamin D$_3$ tert-Butyldimethylsilyl Ethers (23a and 23b)

Protected 19-norvitamin D$_3$ compounds 23a and 23b were obtained by Wittig-Horner coupling of protected 25-hydroxy Grundmann's ketone 19b with the phosphine oxides 18a and 18b performed analogously to the process described above for the preparation of (20R)-isomers 22a and 22b. The protected vitamins were purified on a silica column, using hexane/ethyl acetate (99.5:0.5) solvent system, and they were obtained in ca. 47% yield. Analytical sample of the protected vitamin 23a was obtained by HPLC (10 mm×25 cm Zorbax-Sil column, 4 mL/min) purification using hexane/ethyl acetate (99.7:0.3) solvent system. Pure compound 23a was eluted at $R_V$ 25 mL as a colorless oil. 23a: UV (in EtOH) $\lambda_{max}$ 243.5, 252.5, 262.5 nm; $^1$H NMR (500 MHz, CDCl$_3$) δ −0.024, 0.057, 0.059, and 0.069 (3H, 3H, 6H, and 6H, each s, 6'SiCH$_3$), 0.550 (3H, s, 18-H$_3$), 0.560 (6H, q, J=7.5 Hz, 3×SiCH$_2$), 0.818, 0.895, and 0.923 (each 9H, each s, 3×Si-t-Bu), 0.867 (3H, d, J=7.0 Hz, 21-H$_3$), 0.943 (9H, t, J=7.5 Hz, 3×SiCH$_2$CH$_3$), 1.191 (6H, s, 26- and 27-H$_3$), 1.79 (1H, t, J~12 Hz, 10α-H), 1.90 (1H, m), 2.00 (2H, m), 2.19 (1H, brd, J~13 Hz, 4β-H), 2.27 (1H, brd, J~13 Hz, 4α-H), 2.33 (2H, m, =CH—CH$_2$), 2.79 (1H, br d, J~11.5 Hz, 9β-H), 3.05 (1H, dm, J~12 Hz, 10β-H), 3.62 (2H, m, CH$_2$—CH$_2$—O), 4.34 (1H, m, w/2=20 Hz, 1β-H), 4.80 (1H, br s, 3α-H), 5.47 (1H, t, J=7.0 Hz, HC=C—CH$_2$), 5.88 and 6.11 (1H and 1H, each d, J=11.2 Hz, 7- and 6-H); HRMS (ESI) exact mass calcd for C$_{53}$H$_{104}$O$_4$Si$_4$Na (M$^+$+Na) 939.6909, measured 939.6907.

K. 2-(3'-hydroxypropylidene)-19-nor-1α,25-dihydroxyvitamin D3 (1AGR E and Z isomers) (24a and 24b)

To a solution of the protected vitamins 22a and 22b (5.7 mg, 6.2 μmol) in anhydrous THF (4.3 mL) was added tetrabutylammonium fluoride (1.0 M in THF, 372 μL, 372 μmol). The mixture was stirred under argon at room temperature for 18 hours, poured into brine, and extracted with ethyl acetate and diethyl ether. The organic extracts were washed with brine, dried (MgSO$_4$), and evaporated. The residue was purified by HPLC (10 mm×25 cm Zorbax-Sil column, 4 mL/min) using hexane/2-propanol (8:2) solvent system. Pure mixture of 19-norvitamin 24a and 24b was collected at $R_V$ 37.5 mL. Separation of both isomers was easily achieved by reverse-phase HPLC (6.2 mm×25 cm Zorbax-ODS column, 2 mL/min) using methanol/water (8:2) solvent system. Analytically pure E-isomer 24a (2.8 mg, 97%) was collected at $R_V$ 23 mL and Z-isomer 24b (11 μg) at $R_V$ 29 mL.

24a: UV (in EtOH) $\lambda_{max}$ 243.0, 251.0, 261.5 nm; $^1$H NMR (500 MHz, CDCl$_3$) δ 0.549 (3H, s, 18-H$_3$), 0.940 (3H, d, J=6.3 Hz, 21-H$_3$), 1.22 (6H, s, 26- and 27-H$_3$), 2.33 and 2.55 (1H and 1H, each m, =CH—CH$_2$), 2.47 (2H, narr m, 4α- and 4β-H), 2.82 (1H, br d, J~13 Hz, 9β-H), 3.16 (1H, dd, J=13.0, 4.8 Hz, 10β-H), 3.66 and 3.76 (1H and 1H, each m, CH$_2$—CH$_2$—O), 4.45 (1H, m, w/2=20 Hz, 1β-H), 4.85 (1H, narr m, 3α-H), 5.66 (1H, t, J=7.3 H, HC=C—CH$_2$), 5.88 and 6.31 (1H and 1H, each d, J=11.2 Hz, 7- and 6-H); HRMS (ESI) exact mass calcd for C$_{29}$H$_{48}$O$_4$Na (M$^+$+Na) 483.3450, measured 483.3461.

24b: UV (in EtOH) $\lambda_{max}$ 243.0, 251.5, 262.0 nm; $^1$H NMR (800 MHz, CDCl$_3$) δ 0.553 (3H, s, 18-H$_3$), 0.939 (3H, d, J=6.6 Hz, 21-H$_3$), 1.22 (6H, s, 26- and 27-H$_3$), 2.19 (1H, t, J=11.0 Hz, 4β-H), 2.25 (1H, br d, J=14.6 Hz, 10β-H), 2.40 and 2.56 (1H and 1H, each m, =CH—CH$_2$), 2.74 (1H, dd, J=13.0, 4.8 Hz, 4α-H), 2.81 (1H, br d, J=12.5 Hz, 9β-H), 2.93 (1H, dd, J=14.6, 3.8 Hz, 10α-H), 3.67 and 3.76 (1H and 1H, each m, CH$_2$—CH$_2$—O), 4.48 (1H, m, w/2=19 Hz, 3α-H), 4.89 (1H, narr m, 1β-H), 5.65 (1H, t, J=8.1Hz, HC=C—CH$_2$), 5.85 and 6.40 (1H and 1H, each d, J=11.0 Hz, 7- and 6-H).

L. 2-(3'-hydroxypropylidene)-19-nor-(20S)-1α,25-dihydroxyvitamin D3 (1AGR E and Z isomers) (25a and 25b)

Vitamins 25a and 25b were obtained by hydrolysis of the silyl protecting groups in the 19-norvitamin derivatives 23a and 23b performed analogously to the process described above for the preparation of (20R)-isomers 24a and 24b. The residue was purified by HPLC (10 mm×25 cm Zorbax-Sil column, 4 mL/min) using hexane/2-propanol (8:2) solvent system. Pure mixture of 19-norvitamin 25a and 25b (95% yield) was collected at $R_V$ 36.5 mL. Separation of both isomers was easily achieved by reverse-phase HPLC (6.2 mm×25 cm Zorbax-ODS column, 2 mL/min) using methanol/water (8:2) solvent system. Analytically pure E-isomer 25a was collected at $R_V$ 18 mL and Z-isomer 25b at $R_V$ 28 mL (ratio of 25a:25b=160:1).

25a: UV (in EtOH) $\lambda_{max}$ 243.0, 251.5, 261.0 nm; $^1$H NMR (500 MHz, CDCl$_3$) δ 0.548 (3H, s, 18-H$_3$), 0.858 (3H, d, J=6.4 Hz, 21-H$_3$), 1.21 (6H, s, 26- and 27-H$_3$), 2.35 and 2.54 (1H and 1H, each m, =CH—CH$_2$), 2.47 (2H, narr m, 4α- and 4β-H), 2.82 (1H, br d, J=12.7 Hz, 9β-H), 3.16 (1H, dd, J=13.1, 4.9 Hz, 10β-H), 3.65 and 3.76 (1H and 1H, each m, CH$_2$—CH$_2$—O), 4.45 (1H, m, w/2=25 Hz, 1β-H), 4.85 (1H, narr m, 3α-H), 5.66 (1H, t, J=7.4 Hz, HC=C—CH$_2$), 5.88 and 6.31 (1H and 1H, each d, J=11.4 Hz, 7- and 6-H); HRMS (ESI) exact mass calcd for C$_{29}$H$_{48}$O$_4$Na (M$^+$+Na) 483.3450, measured 483.3427.

25b: UV (in EtOH) $\lambda_{max}$ 243.0, 251.5, 262.0 nm; $^1$H NMR (800 MHz, CDCl$_3$) δ 0.550 (3H, s, 18-H$_3$), 0.854 (3H, d, J=6.6 Hz, 21-H$_3$), 1.21 (6H, s, 26- and 27-H$_3$), 2.19 (1H, t, J~12 Hz, 4β-H), 2.24 (1H, br d, J=14.6 Hz, 10β-H), 2.40 and 2.56 (1H and 1H, each m, =CH—CH$_2$), 2.74 (1H, dd, J=13.2, 4.4 Hz, 4α-H), 2.82 (1H, br d, J=12.4 Hz, 9β-H), 2.92 (1H, dd, J=14.6, 3.7 Hz, 10α-H), 3.61 and 3.72 (1H and 1H, each m, CH$_2$—CH$_2$—O), 4.47 (1H, m, w/2=18 Hz, 3α-H), 4.88 (1H, narr m, 1β-H), 5.65 (1H, t, J~7.5 Hz, HC=C—CH$_2$), 5.85 and 6.40 (1H and 1H, each d, J=11.0 Hz, 7- and 6-H).

Scheme XVIA

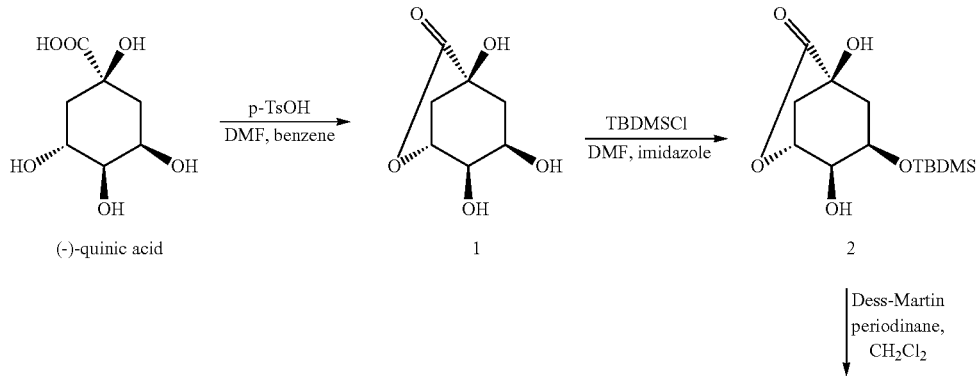

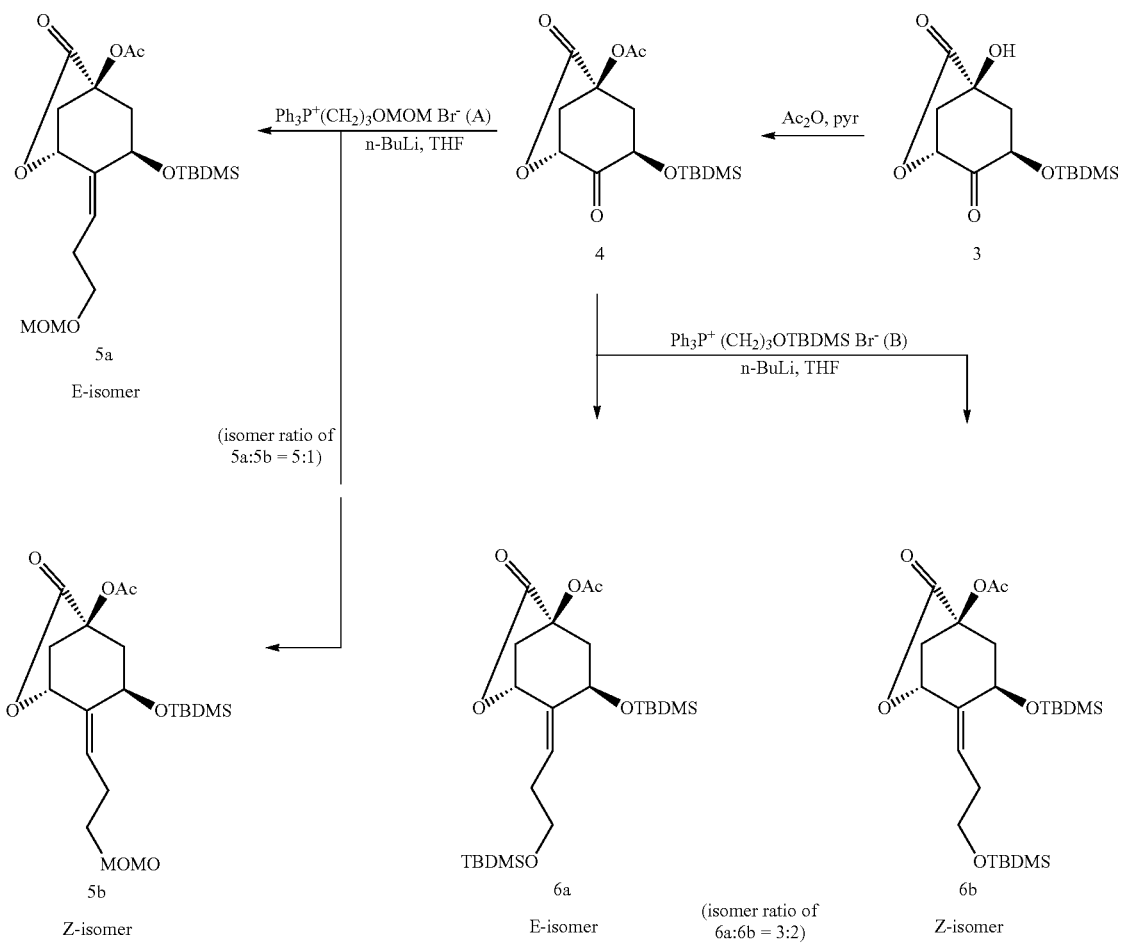
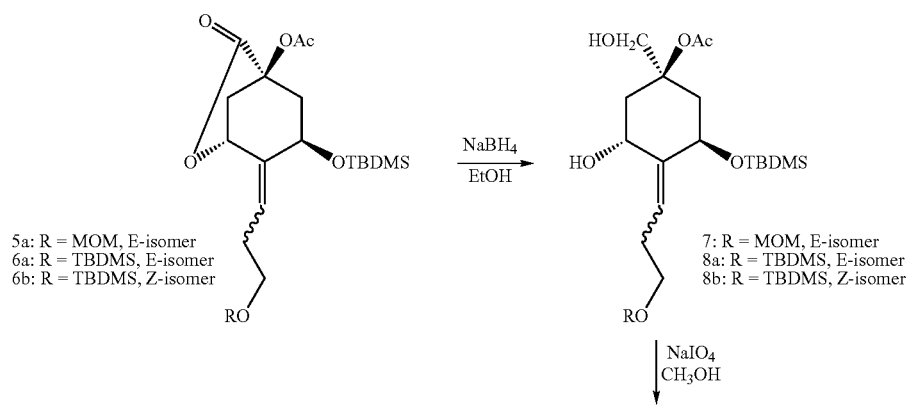
Scheme XVIB

-continued
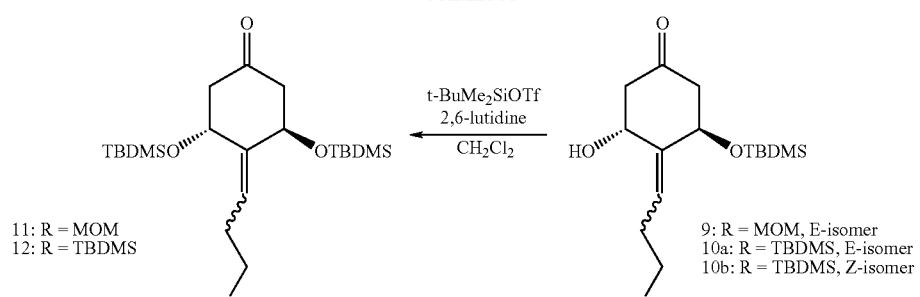
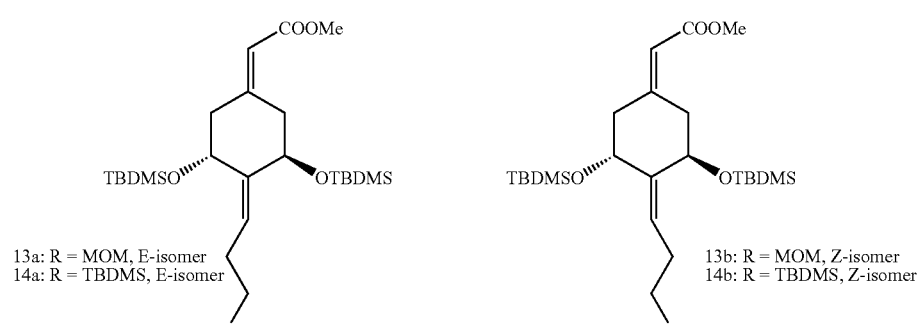
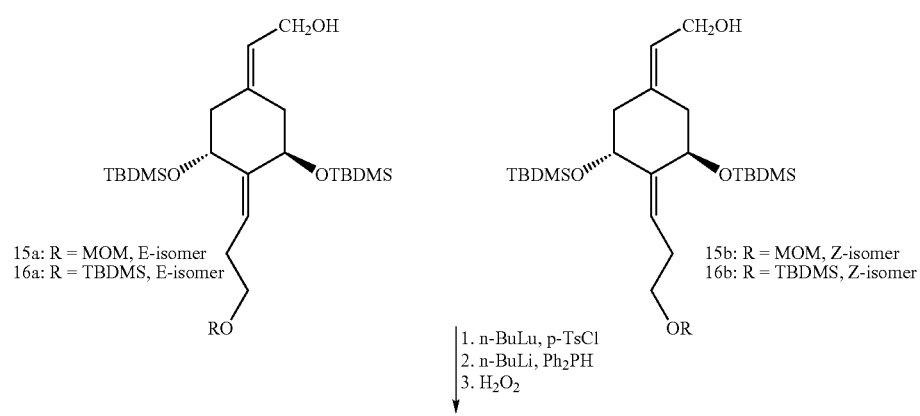

-continued
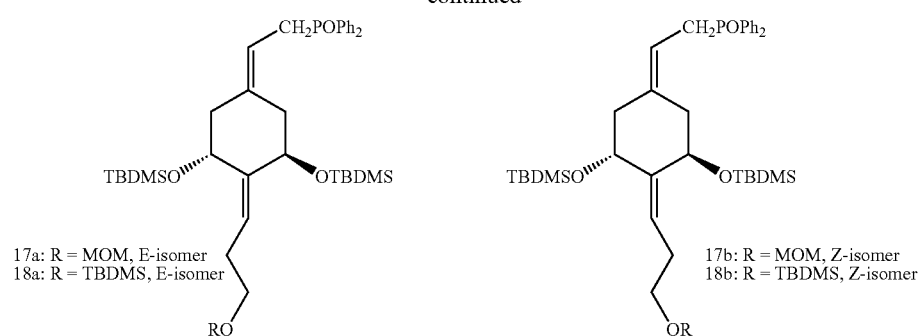
17a: R = MOM, E-isomer
18a: R = TBDMS, E-isomer
17b: R = MOM, Z-isomer
18b: R = TBDMS, Z-isomer
Scheme XVIC
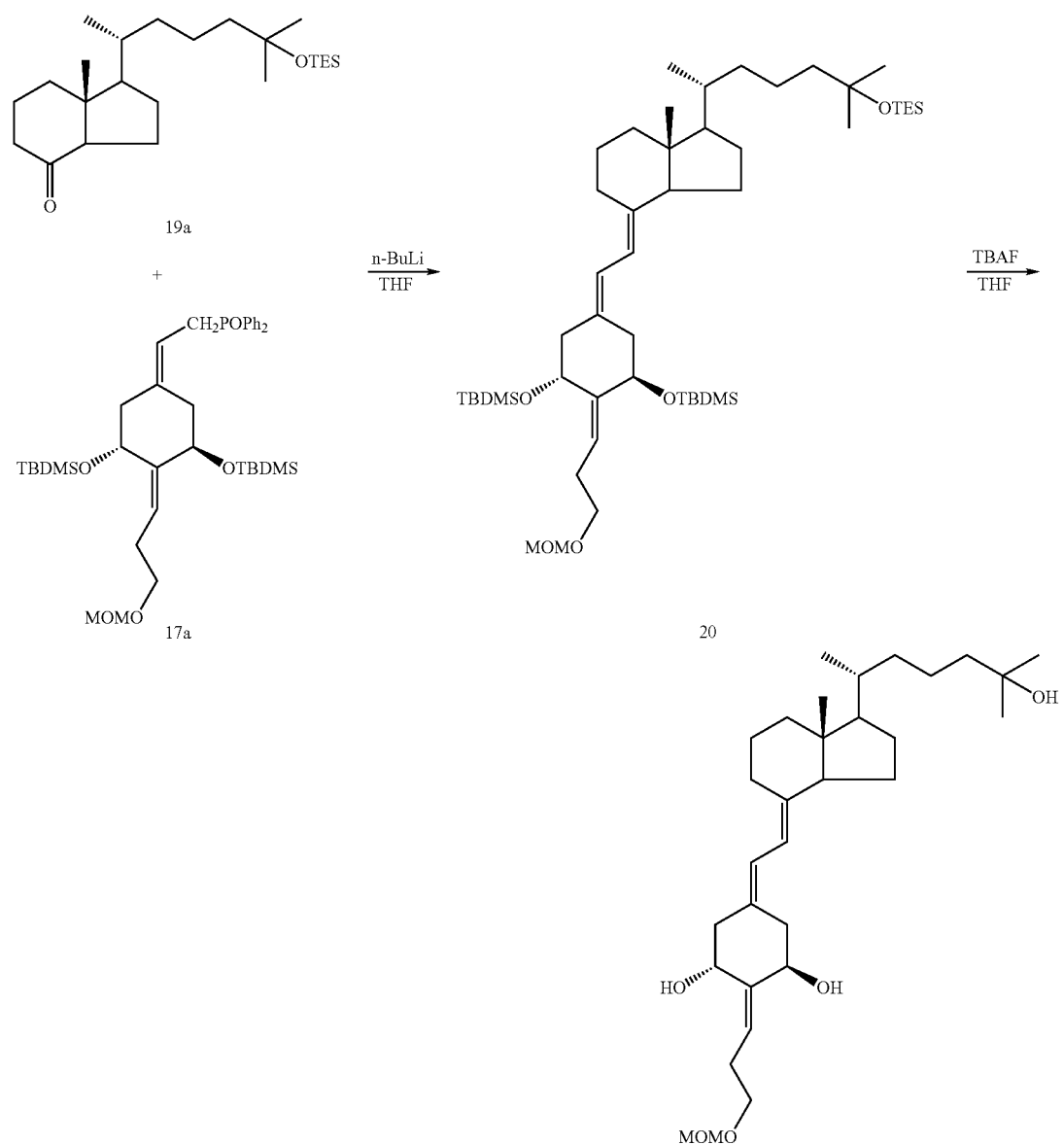

-continued
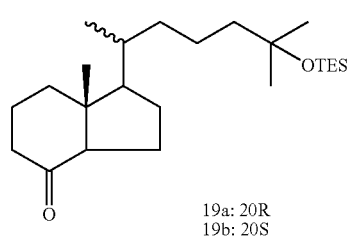
19a: 20R
19b: 20S
+
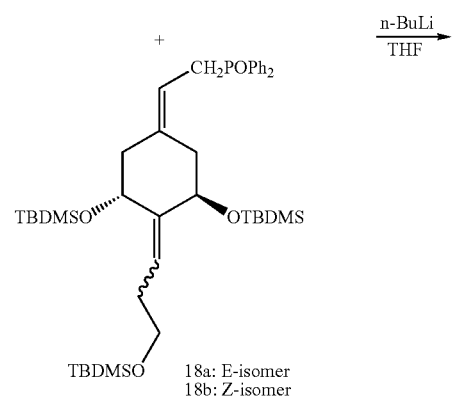
18a: E-isomer
18b: Z-isomer
n-BuLi / THF →
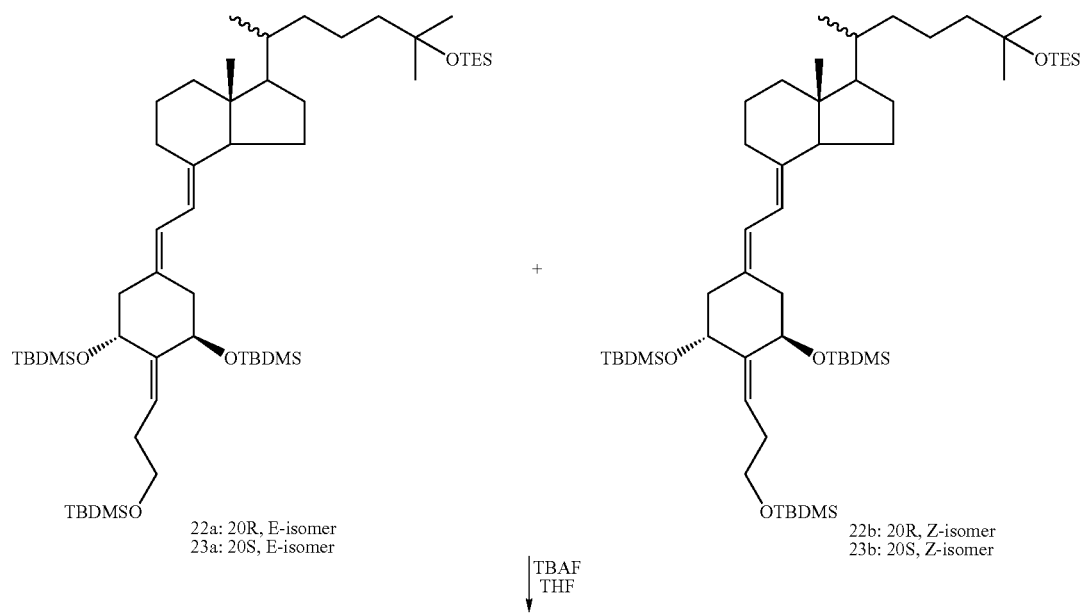
22a: 20R, E-isomer
23a: 20S, E-isomer
+
22b: 20R, Z-isomer
23b: 20S, Z-isomer
↓ TBAF / THF

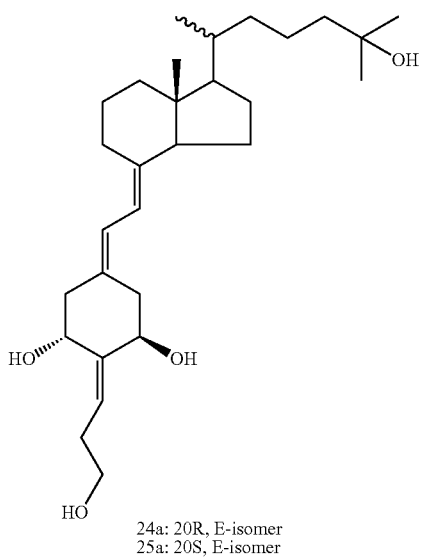

24a: 20R, E-isomer
25a: 20S, E-isomer

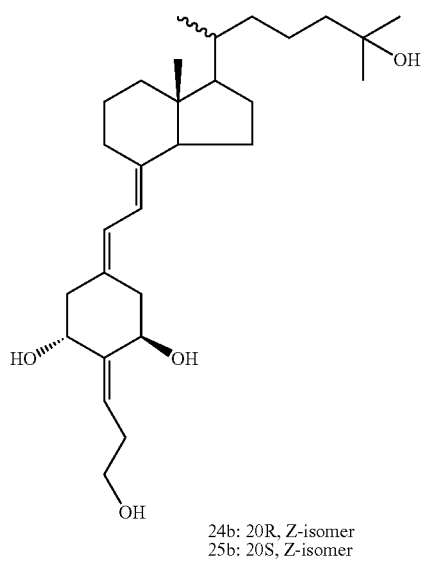

24b: 20R, Z-isomer
25b: 20S, Z-isomer

Biological Activity of Vitamin D Analogs

The following compounds were tested for biological activity with respect to vitamin D receptor binding, HL-60 cell differentiation, intestinal calcium transport, bone calcium mobilization, PTH suppression and hypercalcemia: (20R)-1α-hydroxy-2-methylene-19-nor-bishomopregnacalciferol ((20R)2MbisP); 2α-methyl-19-nor-(20S)-1α-hydroxy-bishomopregnacalciferol ((20S)2αMbisP); 2α-methyl-19-nor-1α-hydroxy-homopregnacalciferol (2α-methyl MP; 2-methylene-19-nor-(20S)-1α-hydroxy-trishomopregnacalciferol (2MtrisP); 2α-methyl-19,26,27-trinor-(20S)-1α-hydroxyvitamin $D_3$ (2α-methyl-19,26,27-trinor); 2-methylene-19,21-dinor-1α-hydroxybishomopregnacalciferol (19,21-dinor); 2-methylene-19-nor-1α-hydroxy-17-ene-homopregnacalciferol (VIT-I); and 2-methylene-18,19-dinor-1α-hydroxyhomopregnacalciferol (18,19-dinor-2MP).

Vitamin D Receptor Binding

Test Material
Protein Source

Full-length recombinant rat receptor was expressed in *E. coli* BL21(DE3) Codon Plus RIL cells and purified to homogeneity using two different column chromatography systems. The first system was a nickel affinity resin that utilizes the C-terminal histidine tag on this protein. The protein that was eluted from this resin was further purified using ion exchange chromatography (S-Sepharose Fast Flow). Aliquots of the purified protein were quick frozen in liquid nitrogen and stored at −80° C. until use. For use in binding assays, the protein was diluted in $TEDK_{50}$ (50 mM Tris, 1.5 mM EDTA, pH 7.4, 5 mM DTT, 150 mM KCl) with 0.1% Chaps detergent. The receptor protein and ligand concentration was optimized such that no more than 20% of the added radiolabeled ligand was bound to the receptor.

Study Drugs

Unlabeled ligands were dissolved in ethanol and the concentrations determined using UV spectrophotometry (1,25 $(OH)_2D_3$: molar extinction coefficient=18,200 and $\lambda_{max}$=265 nm; Analogs: molar extinction coefficient=42,000 and $\lambda_{max}$=252 nm). Radiolabeled ligand ($^3$H-1,25$(OH)_2D_3$, ~159 Ci/mmole) was added in ethanol at a final concentration of 1 nM.

Assay Conditions

Radiolabeled and unlabeled ligands were added to 100 mcl of the diluted protein at a final ethanol concentration of ≦10%, mixed and incubated overnight on ice to reach binding equilibrium. The following day, 100 mcl of hydroxylapatite slurry (50%) was added to each tube and mixed at 10-minute intervals for 30 minutes. The hydroxylapaptite was collected by centrifugation and then washed three times with Tris-EDTA buffer (50 mM Tris, 1.5 mM EDTA, pH 7.4) containing 0.5% Titron X-100. After the final wash, the pellets were transferred to scintillation vials containing 4 ml of Biosafe II scintillation cocktail, mixed and placed in a scintillation counter. Total binding was determined from the tubes containing only radiolabeled ligand.

HL-60 Differentiation

Test Material
Study Drugs

The study drugs were dissolved in ethanol and the concentrations determined using UV spectrophotometry. Serial dilutions were prepared so that a range of drug concentrations could be tested without changing the final concentration of ethanol (≦0.2%) present in the cell cultures.

Cells

Human promyelocytic leukemia (HL60) cells were grown in RPMI-1640 medium containing 10% fetal bovine serum. The cells were incubated at 37° C. in the presence of 5% $CO_2$.

Assay Conditions

HL60 cells were plated at $1.2 \times 10^5$ cells/ml. Eighteen hours after plating, cells in duplicate were treated with drug. Four days later, the cells were harvested and a nitro blue tetrazolium reduction assay was performed (Collins et al., 1979; *J. Exp. Med.* 149:969-974). The percentage of differentiated cells was determined by counting a total of 200 cells and recording the number that contained intracellular black-blue formazan deposits. Verification of differentiation to monocytic cells was determined by measuring phagocytic activity (data not shown).

In Vitro Transcription Assay

Transcription activity was measured in ROS 17/2.8 (bone) cells that were stably transfected with a 24-hydroxylase (24Ohase) gene promoter upstream of a luciferase reporter gene (Arbour et al., 1998). Cells were given a range of doses. Sixteen hours after dosing the cells were harvested and luciferase activities were measured using a luminometer. RLU=relative luciferase units.

Intestinal Calcium Transport and Bone Calcium Mobilization

Male, weanling Sprague-Dawley rats were placed on Diet 11 (0.47% Ca) diet+AEK for one week followed by Diet 11 (0.02% Ca)+AEK for 3 weeks. The rats were then switched to a diet containing 0.47% Ca for one week followed by two weeks on a diet containing 0.02% Ca. Dose administration began during the last week on 0.02% calcium diet. Four consecutive ip doses were given approximately 24 hours apart. Twenty-four hours after the last dose, blood was collected from the severed neck and the concentration of serum calcium determined as a measure of bone calcium mobilization. The first 10 cm of the intestine was also collected for intestinal calcium transport analysis using the everted gut sac method.

PTH Suppression and Hypercalcemia

Species
Adult, female Sprague-Dawley rats were obtained from Harlan (Madison, Wis.).
Animal Husbandry
Upon receipt, the animals were identified by individual tail marks. Animals were housed in suspended, stainless steel, wire-bottom cages. Each cage contained one animal. The animal rooms were maintained at a temperature of 68 to 72° F. and a relative humidity of 25 to 75%. The holding rooms were set to provide 12 hours of light per day. Water and a purified rodent diet (Suda et al., Purified Rodent Diet-Diet 11) containing 0.47% and 0.3% phosphorus and fat soluble vitamins A, D, E and K were provided ad libitum.
Treatment Groups
Animals were randomly assigned to treatment groups (5 animals/group). All doses were administered intraperitoneally in 100 microliters of propylene glycol. Four to seven consecutive doses were given approximately 24 hours apart. Dosing was initiated after the animals had been allowed to acclimate for at least one week.

Dose Preparation

Control Material
A. Negative Control Material
The negative control material was prepared by volumetrically measuring ethanol (<5%) and propylene glycol, mixing, and then placing in storage at 2 to 8° C.
B. Positive Control Material
$1,25(OH)_2D_3$ was prepared by determining the concentration of an ethanol stock solution using UV spectrophotometry (extinction coefficient=18,200; $\lambda_{max}$=265 nm). The required amount of $1,25(OH)_2D_3$ was volumetrically measured into propylene glycol so that there was less than 5% ethanol in the final solution. The solution was mixed and then stored at 2 to 8° C.
Test Material
The analogs were prepared by first determining the concentration of an ethanol stock solution using UV spectrophotometry (extinction coefficient=42,000; $\lambda_{max}$=252 nm). The analog solutions were then volumetrically added to propylene glycol so that there was less than 5% ethanol in the final solution. The solution was mixed and stored at 2 to 8° C.
Dose Administration Method
Both control and test articles were administered by intraperitoneal injection in 100 microliters for 4-7 consecutive days spaced approximately 24 hours apart. $1,25(OH)_2D_3$ was given for 4 consecutive days, whereas, the test drugs were given for 7 consecutive days.
Serum PTH Levels
Twenty-four hours after the final dose, blood was collected from the tail artery and the concentration of bioactive serum PTH was measured using the rat BioActive Intact PTH ELISA Kit from Immutopics, Inc. (San Clemente, Calif.).
Serum Calcium Analysis
Twenty-four hours after the final dose, approximately 1 ml of blood was collected from the tail artery of each experimental animal. The blood was allowed to coagulate at room temperature and then centrifuged at 3000×g for 15 minutes. The serum was transferred to a polypropylene tube and stored frozen at –20° C. The level of calcium was determined by diluting the serum into 0.1% lanthum chloride and measuring the absorbance on an atomic absorption spectrophotometer (Perkin Elmer Model 3110, Shelton, Conn.).

The experiments described above were conducted and showed that 2-methylene-19,21-dinor-1α-hydroxy-bishomopregnacalciferol (19,21-dinor) binds to the recombinant vitamin D receptor, but is about 5 times less active than is 1α,25-dihydroxyvitamin $D_3$ in this respect. Furthermore, 19,21-dinor was active in stimulating transcription of a reporter gene stably transfected in Ros17/2.8 (bone) cells, indicating significant biological activity. 19,21-Dinor was about 15 times less active than 1α,25-dihydroxyvitamin $D_3$ in inducing differentiation of HL-60 cells. 19,21-Dinor had no calcemic activity when measured either by intestinal calcium transport or bone calcium mobilization even when given at 100 times the dose of 1α,25-dihydroxyvitamin $D_3$. However, 19,21-dinor did possess significant activity in suppressing parathyroid hormone levels in normal rats. 19,21-Dinor may thus find use in the treatment of autoimmune diseases such as multiple sclerosis, type I diabetes, rheumatoid arthritis, lupus, and other similar degenerative diseases. 19,21-Dinor should also have significant activity in treating malignant growth such as colorectal, breast and prostate cancers. All of these activities should be evident in the absence of raising serum calcium concentrations. 19,21-Dinor should also be useful in treating secondary hyperparathyroidism found in patients who have lost kidney function such as those on hemodialysis or peritoneal dialysis.

The experiments described above were conducted and showed that 2-methylene-19-nor-(20R)-1α-hydroxy-bishomopregnacalciferol ((20R)2MbisP) is approximately equally effective as 1α,25-$(OH)_2D_3$ in binding to the recombinant vitamin D receptor. However, (20R)2MbisP is about 5 times less active than 1α,25-$(OH)_2D_3$ in causing the differentiation of HL-60 cells in culture. Likewise, (20R)2MbisP is about 5 times less active than 1α,25-$(OH)_2D_3$ in turning on transcription of a reporter gene coupled to the CYP-24 promoter. In vivo testing demonstrated that at even very high concentrations, (20R)2MbisP does not support either intestinal calcium transport or bone calcium mobilization. Additionally, doses as high as 45 nmol/day of (20R)2MbisP failed to cause hypercalcemia in adult rats. On the other hand, (20R)2MbisP showed considerable activity in suppression of parathyroid hormone (PTH) in the plasma of rats illustrating that it has significant in vivo activity albeit not on calcium transport or mobilization of calcium from bone. These properties illustrate that (20R)2MbisP should be very useful in the treatment of diseases where a rise in serum calcium is not desirable. Thus, (20R)2MbisP should find utility in the treatment of secondary hyperparathyroidism of patients suffering from chronic kidney failure because it is undesirable to elevate serum calcium above normal in these patients for fear of calcification of heart, aorta and other vital organs while it suppresses parathyroid gland proliferation and transcription of the preproparathyroid gene. (20R)2MbisP should also be useful in the treatment of malignancy such as breast, colorectal and prostate cancers, or in the treatment of autoimmune diseases such as multiple sclerosis, lupus, rheumatoid arthritis, type 1 diabetes, and inflammatory bowel disease. (20R)2MbisP should also be useful in preventing transplant rejection.

The experiments described above were conducted and showed that 2-methylene-19-nor-(20S)-1α-hydroxy-trishomopregnacalciferol (2-MtrisP) is almost equal to the native hormone in binding to the vitamin D receptor. 2-MtrisP is also equal in activity to 1α,25-(OH)$_2$D$_3$ in inducing differentiation of HL-60 cells. Although 2-MtrisP is not quite as effective as 1α,25-(OH)$_2$D$_3$ in causing transcription, it is within one order of magnitude of the activity of 1α,25-(OH)$_2$D$_3$ in this respect. 2-MtrisP has little bone calcium mobilizing activity even at the very high dose of 2340 pmol/day. However, 2-MtrisP does retain some ability to elevate intestinal calcium transport. 2-MtrisP is remarkably effective in suppressing parathyroid hormone in adult rats, while not raising serum calcium concentrations. 2-MtrisP will find use as an effective therapy for secondary hyperparathroidism of dialysis patients. 2-MtrisP may also be used for the treatment of malignancy of colon, prostate, and breast, and can be used in the therapy of autoimmune diseases such as multiple sclerosis, diabetes type 1 and type 2 diabetes, inflammatory bowel diseases, lupus, rheumatoid arthritis and Lou Gehrig's Disease.

The experiments described above were conducted on 2α-methyl-19-nor-(20S)-1α-hydroxy-bishomopregnacalciferol ((20S)2αMbisP). The introduction of a methyl group at the 2-position, and the elimination of carbons 24, 25, 26 and 27 in the side chain of had little or no effect on binding to the full length recombinant rat vitamin D receptor, as compared to 1α,25-dihydroxyvitamin D$_3$. The compound (20S)2αMbisP bound equally well to the receptor as compared to the standard 1α,25-(OH)$_2$D$_3$. It might be expected from these results that compound (20S)2αMbisP would have equivalent biological activity. Surprisingly, however, compound (20S)2αMbisP is a highly selective analog with unique biological activity. For example, (20S)2αMbisP has very little activity as compared to that of 1α,25(OH)$_2$D$_3$ in stimulating intestinal calcium transport. (20S)2αMbisP also has very little bone calcium mobilization activity, as compared to 1α,25(OH)$_2$D$_3$. (20S)2αMbisP may thus be characterized as having little, if any, calcemic activity. (20S)2αMbisP is almost as potent as 1α,25(OH)$_2$D$_3$ on HL-60 differentiation, making it an excellent candidate for the treatment of psoriasis and cancer, especially against leukemia, colon cancer, breast cancer and prostate cancer. In addition, due to its relatively high cell differentiation activity, (20S)2αMbisP provides a therapeutic agent for the treatment of various skin conditions including wrinkles, lack of adequate dermal hydration, i.e. dry skin, lack of adequate skin firmness, i.e. slack skin, and insufficient sebum secretion. Use of this compound thus not only results in moisturizing of skin but also improves the barrier function of skin. (20S)2αMbisP also has about the same transcriptional activity as 1α,25(OH)$_2$D$_3$ in bone cells. This result, together with the cell differentiation activity, suggests that (20S)2αMbisP will be very effective in psoriasis because it has direct cellular activity in causing cell differentiation and in suppressing cell growth. These data also indicate that (20S)2αMbisP may have significant activity as an anti-cancer agent, especially against leukemia, colon cancer, breast cancer, skin cancer and prostate cancer.

The experiments described above were conducted on 2α-methyl-19-nor-1α-hydroxy-homopregnacalciferol (2α-methyl MP). The introduction of a methyl group at the 2-position, and the elimination of carbons 23, 24, 25, 26 and 27 in the side chain of had little or no effect on binding to the full length recombinant rat vitamin D receptor, as compared to 1α,25-dihydroxyvitamin D$_3$. The compound 2α-methyl MP bound equally well to the receptor as compared to the standard 1α,25-(OH)$_2$D$_3$. It might be expected from these results that 2α-methyl MP would have equivalent biological activity. Surprisingly, however, 2α-methyl MP is a highly selective analog with unique biological activity. For example, 2α-methyl MP has very little activity as compared to that of 1α,25(OH)$_2$D$_3$ in stimulating intestinal calcium transport. 2α-methyl MP also has very little bone calcium mobilization activity, as compared to 1α,25(OH)$_2$D$_3$. 2α-methyl MP may thus be characterized as having little, if any, calcemic activity. 2α-methyl MP is almost as potent as 1α,25(OH)$_2$D$_3$ on HL-60 differentiation, making it an excellent candidate for the treatment of psoriasis and cancer, especially against leukemia, colon cancer, breast cancer and prostate cancer. In addition, due to its relatively high cell differentiation activity, 2α-methyl MP provides a therapeutic agent for the treatment of various skin conditions including wrinkles, lack of adequate dermal hydration, i.e. dry skin, lack of adequate skin firmness, i.e. slack skin, and insufficient sebum secretion. Use of this compound thus not only results in moisturizing of skin but also improves the barrier function of skin. 2α-methyl MP also has about the same transcriptional activity as 1α,25(OH)$_2$D$_3$ in bone cells. This result, together with the cell differentiation activity, suggests that 2α-methyl MP will be very effective in psoriasis because it has direct cellular activity in causing cell differentiation and in suppressing cell growth. These data also indicate that 2α-methyl MP may have significant activity as an anti-cancer agent, especially against leukemia, colon cancer, breast cancer, skin cancer and prostate cancer.

The experiments described above were conducted on 2α-methyl-19,26,27-trinor-(20S)-1α-hydroxyvitamin D$_3$ (2α-methyl 19,26,27-trinor). The introduction of a methyl group in an alpha orientation to the 2-position and the removal of the two methyl groups at the 26 and 27 positions in the side chain had little or no effect on binding to the full length recombinant rat vitamin D receptor, as compared to 1α,25-dihydroxyvitamin D$_3$. 2α-Methyl 19,26,27-trinor bound equally well to the receptor as compared to the standard 1α,25-(OH)$_2$D$_3$. It might be expected from these results that 2α-methyl 19,26,27-trinor would have equivalent biological activity. Surprisingly, however, this compound is a highly selective analog with unique biological activity. 2α-Methyl 19,26,27-trinor has very little bone calcium mobilization activity, as compared to 1α,25(OH)$_2$D$_3$. Thus, 2α-methyl 19,26,27-trinor may be characterized as having little, if any, calcemic activity. 2α-Methyl 19,26,27-trinor is almost as potent as 1 α,25(OH)$_2$D$_3$ on HL-60 differentiation, making it an excellent candidate for the treatment of psoriasis and cancer, especially against leukemia, colon cancer, breast cancer and prostate cancer. In addition, due to its relatively high cell differentiation activity, this compound provides a therapeutic agent for the treatment of various skin conditions including wrinkles, lack of adequate dermal hydration, i.e. dry skin, lack of adequate skin firmness, i.e. slack skin, and insufficient sebum secretion. Use of this compound thus not only results in moisturizing of skin but also improves the barrier function of skin. 2α-Methyl 19,26,27-trinor has transcriptional activity similar to 1α,25-dihydroxyvitamin D$_3$ in bone cells. This result, together with the cell differentiation activity, suggests that 2α-methyl 19,26,27-trinor will be very effective in psoriasis because it has direct cellular activity in causing cell differentiation and in suppressing cell growth. These data also indicate that 2α-methyl 19,26,27-trinor may have significant activity as an anti-cancer agent, especially against leukemia, colon cancer, breast cancer, skin cancer and prostate cancer.

The experiments described above were conducted on 2-methylene-18,19-dinor-1α-hydroxyhomopregnacalciferol (18,19-dinor 2MP)). The introduction of a methylene group to the 2-position, the substitution of a hydrogen for the methyl normally found at the 18 position, and the elimination of carbons 23, 24, 25, 26 and 27 in the side chain had little or no effect on binding to the full length recombinant rat vitamin D receptor, as compared to 1 α,25-dihydroxyvitamin D$_3$. The compound 18,19-dinor 2MP bound equally well to the receptor as compared to the standard 1α,25-(OH)$_2$D$_3$. It might be expected from these results that compound 18,19-dinor 2MP would have equivalent biological activity. Surprisingly, however, 18,19-dinor 2MP is a highly selective analog with unique biological activity. 18,19-Dinor 2MP has very little activity as compared to that of 1α,25(OH)$_2$D$_3$ in stimulating intestinal calcium transport. 18,19-Dinor 2MP has very little bone calcium mobilization activity, as compared to 1α,25 (OH)$_2$D$_3$. 18,19-Dinor 2MP may thus be characterized as having little, if any, calcemic activity. 18,19-Dinor 2MP is almost as potent as 1α,25(OH)$_2$D$_3$ on HL-60 differentiation, making it an excellent candidate for the treatment of psoriasis and cancer, especially against leukemia, colon cancer, breast cancer and prostate cancer. In addition, due to its relatively high cell differentiation activity, this compound provides a therapeutic agent for the treatment of various skin conditions including wrinkles, lack of adequate dermal hydration, i.e. dry skin, lack of adequate skin firmness, i.e. slack skin, and insufficient sebum secretion. Use of this compound thus not only results in moisturizing of skin but also improves the barrier function of skin. 18,19-Dinor 2MP has about the same transcriptional activity as 1α,25(OH)$_2$D$_3$ in bone cells. This result, together with the cell differentiation activity, suggests that 18,19-dinor 2MP will be very effective in psoriasis because it has direct cellular activity in causing cell differentiation and in suppressing cell growth. These data also indicate that 18,19-dinor 2MP may have significant activity as an anti-cancer agent, especially against leukemia, colon cancer, breast cancer, skin cancer and prostate cancer.

The experiments described above were conducted on 2-methylene-19-nor-1α-hydroxy-17-ene-homopregnacalciferol (VIT-I)). The introduction of a methylene group to the 2-position, the introduction of a double bond between the 17 and 20 positions, and the elimination of carbons 23, 24, 25, 26 and 27 in the side chain had little or no effect on binding to the full length recombinant rat vitamin D receptor, as compared to 1α,25(OH)$_2$D$_3$. VIT-I bound equally well to the receptor as compared to the standard 1α,25(OH)$_2$D$_3$. It might be expected from these results that compound VIT-I would have equivalent biological activity. Surprisingly, however, compound VIT-I is a highly selective analog with unique biological activity. VIT-I has very little activity as compared to that of 1α,25(OH)$_2$D$_3$ in stimulating intestinal calcium transport. VIT-I also has very little bone calcium mobilization activity, as compared to 1α,25(OH)$_2$D$_3$. VIT-I may thus be characterized as having little, if any, calcemic activity. VIT-I is almost as potent as 1α,25(OH)$_2$D$_3$ on HL-60 differentiation, making it an excellent candidate for the treatment of psoriasis and cancer, especially against leukemia, colon cancer, breast cancer and prostate cancer. In addition, due to its relatively high cell differentiation activity, this compound provides a therapeutic agent for the treatment of various skin conditions including wrinkles, lack of adequate dermal hydration, i.e. dry skin, lack of adequate skin firmness, i.e. slack skin, and insufficient sebum secretion. Use of this compound thus not only results in moisturizing of skin but also improves the barrier function of skin. VIT-I has about the same transcriptional activity as 1α,25(OH)$_2$D$_3$ in bone cells. This result, together with the cell differentiation activity, suggests that VIT-I will be very effective in psoriasis because it has direct cellular activity in causing cell differentiation and in suppressing cell growth. These data also indicate that VIT-I may have significant activity as an anti-cancer agent, especially against leukemia, colon cancer, breast cancer, skin cancer and prostate cancer.

The experiments described above were conducted on 2-methylene-19,26,27-trinor-(20S)-1α-hydroxyvitamin D$_3$ (OM)). The introduction of a methylene group to the 2-position and the removal of the two methyl groups at the 26 and 27 positions in the side chain had little or no effect on binding to the full length recombinant rat vitamin D receptor, as compared to 1α,25(OH)$_2$D$_3$. The compound OM bound equally well to the receptor as compared to the standard 1α,25(OH)$_2$D$_3$. It might be expected from these results that compound OM would have equivalent biological activity. Surprisingly, however, compound OM is a highly selective analog with unique biological activity. OM has very little activity as compared to that of 1α,25(OH)$_2$D$_3$ in stimulating intestinal calcium transport. OM also has very little bone calcium mobilization activity, as compared to 1 α,25 (OH)$_2$D$_3$. OM may thus be characterized as having little, if any, calcemic activity. OM is also almost as potent as 1α,25 (OH)$_2$D$_3$ on HL-60 differentiation, making it an excellent candidate for the treatment of psoriasis and cancer, especially against leukemia, colon cancer, breast cancer and prostate cancer. In addition, due to its relatively high cell differentiation activity, this compound provides a therapeutic agent for the treatment of various skin conditions including wrinkles, lack of adequate dermal hydration, i.e. dry skin, lack of adequate skin firmness, i.e. slack skin, and insufficient sebum secretion. Use of this compound thus not only results in moisturizing of skin but also improves the barrier function of skin. OM has about the same transcriptional activity as 1 α,25(OH)$_2$D$_3$ in bone cells. This result, together with the cell differentiation activity, suggests that OM will be very effective in psoriasis because it has direct cellular activity in causing cell differentiation and in suppressing cell growth. These data also indicate that OM may have significant activity as an anti-cancer agent, especially against leukemia, colon cancer, breast cancer, skin cancer and prostate cancer.

The experiments described above were conducted on 2-methylene-18,19-dinor-(20S)-1α,25-dihydroxyvitamin D$_3$ (VD-03)). This compound is very active in binding to the full length recombinant rat vitamin D receptor, as compared to 1α,25(OH)$_2$D$_3$. VD-03 exhibited a pattern of biological activity having high potency in promoting the differentiation of malignant cells, relatively high intestinal calcium transport activity and a relatively low ability to mobilize calcium from bone. VD-03 exhibited higher transcriptional activity than 1α,25-dihydroxyvitamin D$_3$ in bone cells. This result, together with the cell differentiation activity, suggests that VD-03 will be very effective in psoriasis because it has direct cellular activity in causing cell differentiation and in suppressing cell growth. These data also indicate that VD-03 may have significant activity as an anti-cancer agent, especially against leukemia, colon cancer, breast cancer, skin cancer and prostate cancer. VD-03 is about as active as 1,25-dihydroxyvitamin D$_3$ in intestinal calcium transport activity. Although VD-03 has some ability to mobilize calcium from bone, it is clearly not as active in this regard as 1α,25-dihydroxyvitamin D$_3$. Thus, VD-03 shows a selective activity profile combining high potency in inducing the differentiation of malignant cells, relatively high intestinal calcium transport activity and relatively low bone calcium mobilization activity.

The experiments described above were conducted on 1AGR, 1AGS, and F-Wit. F-Wit, 1AGR, and 1AGS are all very active in binding to the 1α,25-hydroxyvitamin D$_3$ rat receptor. The 2-propylidene-19-nor compounds exhibit a pattern of biological activity having high potency in promoting the differentiation of malignant cells, relatively high intestinal calcium transport activity and a relatively high ability to mobilize calcium from bone. This is illustrated by the biological assay results obtained for F-Wit, 1AGR, 1AGS, and 1AGS. Differentiation activity of human leukemia cells (HL-60 cells) in culture to monocytes was assessed by a standard differentiation assay, abbreviated as NBT reduction (nitroblue tetrazolium reduction). The results showed that the analogs, F-Wit, 1AGR, and 1AGS are all as potent as 1α,25-dihydroxyvitamin D$_3$ and 2MD in promoting the differentiation of leukemia cells. Thus, in the NBT assay, close to 90% of the cells were induced to differentiate by 1α,25-dihydroxyvitamin D$_3$ at a concentration of $1\times10^{-7}$M, and the same degree of differentiation was observed for F-Wit, 1AGR, and 1AGS at $1\times10^{-7}$M. F-Wit, 1AGR, and 1AGS all have significant transcriptional activity in bone cells. This result, together with the cell differentiation activity, suggests that F-Wit, 1AGR, and 1AGS, will be very effective in psoriasis because they have direct cellular activity in causing cell differentiation and in suppressing cell growth. These data also indicate that F-Wit, 1AGR, and 1AGS may have significant activity as anti-cancer agents, especially against leukemia, colon cancer, breast cancer, skin cancer and prostate cancer. F-Wit, 1AGR, and 1AGS all exhibited relatively high intestinal calcium transport activity, and are more active than 2MD in intestinal calcium transport activity. F-Wit, 1AGR, and 1AGS all exhibited significant ability to mobilize calcium from bone, and were less active in this regard than 2MD. Thus, in summary, F-Wit, 1AGR, and 1AGS, showed a selective activity profile combining high potency in inducing the differentiation of malignant cells, relatively high intestinal calcium transport activity and moderate bone calcium mobilization activity.

Various 19-nor vitamin D analogs were or are tested and found to inhibit the differentiation of preadipocytes into mature adipocytes, to reduce body fat, to inhibit an increase in PPARγ, C/EBPα, and/or SCD-1 gene transcription and to be useful in treating and preventing obesity both in vivo and in vitro. The undifferentiated preadipocyte 3T3-L1 subline, a derivative of the original mouse fibroblast cell line, is one of the most accepted models for investigating the adipogenesis process and was used for the analysis. Two days after reaching confluence, 3T3-L1 cells can be induced to differentiate into adipocytes (see Mackall, J. C. et al. *J. Biol. Chem.*, 251(20), 6462-6464 (1976)) with the addition of a cAMP phosphodiesterase inhibitor, dexamethasone (a glucocortoid), and insulin. After initiation of this treatment, the cells showed or will show increased expression of the transcription factor PPARγ and C/EBPα, which are involved in the induction of adipose-specific genes, leading to the accumulation of fat droplets, and ultimately, the maturation into terminally-differentiated adipocytes (Green, H. et al., *Cell*, 3(2), 127-33 (1974); Mandrup, S. and Lane, M. D., *J. Biol. Chem.* 272, 5367-70 (1997); and Yeh, W. et al., *Genes Dev.* 9, 168-181 (1995)). The induction of PPARγ and C/EBPα is required for adipocyte differentiation. The expression of the adipocyte-specific marker gene, stearoyl-CoA desaturase gene 1 (SCD-1), is maximally increased 3 to 4 days after treatment of confluent cells with the inducer (Casimir, D. A. et al., *J. Biol. Chem.*, 271(47), 29847-29853 (1996)). SCD-1 is an enzyme found in adipocytes that converts saturated fatty acids (C16 and C18) to their monounsaturated forms (C16:1 and C18:1). The deposition of triglyceride can also be detected as early as 3 days, and by the $7^{th}$ to $14^{th}$ days post-confluence, greater than 80% of the cells in the monolayer stain positively with Oil-red-O.

Cell Culture

A 3T3-L1 cell line was grown to confluence in DMEM (high glucose) medium containing 10% fetal bovine or calf serum and 1% penicillin/streptomycin at 37° C. at 10% $CO_2$. Two days after the cells reached confluence (designated as day 0), they were given medium containing dexamethasone (390 ng/mL), insulin (10 µg/mL), and 3-isobutyl-1-methylxanthine (115 µg/mL) (referred to as MDI). Two days later and for the remainder of the experiment, the cells were given medium containing insulin and fetal bovine serum. Starting at day 0, the cells were also treated with a vitamin D analog (1α,25-dihydroxycholecalciferol (calcitriol); (20S)-2-methylene-19-nor-1α,25-dihydroxyvitamin $D_3$ (2-MD); (20S)-1α-hydroxy-2-methylene-19-nor-25-methylvitamin $D_3$ (TMM); (20S)-1α-hydroxy-2-methylene-19-nor-bishomopregnacalciferol (2-MbisP); 1α-hydroxy-2-methylene-19-nor-homopregnacalciferol (2-MP); (20R)-1α-hydroxy-2-methylene-19-nor-bishomopregnacalciferol ((20R)2MbisP); 2-methylene-19-nor-1α-hydroxy-pregnacalciferol (2-Mpregna); 2α-methyl-19-nor-(20S)-1α-hydroxy-bishomopregnacalciferol ((20S)2αMbisP); 2α-methyl-19-nor-1α-hydroxy-homopregnacalciferol (2α-methyl MP); 2-methylene-19-nor-(20S)-1α-hydroxy-trishomopregnacalciferol (2MtrisP); 2-methylene-19,26,27-trinor-(20S)-1α-hydroxyvitamin $D_3$ ((20S)OM); 2-(3'-hydroxypropylidene)-19-nor-(20S)-1α,25-dihydroxyvitamin $D_3$ (1AGS); 2-(3'-hydroxypropylidene)-19-nor-1α,25-dihydroxyvitamin $D_3$ (1AGR); 2-[(3'-methoxymethoxy)-propylidene]-19-nor-1α,25-dihydroxyvitamin $D_3$ (F-Wit); 2-methylene-19-nor-1α-hydroxy-17-ene-homopregnacalciferol (Vitamin I or VIT-I); 2-methylene-18,19-dinor-(20S)-1α,25-dihydroxyvitamin $D_3$ (VD-03); 2-methylene-19-nor-24-epi-1α,25-dihydroxyvitamin $D_2$ ((24epi)$D_2$); 19-nor-1α,25-dihydroxyvitamin $D_2$ (1α,25(OH)$_2$(19nor)$D_2$ or Zemplar); or (20S)-1β-hydroxy-2-methylene-19-nor-bishomo-pregnacalciferol(1β,20S)2MbisP)). The tissue culture medium was replenished every two days along with drug. On day 4 or 5, cells were harvested for the analysis of SCD-1 mRNA. On day 10, additional plates of cells were stained with Oil-red-O (Qiu, Z, et al., *J. Biol. Chem.*, 276(15), 11988-11995, (2001)).

A 3T3-L1 cell line is grown to confluence in DMEM (high glucose) medium containing 10% fetal bovine or calf serum and 1% penicillin/streptomycin at 37° C. at 10% $CO_2$. Two days after the cells reach confluence (designated as day 0), they are given medium containing dexamethasone (390 ng/mL), insulin (10 µg/mL), and 3-isobutyl-1-methylxanthine (115 µg/mL) (referred to as MDI). Two days later and for the remainder of the experiment, the cells are given medium containing insulin and fetal bovine serum. Starting at day 0, the cells are also treated with a vitamin D analog (2α-methyl-19,26,27-trinor-(20S)-1α-hydroxyvitamin $D_3$ (2α-methyl-19,26,27-trinor); 2-methylene-19,21-dinor-1α-hydroxybishomopregnacalciferol (19,21-dinor); or 2-methylene-18,19-dinor-1α-hydroxyhomopregnacalciferol (18,19-dinor-2MP))). The tissue culture medium is replenished every two days along with drug. On day 4 or 5, cells are harvested for the analysis of SCD-1 mRNA. On day 10, additional plates of cells are stained with Oil-red-O (Qiu, Z, et al., *J. Biol. Chem.*, 276(15), 11988-11995, (2001)). Each of the vitamin D compounds is found to inhibit adipocyte differentiation as assessed by Oil-Red-O staining, to inhibit SCD-1 gene transcription, to inhibit PPARγ2 and C/EBPα gene transcription, and to be useful in treating and preventing obesity and preventing weight gain and/or reducing weight.

Analysis of SCD-1 mRNA

Isolation of RNA

Total RNA was isolated from cells by the method of Chomczynski and Sacchi with minor modifications. Chomczynski, P. et al., *Anal. Biochem.* 162(1)156-159 (1987). Briefly, each plate of cells (100 mm dish) was rinsed with phosphate buffered saline followed by the addition of lysis buffer (4 mL containing 4 M guanidinium thiocyanate; 25 mM sodium citrate, pH 7; 0.5% sarkosyl (sodium lauryl sarcosinate); and 0.1M 2-mercaptoethanol) to each plate. The lysis buffer containing the 3T3-L1 cells was transferred to a 50 mL conical tube followed by addition of 0.1 volume of sodium acetate (2 M, pH 4.0) and mixing. To this, an equal volume of water saturated phenol was added followed by 0.3 volume chloroform:isoamyl alcohol (49:1, v:v). The mixture was immediately transferred to a glass Corex tube, cooled on ice for 15 minutes, and subjected to centrifugation at 10,000 rpm for 30 minutes (Sorvall RC5B Plus centrifuge; SS-34-rotor). The aqueous layer was transferred to a fresh Corex tube, and then isopropanol (4 mL) was added. The RNA was precipitated overnight at −20° C. and collected by centrifugation. The pellet was redissolved in 2 mL homogenization buffer to which an equal volume of isopropanol was added followed by precipitation and centrifugation. The RNA pellet was washed with 75% ethanol, followed by centrifugation and addition of water (200 µL) to resuspend the RNA pellet.

Reverse Transcription and Analysis by Quantitative PCR (RT-PCR)

Total RNA (1 µg) was reverse transcribed in a final volume of 25 µL using 15 units AMV reverse transcriptase, 100 pmol random hexamers, 28 units of Rnasin ribonuclease inhibitor, AMV reverse transcriptase reaction buffer (50 mM Tris-HCl, pH 8.3, 25° C.; 50 mM KCl; 10 mM $MgCl_2$; 0.5 mM spermidine; and 10 mM dithiothreitol), and 0.4 mM each of dATP, dCTP, dGTP, and dTTP. The RNA and random hexamers were heated at 65° C. for 3 minutes prior to addition of the other reagents. The reactions were then incubated at 20° C. for 10 minutes followed by incubation at 42° C. for 1 hour. The reactions were diluted with 100 µL of DEPC-treated H$_2$O and heated for 5 minutes at 90° C.

Analysis of adipocyte differentiation was determined by PCR with murine SCD-1 (Stearyol-CoA desaturase 1) primers (SCD-1 upstream=AGT TTC TTT CGT GGC TGG G (SEQ ID NO: 1); downstream=ATG AGT TGG AGG TAG GGA GGA (SEQ ID NO: 2)). Rat glyceraldehyde-3-phosphate dehydrogenase (GAPDH) was run as a housekeeping gene in order to normalize equivalent amounts of cDNA (GAPDH upstream=TGA AGG TCG GTG TGA ACG GAT TTG GC (SEQ ID NO: 3); downstream=CAT GTA GGC CAT GAG GTC CAC CAC (SEQ ID NO: 4)). RT-PCR was carried out using a Roche LightCycler. LightCycler PCR reactions were set up in capillary tubes using 5 µL of cDNA and a master mix containing upstream and downstream PCR primers, MgCl$_2$, and SYBR Green. The final concentrations of the reaction components were 0.5 µM each primer, 4 mM MgCl$_2$ (SCD-1) or 2 mM MgCl$_2$(GAPDH), and 1×SYBR Green master mix. Murine SCD-1 primers have a 63° C. annealing temperature and a 20 second extension time. Rat GAPDH primers have a 58° C. annealing temperature and a 40 second extension time. A dilution series of plasmid DNA for SCD-1 or GAPDH was used as a standard curve for each run; the diluted values were entered as concentration standards in the LightCycler input screen. A no template control was also included in each run-these were negative in all cases. Each sample was run in duplicate, and two runs were performed for each set of templates.

Analysis of PPARγ2 was determined by PCR using murine primers (upstream=TGC TGT TAT GGG TGA MC TCT G (SEQ ID NO: 5); downstream=GM ATC MC TGT GGT AAA GGG C (SEQ ID NO: 6)). RT-PCR was carried out as described above with 0.5 µM each primer, 2 mM MgCl$_2$, and 1×SYBR Green master mix. The murine PPARγ2 primers have a 62° C. annealing temperature and a 10 second extension time.

Analysis of C/EBPα was determined by PCR using murine primers (upstream=CGA GTA GGG GGA GCA AAA A (SEQ ID NO: 7); downstream=GCA AAA AGC MG GGA TTA GGA G (SEQ ID NO: 8)). RT-PCR was carried out as described above with 0.5 µM each primer, 2 mM MgCl$_2$, and 1×SYBR Green master mix. The murine C/EBPα primers have a 60° C. annealing temperature and a 12 second extension time.

Rodent and Animal Studies

The compounds described herein are administered to rodents and other animal subjects in accordance with standard rodent and animal subject obesity models and protocols. Administration of compounds of formula IA and IB, IIA, and IIB and other vitamin D analogs such as compounds of formula IIC, IID, IIE, IIF, IIG, IIH, IIJ, IIK, IIL, IIM, IIN, IIO, IIP, IIQ, IIR, IIS, IIT, IIU, IIV, and IIW to the animal subjects is found to result in a reduction in food intake or a change in energy utilization, to inhibit differentiation of preadipocytes into adipocytes, to reduce body fat, to inhibit an increase in SCD-1 gene transcription, to inhibit PPARγ2 and C/EBPα gene transcription, and to be useful in treating and preventing obesity and preventing weight gain and/or reducing weight.

Interpretation of Data

Figure 3:
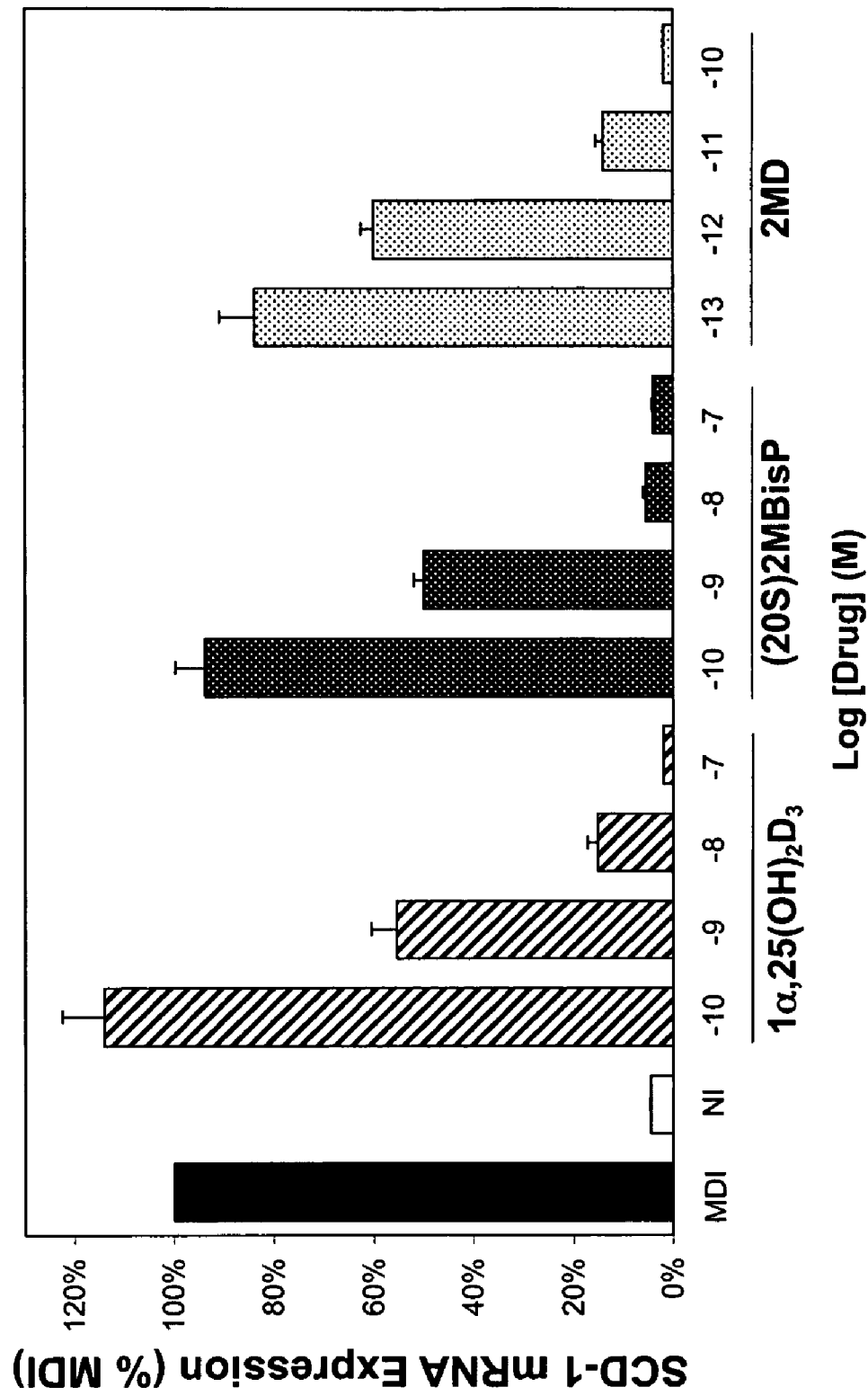
FIG. 3 is a graph representative of two to three independent experiments showing that the EC$_{50}$ for 1α,25(OH)$_2$D$_3$ inhibition of murine 3T3-L1 expression of SCD-1 mRNA is $2.0 \times 10^{-10}$ M, the EC$_{50}$ for (20S)2MbisP inhibition of murine 3T3-L1 expression of SCD-1 mRNA is $5.4 \times 10^{-10}$ M, and the EC$_{50}$ for 2MD inhibition of murine 3T3-L1 expression of SCD-1 mRNA is $2.9 \times 10^{-12}$ M.
Figure 4:
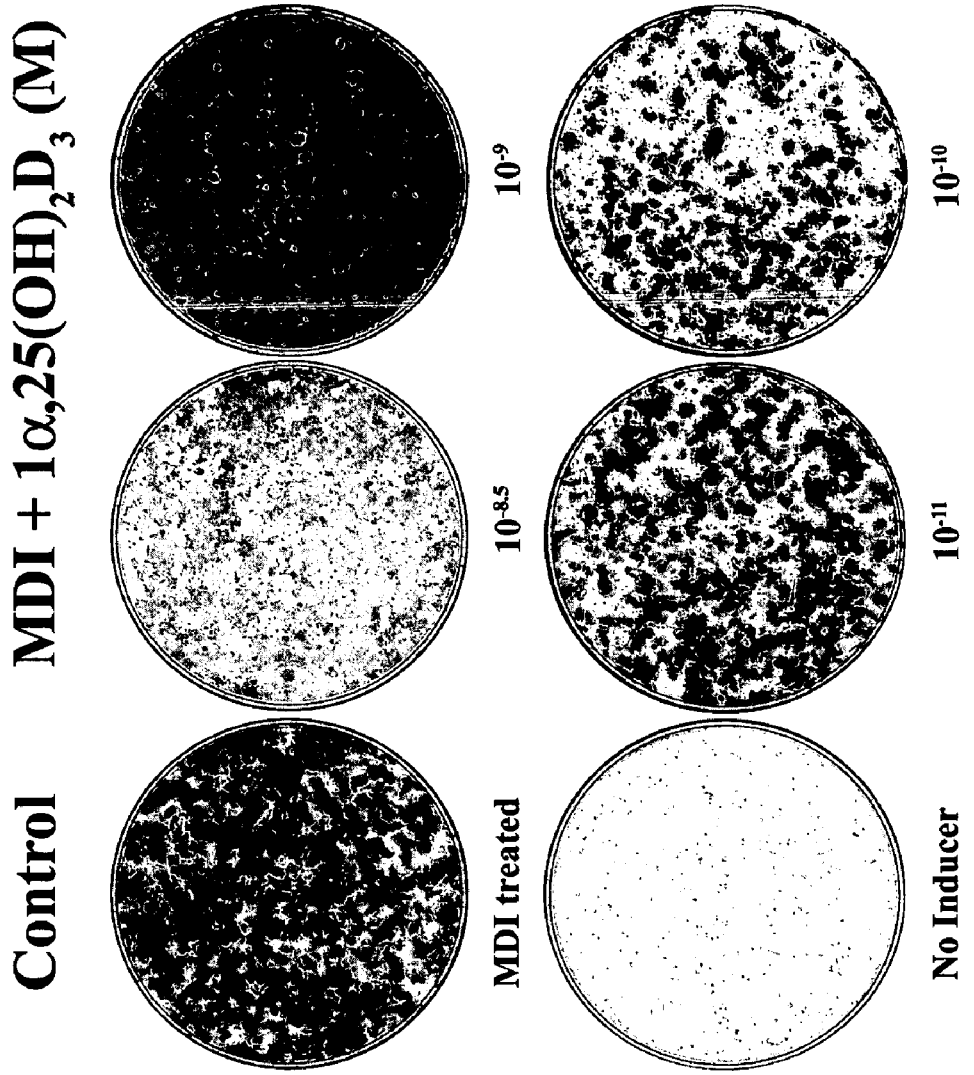
FIG. 4 is a scanned image showing 1α,25(OH)$_2$D$_3$ inhibition of MDI-treated murine 3T3-L1 cells into mature adipocytes at various concentrations ($10^{-8.5}$ M, $10^{-9.0}$ M, (top row left to right), $10^{-10.0}$ M, $10^{-11.0}$ M (bottom row right to left). MDI refers to a mixture containing methylisobutylxanthine, dexamethasone, and insulin.
Figure 5:
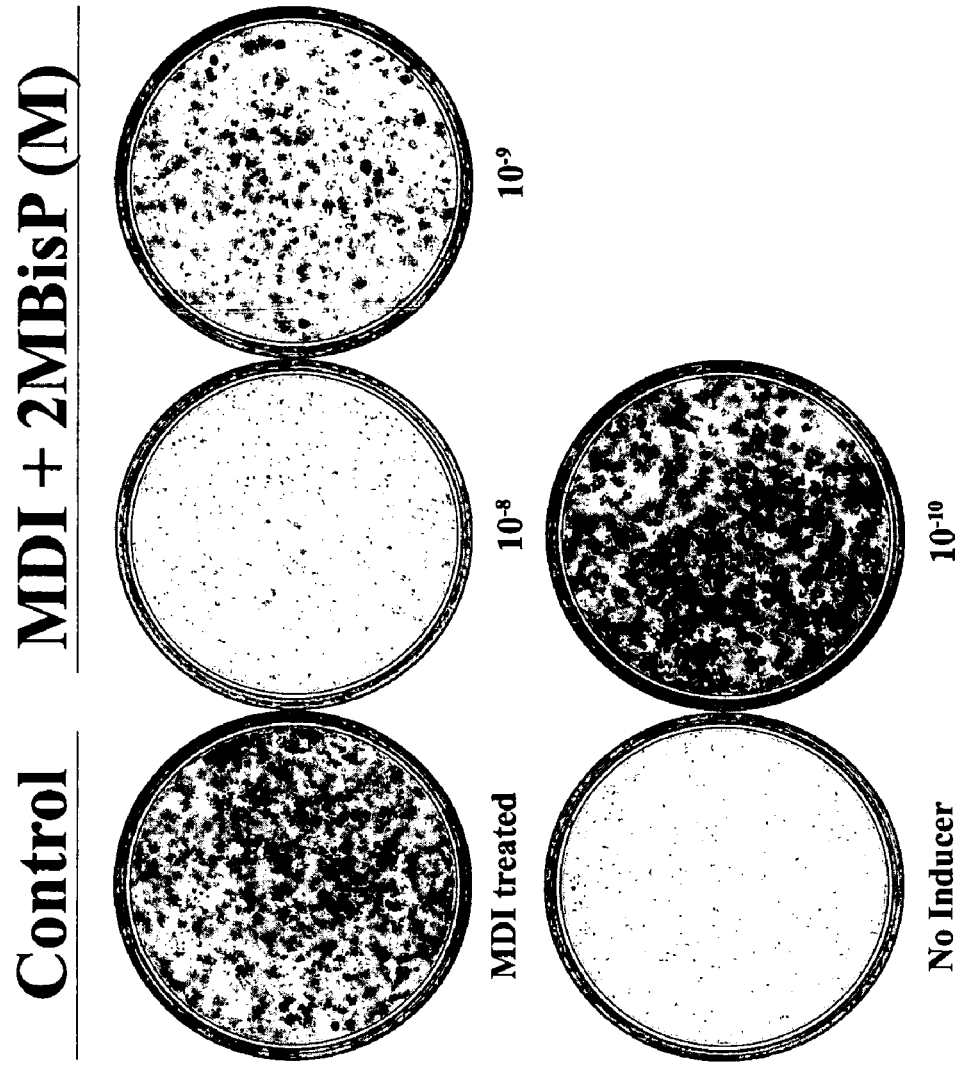
FIG. 5 is a scanned image showing (20S)2MbisP inhibition of MDI-treated murine 3T3-L1 cells into mature adipocytes at various concentrations ($10^{-8}$ M, $10^{-9}$ M, (top row left to right), $10^{-10.0}$ M (bottom row).
Figure 6:
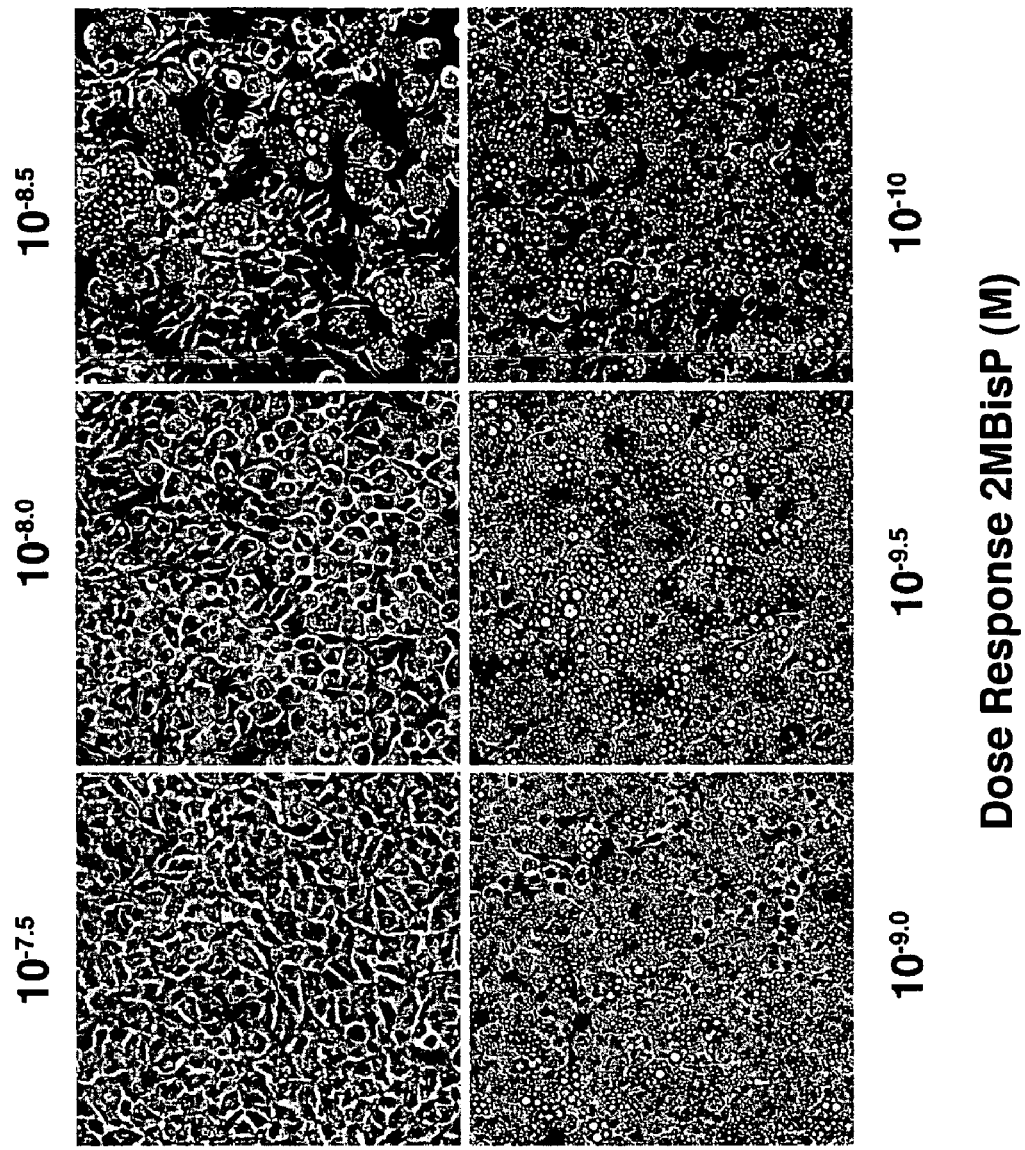
FIG. 6 is a scanned image showing (20S)2M-bisP inhibition of murine MDI-treated 3T3-L1 cells into mature adipocytes at various concentrations ($10^{-7.5}$ M, $10^{-8.0}$ M, $10^{-8.5}$ M, (top row left to right), $10^{-9.0}$ M, $10^{-9.5}$ M, $10^{-10.0}$ M (bottom row left to right).

The data shows that analogs of 1α,25-dihydroxyvitamin D$_3$ and 1α,25-dihydroxyvitamin D$_2$ such as 19-nor vitamin D analogs are highly potent in inhibiting the differentiation of 3T3-L1 cells into mature adipocytes. Collectively, the Oil-Red-O staining at 10 days (FIG. 2), and the analysis of SCD-1 mRNA at 4 days (FIG. 3) demonstrate that the EC$_{50}$ value for inhibition by 2-MD is approximately 2.9×10$^{-12}$ M. Therefore, 2-MD is at least 70 times more potent than the native hormone calcitriol (FIG. 2 and FIG. 3). 2-MbisP and TMM have also been shown to inhibit adipocyte differentiation as assessed by Oil-Red-O staining (FIGS. 2, 5, and 6). The EC$_{50}$ value for inhibition of SCD-1 mRNA induction by 2-MbisP is approximately 5.4×10$^{-10}$ M or 2 to 3 times less potent than the native hormone, 1,25-(OH)$_2$D$_3$.

Figure 7:
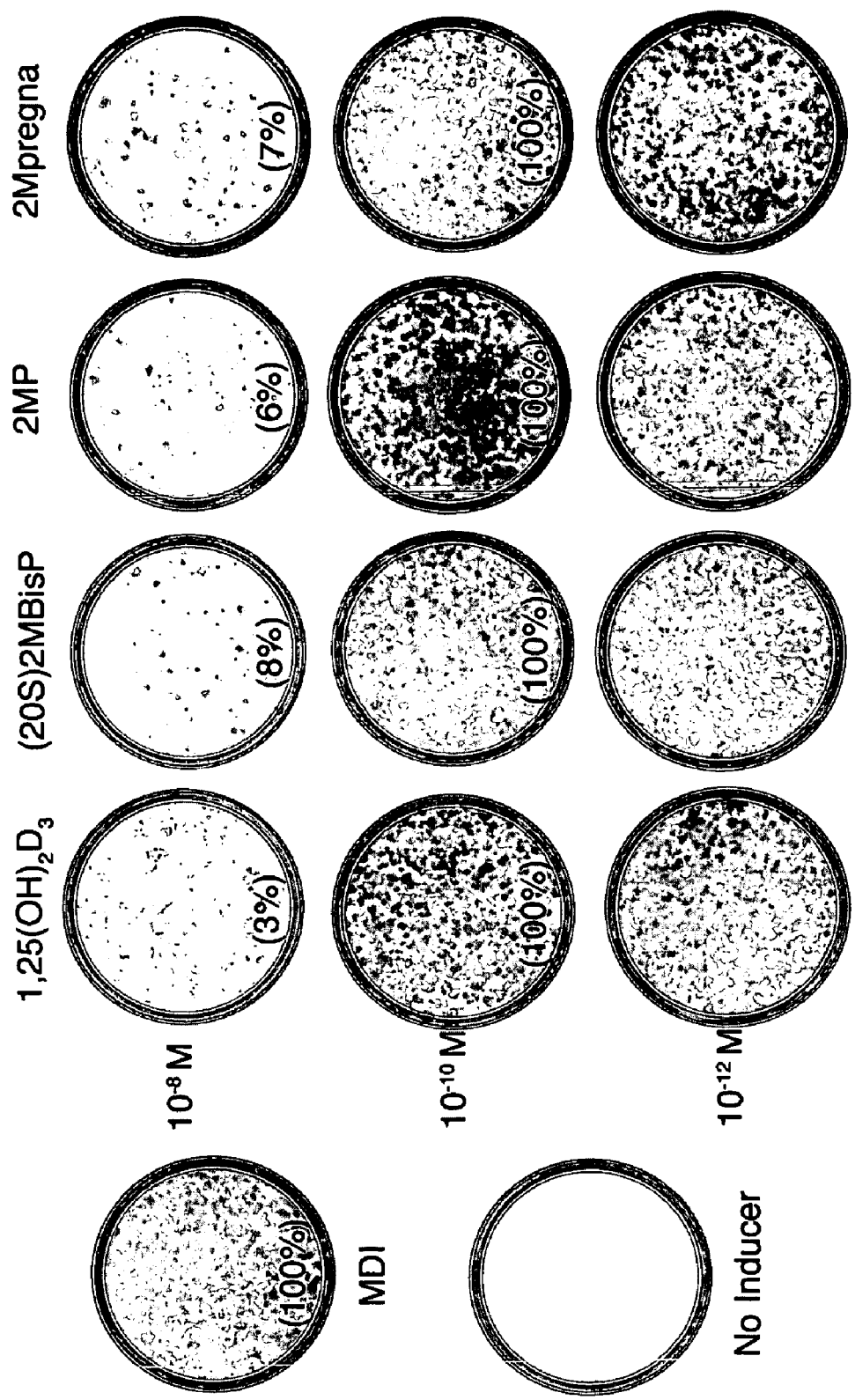
FIG. 7 is a scanned image showing that modification of the 2M-bisP side chain by eliminating 1 carbon atoms (2MP) and 2 carbon atoms (2Mpregna) yields compounds that are still active in inhibiting the differentiation of MDI-treated 3T3-L1 cells into mature adipocytes, as assessed by inhibition of oil-red-O staining and SCD1 mRNA induction (the expression of SCD1 mRNA is expressed as a percentage of that found in cells treated with MDI alone and is shown in the parentheses).
Figure 8:
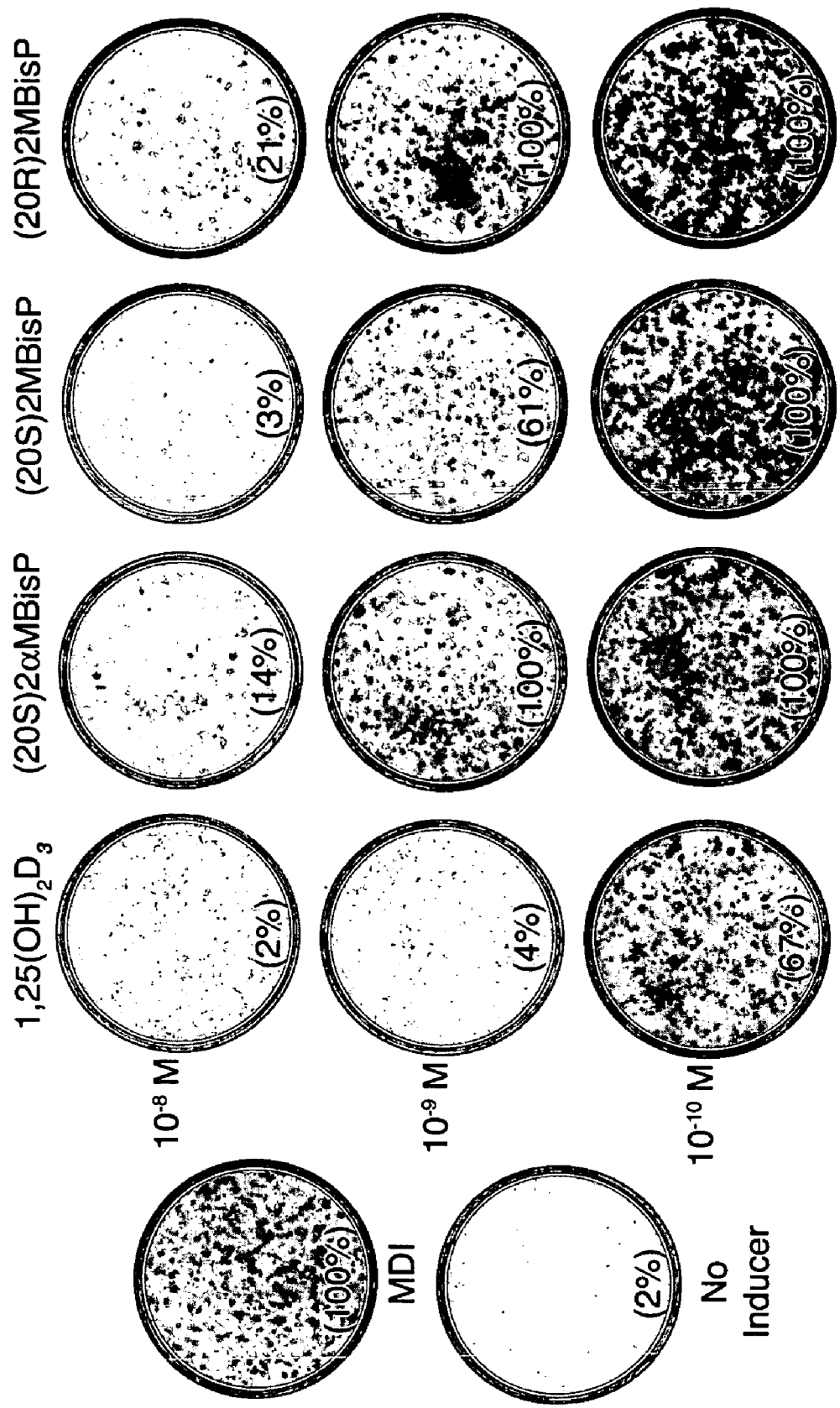
FIG. 8 is a scanned image showing that both 20S and 20R 2M-bisP as well as the 2α-methyl (20S) configuration of this compound are active in inhibiting the differentiation of MDI-treated 3T3-L1 cells into mature adipocytes, as assessed by inhibition of oil-red-O staining and SCD1 mRNA induction (the expression of SCD1 mRNA is expressed as a percentage of that found in cells treated with MDI alone and is shown in the parentheses). All compounds were tested at a concentration of $1 \times 10^{-8.5}$ M.
Figure 10A:
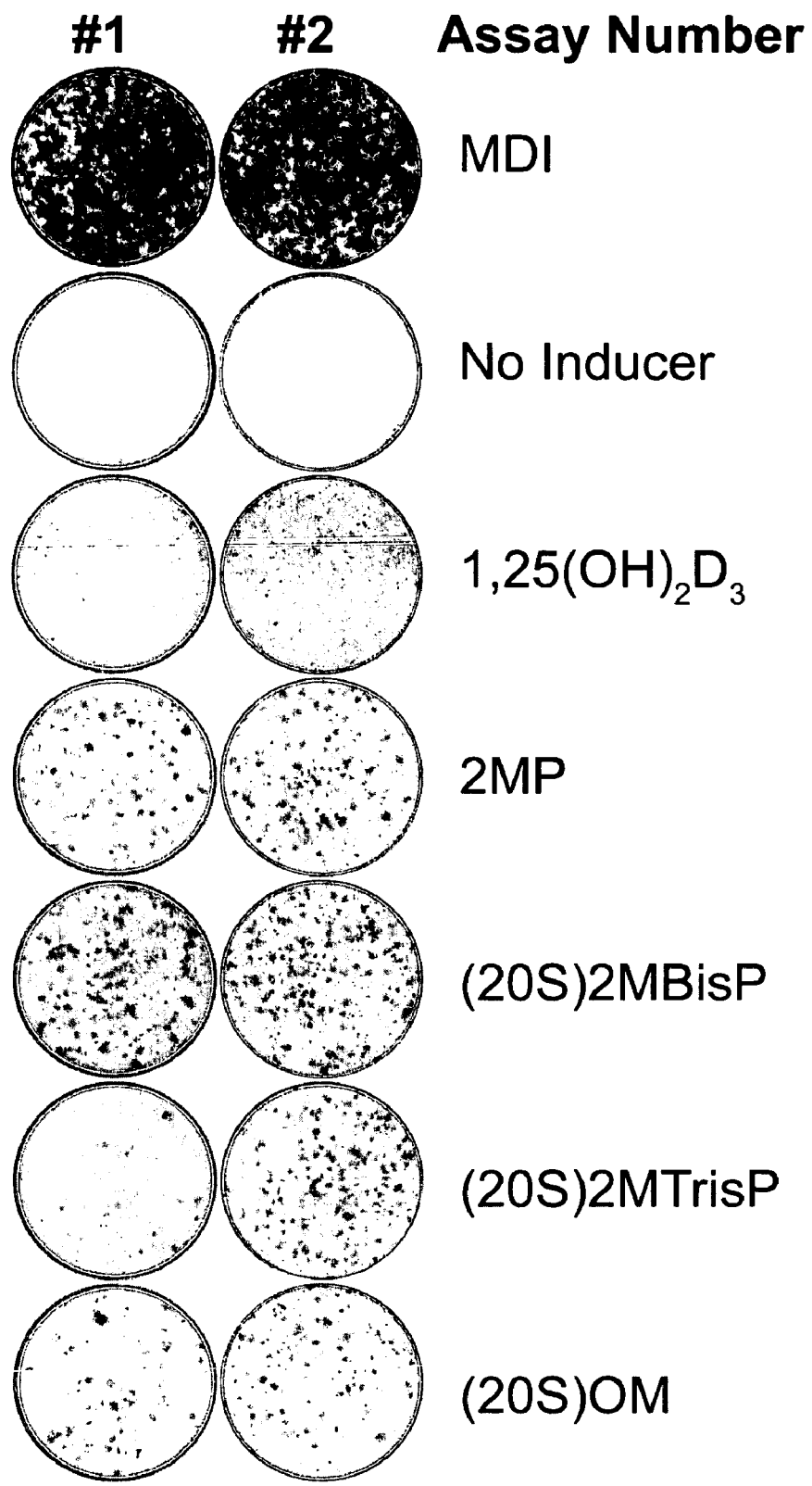
FIGS. 10A and 10B show that lengthening the vitamin D side chain found in the (20S)2MbisP compound by one carbon atom, (20S)2M-trisP, and two carbon atoms, (20S)OM) yields compounds that still possess activity in inhibiting the differentiation of MDI-treated 3T3-L1 cells into mature adipocytes, as assessed by a oil-red-O staining (FIG. 10A) and SCD1 mRNA induction (FIG. 10B).
Figure 10B:
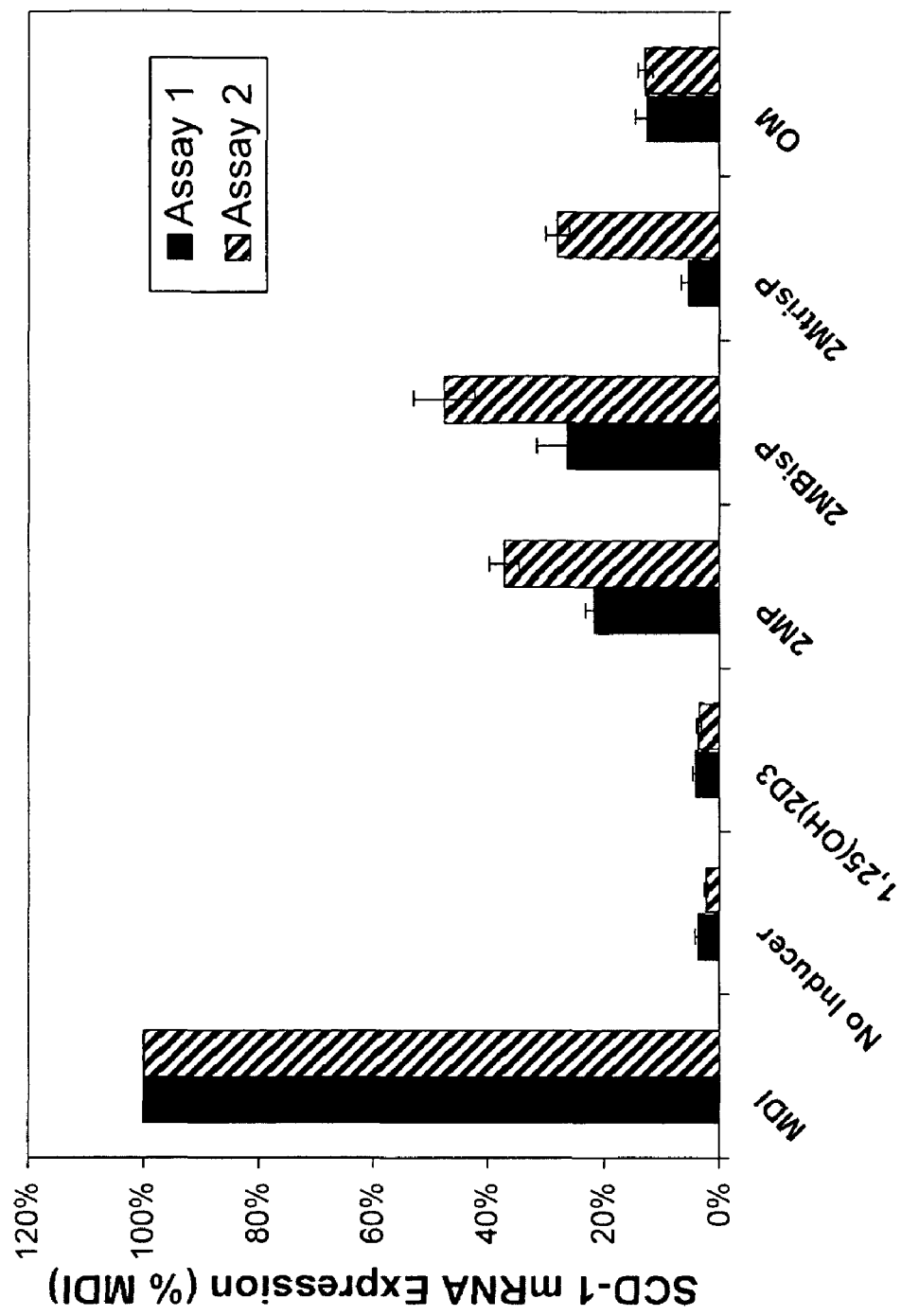

The effect of shortening the vitamin D side chain and eliminating the 25-hydroxy group of the 19-nor analogs is described in FIGS. 7-10. FIG. 7 shows that (20S)2-MbisP, 2-MP and 2-Mpregna are nearly as potent as the native hormone in inhibiting differentiation as assessed by Oil-Red-O staining and inhibition of SCD-1 mRNA. Thus, these shortened side chain 19-nor, 2-methylene analogs or 1α,25-(OH)$_2$D$_3$ containing only two to four carbons in the side chain and without a hydroxyl group on the side chain are active in inhibiting adipocyte differentiation. FIGS. 8 and 9 show that compounds containing the 2α-methyl substitution (2α-methyl bisP, 2α-methyl P) are nearly equal to their respective 2-methylene counterparts (2-MbisP, 2-MP). In addition, the 20R epimer of 2-MBisP is nearly equipotent to the 20S epimer (FIG. 8). FIG. 9 also shows that 17-ene compound VIT-I has activity. FIGS. 10A and 10B shows that when the side chain contains 5 (2-MtrisP) or 6 (OM) carbons without a hydroxyl group, the potency of the analog compared to those with shorter side chains is increased slightly as assessed by the reduction in Oil-Red-O staining compared to the sample treated with MDI inducer showing maximal differentiation, and in the reduction in SCD-1 mRNA induction.

Figure 11:
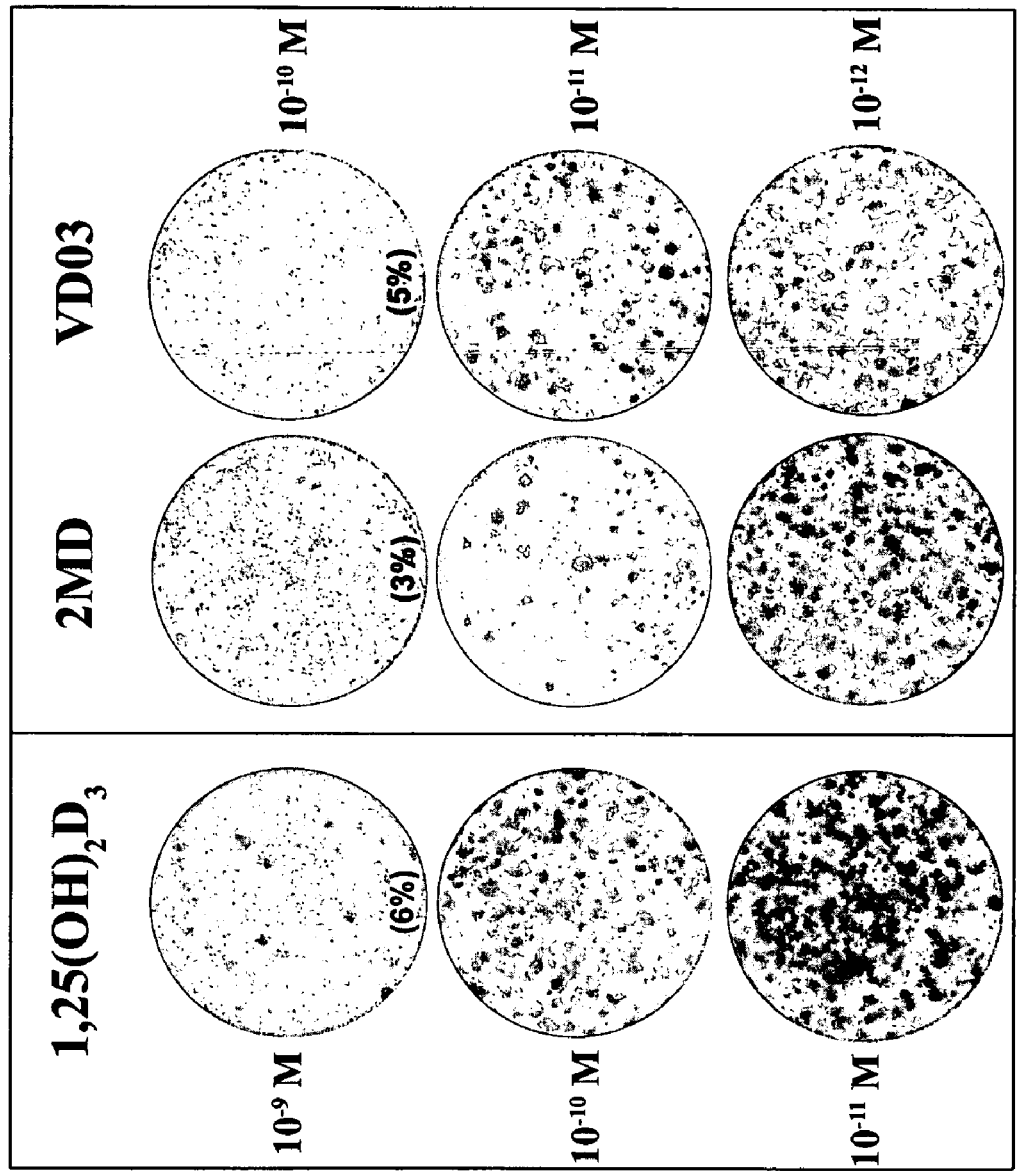
FIG. 11 is a scanned image showing that 2-methylene-18, 19-dinor vitamin D analogs such as VD-03 are active in inhibiting the differentiation of MDI-treated 3T3-L1 cells into mature adipocytes, as assessed by a oil-red-O staining and SCD1 mRNA induction (the expression of SCD1 mRNA is expressed as a percentage of that found in cells treated with MDI alone and is shown in the parentheses).

FIG. 11 shows that the (20S)-2-methylene-18,19-dinor-1α,25-dihydroxyvitamin D$_3$, VD-03, is approximately 10-fold more active than the native hormone, 1α,25-(OH)$_2$D$_3$, in inhibition Oil-Red-O staining. Other 19-nor analogs of 1α,25-(OH)$_2$D$_2$ also show good activity as described below.

Figure 12:
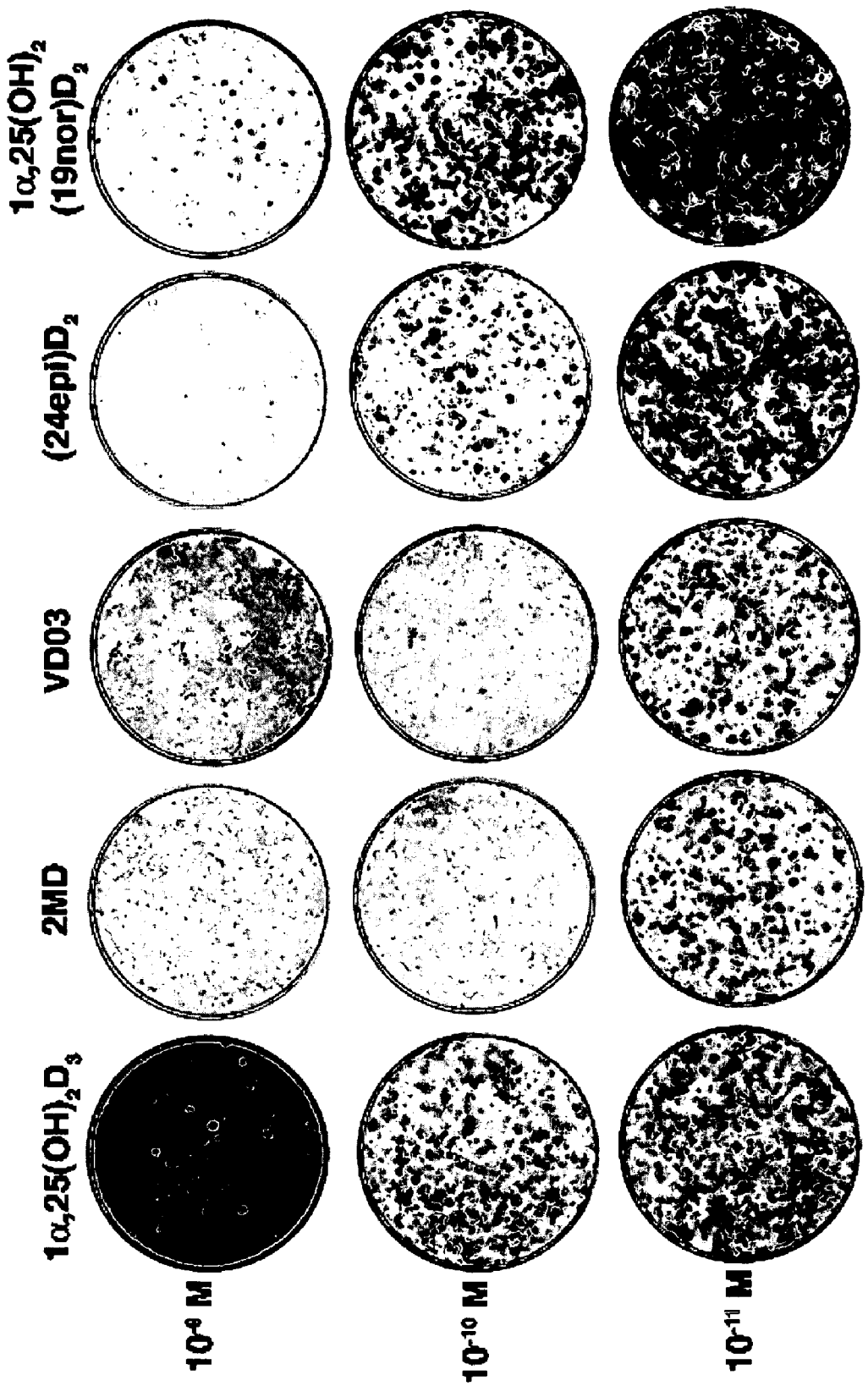
FIG. 12 is a scanned image showing that 2-methylene compounds with a vitamin $D_2$ side chain such as (24epi)$D_2$ and 1α,25(OH)$_2$(19nor)$D_2$ are active in inhibiting the differentiation of MDI-treated 3T3-L1 cells into mature adipocytes, as assessed by inhibition of oil-red-O staining.

The 19-nor derivative of the 1α,25-dihydroxyvitamin D$_3$ analog in the ergosterol series (i.e. 19-nor-1α,25-dihydroxyvitamin D$_2$ (1α,25(OH)$_2$(19nor)D$_2$)) also shows activity in inhibiting the differentiation of adipocyte differentiation that is equivalent in potency to the native hormone, 1α,25-(OH)$_2$D$_3$ (FIG. 12). The potency of this 19-nor vitamin D$_2$ analog is improved by the addition of a methylene group in the 2 position and the 24-epi configuration (2-methylene-19-nor-24-epi-1α,25-dihydroxyvitamin D$_2$ (24epi)D$_2$). Thus, both 24S and 24R derivatives of the 19-nor 1,25-dihydroxyvitamin D$_2$ analogs have activity.

The 2-(3'-hydroxypropylidene)-19-nor-1α,25-dihydroxyvitamin D$_3$ compounds (1AGR and 1AGS) are nearly equipotent in activity with the very potent 2-MD compound in inhibiting the differentiation of 3T3-L1 preadipocytes into mature adipocytes as assessed by Oil-Red-O staining and in the inhibition of SCD-1 mRNA induction. The compound with the 20S configuration (LAGS) is slightly more active than the 20R configuration (1AGR). The compound with a 3'-methoxymethoxy)propylidene group on the 2 position (F-Wit) is also active, but the activity of this compound is less than that observed with the 3'-hydroxypropylidene modification.

Thus, 2-MD, 2-MbisP, TMM, and the other vitamin D analogs described herein are effective at inhibiting the differentiation of 3T3-L1 cells, and the 2-MD and 1AGS compound have so far shown the highest activity. The ability of the 19-nor vitamin D analogs to inhibit the increase in SCD-1 gene transcription that precedes fat cell differentiation is highly significant as loss of this gene has been shown to protect mice against adiposity (Ntambi, J. M. et al., Proc. Natl. Acad. Sci. USA, 99(17), 11482-11486 (2002)). Furthermore, leptin, an adipocyte derived hormone whose loss is associated with the appearance of obesity, also specifically represses SCD-1 mRNA levels in vivo (Cohen, P. et al., Science, 297(5579), 240-243 (2002)). The surprising and unexpected ability of the 19-nor vitamin D analogs to both repress SCD-1 and prevent overt adipocyte differentiation and fat droplet accumulation strongly supports that these compounds will be effective agents in treating obesity.

Figure 14A:
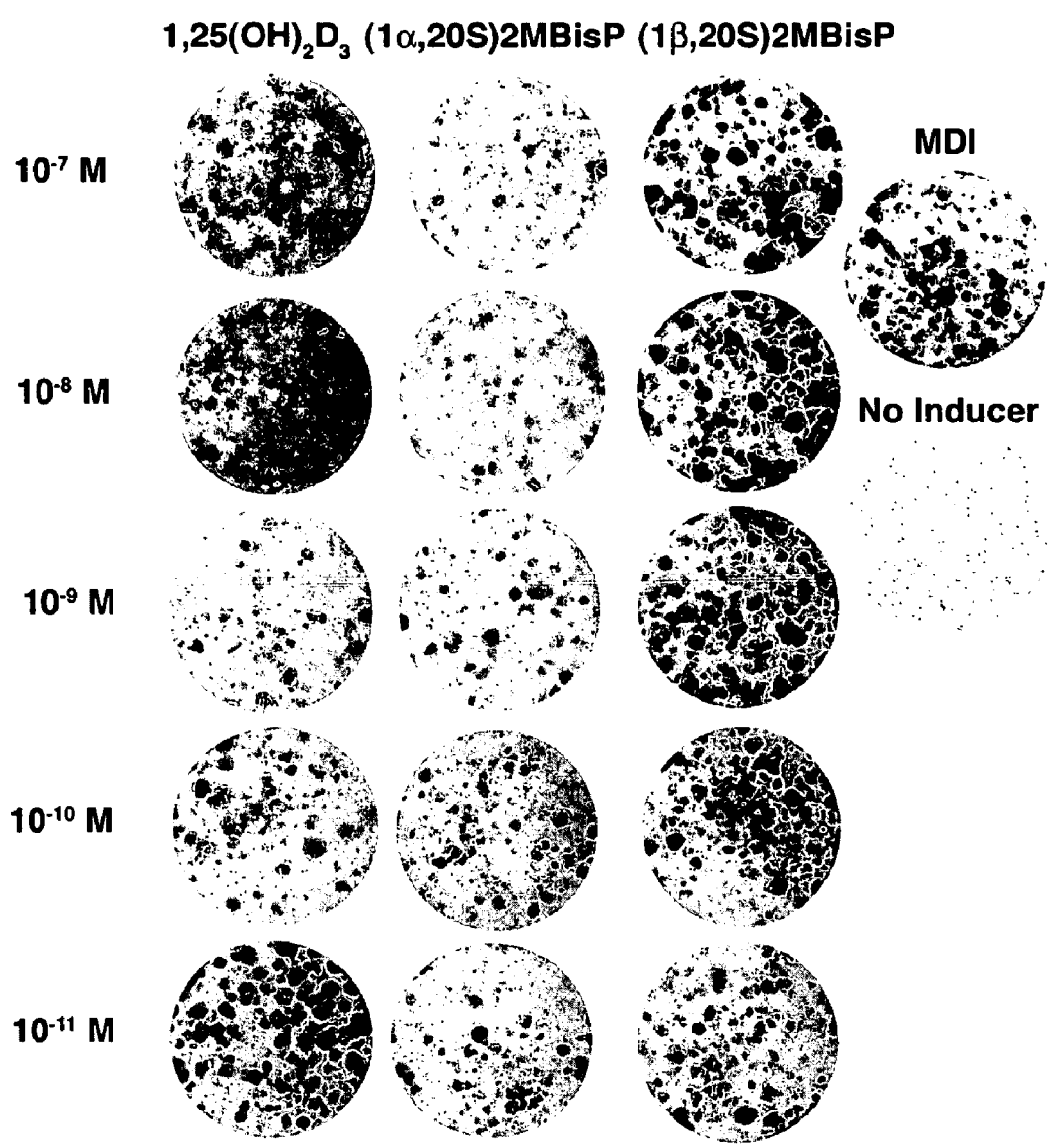
FIGS. 14A and 14B show inhibition of oil-red-O staining and SCD1 mRNA induction by 1α,25(OH)$_2$D$_3$ and (1α,20S)2MbisP.
Figure 14B:
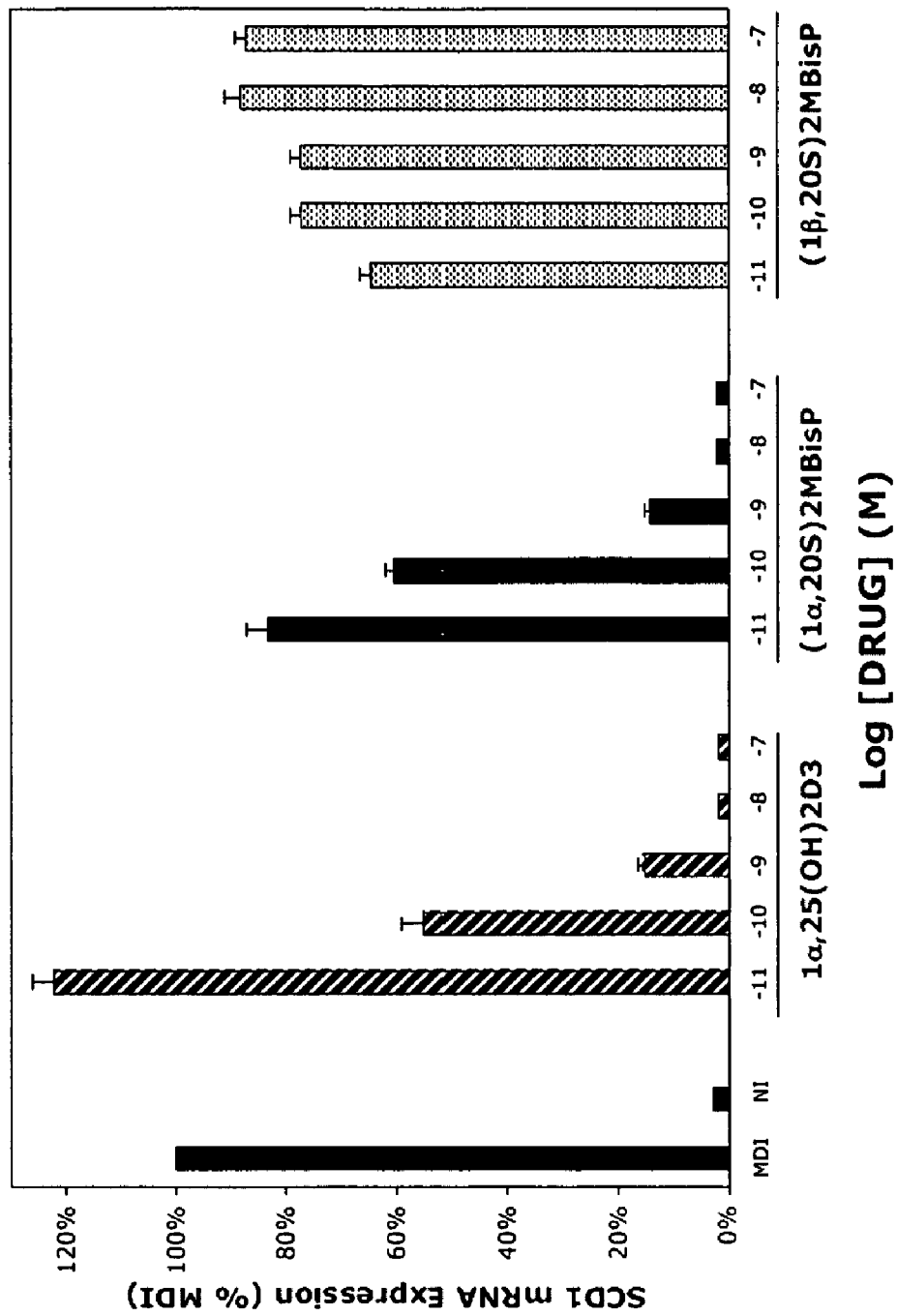
Figure 15:
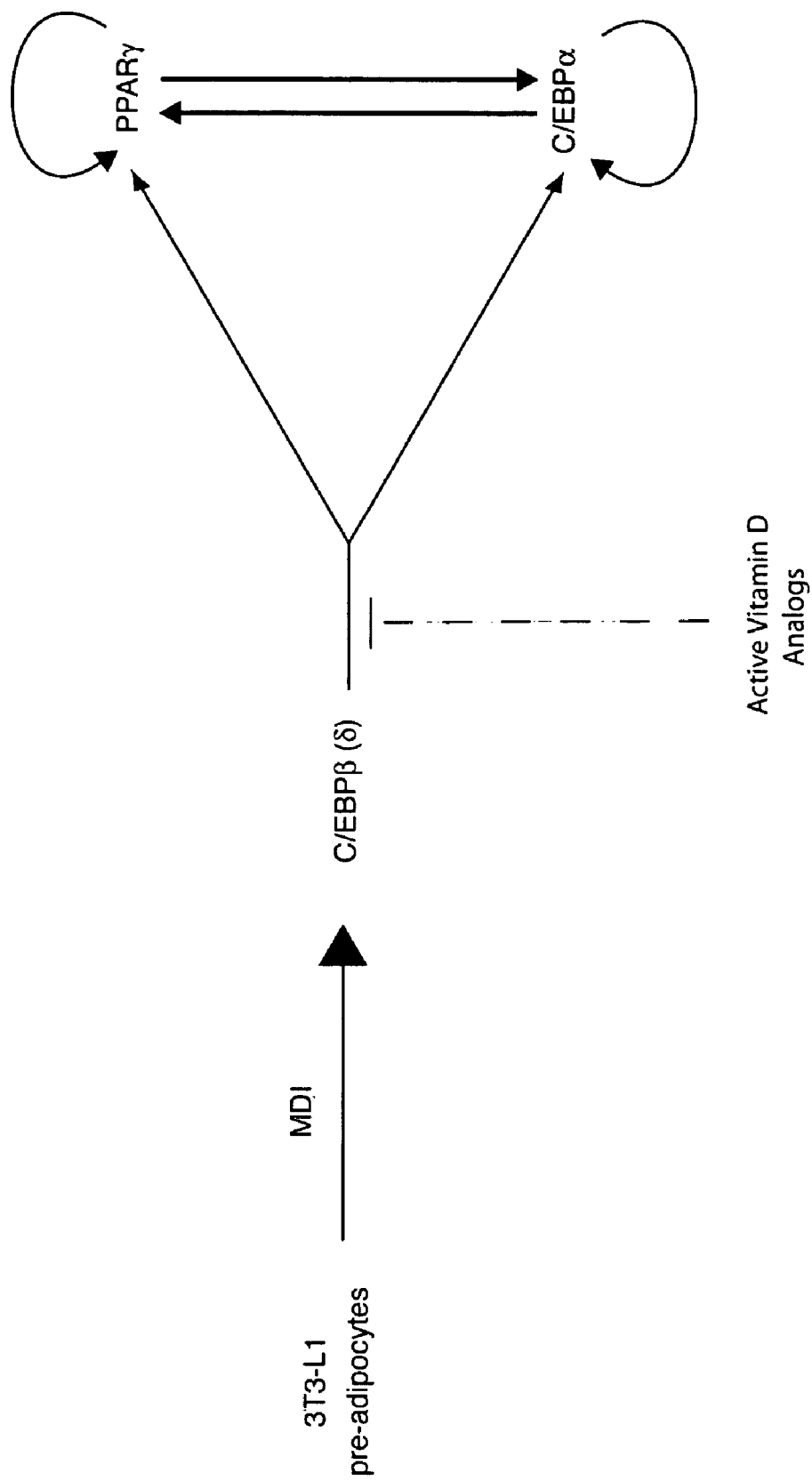
FIG. 15 shows the proposed pathway that is activated in 3T3-L1 cells by MDI induction leading to adipocyte differentiation, and the site at which vitamin D analogs are proposed to inhibit this process. Addition of MDI inducer promotes the induction of C/EBPβ(δ), which then leads to the transcription of the target transcription factors, PPARγ and C/EBPα, which then lead to expression of genes involved in establishing the mature adipocyte phenotype, such as SCD1 and Glut4. Active vitamin D analogs prevent the expression of the early transcription factors PPARγ and C/EBPα that are essential for the differentiation (see FIGS. 16-18).

The 1α configuration is preferred for activity in inhibiting adipocyte differentiation, as the 1-(20S)2-MbisP analog was unable to inhibit the appearance of Oil-Red-O staining in MDI-induced 3T3-L1 cells (FIG. 14A) or to inhibit the induction of SCD-1 mRNA (FIG. 14B), whereas the 1α-(20S)2-MbisP and the native hormone were nearly equipotent (<0.5 log unit difference) in inhibiting this differentiation. This is significant because the 1β-(20S)2-MbisP analog binds poorly, if at all, to the rat recombinant vitamin D receptor whereas the 1α-(20S)2-MbisP analog binds with nearly the same affinity as does the native 1α,25-dihydroxyvitamin $D_3$ hormone. It has also been documented previously, that 1α,25-dihydroxyvitamin $D_3$ shows very poor binding to the recombinant human vitamin D receptor (Peleg, S. Chapter 60: Molecular Basis for Differential Action of Vitamin D Analogs, In: Vitamin D (Feldman, Glorieux and Pike) 1977 pp. 1011-1025.

2-MD (Sicinski, R. et al., *J. Med. Chem.* 41(23), 4662-4674 (1998)), VD-03, VIT-I, and the 19-nor-1α,25-dihydroxyvitamin $D_2$ compound compete for tritiated hormone binding to the vitamin D receptor as well as the native hormone, calcitriol (1,25-$(OH)_2D_3$), and the 2-methylene-19-nor-24-epi-1α,25-dihydroxyvitamin $D_2$ analog actually show higher affinity binding than does the native hormone (approximately 0.5 log units). The AGS, AGR, and F-Wit analogs are all less than five times less potent in competing for tritiated hormone binding to the vitamin D receptor compared to the native hormone. The shortened side chain analogs including 2-Mpregna (U.S. Pat. No. 6,566,352), 2-MP (U.S. Pat. No. 6,579,861), (20S)2-MbisP (U.S. Pat. No. 6.627,622 B2), 2-MtrisP, and (20S)OM are as or nearly effective as calcitriol in binding to the vitamin D receptor although TMM, 2α-methylP, 2α-methylbisP, and (20R)2-MbisP are approximately 7 to 10-fold less effective at binding to the receptor. Thus, vitamin D receptor binding affinity alone cannot explain the differences in the potency of compounds to inhibit adipocyte differentiation.

As described, 2-MbisP, 2-MP (U.S. Pat. No. 6,579,861) 2-Mpregna (U.S. Pat. No. 6,566,352), have little, if any, activity in mobilizing calcium from bone or in promoting intestinal calcium transport, whereas the native hormone calcitriol (1α,25-$(OH)_2D_3$) is quite potent in both of these effects using a vitamin D deficient rat model. The above-cited patents are all hereby incorporated by reference in their entireties and for all purposes as if fully set forth herein. See also Plum L. A. et al., *Proc. Natl. Acad. Sci. USA* 101(18), 6900-9004 (2004). Likewise, 2α-methylP, (20R)2-MbisP, 2α-methylbisP, 2-MtrisP, (20S)-OM, and VIT-I, have very little bone calcium mobilization activity as compared to equimolar doses of the native hormone, 1α,25-$(OH)_2D_3$. Furthermore, these compounds have less activity as compared to that of 1,25-$(OH)_2D_3$ in stimulating intestinal calcium transport. In normal vitamin D sufficient rats, very high oral doses of 2-MP and 2-MbisP may be administered without producing an increase in serum calcium whereas similar doses of the native hormone produce frank hypercalcemia and even death. Therefore, 2-MP, 2α-methylP, (20S)2-MbisP, (20R)2-MbisP, 2α-methylbisP, 2MtrisP, OM and certain other vitamin D analogs may be used at much higher does than can the native hormone making them feasible for use in the treatment of obesity in humans and other animal subjects.

As described above, VD-03 exhibits a relatively low ability to mobilize calcium from bone, yet retains approximately the same activity as the native hormone, 1α,25-$(OH)_2D_3$ in promoting intestinal calcium transport. Because this alkylidene-18,19-dinor compound is approximately 10-fold more potent than 1α,25-$(OH)_2D_3$ in the inhibition of adipocyte differentiation and is less active in mobilizing calcium from bone, it, and other compounds, may be used at a higher doses than can the native hormone making them feasible for use in the treatment of obesity in humans and other animal subjects.

The 19-nor 1α,25-dihydroxyvitamin $D_2$ analog, 19-nor-1α,25-dihydroxyvitamin $D_2$ shows very low bone calcium mobilizing activity and the 2-methylene-19-nor-24-epi-1α,25-dihydroxyvitamin $D_2$ is less active than an equimolar dose of 1α,25$(OH)_2D_3$ in promoting bone calcium mobilization and intestinal calcium transport in the vitamin D deficient rat model. Because the $D_2$ analogs are both more active than the native hormone in inhibiting adipocyte differentiation, and are less calcemic, they may be used at higher doses than can the native hormone improving their potential for use in the treatment of obesity in humans and other animal subjects.

Figure 13:
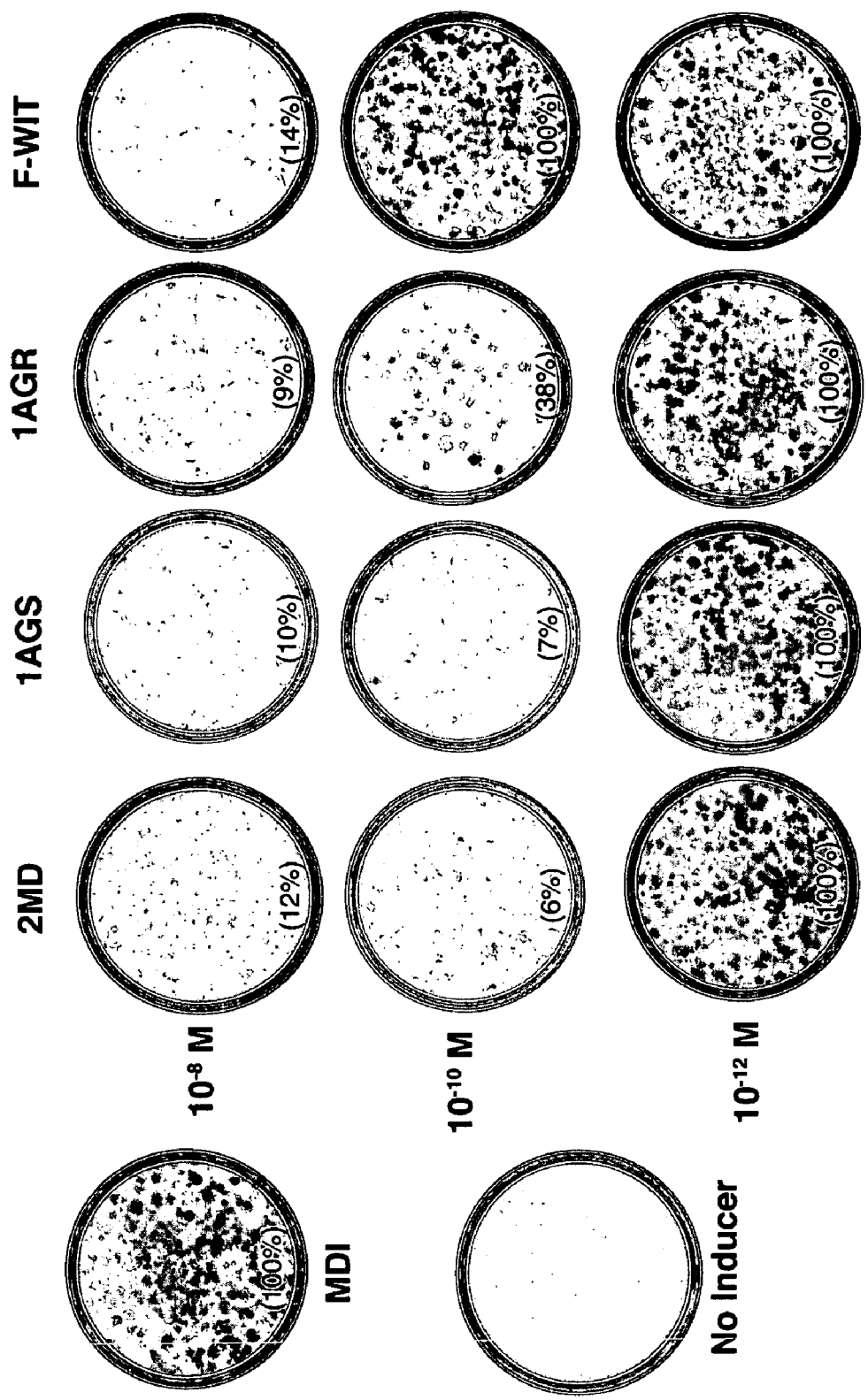
FIG. 13 is a scanned image showing that both 20S and 20R configurations of a 19-nor 1α,25-dihydroxyvitamin D compound further modified in the 2 position with the addition of a 3'-hydroxypropylidene group (1AGS and 1AGR), and the 20R 19-nor 1α,25-dihydroxyvitamin compound modified in the 2 position with the addition of a (3'-methoxymethoxy) propylidene group (F-Wit), are active in inhibiting the differentiation of MDI-treated 3T3-L1 cells into mature adipocytes, as assessed by inhibition of oil-red-O staining and SCD1 mRNA induction (the expression of SCD1 mRNA is expressed as a percentage of that found in cells treated with MDI alone and is shown in the parentheses).

2-MD, TMM, 1AGS, 1AGR, and F-Wit, like calcitriol, are active in promoting bone calcium mobilization and intestinal calcium transport (see Sicinski, R. R. et al., *J. Med. Chem.*, 41, 4662-4674 (1998). However, because the activity of 2-MD, 1AGR, and 1AGS in inhibiting adipocyte differentiation (FIG. 2 and FIG. 13) is so much greater that that of calcitriol relative to the doses of each that cause the above-described effects, it is likely that 2-MD, 1AGS, and/or 1AGR may be used for the prevention of obesity at doses that are non-calcemic in vivo.

Figure 16:
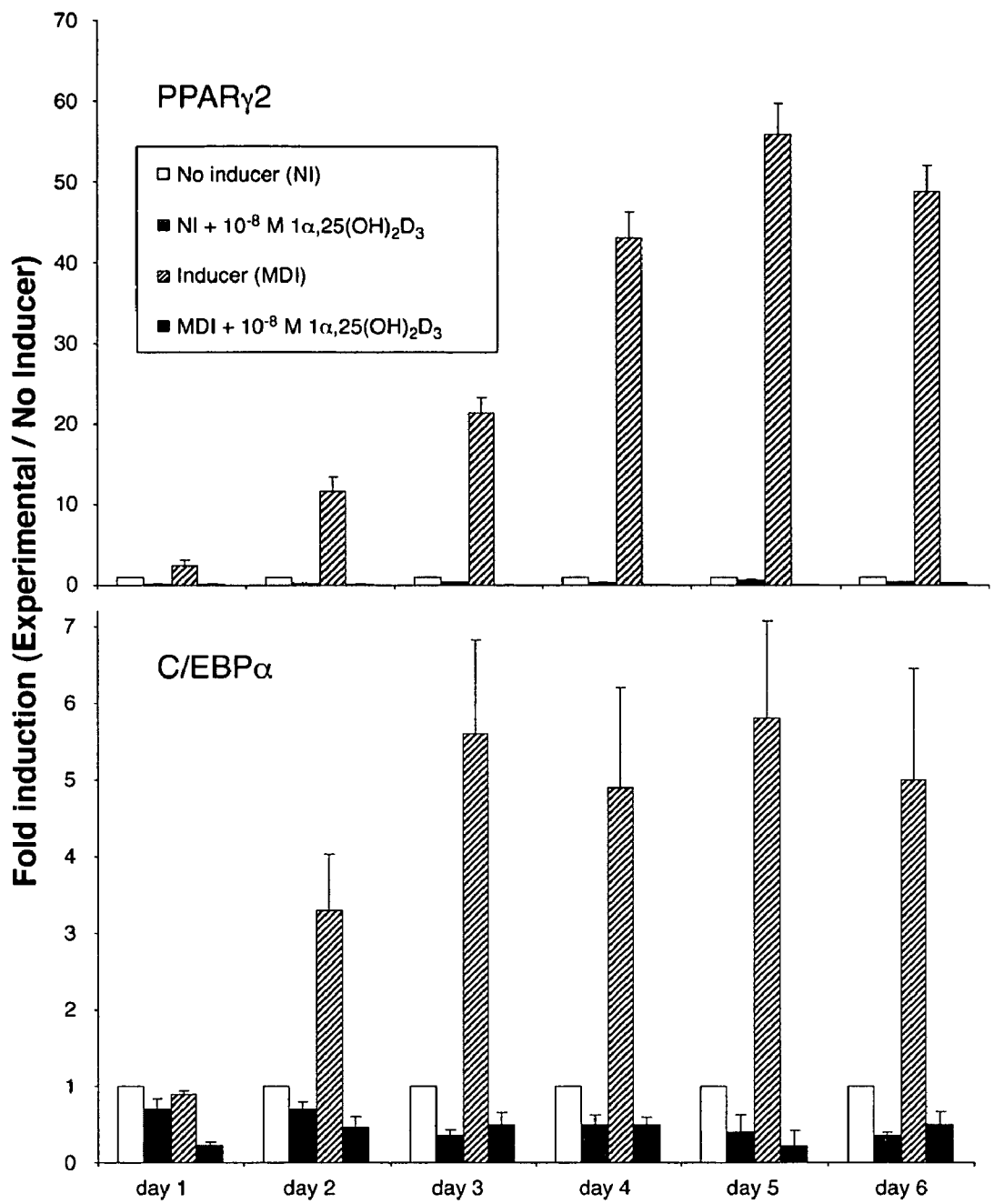
FIG. 16 shows that the PPARγ and C/EBPα mRNAs are not induced by MDI when 1α,25(OH)$_2$D$_3$ is present at $1 \times 10^{-8}$ M. Values from the transcription factor mRNAs are normalized to the no inducer sample.
Figure 17:
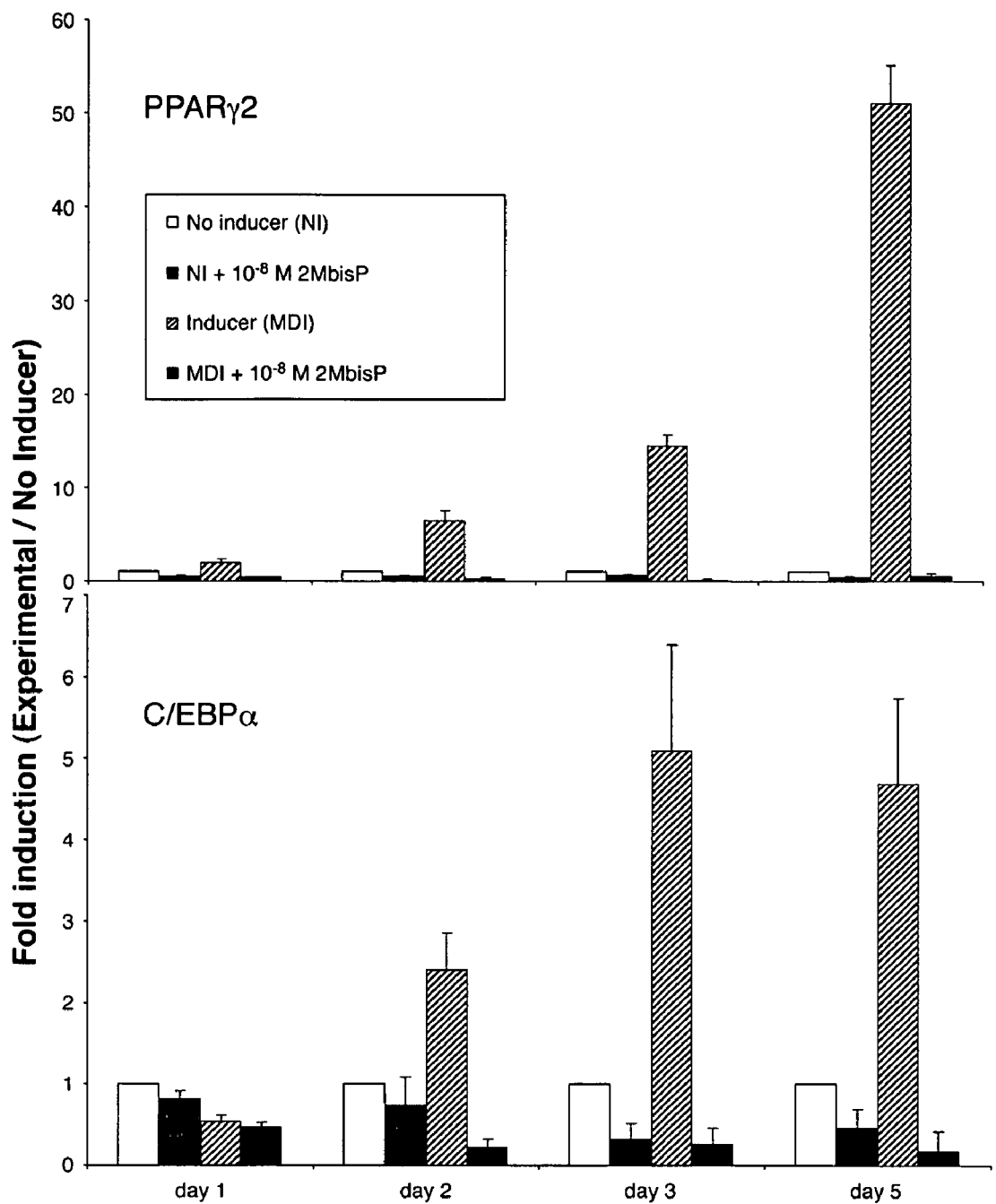
FIG. 17 shows that the PPARγ and C/EBPα mRNAs are not induced by MDI when (20S)2MbisP is present at $1 \times 10^{-8}$ M. Values from the transcription factor mRNAs are normalized to the no inducer sample.
Figure 18:
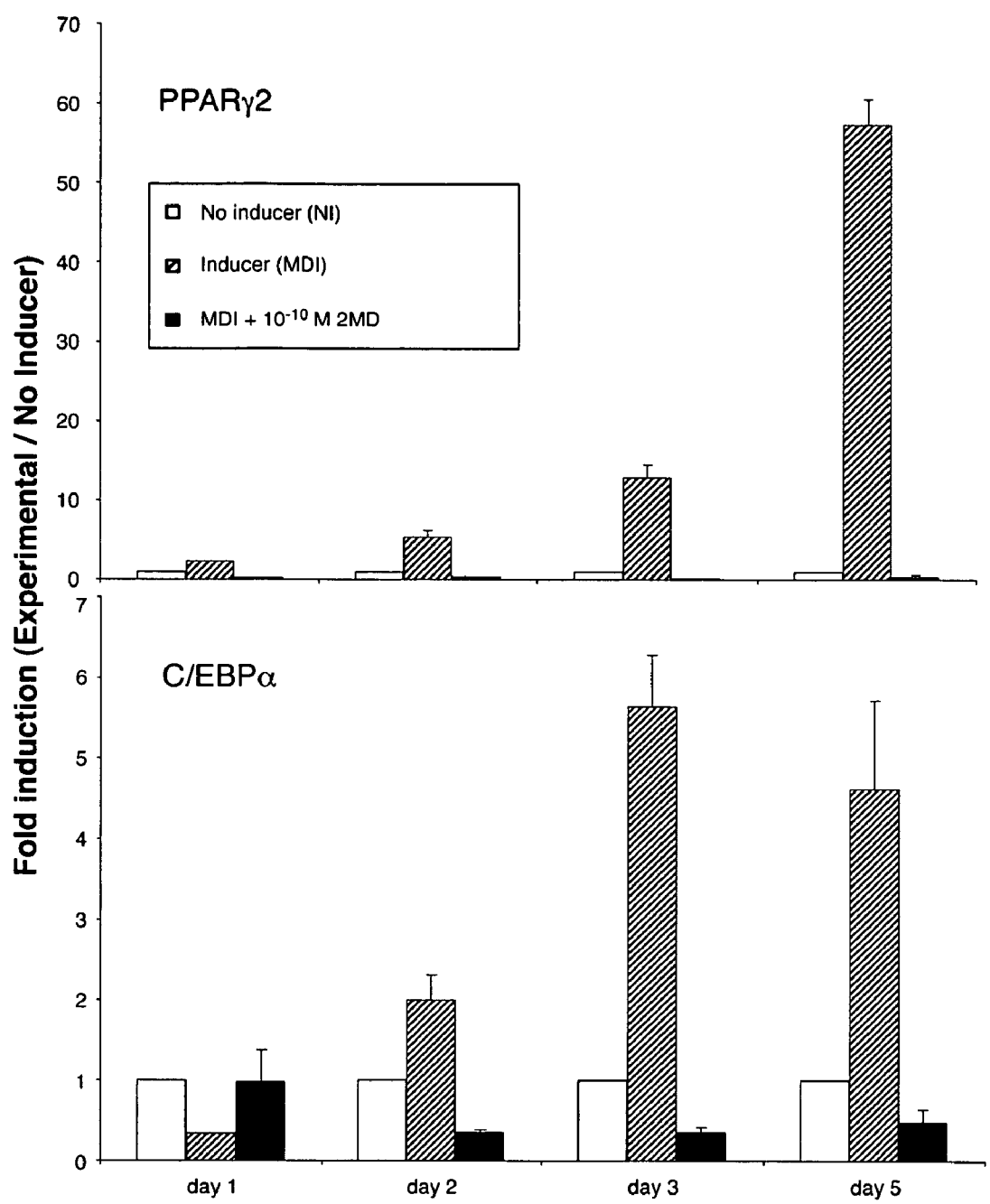
FIG. 18 shows that the PPARγ and C/EBPα mRNAs are not induced by MDI when 2-MD is present at $1 \times 10^{-10}$ M. Values from the transcription factor mRNAs are normalized to the no inducer sample.

The proposed pathway that is activated in 3T3-L1 cells by MDI induction that ultimately leads to adipocyte differentiation, and the site at which the vitamin D analogs of the invention are proposed to act is to prevent the induction of PPARγ2 and C/EBPα mRNAs. An increase in the transcription factors, PPARγ and C/EBPα, is essential for the expression of downstream genes (such as SCD-1) to establish the mature adipocyte phenotype. FIG. 16 shows that PPARγ2 and C/EBPα mRNAs are not induced by MDI when 1α,25$(OH)_2D_3$ is present at $1\times10^{-8}$ M. Furthermore, PPARγ and C/EBPα mRNAs are not induced by MDI when (20S)2MbisP is present at $1\times10^{-8}$ M. Tests on 2-MD also showed that it prevented these mRNAs from being upregulated when used at a concentration of $1\times10^{-10}$ M.

The results illustrate that analogs of 1α,25-dihydroxyvitamin D3 and 1α,25-dihydroxyvitamin $D_2$ have utility in treating obesity because they: (1) exhibit significant inhibition of adipocyte differentiation; (2) inhibit SCD-1 gene transcription; (3) prevent the induction of PPARγ2 and C/EBPα mRNAs and (4) may, in some compounds be used at doses that are devoid of hypercalcemic liability, unlike the native hormone 1α,25-dihydroxycholecalciferol (calcitriol).

All references cited herein are hereby incorporated by reference in their entireties and for all purposes as if fully set forth herein.

It is understood that the invention is not limited to the embodiments set forth herein for illustration, but embraces all such forms thereof as come within the scope of the following claims.

What is claimed is:

1. A method for inhibiting adipocyte differentiation, inhibiting SCD-1 gene transcription, and/or reducing body fat in an animal subject in need thereof, comprising administering to the animal subject, an effective amount of a 19-nor vitamin D compound or a pharmaceutical composition comprising the compound, wherein the compound administered to the subject inhibits adipocyte differentiation, inhibits SCD-1 gene transcription, and/or reduces body fat in the animal subject, and further wherein the compound is selected from a compound of formula IID, a compound of formula IIE, a compound of formula IIF, a compound of formula IIG, a compound of formula IIH, a compound of formula IIJ, a compound of formula IIK, a compound of formula IIL, a compound of formula IIM, a compound of formula IIN, a compound of formula IIO, a compound of formula IIP, a compound of formula IIQ,

IID

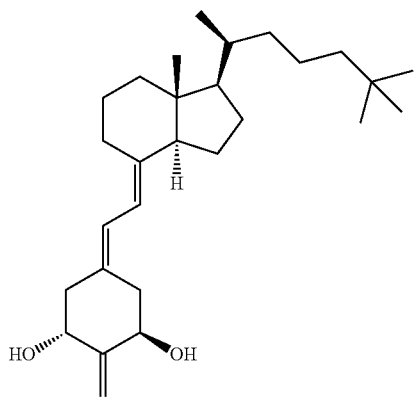

IIE

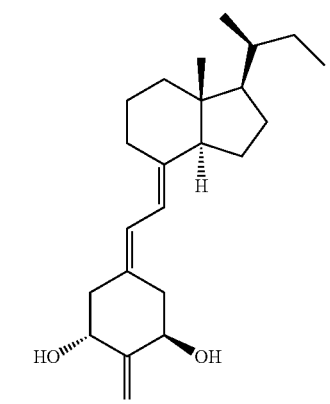

-continued

IIF

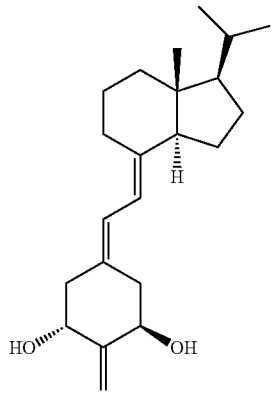

IIG

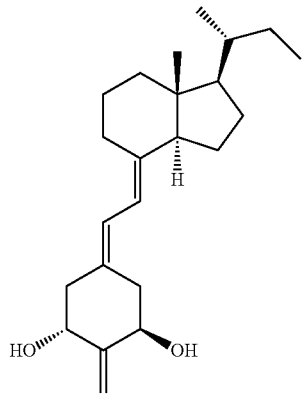

IIH

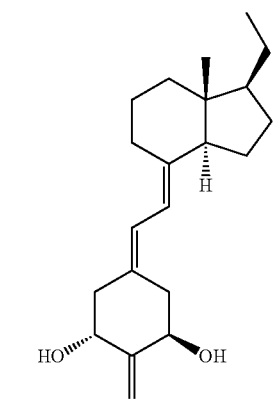

139
-continued
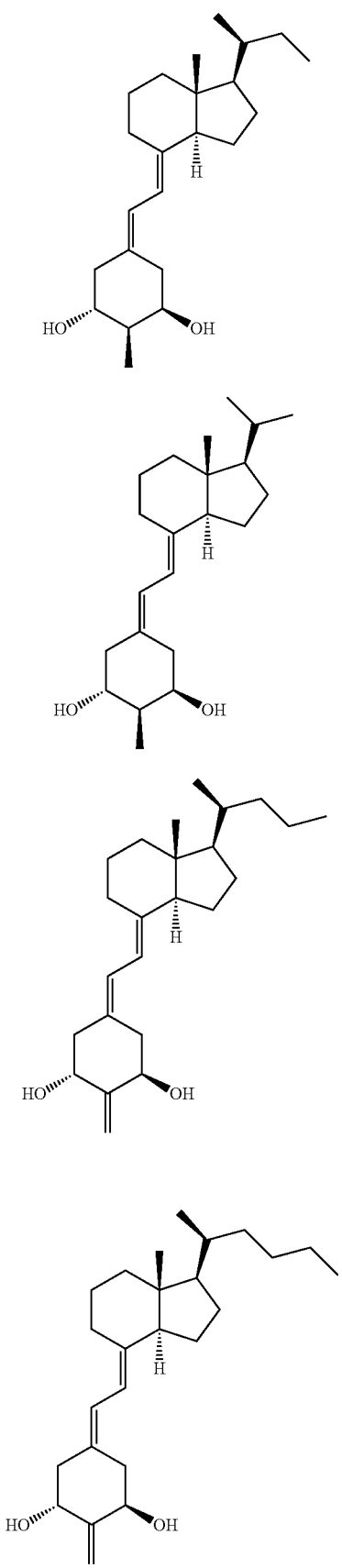
IIJ
IIK
IIL
IIM
140
-continued
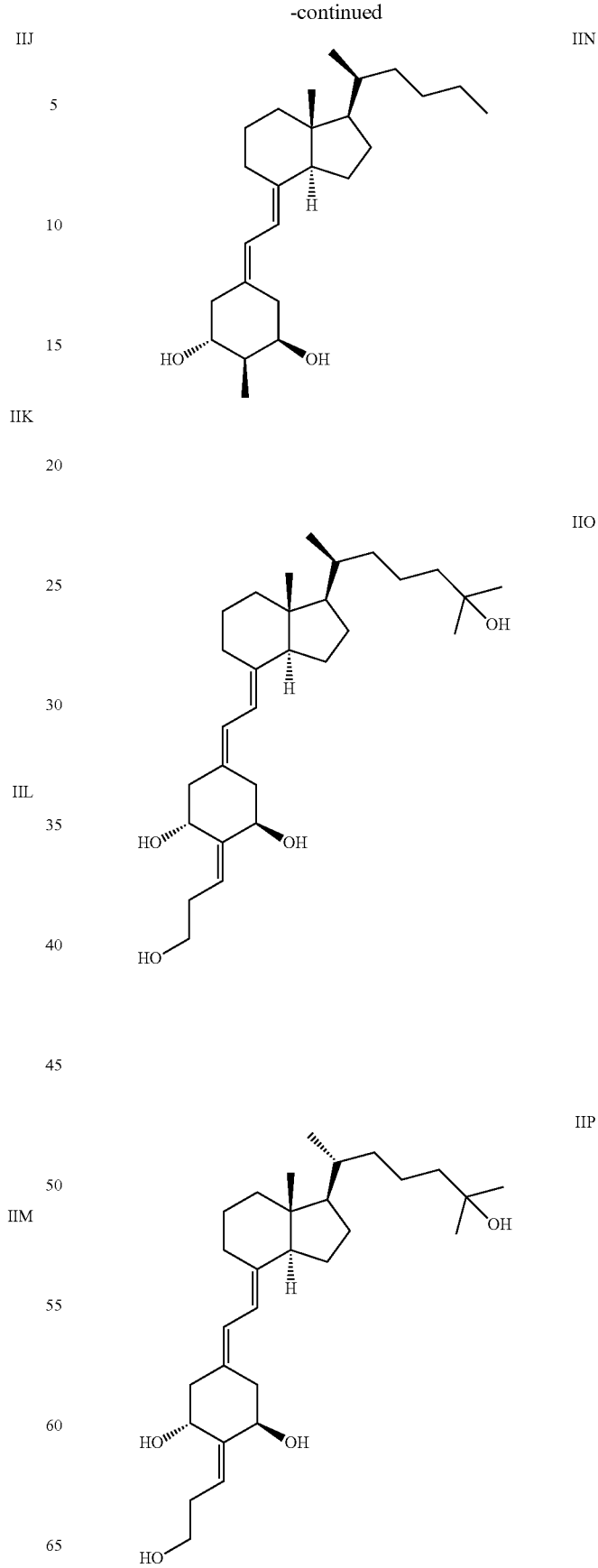
IIN
IIO
IIP -continued

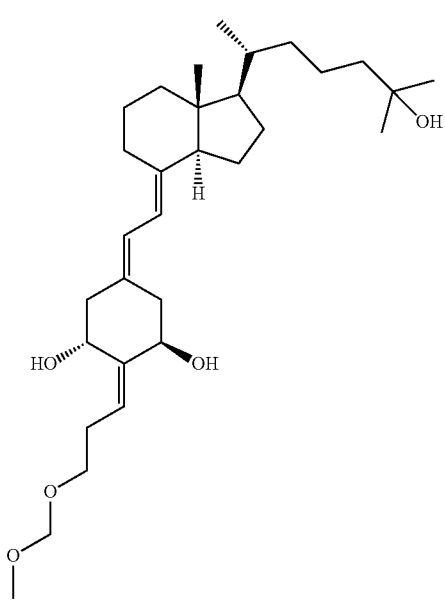

IIQ or is a combination thereof.

2. The method of claim 1, wherein the compound has the formula IID

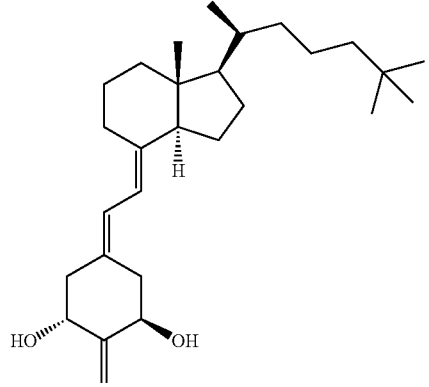

IID

3. The method of claim 1, wherein the compound has the formula IIE

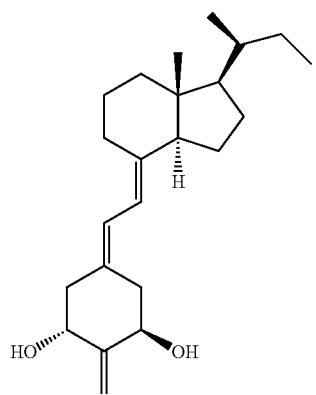

IIE

4. The method of claim 1, wherein the compound has the formula IIF

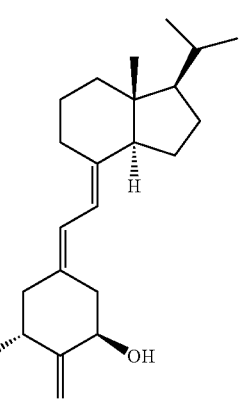

IIF

5. The method of claim 1, wherein the compound has the formula IIG

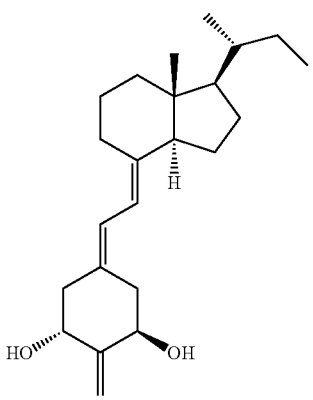

IIG

6. The method of claim 1, wherein the compound has the formula IIH

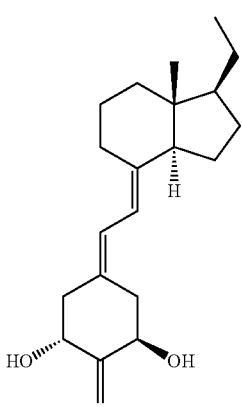

IIH

7. The method of claim 1, wherein the compound has the formula IIJ

IIJ

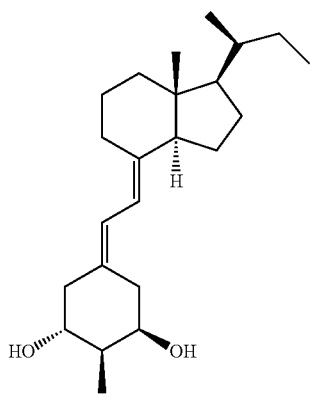

8. The method of claim 1, wherein the compound has the formula IIK

IIK

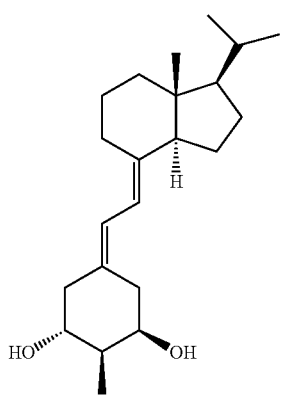

9. The method of claim 1, wherein the compound has the formula IIL

IIL

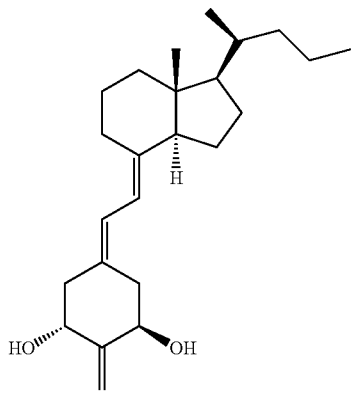

10. The method of claim 1, wherein the compound has the formula IIM

IIM

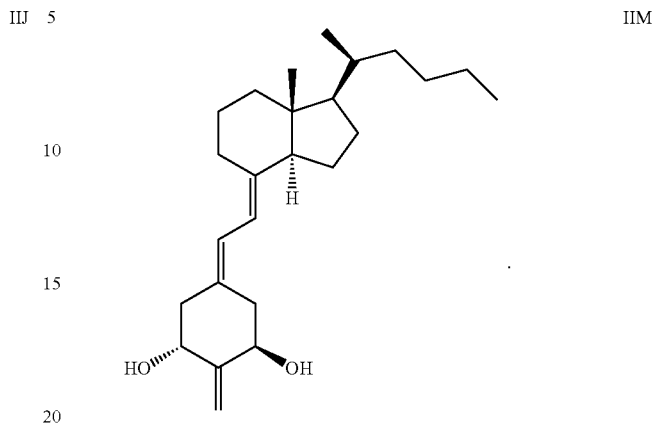

11. The method of claim 1, wherein the compound has the formula IIN

IIN

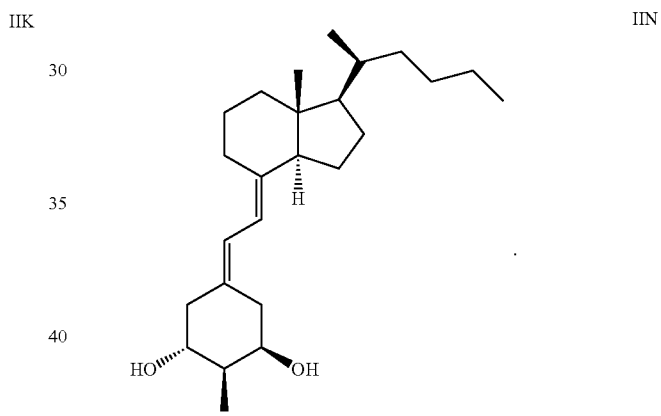

12. The method of claim 1, wherein the compound has the formula IIO

IIO

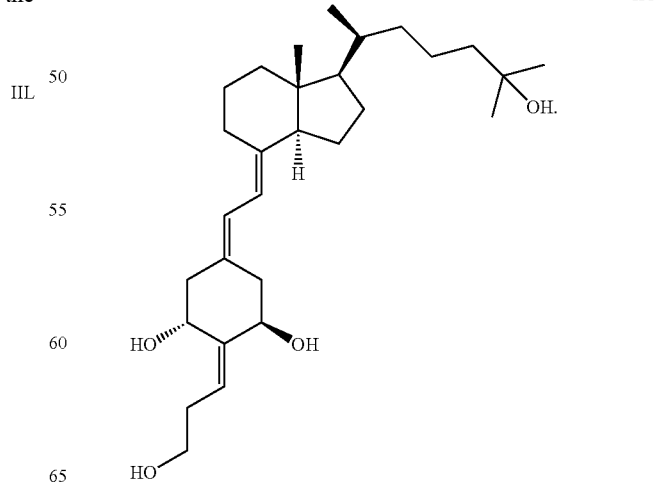

13. The method of claim 1, wherein the compound has the formula IIP
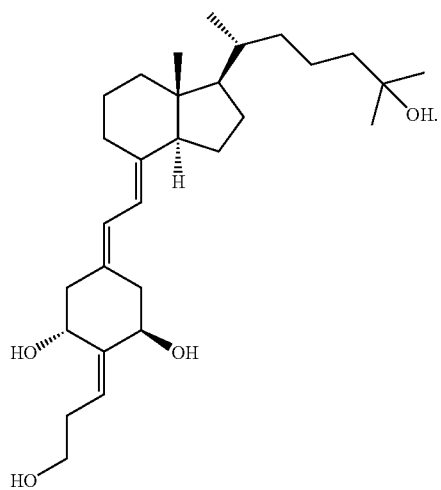
14. The method of claim 1, wherein the compound has the formula IIQ
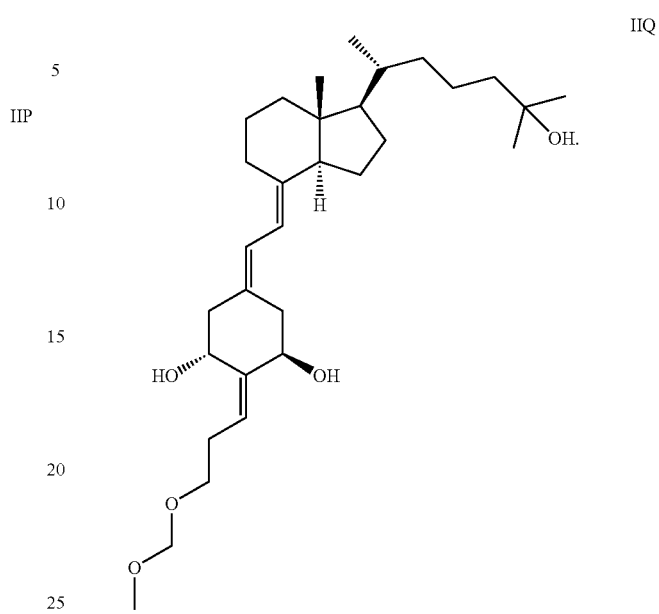
* * * * *

SEQUENCE LISTING

<160> NUMBER OF SEQ ID NOS: 8

<210> SEQ ID NO 1
<211> LENGTH: 19
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 1
agtttctttc gtggctggg                                                19

<210> SEQ ID NO 2
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
atgagttgga ggtagggagg a                                             21

<210> SEQ ID NO 3
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
tgaaggtcgg tgtgaacgga tttggc                                        26

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
catgtaggcc atgaggtcca ccac                                          24

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
tgctgttatg ggtgaaactc tg                                            22

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gaaatcaact gtggtaaagg gc                                            22

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 7
cgagtagggg gagcaaaaa                                              19

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gcaaaaagca agggattagg ag                                          22
```